US012485121B2

(12) United States Patent
Kurkin et al.

(10) Patent No.: US 12,485,121 B2
(45) Date of Patent: Dec. 2, 2025

(54) ANTIVIRAL AGENTS FOR THE TREATMENT AND PREVENTION OF HIV INFECTION

(71) Applicant: Pharmasyntez, Joint Stock Company, Irkutsk (RU)

(72) Inventors: Alexander Vitalievich Kurkin, Moscow (RU); Ekaterina Vladimirovna Manasova, Moscow (RU); Denis Nikolaevich Kazyulkin, Moscow (RU); Vladimir Nikolaevich Ivanov, Yelets (RU); Mikhail Gennadievich Shurygin, Markova (RU)

(73) Assignee: PHARMASYNTEZ, JOINT STOCK COMPANY, Irkutsk (RU)

( * ) Notice: Subject to any disclaimer, the term of this patent is extended or adjusted under 35 U.S.C. 154(b) by 684 days.

(21) Appl. No.: 17/891,979

(22) Filed: Aug. 19, 2022

(65) Prior Publication Data

US 2023/0120294 A1 Apr. 20, 2023

Related U.S. Application Data

(63) Continuation of application No. PCT/RU2021/000070, filed on Feb. 18, 2021.

(30) Foreign Application Priority Data

Feb. 19, 2020 (RU) ........................... RU2020107455

(51) Int. Cl.
*A61K 31/517* (2006.01)
*A61K 45/06* (2006.01)
*A61P 31/18* (2006.01)

(52) U.S. Cl.
CPC ........... *A61K 31/517* (2013.01); *A61K 45/06* (2013.01); *A61P 31/18* (2018.01)

(58) Field of Classification Search
CPC ...... A61K 31/517; A61K 45/06; A61K 31/55; A61K 31/519; A61P 31/18; C07D 239/70; C07D 239/91; C07D 401/12; C07D 487/02; C07D 471/04; C07D 487/04
See application file for complete search history.

(56) References Cited

FOREIGN PATENT DOCUMENTS

| | | | |
|---|---|---|---|
| WO | 2006035067 | A2 | 4/2006 |
| WO | 2006035068 | A2 | 4/2006 |
| WO | 2006035369 | A2 | 4/2006 |
| WO | 2006045828 | A1 | 5/2006 |
| WO | 2006087387 | A1 | 8/2006 |
| WO | 2006094930 | A1 | 9/2006 |
| WO | 2018000450 | A1 | 1/2018 |

OTHER PUBLICATIONS

Kang et al. Journal of Medicinal Chemistry 2020 63 (3), 1298-1312. (Year: 2020).*
Das, K. et al. Roles of Conformational and Positional Adaptability in Structure-Based Design of TMC125-R165335 (Etravirine) and Related Non-nucleoside Reverse Transcriptase Inhibitors That Are Highly Potent and Effective against Wild-Type and Drug-Resistant HIV-1 Variants. J. Med. Chem. 2004, 47, 2550-2560.
Guillemont, J. et al. Synthesis of Novel Diarylpyrimidine Analogues and Their Antiviral Activity against Human Immunodeficiency Virus Type 1. J. Med. Chem. 2005, 48, 2072-2079.
Janssen, P.A. et al. In Search of a Novel Anti-HIV Drug: Multidisciplinary Coordination in the Discovery of 4-[[4-[[4-(1E)-2-Cyanoethenyl]-2,6-dimethylphenyl]amino]-2-pyrimidinyl]amino]benzonitrile (R278474, Rilpivirine). J. Med. Chem. 2005, 48, 1901-1909.
International Search Report and Written Opinion issued by the International Searching Authority on Aug. 26, 2021 for corresponding International Patent Application No. PCT/RU2021/000070.
International Preliminary Report on Patentability issued by the International Bureau on Aug. 23, 2022 for corresponding International Patent Application No. PCT/RU2021/000070.
Kang, D. et al. Discovery and Characterization of Fluorine-Substituted Diarylpyrimidine Derivatives as Novel HIV-1 NNRTIs with Highly Improved Resistance Profiles and Low Activity for the hERG Ion Channel. Journal of Medicinal Chemistry, vol. 63, No. 3. Feb. 13, 2020, pp. 1298-1312.

* cited by examiner

*Primary Examiner* — Joseph K Mckane
*Assistant Examiner* — Ashli Ariana Chicks
(74) *Attorney, Agent, or Firm* — Anton J. Hopen; Trenam Law

(57) ABSTRACT

Novel pyrimidine derivatives, as well as pharmaceutical compositions and drugs contained in them, capable of inhibiting HIV replication are presented. These novel pyrimidine compounds, as well as pharmaceutical compositions and drugs contained in them, are capable of treating and preventing HIV-mediated diseases. The treatment and/or prevention of HIV in subjects with HIV-infection (human immunodeficiency virus) or having risk of getting HIV-infection with the compounds and compositions is also presented.

33 Claims, No Drawings

ANTIVIRAL AGENTS FOR THE TREATMENT AND PREVENTION OF HIV INFECTION

CROSS REFERENCE TO RELATED APPLICATIONS

This application is a continuation of PCT Application No. PCT/RU2021/000070, entitled "Pyrimidine-Based Bicycles as Antiviral Agents for the Treatment and Prevention of HIV Infection", filed on Feb. 18, 2021, which claims priority to Russian Application No. 2020107455, filed on Feb. 19, 2020, the contents of which are herein incorporated by reference.

FIELD OF THE INVENTION

This invention relates to pyrimidine derivatives capable of inhibiting HIV replication. The present invention provides new pyrimidine compounds of formula I. The compounds can be used for the treatment and/or prevention of HIV-mediated diseases. The invention further relates to methods of obtaining said compounds and pharmaceutical compositions contained thereof. The invention also relates to the use of the above mentioned compounds for the treatment and/or prevention of HIV in subjects with HIV-infection (human immunodeficiency virus) or having risk of getting HIV-infection.

BACKGROUND OF THE INVENTION

Compounds structurally related to the present antiviral compounds are disclosed in the following prior art:

J. Guillemont et al., application WO 2006/035068, published on Apr. 6, 2006,

J. Guillemont et al., application WO 2006/035067, published on Apr. 6, 2006,

J. Guillemont et al., application WO 2006/045828, published on May 4, 2006,

J. Guillemont et al., application WO 2006/035369, published on Apr. 6, 2006,

H. A. De Koek and P. Wigerinck, application WO 2006/094930, published on Sep. 14, 2006.

H. A. De Koek and P. Wigerinck, application WO 2006/087387, published on Aug. 24, 2006.

P. A. J. Jansen et al., J. Med Chem., 48(6), 1901-1909 (2005)

K. Das et al., J. Med. Chem., 47(10), 2550-2660 (2004).

J. Guillemont et al., J. Med. Chem., 48(6), 2072-2079 (2005).

SUMMARY OF THE INVENTION

The inventors have produced the novel compound of formula I, the compound comprising

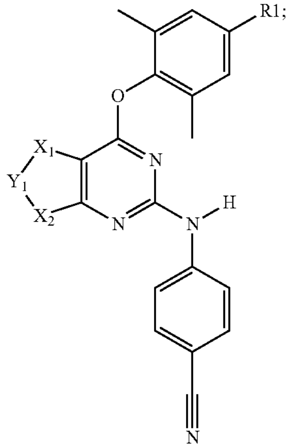

(I)

where $R^1$ is independently selected and represents H—, —CN, CN—CH═CH—;

$X^1$, $X^2$ is a substituent of $(CH_2)_n$ type, wherein n is independently selected for $X_1$, $X_2$ and may have values of between 1 and 3;

$Y^1$ is independently selected and represents —O—, —S—, —S(═O)—, —S(═O)$_2$—, or substitutents of the following type:

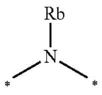 ,
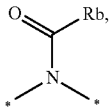
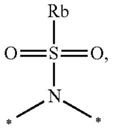
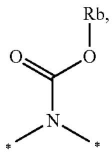

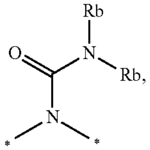
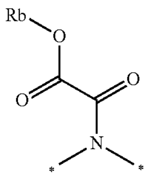
or
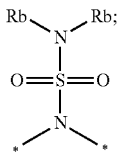

$R^b$ is independently selected and represents —H, substituted or unsubstituted —$C_1$-$C_6$-alkyl, substituted or unsubstituted —$C_1$-$C_6$-alkenyl, substituted or unsubstituted —$C_6$-aryl, substituted or unsubstituted -5-6-membered-heteroaryl containing 1 to 4 heteroatoms independently selected from N, S and/or O, substituted or unsubstituted —$C_3$-$C_9$-cycloalkyl, or substituted or unsubstituted 4-9-membered heterocyclyl containing 1 to 4 heteroatoms independently selected from N, S and/or O; or pharmaceutically acceptable salts thereof.

Compounds of formula I inhibit HIV-1 reverse transcriptase and can be used in the method for the treatment and/or prevention of HIV-mediated diseases.

The present invention further relates to the composition, containing compounds of formula I, which can be used for the treatment and/or prevention of HIV-mediated diseases. This invention also relates to compounds of formula I, which can be used for the treatment as a single therapeutic agent or in combination with other antiviral agents.

In one embodiment, the present invention relates to one of the following compounds:

| | Structural formula | Name |
|---|---|---|
| 0272161 | 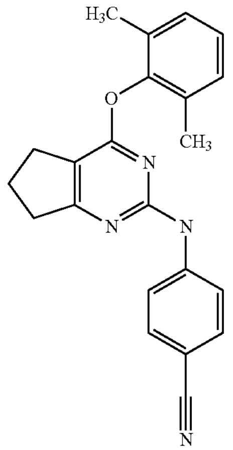 [SMILES: Cc1cccc(C)c1Oc1nc(Nc2ccc(C#N)cc2)nc2c1CCC2] | 4-((4-(2,6-Dimethylphenoxy)-6,7-dihydro-5H-cyclopenta[d]pyrimidine-2-yl)amino)-benzonitrile |
| 0272208 | 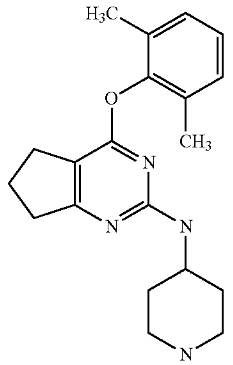 [SMILES: Cc1cccc(C)c1Oc1nc(NC2CCNCC2)nc2c1CCC2] | 4-(2,6-Dimethylphenoxy)-N-(piperidine-4-yl)-6,7-dihydro-5H-cyclopenta[d]pyrimidine-2-amine |
| 0273457 | 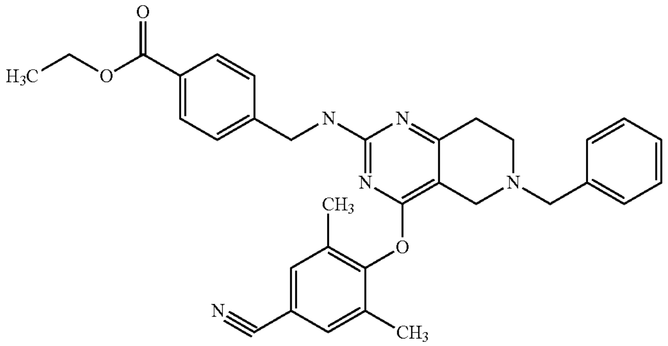 [SMILES: CCOC(=O)c1ccc(CNc2nc3c(c(Oc4c(C)cc(C#N)cc4C)n2)CN(Cc2ccccc2)CC3)cc1] | Ethylic ether 4-(((6-benzyl-4-(4-cyano-2,6-dimethylphenoxy)-5,6,7,8-tetrahydropyrido[4,3-d]pyrimidine-2-yl)amino)methyl)benzoic acid |
| 0273458 | 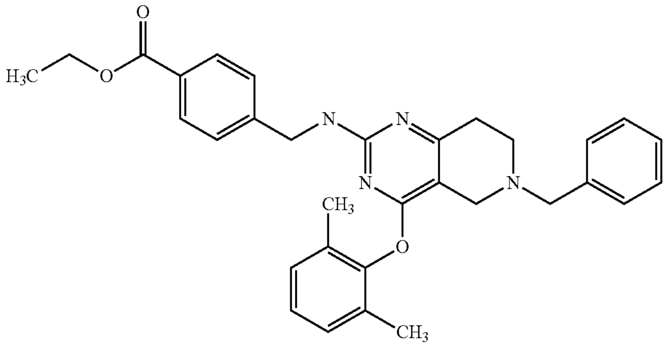 [SMILES: CCOC(=O)c1ccc(CNc2nc3c(c(Oc4c(C)cccc4C)n2)CN(Cc2ccccc2)CC3)cc1] | Ethylic ether 4-(((6-benzyl-4-(2,6-dimethylphenoxy)-5,6,7,8-tetrahydropyrido[4,3-d]pyrimidine-2-yl)amino)methyl)benzoic acid |

-continued

| | Structural formula | Name |
|---|---|---|
| 0273459 | 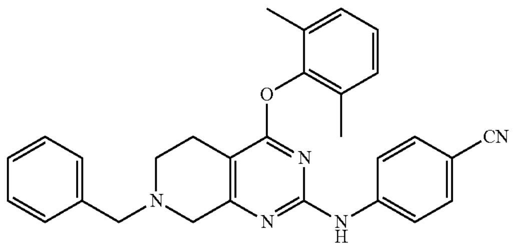 [SMILES: Cc1cccc(C)c1Oc1nc(Nc2ccc(C#N)cc2)nc2c1CCN(Cc1ccccc1)C2] | 4-(((7-Benzyl-4-(2,6-dimethylphenoxy)-5,6,7,8-tetrahydropyrido[3,4-d]pyrimidine-2-yl)amino)methyl)benzonitrile |
| 0273460 | 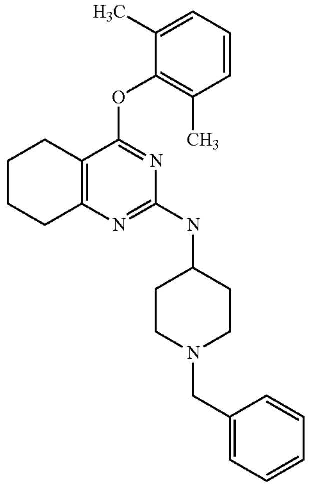 [SMILES: Cc1cccc(C)c1Oc1nc(NC2CCN(Cc3ccccc3)CC2)nc2c1CCCC2] | N-(1-Benzylpiperidine-4-yl)-4-(2,6-dimethylphenoxy)-5,6,7,8-tetrahydroquinazoline-2-amine |
| 0273461 | 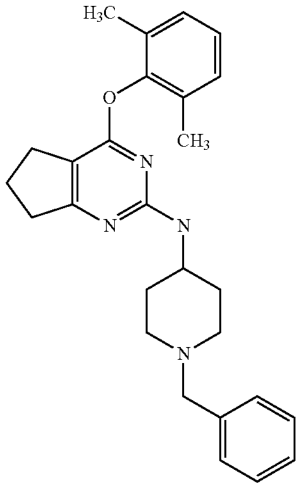 [SMILES: Cc1cccc(C)c1Oc1nc(NC2CCN(Cc3ccccc3)CC2)nc2c1CCC2] | N-(1-Benzylpiperidine-4-yl)-4-(2,6-dimethylphenoxy)-6,7-dihydro-5H-cyclopenta[d]pyrimidine-2-amine |
| 0273774 | 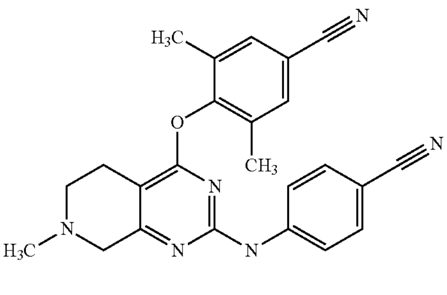 [SMILES: Cc1cc(C#N)cc(C)c1Oc1nc(Nc2ccc(C#N)cc2)nc2c1CCN(C)C2] | 4-((2-((4-Cyanophenyl)amino)-7-methyl-5,6,7,8-tetrahydropyrido[3,4-d]pyrimidine-4-yl)oxy)-3,5-dimethylbenzonitrile |

-continued
| | Structural formula | Name |
|---|---|---|
| 0273775 | 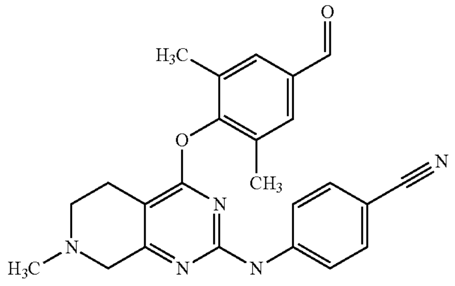 [SMILES: Cc1cc(C=O)cc(C)c1Oc1nc(Nc2ccc(C#N)cc2)nc2c1CCN(C)C2] | 4-((4-(4-Formyl-2,6-dimethylphenoxy)-7-methyl-5,6,7,8-tetrahydro[3,4-d]pyrimidine-2-yl)amino)benzonitrile |
| 0273892 | 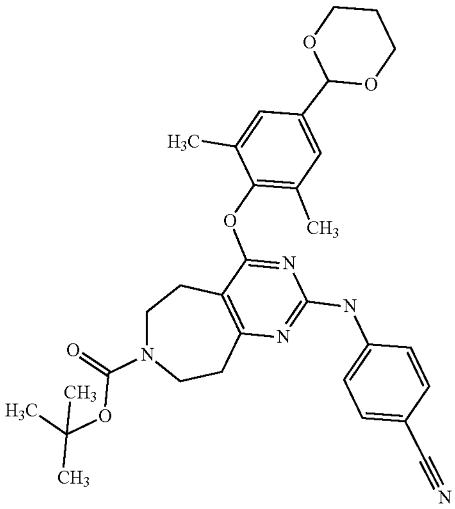 | Tert-butyl 4-(4-(1,3-dioxolane-2-yl)-2,6-dimethylphenoxy)-2-((4-cyanophenyl)amino)-8,9-dihydro-5H-pyrimido[4,5-d]azepine-7(6H)-carboxylate |
| 0273943 | 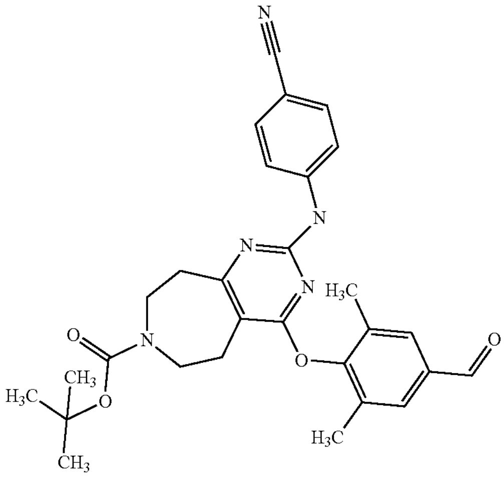 [SMILES: Cc1cc(C=O)cc(C)c1Oc1nc(Nc2ccc(C#N)cc2)nc2c1CCN(C(=O)OC(C)(C)C)CC2] | Tert-butyl 2-((4-cyanophenyl)amino)-4-(4-formyl-2,6-dimethylphenyoxy)-8,9-dihydro-5H-pyrimido[4,5-d]azepine-7(6H)-carboxylate |

-continued
| | Structural formula | Name |
|---|---|---|
| 0273961 | 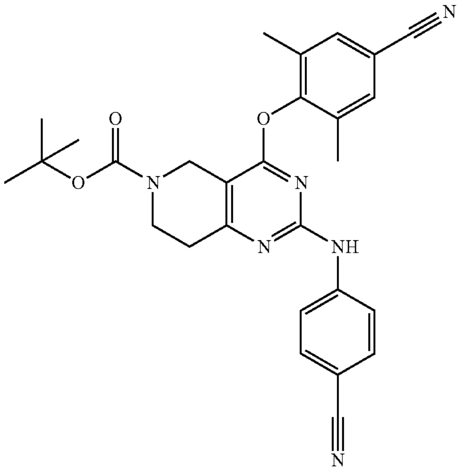 [SMILES: Cc1cc(C#N)cc(C)c1Oc1nc(Nc2ccc(C#N)cc2)nc2c1CN(C(=O)OC(C)(C)C)CC2] | Tert-butyl 4-(4-cyano-2,6-dimethylphenoxy)-2-((4-cyanophenyl)amino)-7,8-dihydropyrido[4,3-d]pyrimidine-6(5H)-carboxylate |
| 0273963 | 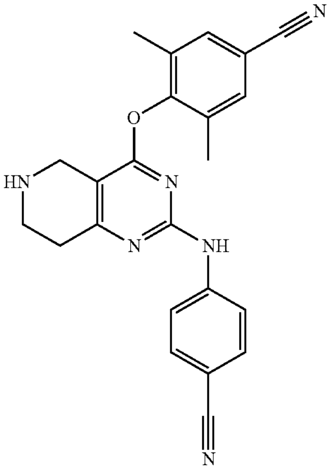 [SMILES: Cc1cc(C#N)cc(C)c1Oc1nc(Nc2ccc(C#N)cc2)nc2c1CNCC2] | 4-((2-((4-Cyanophenyl)amino)-5,6,7,8-tetrahydropyrido[4,3-d]pyrimidine-4-yl)oxy)-3,5-dimethylbenzonitrile |
| 0273964 | 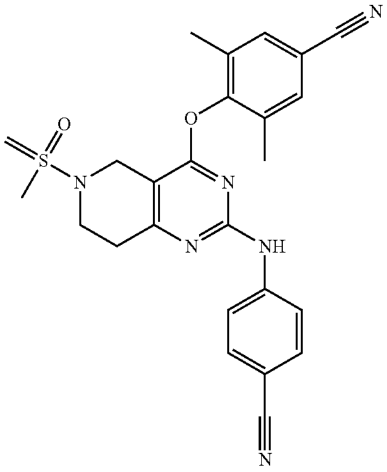 [SMILES: C=S(C)(=O)N1CCc2nc(Nc3ccc(C#N)cc3)nc(Oc3c(C)cc(C#N)cc3C)c2C1] | 4-((2-((4-Cyanophenyl)amino)-6-(methylsulfonyl)-5,6,7,8-tetrahydropyrido[4,3-d]pyrimidine-4-yl)oxy)-3,5-dimethylbenzonitrile |

-continued
| | Structural formula | Name |
|---|---|---|
| 0273965 | 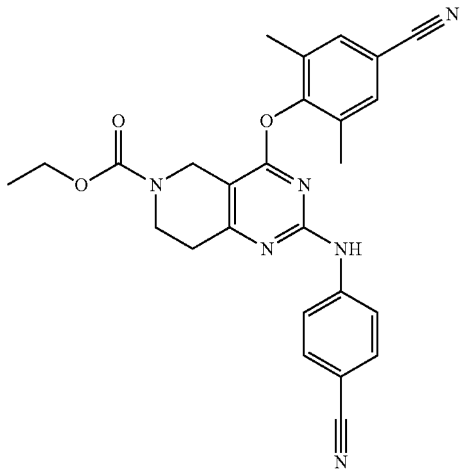 [SMILES: CCOC(=O)N1CCc2nc(Nc3ccc(C#N)cc3)nc(Oc3c(C)cc(C#N)cc3C)c2C1] | Ethyl 4-(4-cyano-2,6-dimethylphenoxy)-2-((4-cyanophenyl)amino)-7,8-dihydropyrido[4,3-d]pyrimidine-6(5H)-carboxylate |
| 0273969 | 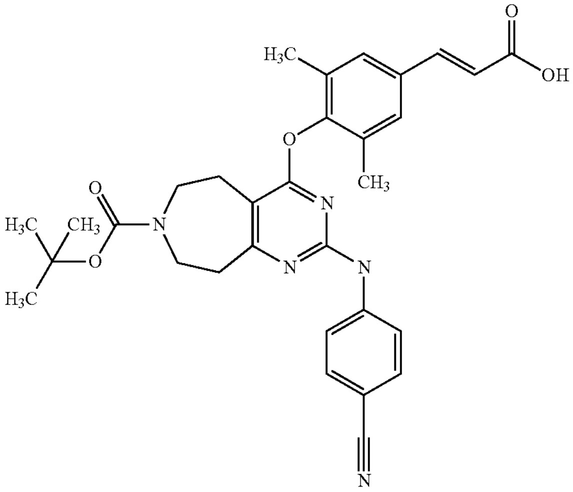 [SMILES: Cc1cc(/C=C/C(=O)O)cc(C)c1Oc1nc(Nc2ccc(C#N)cc2)nc2c1CCN(C(=O)OC(C)(C)C)CC2] | (E)-3-(4-((7-(Tert-butoxycarbonyl)-2-((4-cyanophenyl)amino)-6,7,8,9-tetrahydro-5H-pyrimido[4,5-d]azepine-4-yl)oxy)-3,5-dimethylphenyl)acrylic acid |
| 0273972 | 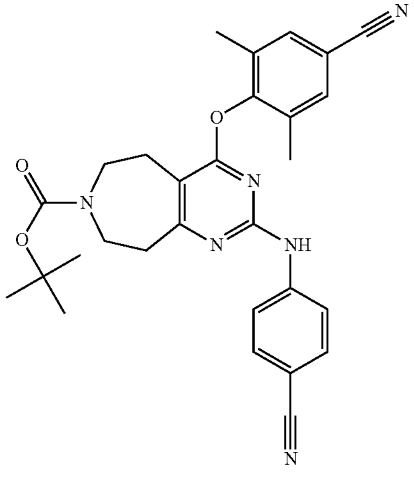 [SMILES: Cc1cc(C#N)cc(C)c1Oc1nc(Nc2ccc(C#N)cc2)nc2c1CCN(C(=O)OC(C)(C)C)CC2] | Tert-butyl 4-(4-cyano-2,6- dimethylphenoxy)-2-((4-cyanophenyl)amino)-8,9-dihydro-5H-pyrimido[4,5-d]azepine-7(6H)-carboxylate |

-continued
| | Structural formula | Name |
| --- | --- | --- |
| 0273976 | 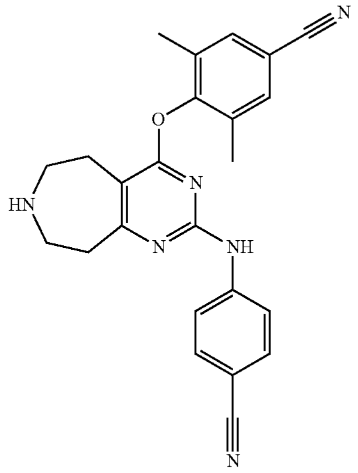 [SMILES: Cc1cc(C#N)cc(C)c1Oc1nc(Nc2ccc(C#N)cc2)nc2c1CCNCC2] | 4-((2-((4-Cyanophenyl)amino)-6,7,8,9-tetrahydro-5H-pyrimido[4,5-d]azepine-4-yl)oxy)-3,5-dimethylbenzonitrile |
| 0274009 | 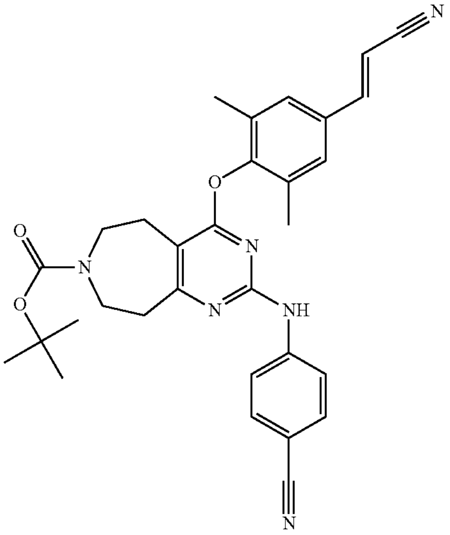 [SMILES: Cc1cc(/C=C/C#N)cc(C)c1Oc1nc(Nc2ccc(C#N)cc2)nc2c1CCN(C(=O)OC(C)(C)C)CC2] | Tert-butyl 2-((4-cyanophenyl)amino)-4-(4-(2-cyanovinyl)-2,6-dimethylphenoxy)-8,9-dihydro-5H-pyrimido[4,5-d]azepine-7(6H)-carboxylate |
| 0274010 | 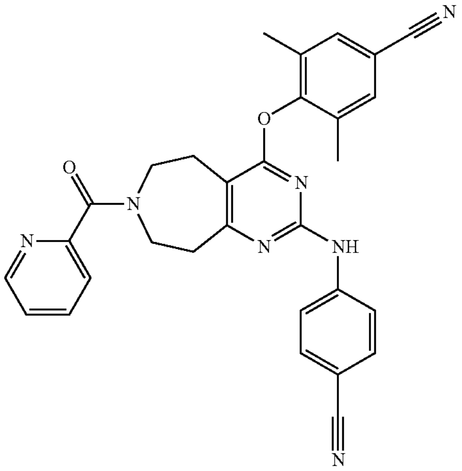 | 4-((2-((4-Cyanophenyl)amino)-7-picolynoyl-6,7,8,9-tetrahydro-5H-pyrimido[4,5-d]azepine-4-yl)oxy)-3,5-dimethylbenzonitrile |

-continued
| | Structural formula | Name |
|---|---|---|
| 0274011 | 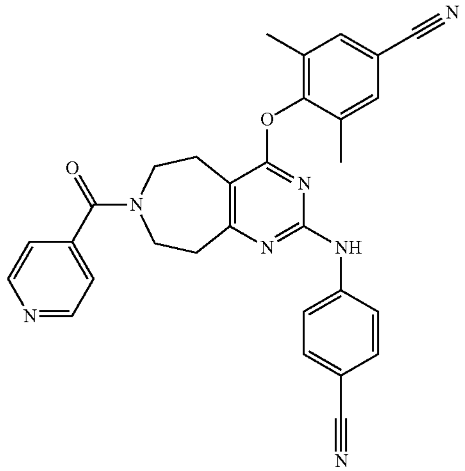 [SMILES: Cc1cc(C#N)cc(C)c1Oc1nc(Nc2ccc(C#N)cc2)nc2c1CCN(C(=O)c1ccncc1)CC2] | 4-((2-((4-Cyanophenyl)amino)-7-isonicotinoyl-6,7,8,9-tetrahydro-5H-pyrimido[4,5-d]azepine-4-yl)oxy)-3,5-dimethylbenzonitrile |
| 0274012 | 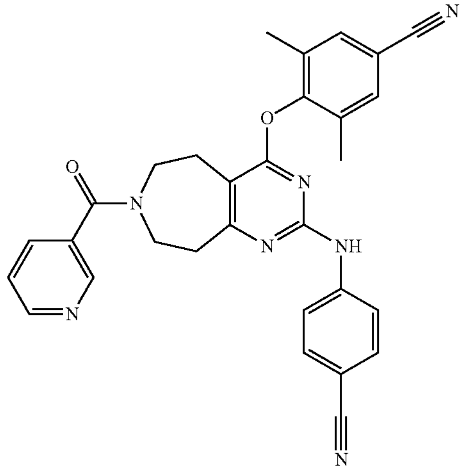 [SMILES: Cc1cc(C#N)cc(C)c1Oc1nc(Nc2ccc(C#N)cc2)nc2c1CCN(C(=O)c1cccnc1)CC2] | 4-((2-((4-Cyanophenyl)amino)-7-nicotinoyl-6,7,8,9-tetrahydro-5H-pyrimido[4,5-d]azepine-4-yl)oxy)-3,5-dimethylbenzonitrile |
| 0274014 | 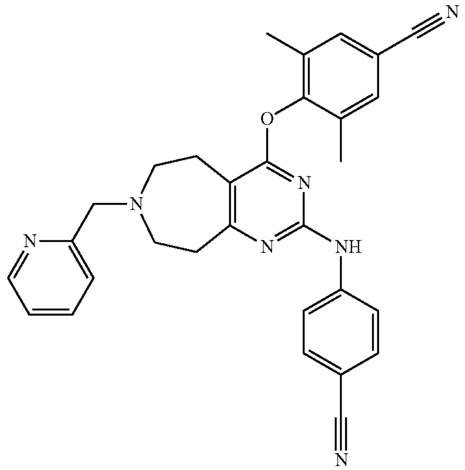 [SMILES: Cc1cc(C#N)cc(C)c1Oc1nc(Nc2ccc(C#N)cc2)nc2c1CCN(Cc1ccccn1)CC2] | 4-((2-((4-Cyanophenyl)amino)-7-(pyridine-2-ylmethyl)-6,7,8,9-tetrahydro-5H-pyrimido[4,5-d]azepine-4-yl)oxy)-3,5-dimethylbenzonitrile |

-continued
| | Structural formula | Name |
|---|---|---|
| 0274015 | 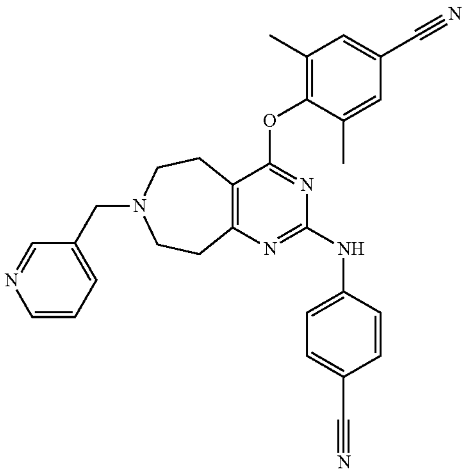 [SMILES: Cc1cc(C#N)cc(C)c1Oc1nc(Nc2ccc(C#N)cc2)nc2c1CCN(Cc1cccnc1)CC2] | 4-((2-((4-Cyanophenyl)amino)-7-(pyridine-3-ylmethyl)-6,7,8,9-tetrahydro-5H-pyrimido[4,5-d]azepine-4-yl)oxy)-3,5-dimethylbenzonitrile |
| 0274016 | 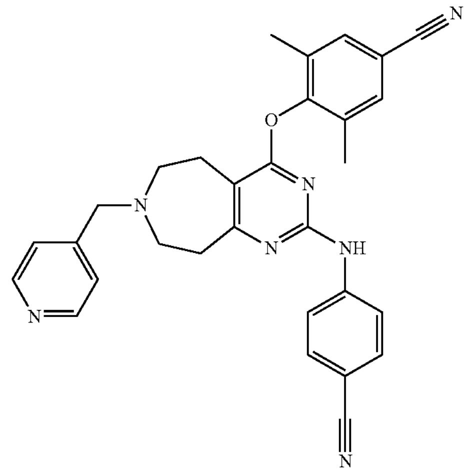 [SMILES: Cc1cc(C#N)cc(C)c1Oc1nc(Nc2ccc(C#N)cc2)nc2c1CCN(Cc1ccncc1)CC2] | 4-((2-((4-Cyanophenyl)amino)-7-(pyridine-4-ylmethyl)-6,7,8,9-tetrahydro-5H-pyrimido[4,5-d]azepine-4-yl)oxy)-3,5-dimethylbenzonitrile |
| 0274021 | 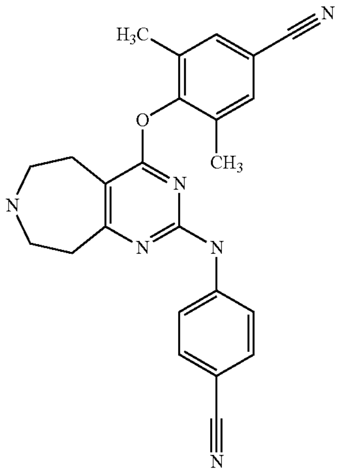 [SMILES: Cc1cc(C#N)cc(C)c1Oc1nc(Nc2ccc(C#N)cc2)nc2c1CCNCC2] | 4-((2-((4-Cyanophenyl)amino)-6,7,8,9-tetrahydro-5H-pyrimido[4,5-d]azepine-4-yl)oxy)-3,5-dimethylbenzonitrile |

-continued

| | Structural formula | Name |
|---|---|---|
| 0274025 | 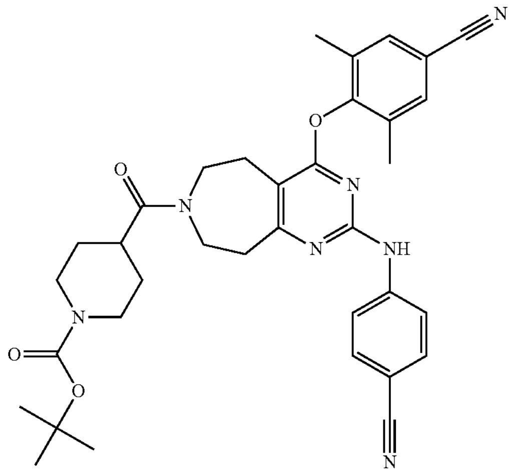 [SMILES: Cc1cc(C#N)cc(C)c1Oc1nc(Nc2ccc(C#N)cc2)nc2c1CCN(C(=O)C1CCN(C(=O)OC(C)(C)C)CC1)CC2] | Tert-butyl 4-(4-(4-cyano-2,6-dimethylphenoxy)-2-((4-cyanophenyl)amino)-6,7,8,9-tetrahydro-5H-pyrimido[4,5-d]asein-7-carbonyl)piperidine-1-carboxylate |
| 0274026 | 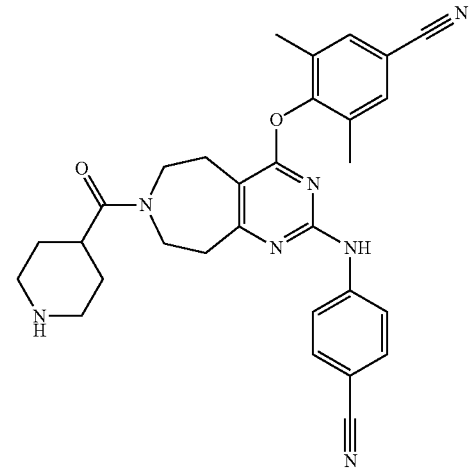 [SMILES: Cc1cc(C#N)cc(C)c1Oc1nc(Nc2ccc(C#N)cc2)nc2c1CCN(C(=O)C1CCNCC1)CC2] | 4-((2-((4-Cyanophenyl)amino)-7-(piperidine-4-carbonyl)-6,7,8,9-tetrahydro-5H-pyrimido[4,5-d]azepine-4-yl)oxy)-3,5-dimethylbenzonitrile |
| 0274027 | 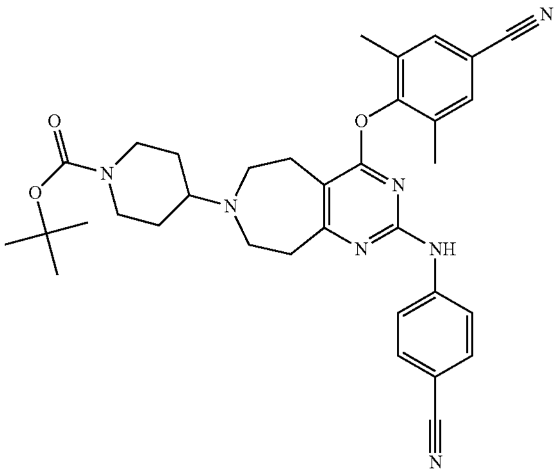 [SMILES: Cc1cc(C#N)cc(C)c1Oc1nc(Nc2ccc(C#N)cc2)nc2c1CCN(C1CCN(C(=O)OC(C)(C)C)CC1)CC2] | Tert-butyl 4-(4-(4-cyano-2,6-dimethylphenoxy)-2-((4-cyanophenyl)amino)-8,9-dihydro-5H-pyrimido[4,5-d]azepine-7(6H)-yl)piperidine-1-carboxylate |

-continued
| | Structural formula | Name |
|---|---|---|
| 0274028 | 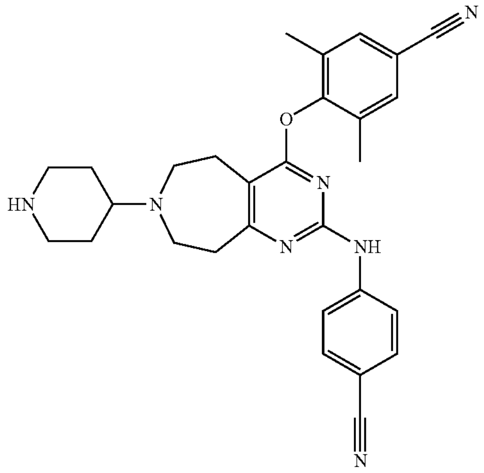 [SMILES: Cc1cc(C#N)cc(C)c1Oc1nc(Nc2ccc(C#N)cc2)nc2c1CCN(C1CCNCC1)CC2] | 4-((2-((4-Cyanophenyl)amino)-7-(piperidine-4-yl)-6,7,8,9-tetrahydro-5H-pyrimido[4,5-d]azepine-4-yl)oxy)-3,5-dimethylbenzonitrile |
| 0274051 | 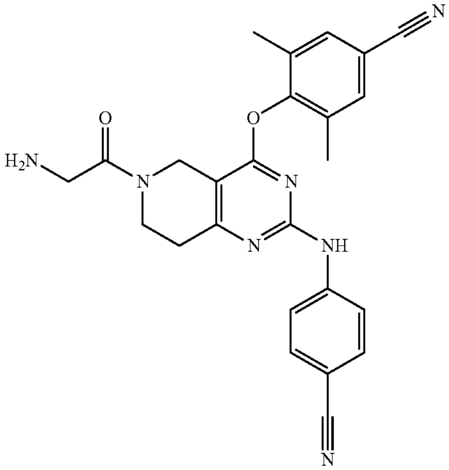 [SMILES: Cc1cc(C#N)cc(C)c1Oc1nc(Nc2ccc(C#N)cc2)nc2c1CN(C(=O)CN)CC2] | 4-((6-(2-Aminoacetyl)-2-((4-cyanophenyl)amino)-5,6,7,8-tetrahydropyrido[4,3-d]pyrimidine-4-yl)oxy)-3,5-dimethylbenzonitrile |
| 0274052 | 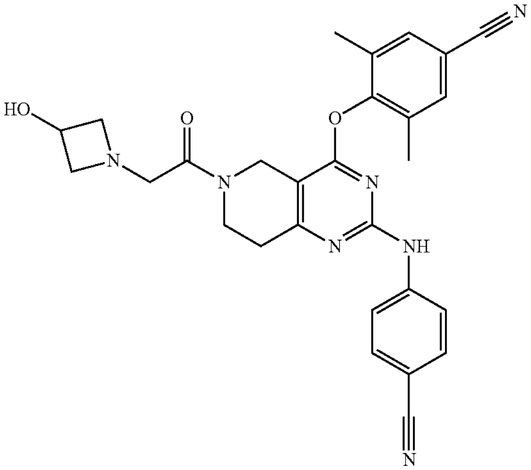 [SMILES: Cc1cc(C#N)cc(C)c1Oc1nc(Nc2ccc(C#N)cc2)nc2c1CN(C(=O)CN1CC(O)C1)CC2] | 4-((2-((4-Cyanophenyl)amino)-6-(2-(3-hydroxyazetidine-1-yl)acetyl)-5,6,7,8-tetrahydropyrido[4,3-d]pyrimidine-4-yl)oxy)-3,5-dimethylbenzonitrile |

-continued
| | Structural formula | Name |
|---|---|---|
| 0274053 | 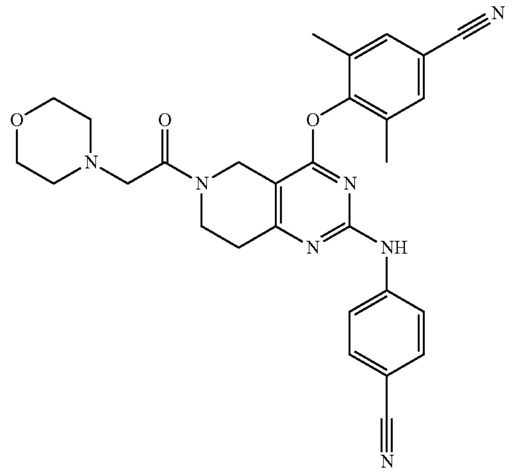 [SMILES: Cc1cc(C#N)cc(C)c1Oc1nc(Nc2ccc(C#N)cc2)nc2c1CN(C(=O)CN1CCOCC1)CC2] | 4-({2-[(4-Cyanophenyl)amino]-6-[2-(morpholine-4-yl)acetyl]-5H,6H,7H,8H-pyrido[4,3-d]pyrimidine-4-yl}oxy)-3,5-dimethylbenzonitrile |
| 0274054 | 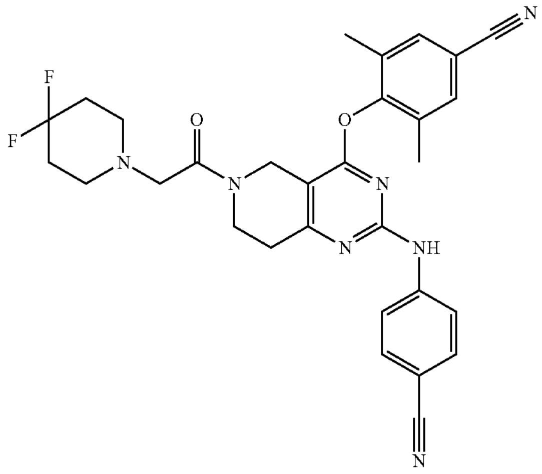 [SMILES: Cc1cc(C#N)cc(C)c1Oc1nc(Nc2ccc(C#N)cc2)nc2c1CN(C(=O)CN1CCC(F)(F)CC1)CC2] | 4-({2-[(4-Cyanophenyl)amino]-6-[2-(4,4-difluoropiperidine-1-yl)acetyl]-5H,6H,7H,8H-pyrido[4,3-d]pyrimidine-4-yl}oxy)-3,5-dimethylbenzonitrile |
| 0274055 | 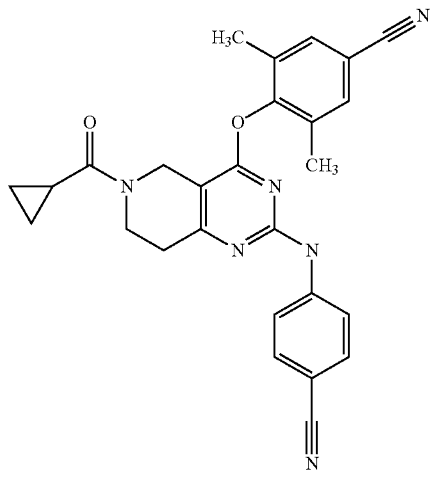 [SMILES: Cc1cc(C#N)cc(C)c1Oc1nc(Nc2ccc(C#N)cc2)nc2c1CN(C(=O)C1CC1)CC2] | 4-((2-((4-Cyanophenyl)amino)-7-(cyclopropanecarbonyl)-5,6,7,8-tetrahydro-[4,3-d]pyrimidine-4-yl)oxy)-3,5-dimethylbenzonitrile |

-continued
| | Structural formula | Name |
|---|---|---|
| 0274056 | 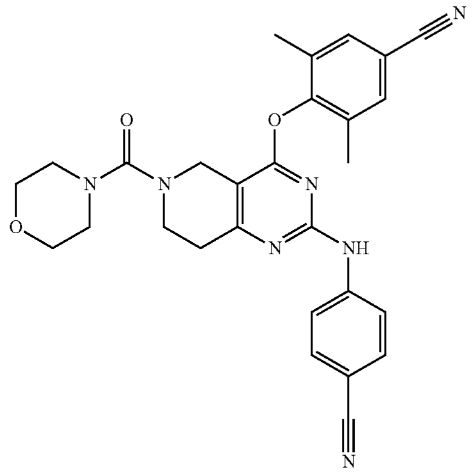 [SMILES: Cc1cc(C#N)cc(C)c1Oc1nc(Nc2ccc(C#N)cc2)nc2c1CN(C(=O)N1CCOCC1)CC2] | 4-({2-[(4-Cyanophenyl)amino]-6-(morpholine-4-carbonyl)-5H,6H,7H,8H-pyrido[4,3-d]pyrimidine-4-yl}oxy)-3,5-dimethylbenzonitrile |
| 0274057 | 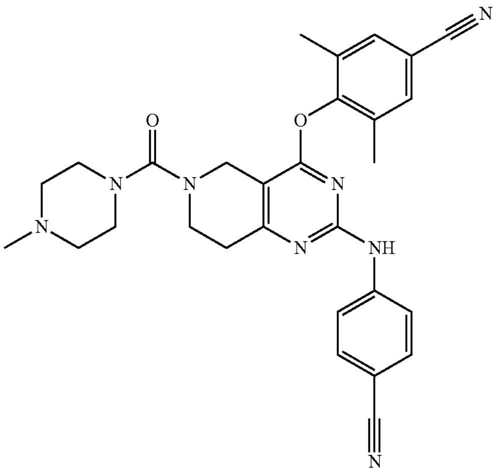 [SMILES: Cc1cc(C#N)cc(C)c1Oc1nc(Nc2ccc(C#N)cc2)nc2c1CN(C(=O)N1CCN(C)CC1)CC2] | 4-({2-[(4-Cyanophenyl)amino]-6-(4-methylpiperazine-1-carbonyl)-5H,6H,7H,8H-pyrido[4,3-d]pyrimidine-4-yl}oxy)-3,5-dimethylbenzonitrile |
| 0274063 | 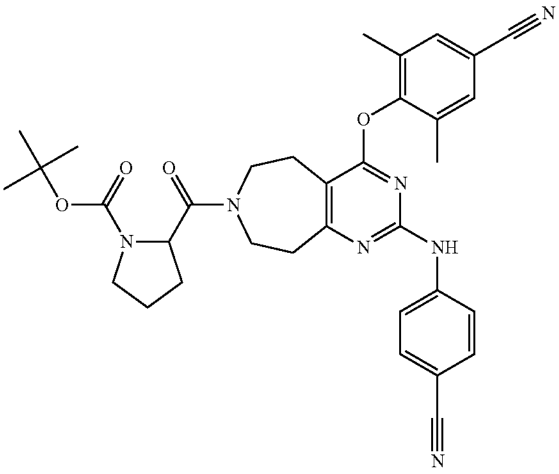 | Tert-butyl 2-(4-(4-cyano-2,6-dimethylphenoxy)-2-((cyanophenyl)amino)-6,7,8,9-tetrahydro-5H-pyrimido[4,5-d]azepine-7-carbonyl)pyrrolidine-1-carboxylate |

-continued

| | Structural formula | Name |
|---|---|---|
| 0274064 | 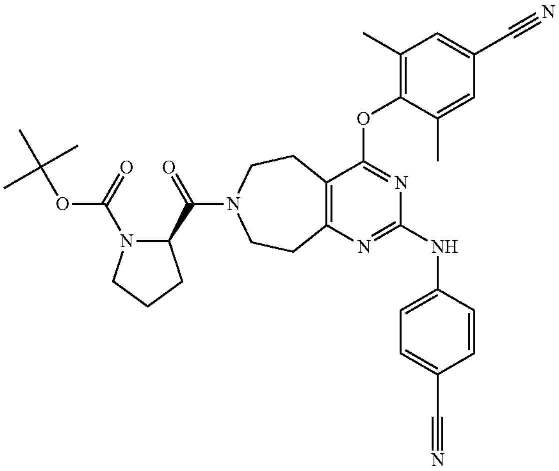 Chiral | (R)-Tert-butyl 2-(4-(4-cyano-2,6-dimethylphenoxy)-2-((cyanophenyl)amino)-6,7,8,9-tetrahydro-5H-pyrimido[4,5-d]azepine-7-carbonyl)pyrrolidine-1-carboxylate |
| 0274065 | 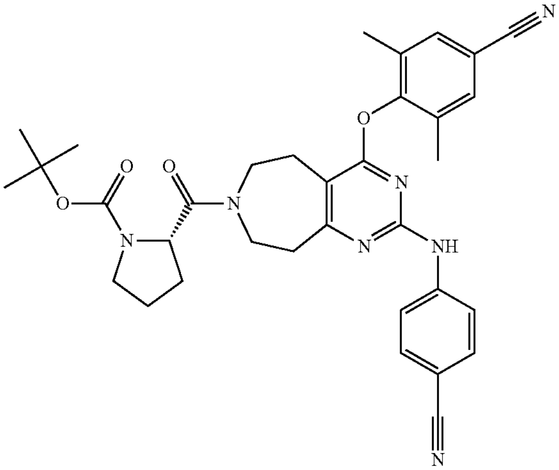 [SMILES: Cc1cc(C#N)cc(C)c1Oc1nc(Nc2ccc(C#N)cc2)nc2c1CCN(C(=O)C1CCCN1C(=O)OC(C)(C)C)CC2] Chiral | (S)-Tert-butyl 2-(4-(4-cyano-2,6-dimethylphenoxy)-2-((cyanophenyl)amino)-6,7,8,9-tetrahydro-5H-pyrimido[4,5-d]azepine-7-carbonyl)pyrrolidine-1-carboxylate |
| 0274072 | 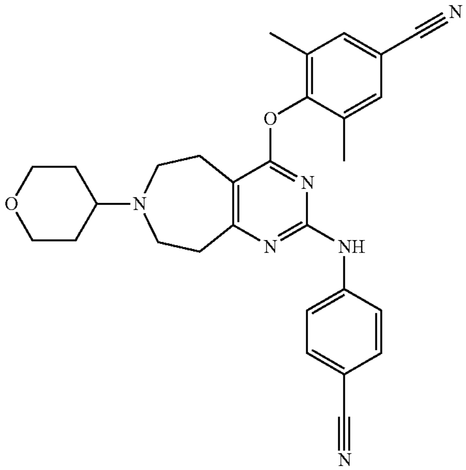 [SMILES: Cc1cc(C#N)cc(C)c1Oc1nc(Nc2ccc(C#N)cc2)nc2c1CCN(C1CCOCC1)CC2] | 4-((2-((4-Cyanophenyl)amino)-7-(tetrahydro-2H-pyran-4-yl)-6,7,8,9-tetrahydro-5H-pyrimido[4,5-d]azepine-4-yl)oxy)-3,5-dimethylbenzonitrile |

-continued
| | Structural formula | Name |
|---|---|---|
| 0274073 | 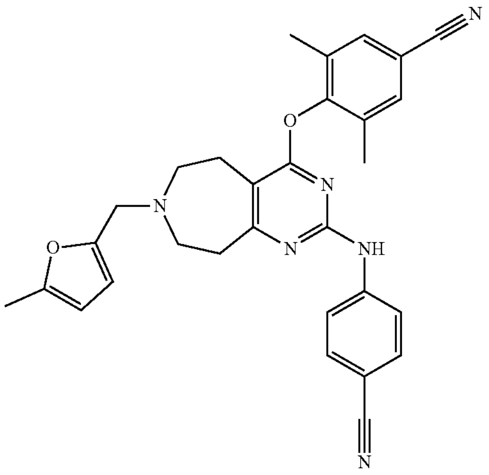 [SMILES: Cc1ccc(CN2CCc3nc(Nc4ccc(C#N)cc4)nc(Oc4c(C)cc(C#N)cc4C)c3CC2)o1] | 4-((2-((4-Cyanophenyl)amino)-7-(5-methylfuran-2-yl)methyl)-6,7,8,9-tetrahydro-5H-pyrimido[4,5-d]azepine-4-yl)oxy)-3,5-dimethylbenzonitrile |
| 0274074 | 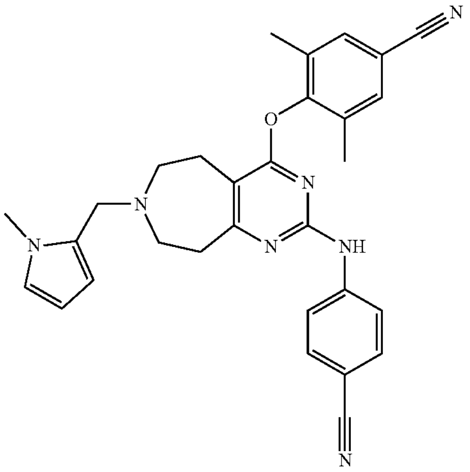 [SMILES: Cc1cc(C#N)cc(C)c1Oc1nc(Nc2ccc(C#N)cc2)nc2c1CCN(Cc1cccn1C)CC2] | 4-((2-((4-Cyanophenyl)amino)-7-(1-methyl-1H-pyrrol-2-yl)methyl)-6,7,8,9-tetrahydro-5H-pyrimido[4,5-d]azepine-4-yl)oxy)-3,5-dimethylbenzonitrile |
| 0274075 | 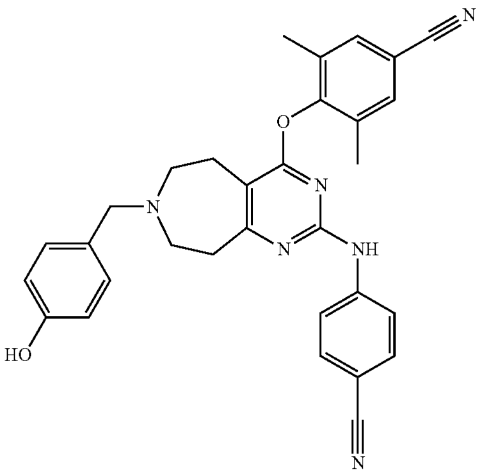 [SMILES: Cc1cc(C#N)cc(C)c1Oc1nc(Nc2ccc(C#N)cc2)nc2c1CCN(Cc1ccc(O)cc1)CC2] | 4-((2-((4-Cyanophenyl)amino)-7-(4-hydroxybenzyl)-6,7,8,9-tetrahydro-5H-pyrimido[4,5-d]azepine-4-yl)oxy)-3,5-dimethylbenzonitrile |

-continued

| | Structural formula | Name |
|---|---|---|
| 0274080 | 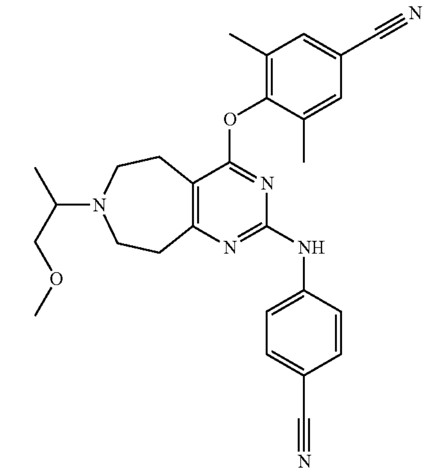 [SMILES: COCC(C)N1CCc2nc(Nc3ccc(C#N)cc3)nc(Oc3c(C)cc(C#N)cc3C)c2CC1] | 4-((2-((4-Cyanophenyl)amino)-7-(1-methoxypropane-2-yl-6,7,8,9-tetrahydro-5H-pyrimido[4,5-d]azepine-4-yl)oxy)-3,5-dimethylbenzonitrile |
| 0274097 | 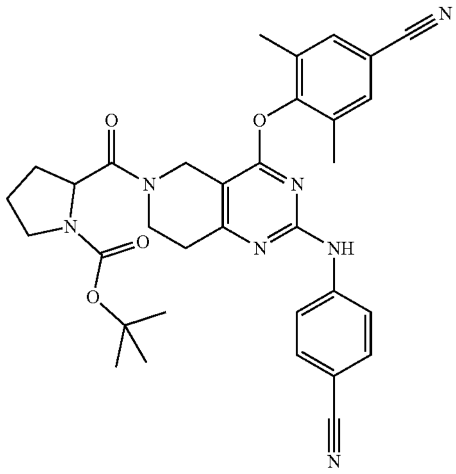 [SMILES: Cc1cc(C#N)cc(C)c1Oc1nc(Nc2ccc(C#N)cc2)nc2c1CN(C(=O)C1CCCN1C(=O)OC(C)(C)C)CC2] | Tert-butyl 2-(4-(4-cyano-2,6-dimethylphenoxy)-2-((4-cyanophenyl)amino)-5,6,7,8-tetrahydropyrido[4,3-d]pyrimidine-6-carbonyl)pyrrolidine-1-carboxylate |
| 0274098 | 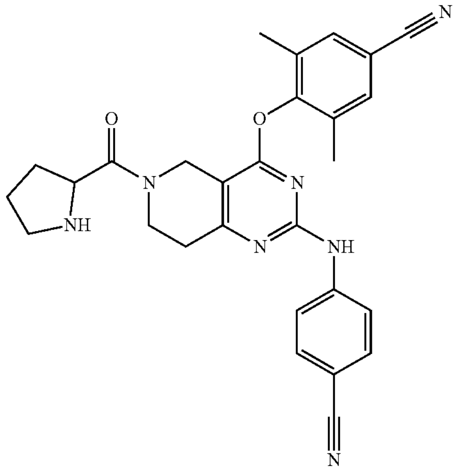 [SMILES: Cc1cc(C#N)cc(C)c1Oc1nc(Nc2ccc(C#N)cc2)nc2c1CN(C(=O)C1CCCN1)CC2] | 4-((2-((4-Cyanophenyl)amino)-6-(pyrrolidine-2-carbonyl)-5,6,7,8-tetrahydropyrido[4,3-d]pyrimidine-4-yl)oxy)-3,5-dimethylbenzonitrile |

-continued
| | Structural formula | Name |
|---|---|---|
| 0274099 | 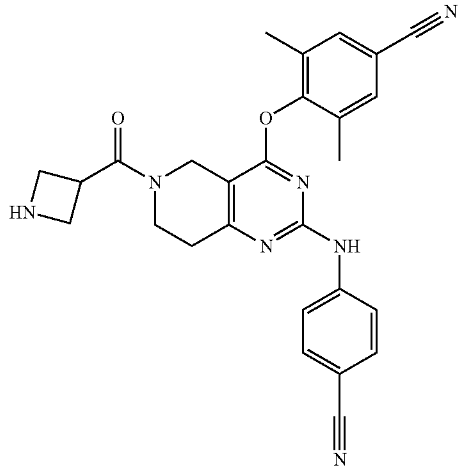 [SMILES: Cc1cc(C#N)cc(C)c1Oc1nc(Nc2ccc(C#N)cc2)nc2c1CN(C(=O)C1CNC1)CC2] | 4-((6-(Azetidine-3-carbonyl)-2-((4-cyanophenyl)amino)-5,6,7,8-tetrahydropyrido[4,3-d]pyrimidine-4-yl)oxy)-3,5-dimethylbenzonitrile |
| 0274100 | 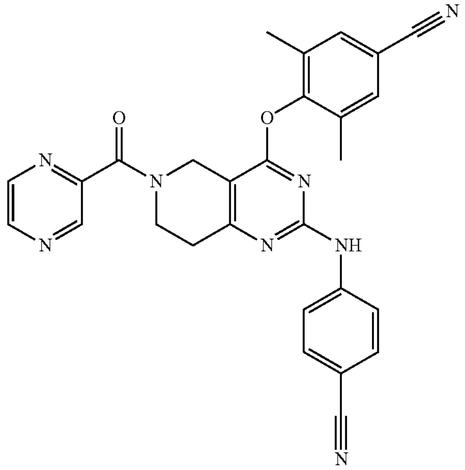 [SMILES: Cc1cc(C#N)cc(C)c1Oc1nc(Nc2ccc(C#N)cc2)nc2c1CN(C(=O)c1cnccn1)CC2] | 4-((2-((4-Cyanophenyl)amino)-6-(pyrazine-2-carbonyl)-5,6,7,8-tetrahydropyrido[4,3-d]pyrimidine-4-yl)oxy)-3,5-dimethylbenzonitrile |
| 0274101 | 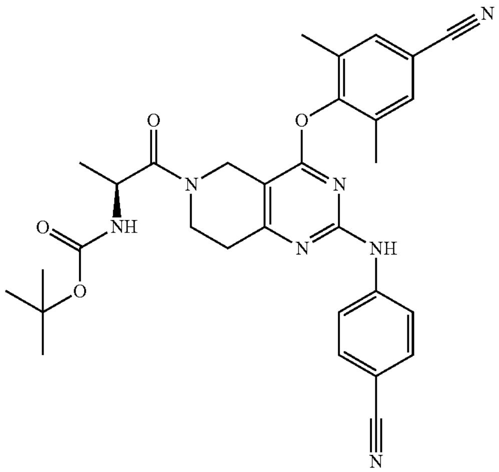 Chiral | (S)-Tert-butyl (1-(4-(4-cyano-2,6-dimethylphenoxy)-2-((4-cyanophenyl)amino)-7,8-dihydropyrido[4,3-d]pyrimidine-6(5H)-yl)-1-oxopropane-2-yl)carbamate |

-continued

| | Structural formula | Name |
|---|---|---|
| 0274102 | 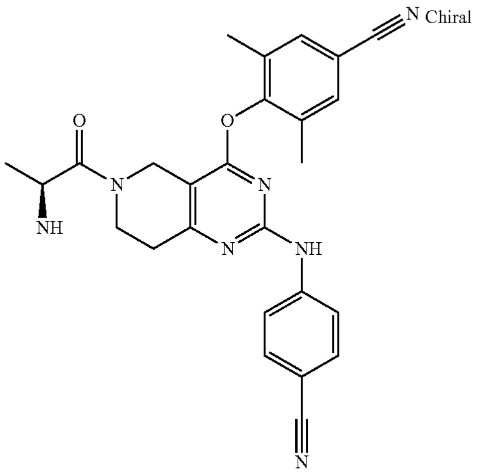 [SMILES: Cc1cc(C#N)cc(C)c1Oc1nc(Nc2ccc(C#N)cc2)nc2c1CN(C(=O)[C@H](C)N)CC2] | (S)-4-((6-(2-Aminopropanoyl)-2-((4-cyanophenyl)amino)-5,6,7,8-tetrahydropyrido[4,3-d]pyrimidine-4-yl)oxy)-3,5-dimethylbenzonitrile |
| 0274103 | 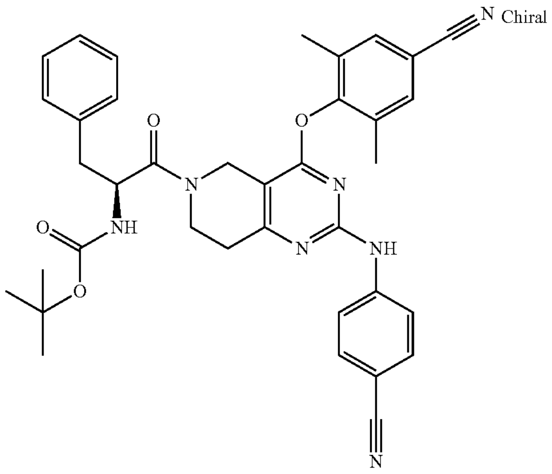 [SMILES: Cc1cc(C#N)cc(C)c1Oc1nc(Nc2ccc(C#N)cc2)nc2c1CN(C(=O)[C@H](Cc1ccccc1)NC(=O)OC(C)(C)C)CC2] | (S)-Tert-butyl (1-(4-(4-cyano-2,6-dimethylphenoxy)-2-((4-cyanophenyl)amino)-7,8-dihydropyrido[4,3-d]pyrimidine-6(5H)-yl)-1-oxo-3-phenylpropane-2-yl)carbamate |
| 0274111 | 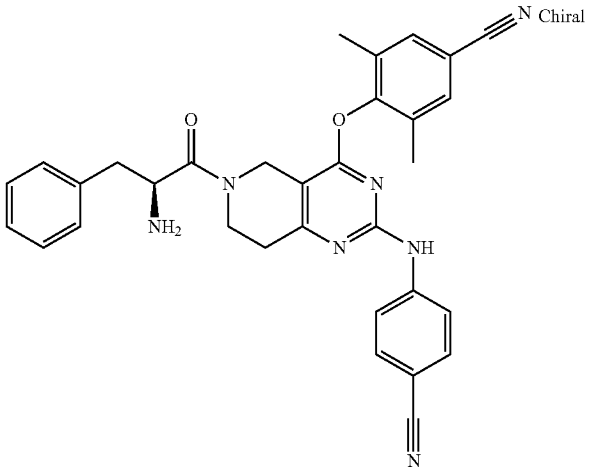 [SMILES: Cc1cc(C#N)cc(C)c1Oc1nc(Nc2ccc(C#N)cc2)nc2c1CN(C(=O)[C@@H](N)Cc1ccccc1)CC2] | (S)-4-((6-(2-Amino-3-phenylpropanoyl)-2-((4-cyanophenyl)amino)-5,6,7,8-tetrahydropyrido[4,3-d]pyrimidine-4-yl)oxy)-3,5-dimethylbenzonitrile |

-continued

| | Structural formula | Name |
|---|---|---|
| 0274118 | 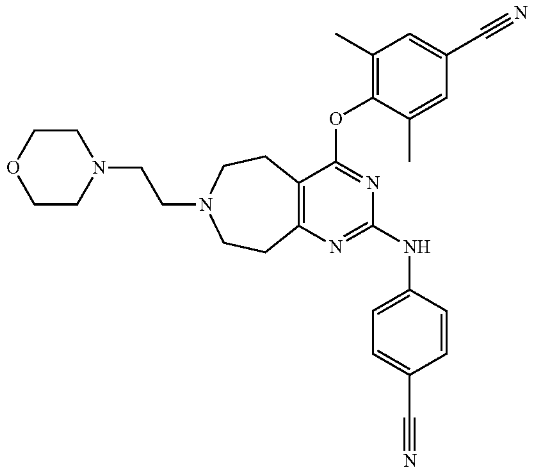 [SMILES: Cc1cc(C#N)cc(C)c1Oc1nc(Nc2ccc(C#N)cc2)nc2c1CCN(CCN1CCOCC1)CC2] | 4-((2-((4-Cyanophenyl)amino)-7-(2-morpholineethyl)-6,7,8,9-tetrahydro-5H-pyrimido[4,5-d]azepine-4-yl)oxy)-3,5-dimethylbenzonitrile |
| 0274119 | 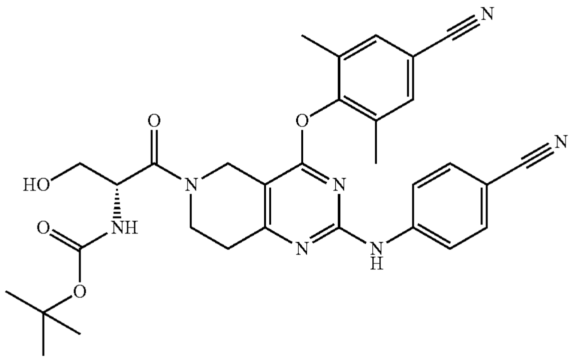 [SMILES: Cc1cc(C#N)cc(C)c1Oc1nc(Nc2ccc(C#N)cc2)nc2c1CN(C(=O)[C@@H](CO)NC(=O)OC(C)(C)C)CC2] | (R)-Tert-butyl (1-(4-(4-cyano-2,6-dimethylphenoxy)-2-((4-cyanophenyl)amino)-7,8-dihydropyrido[4,3-d]pyrimidine-6(5H)-yl)-3-hydroxy-1-oxopropane-2-yl)carbamate |
| 0274120 | 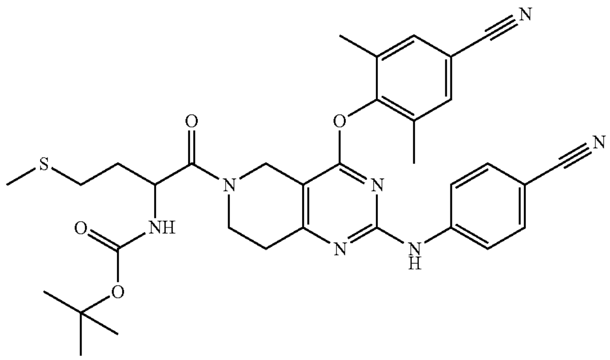 [SMILES: CSCCC(NC(=O)OC(C)(C)C)C(=O)N1CCc2nc(Nc3ccc(C#N)cc3)nc(Oc3c(C)cc(C#N)cc3C)c2C1] | Tert-butyl (1-(4-(4-cyano-2,6-dimethylphenoxy)-2-((4-cyanophenyl)amino)-7,8-dihydropyrido[4,3-d]pyrimidine-6(5H)-yl)-4-(methylthio)-1-oxobutane-2-yl)carbamate |

-continued

| | Structural formula | Name |
|---|---|---|
| 0275622 | 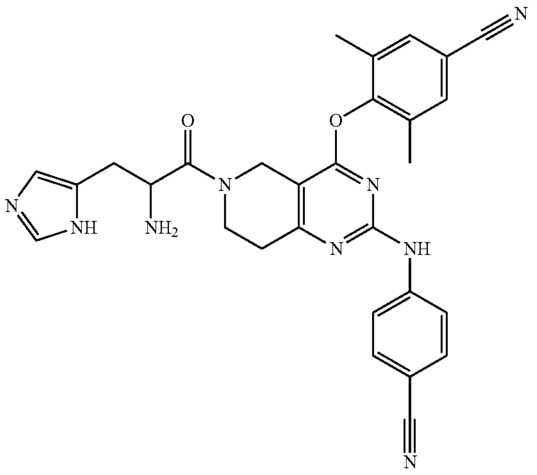 [SMILES: Cc1cc(C#N)cc(C)c1Oc1nc(Nc2ccc(C#N)cc2)nc2c1CN(C(=O)C(N)Cc1cnc[nH]1)CC2] | 4-({6-[2-Amino-3-(1H-imidazole-5-yl)propanoyl]-2-[(4-cyanophenyl)amino]-5H,6H,7H,8H-pyrido[4,3-d]pyrimidine-4-yl}oxy)-3,5-dimethylbenzonitrile |
| 0274121 | 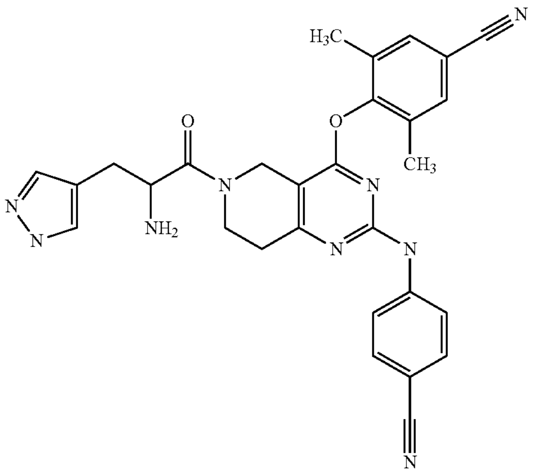 [SMILES: Cc1cc(C#N)cc(C)c1Oc1nc(Nc2ccc(C#N)cc2)nc2c1CN(C(=O)C(N)Cc1cn[nH]c1)CC2] | 4-((6-(2-Amino-3-(1H-pyrazole-4-yl)propanoyl)-2-((4-cyanophenyl)amino)-5,6,7,8-tetrahydropyrido[4,3-d]pyrimidine-4-yl)oxy)-3,5-dimethylbenzonitrile |
| 0274122 | 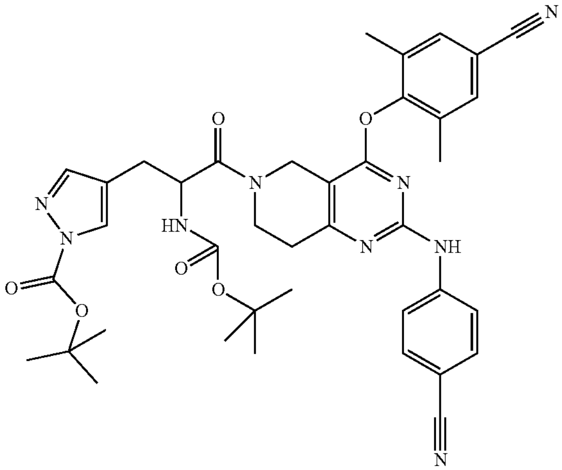 [SMILES: Cc1cc(C#N)cc(C)c1Oc1nc(Nc2ccc(C#N)cc2)nc2c1CN(C(=O)C(Cc1cnn(C(=O)OC(C)(C)C)c1)NC(=O)OC(C)(C)C)CC2] | Tert-butyl 4-(2-((tert-butoxycarbonyl)amino)-3-(4-(4-cyano-2,6-dimethylphenoxy)-2-((4-cyanophenyl)amino)-7,8-dihydropyrido[4,3-d]pyrimidine-6(5H)-yl)-3-oxopropyl)-1H-pyrazole-1-carboxylate |

-continued

| | Structural formula | Name |
|---|---|---|
| 0274123 | 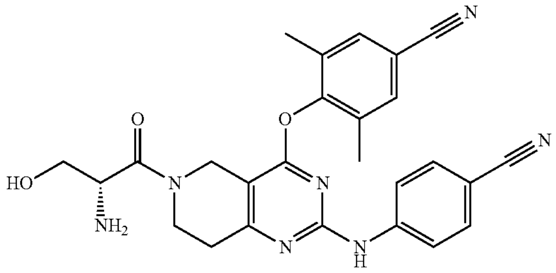 [SMILES: Cc1cc(C#N)cc(C)c1Oc1nc(Nc2ccc(C#N)cc2)nc2c1CN(C(=O)[C@H](N)CO)CC2] | (R)-4-((6-(2-Amino-3-hydroxypropanoyl)-2-((4-cyanophenyl)amino)-5,6,7,8-tetrahydropyrido[4,3-d]pyrimidine-4-yl)oxy)-3,5-dimethylbenzonitrile |
| 0274124 | 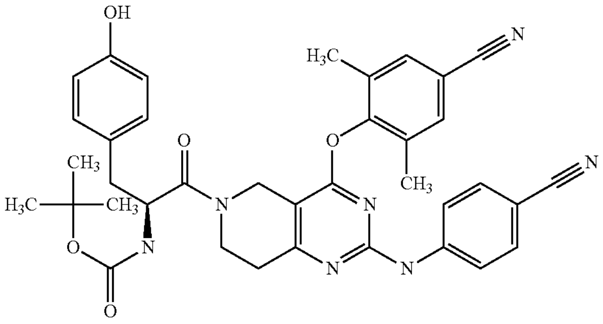 [SMILES: Cc1cc(C#N)cc(C)c1Oc1nc(Nc2ccc(C#N)cc2)nc2c1CN(C(=O)[C@H](Cc1ccc(O)cc1)NC(=O)OC(C)(C)C)CC2] | (S)-Tert-butyl (1-(4-(4-cyano-2,6-dimethylphenoxy)-2-((4-cyanophenyl)amino)-7,8-dihydropyrido[4,3-d]pyrimidine-6(5H)-yl)-3-(4-hydroxyphenyl)-1-oxopropane-2-yl)carbamate |
| 0274125 | 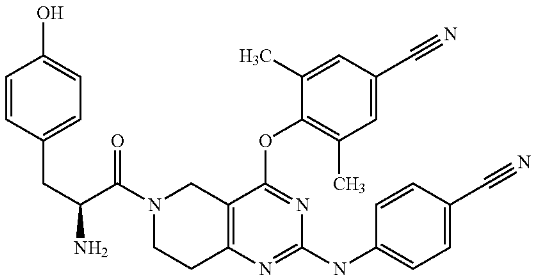 [SMILES: Cc1cc(C#N)cc(C)c1Oc1nc(Nc2ccc(C#N)cc2)nc2c1CN(C(=O)[C@@H](N)Cc1ccc(O)cc1)CC2] | (S)-4-((6-(2-Amino-3-(4-hydroxyphenyl) propanoyl)-2-((4-cyanophenyl)amino)-5,6,7,8-tetrahydropyrido[4,3-d]pyrimidine-4-yl)oxy)-3,5-dimethylbenzonitrile |
| 0274126 | 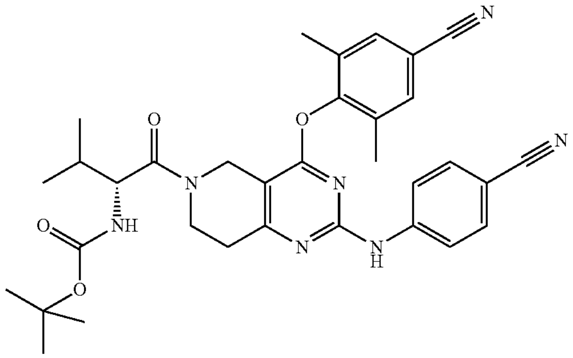 [SMILES: Cc1cc(C#N)cc(C)c1Oc1nc(Nc2ccc(C#N)cc2)nc2c1CN(C(=O)[C@H](NC(=O)OC(C)(C)C)C(C)C)CC2] | (R)-Tert-butyl (1-(4-(4-cyano-2,6-dimethylphenoxy)-2-((4-cyanophenyl)amino)-7,8-dihydropyrido[4,3-d]pyrimidine-6(5H)-yl)-3-methyl-1-oxobutane-2-yl)carbamate |
| 0274127 | 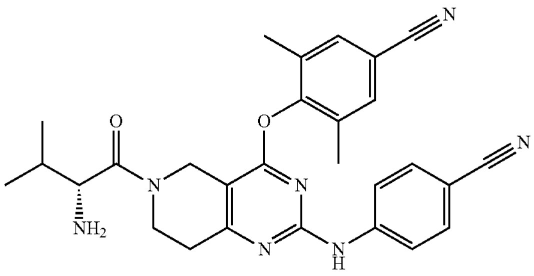 [SMILES: Cc1cc(C#N)cc(C)c1Oc1nc(Nc2ccc(C#N)cc2)nc2c1CN(C(=O)[C@H](N)C(C)C)CC2] | (R)-4-((6-(2-Amino-3-methylbutanoyl)-2-((4-cyanophenyl)amino)-5,6,7,8-tetrahydropyrido[4,3-d]pyrimidine-4-yl)oxy)-3,5-dimethylbenzonitrile |

-continued

| | Structural formula | Name |
|---|---|---|
| 0274128 | 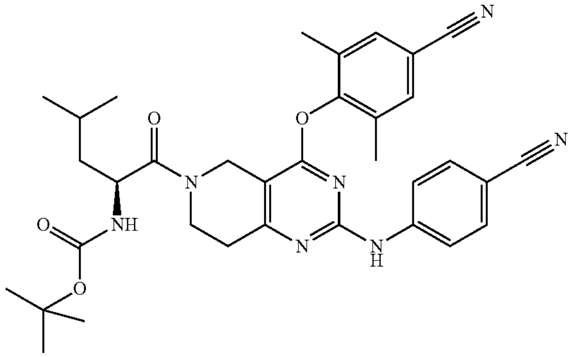 [SMILES: Cc1cc(C#N)cc(C)c1Oc1nc(Nc2ccc(C#N)cc2)nc2c1CN(C(=O)[C@H](CC(C)C)NC(=O)OC(C)(C)C)CC2] | (S)-Tert-butyl (1-(4-(4-cyano-2,6-dimethylphenoxy)-2-((4-cyanophenyl)amino)-7,8-dihydropyrido[4,3-d]pyrimidine-6(5H)-yl)-4-methyl-1-oxopentane-2-yl)carbamate |
| 0274129 | 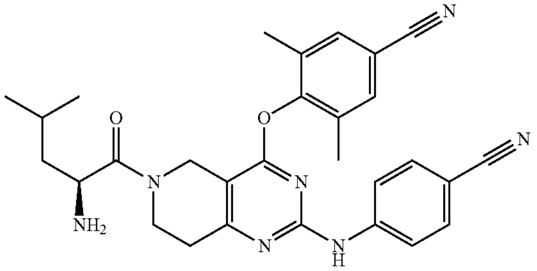 [SMILES: Cc1cc(C#N)cc(C)c1Oc1nc(Nc2ccc(C#N)cc2)nc2c1CN(C(=O)[C@@H](N)CC(C)C)CC2] | (S)-4-((6-(2-Amino-4-methylpentanoyl)-2-((4-cyanophenyl)amino)-5,6,7,8-tetrahydropyrido[4,3-d]pyrimidine-4-yl)oxy)-3,5-dimethylbenzonitrile |
| 0274130 | 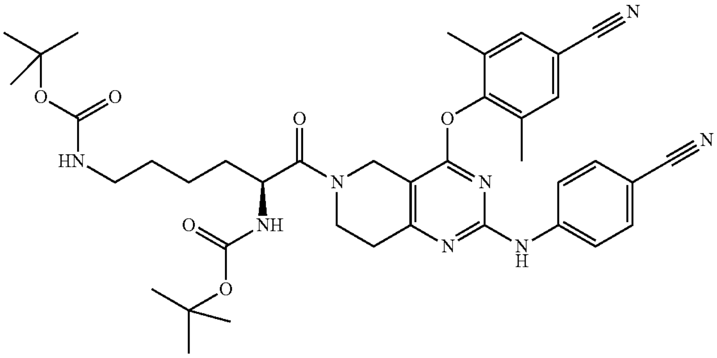 [SMILES: Cc1cc(C#N)cc(C)c1Oc1nc(Nc2ccc(C#N)cc2)nc2c1CN(C(=O)[C@H](CCCCNC(=O)OC(C)(C)C)NC(=O)OC(C)(C)C)CC2] | (S)-Di-tert-butyl (6-(4-(4-cyano-2,6-dimethylphenoxy)-2-((4-cyanophenyl)amino)-7,8-dihydropyrido[4,3-d]pyrimidine-6(5H)-yl)-6-oxohexane-1,5-diyl)dicarbamate |
| 0274131 | 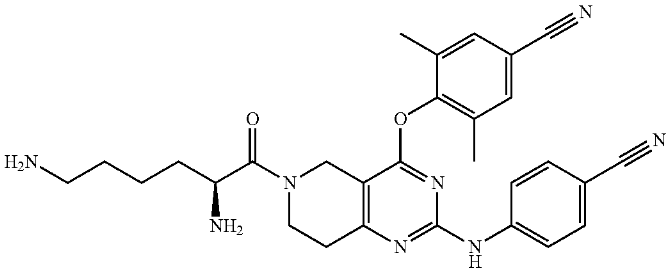 [SMILES: Cc1cc(C#N)cc(C)c1Oc1nc(Nc2ccc(C#N)cc2)nc2c1CN(C(=O)[C@@H](N)CCCCN)CC2] | (S)-4-((2-((4-Cyanophenyl)amino)-6-(2,6-diaminohexanoyl)-5,6,7,8-tetrahydropyrido[4,3-d]pyrimidine-4-yl)oxy)-3,5-dimethylbenzonitrile |
| 0274132 | 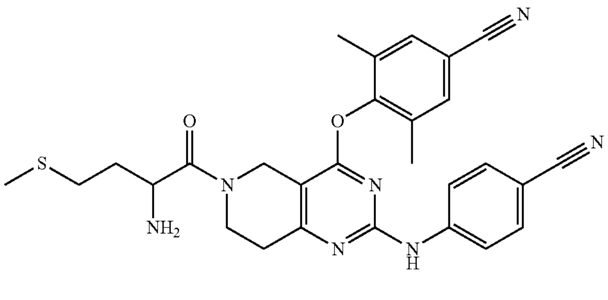 [SMILES: CSCCC(N)C(=O)N1CCc2nc(Nc3ccc(C#N)cc3)nc(Oc3c(C)cc(C#N)cc3C)c2C1] | 4-((2-((4-cyanophenyl)amino)-6-methionyl-5,6,7,8-tetrahydropyrido[4,3-d]pyrimidin-4-yl)oxy)-3,5-dimethylbenzonitrile |

-continued
| | Structural formula | Name |
|---|---|---|
| 0274133 | 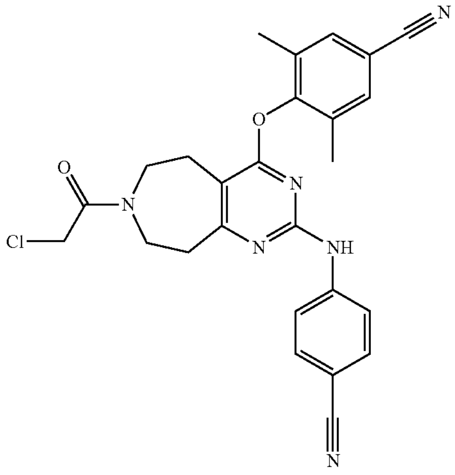 [SMILES: Cc1cc(C#N)cc(C)c1Oc1nc(Nc2ccc(C#N)cc2)nc2c1CCN(C(=O)CCl)CC2] | 4-((7-(2-Chloroacetyl)-2-((4-cyanophenyl)amino)-6,7,8,9-tetrahydro-5H-pyrimido[4,5-d]azepine-4-yl)oxy)-3,5-dimethylbenzonitrile |
| 0274134 | 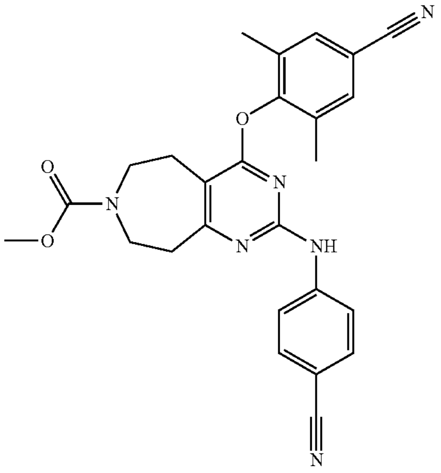 [SMILES: COC(=O)N1CCc2nc(Nc3ccc(C#N)cc3)nc(Oc3c(C)cc(C#N)cc3C)c2CC1] | Methyl 4-(4-cyano-2,6-dimethylphenoxy)-2-((4-4-cyanophenyl) amino)-8,9-dihydro-5H-pyrimido[4,5-d]azepine-7(6H)-carboxylate |
| 0274135 | 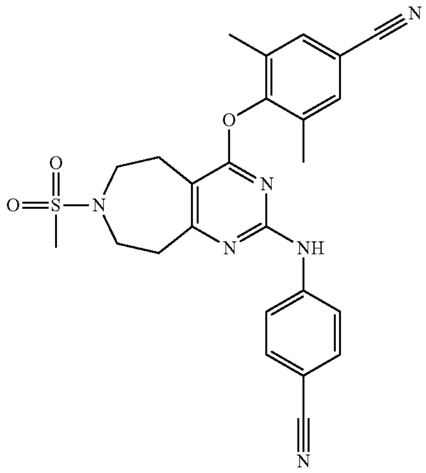 [SMILES: Cc1cc(C#N)cc(C)c1Oc1nc(Nc2ccc(C#N)cc2)nc2c1CCN(S(C)(=O)=O)CC2] | 4-((2-((4-Cyanophenyl)amino)-7-(methylsulfonyl)-6,7,8,9-tetrahydro-5H-pyrimido[4,5-d]azepine-4-yl)oxy)-3,5-dimethylbenzonitrile |

-continued
| | Structural formula | Name |
|---|---|---|
| 0274137 | 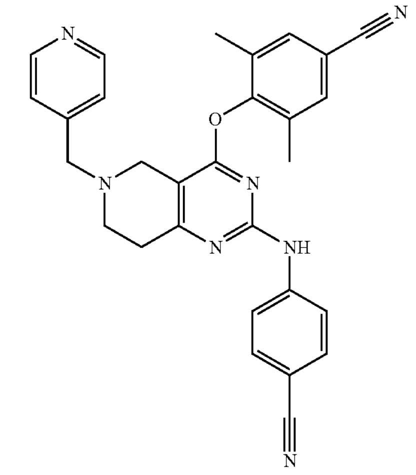 [SMILES: Cc1cc(C#N)cc(C)c1Oc1nc(Nc2ccc(C#N)cc2)nc2c1CN(Cc1ccncc1)CC2] | 4-((2-((4-Cyanophenyl)amino)-6-(pyridine-4-ylmethyl)-5,6,7,8-tetrahydropyrido[4,3-d]pyrimidine-4-yl)oxy)-3,5-dimethylbenzonitrile |
| 0274138 | 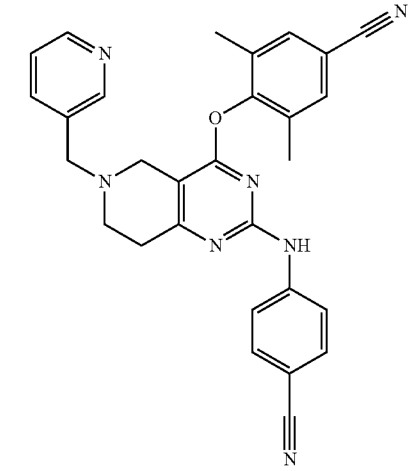 [SMILES: Cc1cc(C#N)cc(C)c1Oc1nc(Nc2ccc(C#N)cc2)nc2c1CN(Cc1cccnc1)CC2] | 4-((2-((4-Cyanophenyl)amino)-6-(pyridine-3-ylmethyl)-5,6,7,8-tetrahydropyrido[4,3-d]pyrimidine-4-yl)oxy)-3,5-dimethylbenzonitrile |
| 0274140 | 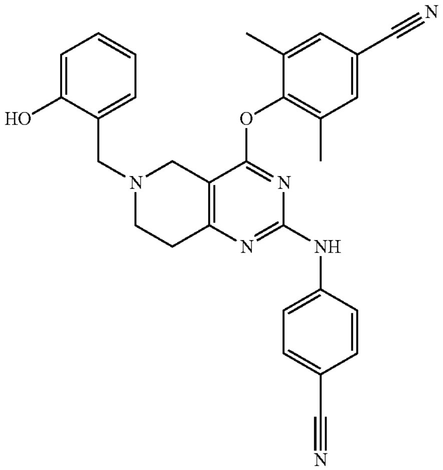 [SMILES: Cc1cc(C#N)cc(C)c1Oc1nc(Nc2ccc(C#N)cc2)nc2c1CN(Cc1ccccc1O)CC2] | 4-((2-((4-Cyanophenyl)amino)-6-(2-hydroxybenzyl)-5,6,7,8-tetrahydropyrido[4,3-d]pyrimidine-4-yl)oxy)-3,5-dimethylbenzonitrile |

-continued
| | Structural formula | Name |
|---|---|---|
| 0274141 | 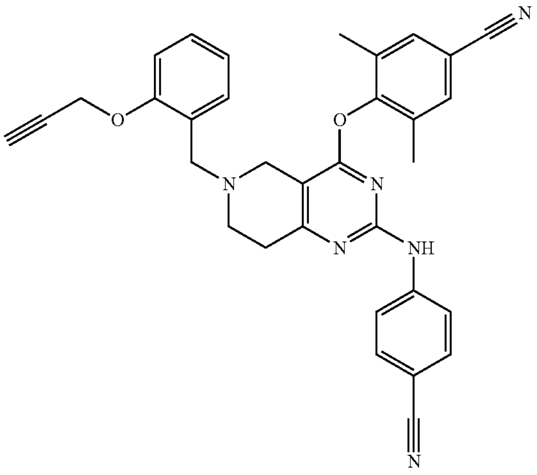 [SMILES: C#CCOc1ccccc1CN1CCc2nc(Nc3ccc(C#N)cc3)nc(Oc3c(C)cc(C#N)cc3C)c2C1] | 4-((2-((4-Cyanophenyl)amino)-6-(2-(prop-2-in-1-yloxy)benzyl)-5,6,7,8-tetrahydropyrido[4,3-d]pyrimidine-4-yl)oxy)-3,5-dimethylbenzonitrile |
| 0274143 | 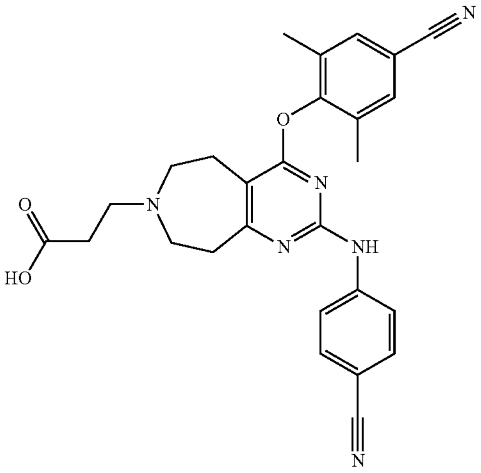 [SMILES: Cc1cc(C#N)cc(C)c1Oc1nc(Nc2ccc(C#N)cc2)nc2c1CCN(CCC(=O)O)CC2] | 3-(4-(4-Cyano-2,6-dimethylphenoxy)-2-((4-cyanophenyl)amino)-8,9-dihydro-5H-pyrimido[4,5-d]azepine-7(6H)-yl)propanoic acid |
| 0274144 | 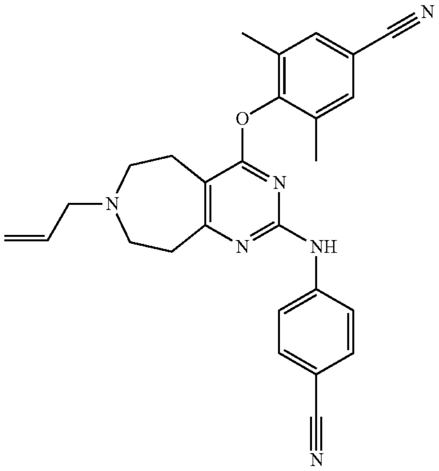 [SMILES: C=CCN1CCc2nc(Nc3ccc(C#N)cc3)nc(Oc3c(C)cc(C#N)cc3C)c2CC1] | 4-((7-Allyl-2-((4-cyanophenyl)amino)-6,7,8,9-tetrahydro-5H-pyrimido[4,5-d]azepine-4-yl)oxy)-3,5-dimethylbenzonitrile |

-continued
| | Structural formula | Name |
|---|---|---|
| 0274145 | 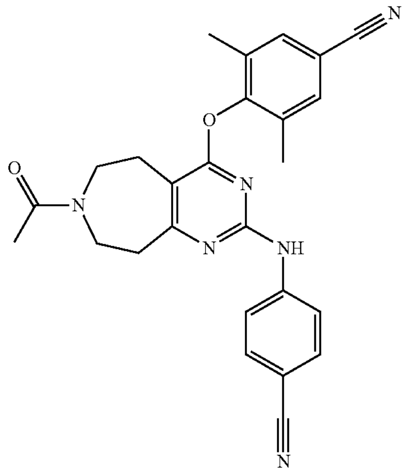 [SMILES: CC(=O)N1CCc2nc(Nc3ccc(C#N)cc3)nc(Oc3c(C)cc(C#N)cc3C)c2CC1] | 4-((7-Acetyl-2-((4-cyanophenyl)amino)-6,7,8,9-tetrahydro-5H-pyrimido[4,5-d]azepine-4-yl)oxy)-3,5-dimethylbenzonitrile |
| 0274227 | 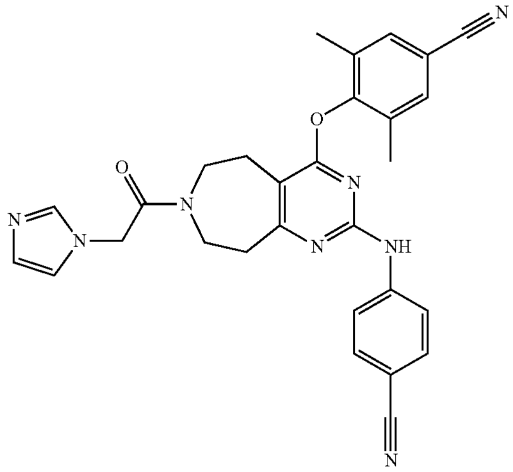 [SMILES: Cc1cc(C#N)cc(C)c1Oc1nc(Nc2ccc(C#N)cc2)nc2c1CCN(C(=O)Cn1ccnc1)CC2] | 4-((7-(2-(1H-Imidazole-1-yl)acetyl)-2-((4-cyanophenyl)amino)-6,7,8,9-tetrahydro-5H-pyrimido[4,5-d]azepine-4-yl)oxy)-3,5-dimethylbenzonitrile |
| 0274236 | 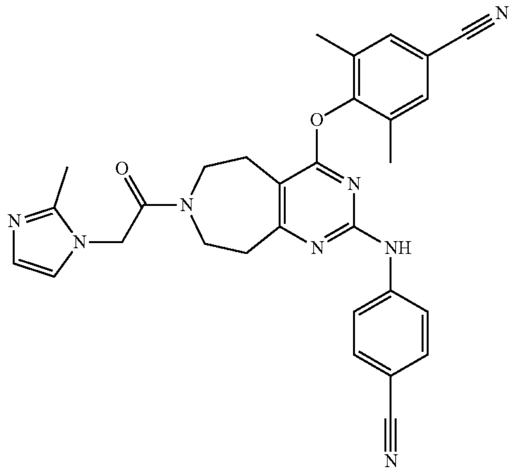 [SMILES: Cc1cc(C#N)cc(C)c1Oc1nc(Nc2ccc(C#N)cc2)nc2c1CCN(C(=O)Cn1ccnc1C)CC2] | 4-((2-((4-Cyanophenyl)amino)-7-(2-(methyl-1H-imidazole-1-yl)acetyl)-6,7,8,9-tetrahydro-5H-pyrimido[4,5-d]azepine-4-yl)oxy)-3,5-dimethylbenzonitrile |

-continued
| | Structural formula | Name |
|---|---|---|
| 0274239 | 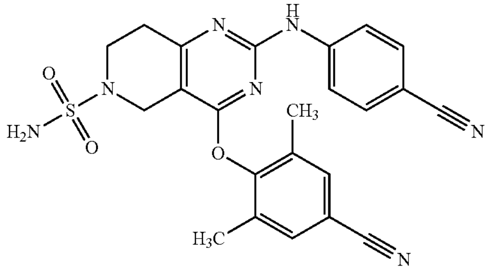 [SMILES: Cc1cc(C#N)cc(C)c1Oc1nc(Nc2ccc(C#N)cc2)nc2c1CN(S(N)(=O)=O)CC2] | 4-(4-Cyano-2,6-dimethylphenoxy)-2-[(4-cyanophenyl)amino]-5H,6H,7H,8H-pyrido[4,3-d]pyrimidine-6-sulfonamide |
| 0274312 | 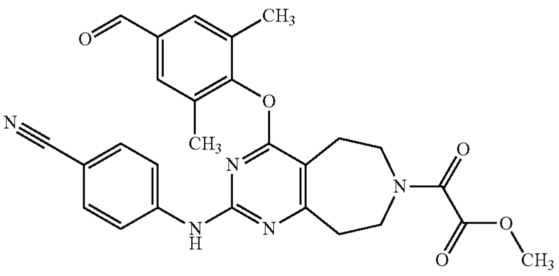 [SMILES: COC(=O)C(=O)N1CCc2nc(Nc3ccc(C#N)cc3)nc(Oc3c(C)cc(C=O)cc3C)c2CC1] | Methyl 2-{2-[(4-cyanophenyl)amino]-4-(4-formyl-2,6-dimethylphenoxy)-5H,6H,7H,8H,9H-pyrimido [4,5-d]azepine-7-yl}-2-oxoacetate |
| 0274337 | 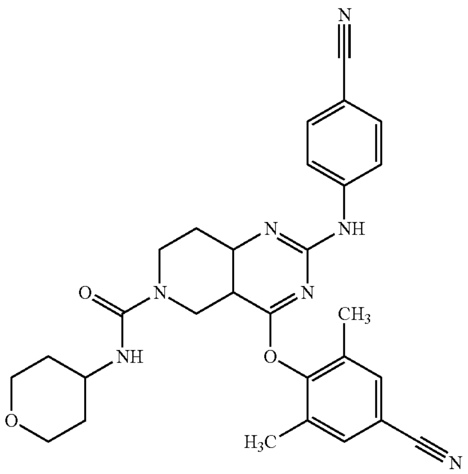 [SMILES: Cc1cc(C#N)cc(C)c1OC1=NC(Nc2ccc(C#N)cc2)=NC2CCN(C(=O)NC3CCOCC3)CC12] | 4-(4-Cyano-2,6-dimethylphenoxy)-2-[(4-cyanophenyl)amino]-N-(oxan-4-yl)-4aH,5H,6H,7H,8H,8aH-pyrido [4,3-d]pyrimidine-6-carboxamide |

DETAILED DESCRIPTION OF THE INVENTION

In one embodiment, the present invention relates to a compound of formula I (I)

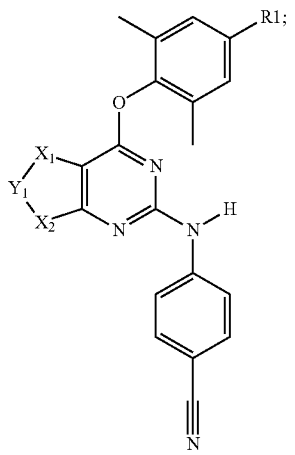

where $R^1$ is independently selected and represents H—, —CN, CN—CH═CH—;

$X^1$, $X^2$ are substituents of $(CH_2)_n$ type, wherein n is independently selected for $X_1$, $X_2$ and may have values from 1 to 3;

$Y^1$ is independently selected and represents —O—, —S—, —S(═O)—, —S(═O)$_2$—, or substituents of the following type:

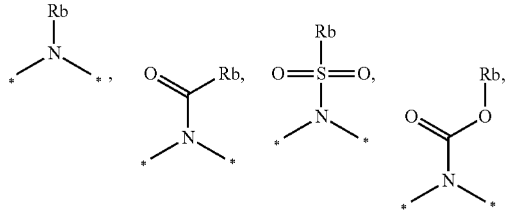

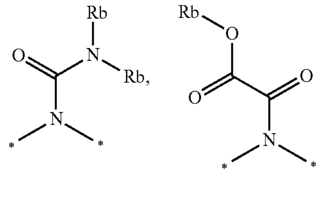

or

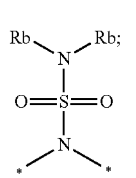

$R^b$ is independently selected and represents —H, substituted or unsubstituted —$C_1$-$C_6$-alkyl, substituted or unsubstituted —$C_1$-$C_6$-alkenyl, substituted or unsubstituted —$C_6$-aryl, substituted or unsubstituted -5-6-membered-heteroaryl, containing from 1 to 4 heteroatoms, independently selected from N, S and/or O, substituted or unsubstituted —$C_3$-$C_9$-cycloalkyl, or substituted or unsubstituted 4-9-membered heterocyclyl, containing from 1 to 4 heteroatoms, independently selected from N, S and/or O; or pharmaceutically acceptable salts thereof, Wherein $R^b$ may be attached to the remaining part of the molecule through a linker of $(CH_2)_n$ type, n is selected from 1 to 3.

In another embodiment, the invention relates to a compound of formula I (1)

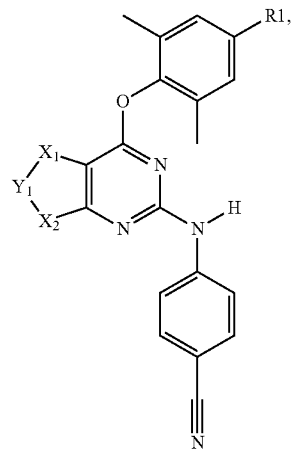

wherein $R^1$ is independently selected and represents H, CN, CN—CH═CH, C═O, CH═CH—COOH, substituted or unsubstituted 4-6-membered heterocyclyl, containing 1-2 heteroatom O; aminocarbonyl; $NH_2$; substituted or unsubstituted $C_{1-6}$alkyl; halogen; substituted or unsubstituted $C_{1-6}$alkyloxy; $NHR^9$; $NR^9R^{10}$; —C(═O)—$NHR^9$; —C(═O)—$NR^9R^{10}$; —C(═O)—$R^9$; —CH═N—NH—C(═O)—$R^9$; substituted or unsubstituted $C_{1-6}$alkyloxy$C_{1-6}$alkyl, substituted or unsubstituted $C_{2-6}$alkenyl; substituted or unsubstituted $C_{2-6}$alkynyl; —C(═N—O—$R^8$)—$C_{1-4}$alkyl; $R^7$ and —Rb-$R^7$;

$X^1$, $X^2$ are substituent of $(CH_2)_n$ type, wherein n is independently selected for $X_1$, $X_2$;

$Y^1$ is independently selected and represents —O—, —S—, —S(═O)—, —S(═O)$_2$—, or substituents of the following type:

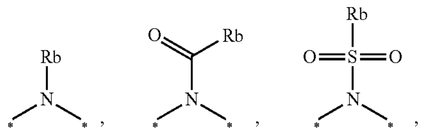

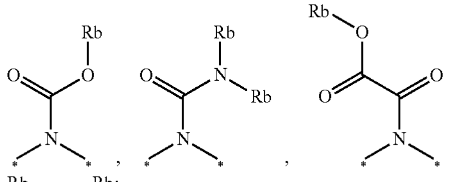

or

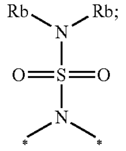

$R^b$ is selected independently and represents —H, cyano, aminocarbonyl, substituted or unsubstituted —$C_1$-$C_6$-alkyl, substituted or unsubstituted —C2-$C_6$-alkenyl, substituted or unsubstituted —C2-$C_6$-alkynyl, substituted or unsubstituted —$C_3$-$C_6$-aryl, substituted or unsubstituted 4-6-membered-heteroaryl, containing from 1 to 4 heteroatoms, independently selected from N, S and/or O, substituted or unsubstituted —$C_3$-$C_9$-cycloalkyl, substituted or unsubstituted 4-9-membered heterocyclyl, containing from 1 to 4 heteroatoms, independently selected from N, S and/or O, $R^7$ or $R^9$, wherein $R^b$ may be attached to the remaining part of the molecule through a linker of $(CH_2)_n$ type $R^7$— is a monocyclic, bicyclic or tricyclic, saturated, partially saturated or aromatic carbocycle or monocyclic, bicyclic or tricyclic, saturated, partially saturated or aromatic 4-6 membered heterocycle, containing from 1 to 4 heteroatoms, independently selected from S, N and O, wherein each of said carbocycle or heterocycle may be optionally substituted by one, two, three, four or five substituents, each of which is independently selected from halogen, hydroxy, mercapto, $C_{1-6}$alkyl, hydroxy$C_{1-6}$alkyl, amino$C_{1-6}$alkyl, mono- and di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, —C(═N—O—$R^8$), $R^{7a}$, —$R^b$—$R^{7a}$, and $R^{7a}$—$C_{1-4}$alkyl;

$R^{7a}$ is a monocyclic, bicyclic or tricyclic, saturated, partially saturated or aromatic carbocycle or monocyclic, bicyclic or tricyclic, saturated, partially saturated or aromatic 4-6 membered heterocycle, containing from 1 to 4 heteroatoms, independently selected from S, N and O, wherein each of said carbocycle or heterocycle may be optionally substituted by one, two, three, four or five substituents, each of which is independently selected from halogen, hydroxy, mercapto, $C_{1-6}$alkyl, hydroxy$C_{1-6}$alkyl, amino$C_{1-6}$alkyl, mono- or di($C_{1-6}$ alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl and —CH(═N—O—$R^8$);

$R^8$ is hydrogen, $C_{1-4}$alkyl, aryl or aryl$C_{1-4}$alkyl.

Each of $R^9$ and $R^{10}$ is independently hydrogen; cyano, aminocarbonyl, hydroxy group; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; —CH(═$NR^{11}$) or $R^7$, wherein each of said $C_{1-6}$alkyl may be optionally, independently, substituted by one or two substituents, each of which is independently selected from hydroxy, $C_{1-6}$alkyloxy, hydroxy$C_{1-6}$alkyloxy, carboxyl, $C_{1-6}$alkyloxycarbonyl, cyano, amino, aminocarbonyl, imino, mono- and di($C_{1-4}$alkyl)amino, polyhalomethyl, polyhalomethyloxy; polyhalomethylthio, —$S(═O)_pR^8$, —NH—S$(═O)_pR^8$, —C(═O)$R^8$, —NHC(═O)H, —C(═O)$NHNH_2$, NHC(═O)$R^8$, C(═NH)$R^8$, $R^7$ wherein substituents of $R^1$, $R^b$ each independently are selected from the group comprising: COO-isobutyl, OH, CN, $NH_2$, $C_{1-4}$-alkoxy, $C_{1-4}$alkyl, 4-6-membered heteroaryl, containing from 1 to 4 heteroatoms, independently selected from S, N and O, wherein said heteroaryl is unsubstituted or substituted by CN, $NH_2$, OH, $C_{1-6}$-alkyl, O or $R^c$; BOC, COOH, $R^c$, $C_{3-6}$-aryl optionally substituted by CN, NH2, OH, O or OCH2C≡CH, 4-6-membered heterocyclyl containing 1-3 heteroatom selected from N, S and O, O, N, S—C1-6-alkyl, halogen, $NR^9R^{10}$, —C(═O)—$NR^9R^{10}$, —C(═O)—$C_{1-6}$alkyl.

$R^c$ represents NHCOO—C1-6-alkyl, n may have values from 1 to 3.

In a further embodiment, the invention relates to a compound as defined above, wherein $R^1$ is independently selected and represents H, CN, CN—CH═CH, C═O, CH═CH—COOH, 4-6-membered heterocyclyl, containing 1-2 heteroatom O;

$R^b$ is independently selected and represents:

—H, substituted or unsubstituted —$C_1$-$C_6$-alkyl, substituted or unsubstituted —$C_1$-$C_6$-alkenyl, substituted or unsubstituted —$C_3$-$C_6$-aryl, substituted or unsubstituted 5-6-membered-heteroaryl, containing from 1 to 4 heteroatoms, independently selected from N, S and/or O, substituted or unsubstituted —$C_3$-$C_9$-cycloalkyl, or substituted or unsubstituted 4-9-membered heterocyclyl, containing from 1 to 4 heteroatoms, independently selected from N, S and/or O, wherein substituents $R^b$ mentioned above each is independently selected from a group, comprising:

COO-isobutyl, $NH_2$,

CN, $C_{1-4}$-alkoxy, 4-6-membered heteroaryl, containing from 1 to 4 heteroatoms, independently selected from S, N and O, wherein said heteroaryl is unsubstituted or substituted with OH, C1-6-alkyl, O or Rc;

BOC;

COOH;

$R^c$;

$C_{3-6}$-aryl, optionally substituted with OH, O or $OCH_2C$≡CH, 4-6-membered heterocyclyl, containing 1-2 heteroatom, selected from N and O,

O, N,

S—$C_{1-6}$-alkyl, halogen,

The remaining substituents are defined in the present invention.

In another embodiment, the invention relates to a compound of the present invention, wherein $R^1$ is independently selected and represents H, —CN, —CH═CH—CN, —C═O or —CH═CH—COOH.

In another embodiment, the invention relates to a compound of the present invention, wherein $R^1$ is independently selected and represents 4-6-membered heterocyclyl, containing 1-2 heteroatoms 0.

In another embodiment, the invention relates to the compound of the present invention, wherein $R^1$ is oxetane, tetrahydrofuran or tetrahydropyran.

In another embodiment, the invention relates to a compound of the present invention, wherein $Y^1$ is —O—, —S—, —S(═O)— or —$S(═O)_2$—.

In another embodiment, the invention relates to a compound of the present invention, wherein $Y^1$ is substituents of the following type:

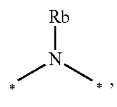,
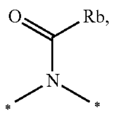,
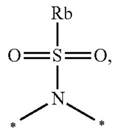,
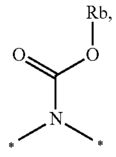

-continued

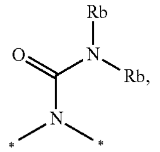
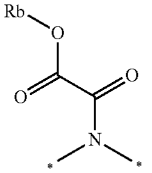 or 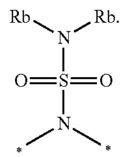

In another embodiment, the invention relates to a compound of the present invention, wherein $Y^1$ is substituents of the following type:

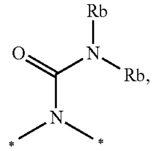
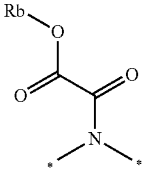 or 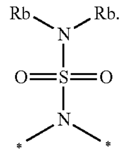

In another embodiment, the invention relates to a compound of the present invention, wherein Rb is substituted or unsubstituted methyl, ethyl, propyl, n-propyl, isopropyl, butyl, n-butyl, sec-butyl, tert-butyl or pentyl, wherein substituents are defined in the present invention.

In another embodiment, the invention relates to a compound of the present invention, wherein Rb is substituted or unsubstituted ethenyl, 1-propenyl, 2-propenyl, 1-butenyl, 2-butenyl, 3-butenyl, 2-methyl-1-propenyl, 2-methyl-2-propenyl, wherein substituents are defined in the present invention.

In another embodiment, the invention relates to a compound of the present invention, wherein Rb is substituted or unsubstituted phenyl, wherein substituents are defined in the present invention.

In another embodiment, the invention relates to a compound of the present invention, wherein Rb is substituted or unsubstituted thienyl, pyrrolyl, imidazolyl, pyrazolyl, pyridyl, pyrimidinyl, pyridazinyl, triazinyl, tetrazolyl, benzo[b]thienyl, isobenzofuranyl, isoindolile, benzimidazolyl, wherein substituents are defined in the present invention.

In another embodiment, the invention relates to a compound of the present invention, wherein Rb is substituted or unsubstituted cyclopropyl, cyclopentyl, cyclohexyl, bicyclo[2.2.2]octanyl, spiro[5.5]undecanyl, wherein substituents are defined in the present invention.

In another embodiment, the invention relates to a compound of the present invention, wherein Rb is substituted or unsubstituted pyrimidine, piperidine, azetidine, morpholine, piperazine, pyrrolidine, tetrahydropyran, furan, pyrrol, pyrazine, imidazole or pyrazole.

In another embodiment, the invention relates to a compound of the present invention, wherein $Y^1$ is substituents of the following type:

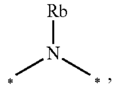, 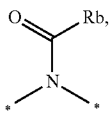 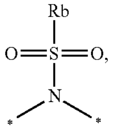 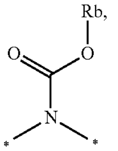

and Rb is substituted or unsubstituted 5-6-membered-heteroaryl or heterocyclyl, containing from 1 to 4 heteroatoms, independently selected from N, S and/or O, wherein substituents are defined in the present invention.

In another embodiment, the invention relates to a compound of the present invention, wherein $Y^1$ is substituents of the following type:

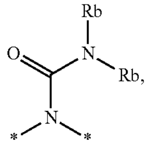
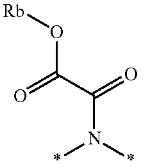 or 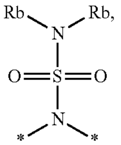

and Rb is substituted or unsubstituted —$C_3$-$C_6$-aryl or substituted or unsubstituted —$C_3$-$C_9$-cycloalkyl, wherein substituents are defined in the present invention.

In another embodiment, the invention relates to a compound selected from:

4-((4-(2,6-Dimethylphenoxy)-6,7-dihydro-5H-cyclopenta[d]pyrimidine-2-yl)amino)-benzonitrile 4-(2,6-Dimethylphenoxy)-N-(piperidine-4-yl)-6,7-dihydro-5H-cyclopenta[d]pyrimidine-2-amine Ethylic ether 4-(((6-benzyl-4-(4-cyano-2,6-dimethylphenoxy)-5,6,7,8-tetrahydropyrido[4,3-d]pyrimidine-2-yl)amino)methyl)benzoic acid Ethylic ether 4-(((6-benzyl-4-(2,6-dimethylphenoxy)-5,6,7,8-tetrahydropyrido[4,3-d]pyrimidine-2-yl)amino)methyl)benzoic acid 4-(((7-Benzyl-4-(2,6-dimethylphenoxy)-5,6,7,8-tetrahydropyrido[3,4-d]pyrimidine-2-yl)amino)methyl)benzonitrile N-(1-Benzylpiperidine-4-yl)-4-(2,6-dimethylphenoxy)-5,6,7,8-tetrahydroquinazoline-2-amine N-(1-Benzylpiperidine-4-yl)-4-(2,6-dimethylphenoxy)-6,7-dihydro-5H-cyclopenta[d]pyrimidine-2-amine 4-((2-((4-Cyanophenyl)amino)-7-methyl-5,6,7,8-tetrahydropyrido[3,4-d]pyrimidine-4-yl)oxy)-3,5-dimethylbenzonitrile 4-((4-(4-Formyl-2,6-dimethylphenoxy)-7-methyl-5,6,7,8-tetrahydro[3,4-d]pyrimidine-2-yl)amino)benzonitrile Tert-butyl 4-(4-(1,3-dioxolane-2-yl)-2,6-dimethylphenoxy)-2-((4-cyanophenyl)amino)-8,9-dihydro-5H-pyrimido[4,5-d]azepine-7(6H)-carboxylate Tert-butyl 2-((4-cyanophenyl)amino)-4-(4-formyl-2,6-dimethylphenyoxy)-8,9-dihydro-5H-pyrimido[4,5-d]azepine-7(6H)-carboxylate Tert-butyl 4-(4-cyano-2,6-dimethylphenoxy)-2-((4-cyanophenyl)amino)-7,8-dihydropyrido[4,3-d]pyrimidine-6(5H)-carboxylate 4-((2-((4-Cyanophenyl)amino)-5,6,7,8-tetrahydropyrido[4,3-d]pyrimidine-4-yl)oxy)-3,5-dimethylbenzonitrile 4-((2-((4-Cyanophenyl)amino)-6-(methylsulfonyl)-5,6,7,8-tetrahydropyrido[4,3-d]pyrimidine-4-yl)oxy)-3,5-dimethylbenzonitrile Ethyl 4-(4-cyano-2,6-dimethylphenoxy)-2-((4-cyanophenyl)amino)-7,8-dihydropyrido[4,3-d]pyrimidine-6(5H)-carboxylate (E)-3-(4-((7-(Tert-butoxycarbonyl)-2-((4-cyanophenyl)amino)-6,7,8,9-tetrahydro-5H-pyrimido[4,5-d]azepine-4-yl)oxy)-3,5-dimethylphenyl)acrylic acid Tert-butyl 4-(4-cyano-2,6-dimethylphenoxy)-2-((4-cyanophenyl)amino)-8,9-dihydro-5H-pyrimido[4,5-d]azepine-7(6H)-carboxylate 4-((2-((4-Cyanophenyl)amino)-6,7,8,9-tetrahydro-5H-pyrimido[4,5-d]azepine-4-yl)oxy)-3,5-dimethylbenzonitrile Tert-butyl 2-((4-cyanophenyl)amino)-4-(4-(2-cyanovinyl)-2,6-dimethylphenoxy)-8,9-dihydro-5H-pyrimido[4,5-d]azepine-7(6H)-carboxylate 4-((2-((4-Cyanophenyl)amino)-7-picolynoyl-6,7,8,9-tetrahydro-5H-pyrimido[4,5-d]azepine-4-yl)oxy)-3,5-dimethylbenzonitrile 4-((2-((4-Cyanophenyl)amino)-7-isonicotinoyl-6,7,8,9-tetrahydro-5H-pyrimido[4,5-d]azepine-4-yl)oxy)-3,5-dimethylbenzonitrile 4-((2-((4-Cyanophenyl)amino)-7-nicotinoyl-6,7,8,9-tetrahydro-5H-pyrimido[4,5-d]azepine-4-yl)oxy)-3,5-dimethylbenzonitrile 4-((2-((4-Cyanophenyl)amino)-7-(pyridine-2-ylmethyl)-6,7,8,9-tetrahydro-5H-pyrimido[4,5-d]azepine-4-yl)oxy)-3,5-dimethylbenzonitrile 4-((2-((4-Cyanophenyl)amino)-7-(pyridine-3-ylmethyl)-6,7,8,9-tetrahydro-5H-pyrimido[4,5-d]azepine-4-yl)oxy)-3,5-dimethylbenzonitrile 4-((2-((4-Cyanophenyl)amino)-7-(pyridine-4-ylmethyl)-6,7,8,9-tetrahydro-5H-pyrimido[4,5-d]azepine-4-yl)oxy)-3,5-dimethylbenzonitrile 4-((2-((4-Cyanophenyl)amino)-6,7,8,9-tetrahydro-5H-pyrimido[4,5-d]azepine-4-yl)oxy)-3,5-dimethylbenzonitrile Tert-butyl 4-(4-(4-cyano-2,6-dimethylphenoxy)-2-((4-cyanophenyl)amino)-6,7,8,9-tetrahydro-5H-pyrimido[4,5-d]asepin-7-carbonyl)piperidine-1-carboxylate 4-((2-((4-Cyanophenyl)amino)-7-(piperidine-4-carbonyl)-6,7,8,9-tetrahydro-5H-pyrimido[4,5-d]azepine-4-yl)oxy)-3,5-dimethylbenzonitrile Tert-butyl 4-(4-(4-cyano-2,6-dimethylphenoxy)-2-((4-cyanophenyl)amino)-8,9-dihydro-5H-pyrimido[4,5-d]azepine-7(6H)-yl)piperidine-1-carboxylate 4-((2-((4-Cyanophenyl)amino)-7-(piperidine-4-yl)-6,7,8,9-tetrahydro-5H-pyrimido[4,5-d]azepine-4-yl)oxy)-3,5-dimethylbenzonitrile 4-((6-(2-Aminoacetyl)-2-((4-cyanophenyl)amino)-5,6,7,8-tetrahydropyrido[4,3-d]pyrimidine-4-yl)oxy)-3,5-dimethylbenzonitrile 4-((2-((4-Cyanophenyl)amino)-6-(2-(3-hydroxyazetidine-1-yl)acetyl)-5,6,7,8-tetrahydropyrido[4,3-d]pyrimidine-4-yl)oxy)-3,5-dimethylbenzonitrile 4-({2-[(4-Cyanophenyl)amino]-6-[2-(morpholine-4-yl)acetyl]-5H,6H,7H,8H-pyrido[4,3-d]pyrimidine-4-yl}oxy)-3,5-dimethylbenzonitrile 4-({2-[(4-Cyanophenyl)amino]-6-[2-(4,4-difluoropiperidine-1-yl)acetyl]-5H,6H,7H,8H-pyrido[4,3-d]pyrimidine-4-yl}oxy)-3,5-dimethylbenzonitrile 4-((2-((4-Cyanophenyl)amino)-7-(cyclopropanecarbonyl)-5,6,7,8-tetrahydro-[4,3-d]pyrimidine-4-yl)oxy)-3,5-dimethylbenzonitrile 4-({2-[(4-Cyanophenyl)amino]-6-(morpholine-4-carbonyl)-5H,6H,7H,8H-pyrido[4,3-d]pyrimidine-4-yl}oxy)-3,5-dimethylbenzonitrile 4-({2-[(4-Cyanophenyl)amino]-6-(4-methylpiperazine-1-carbonyl)-5H,6H,7H,8H-pyrido[4,3-d]pyrimidine-4-yl}oxy)-3,5-dimethylbenzonitrile Tert-butyl 2-(4-(4-cyano-2,6-dimethylphenoxy)-2-((cyanophenyl)amino)-6,7,8,9-tetrahydro-5H-pyrimido[4,5-d]azepine-7-carbonyl)pyrrolidine-1-carboxylate (R)-Tert-butyl 2-(4-(4-cyano-2,6-dimethylphenoxy)-2-((cyanophenyl)amino)-6,7,8,9-tetrahydro-5H-pyrimido[4,5-d]azepine-7-carbonyl)pyrrolidine-1-carboxylate (S)-Tert-butyl 2-(4-(4-cyano-2,6-dimethylphenoxy)-2-((cyanophenyl)amino)-6,7,8,9-tetrahydro-5H-pyrimido[4,5-d]azepine-7-carbonyl)pyrrolidine-1-carboxylate 4-((2-((4-Cyanophenyl)amino)-7-(tetrahydro-2H-pyran-4-yl)-6,7,8,9-tetrahydro-5H-pyrimido[4,5-d]azepine-4-yl)oxy)-3,5-dimethylbenzonitrile 4-((2-((4-Cyanophenyl)amino)-7-(5-methylfuran-2-yl)methyl)-6,7,8,9-tetrahydro-5H-pyrimido[4,5-d]azepine-4-yl)oxy)-3,5-dimethylbenzonitrile 4-((2-((4-Cyanophenyl)amino)-7-(1-methyl-1H-pyrrol-2-yl)methyl)-6,7,8,9-tetrahydro-5H-pyrimido[4,5-d]azepine-4-yl)oxy)-3,5-dimethylbenzonitrile 4-((2-((4-Cyanophenyl)amino)-7-(4-hydroxybenzyl)-6,7,8,9-tetrahydro-5H-pyrimido[4,5-d]azepine-4-yl)oxy)-3,5-dimethylbenzonitrile 4-((2-((4-Cyanophenyl)amino)-7-(1-methoxypropane-2-yl)-6,7,8,9-tetrahydro-5H-pyrimido[4,5-d]azepine-4-yl)oxy)-3,5-dimethylbenzonitrile Tert-butyl 2-(4-(4-cyano-2,6-dimethylphenoxy)-2-((4-cyanophenyl)amino)-5,6,7,8-tetrahydropyrido[4,3-d]pyrimidine-6-carbonyl)pyrrolidine-1-carboxylate 4-((2-((4-Cyanophenyl)amino)-6-(pyrrolidine-2-carbonyl)-5,6,7,8-tetrahydropyrido[4,3-d]pyrimidine-4-yl)oxy)-3,5-dimethylbenzonitrile 4-((6-(Azetidine-3-carbonyl)-2-((4-cyanophenyl)amino)-5,6,7,8-tetrahydropyrido[4,3-d]pyrimidine-4-yl)oxy)-3,5-dimethylbenzonitrile 4-((2-((4-Cyanophenyl)amino)-6-(pyrazine-2-carbonyl)-5,6,7,8-tetrahydropyrido[4,3-d]pyrimidine-4-yl)oxy)-3,5-dimethylbenzonitrile (S)-Tert-butyl (1-(4-(4-cyano-2,6-dimethylphenoxy)-2-((4-cyanophenyl)amino)-7,8-dihydropyrido[4,3-d]pyrimidine-6(5H)-yl)-1-oxopropane-2-yl)carbamate (S)-4-((6-(2-Aminopropanoyl)-2-((4-cyanophenyl)amino)-5,6,7,8-tetrahydropyrido[4,3-d]pyrimidine-4-yl)oxy)-3,5-dimethylbenzonitrile (S)-Tert-butyl (1-(4-(4-cyano-2,6-dimethylphenoxy)-2-((4-cyanophenyl)amino)-7,8-dihydropyrido[4,3-d]pyrimidine-6(5H)-yl)-1-oxo-3-phenylpropane-2-yl)carbamate (S)-4-((6-(2-Amino-3-phenylpropanoyl)-2-((4-cyanophenyl)amino)-5,6,7,8-tetrahydropyrido[4,3-d]pyrimidine-4-yl)oxy)-3,5-dimethylbenzonitrile 4-((2-((4-Cyanophenyl)amino)-7-(2-morpholinoethyl)-6,7,8,9-tetrahydro-5H-pyrimido[4,5-d]azepine-4-yl)oxy)-3,5-dimethylbenzonitrile (R)-Tert-butyl (1-(4-(4-cyano-2,6-dimethylphenoxy)-2-((4-cyanophenyl)amino)-7,8-dihydropyrido[4,3-d]pyrimidine-6(5H)-yl)-3-hydroxy-1-oxopropane-2-yl)carbamate Tert-butyl (1-(4-(4-cyano-2,6-dimethylphenoxy)-2-((4-cyanophenyl)amino)-7,8-dihydropyrido[4,3-d]pyrimidine-6(5H)-yl)-4-(methylthio)-1-oxobutane-2-yl)carbamate 4-({6-[2-Amino-3-(1H-imidazole-5-yl)propanoyl]-2-[(4-cyanophenyl)amino]-5H,6H,7H,8H-pyrido[4,3-d]pyrimidine-4-yl}oxy)-3,5-dimethylbenzonitrile 4-((6-(2-Amino-3-(1H-pyrazole-4-yl)propanoyl)-2-((4-cyanophenyl)amino)-5,6,7,8-tetrahydropyrido[4,3-d]pyrimidine-4-yl)oxy)-3,5-dimethylbenzonitrile Tert-butyl 4-(2-((tert-butoxycarbonyl)amino)-3-(4-(4-cyano-2,6-dimethylphenoxy)-2-((4-cyanophenyl)amino)-7,8-dihydropyrido[4,3-d]pyrimidine-6(5H)-yl)-3-oxopropyl)-1H-pyrazole-1-carboxylate (R)-4-((6-(2-Amino-3-hydroxypropanoyl)-2-((4-cyanophenyl)amino)-5,6,7,8-tetrahydropyrido[4,3-d]pyrimidine-4-yl)oxy)-3,5-dimethylbenzonitrile (S)-Tert-butyl (1-(4-(4-cyano-2,6-dimethylphenoxy)-2-((4-cyanophenyl)amino)-7,8-dihydropyrido[4,3-d]pyrimidine-6(5H)-yl)-3-(4-hydroxyphenyl)-1-oxopropane-2-yl)carbamate (S)-4-((6-(2-Amino-3-(4-hydroxyphenyl)propanoyl)-2-((4-cyanophenyl)amino)-5,6,7,8-tetrahydropyrido[4,3-d]pyrimidine-4-yl)oxy)-3,5-dimethylbenzonitrile (R)-Tert-butyl (1-(4-(4-cyano-2,6-dimethylphenoxy)-2-((4-cyanophenyl)amino)-7,8-dihydropyrido[4,3-d]pyrimidine-6(5H)-yl)-3-methyl-1-oxobutane-2-yl)carbamate (R)-4-((6-(2-Amino-3-methylbutanoyl)-2-((4-cyanophenyl)amino)-5,6,7,8-tetrahydropyrido[4,3-d]pyrimidine-4-yl)oxy)-3,5-dimethylbenzonitrile (S)-Tert-butyl (1-(4-(4-cyano-2,6-dimethylphenoxy)-2-((4-cyanophenyl)amino)-7,8-dihydropyrido[4,3-d]pyrimidine-6(5H)-yl)-4-methyl-1-oxopentane-2-yl)carbamate (S)-4-((6-(2-Amino-4-methylpentanoyl)-2-((4-cyanophenyl)amino)-5,6,7,8-tetrahydropyrido[4,3-d]pyrimidine-4-yl)oxy)-3,5-dimethylbenzonitrile (S)-Di-tert-butyl (6-(4-(4-cyano-2,6-dimethylphenoxy)-2-((4-cyanophenyl)amino)-7,8-dihydropyrido[4,3-d]pyrimidine-6(5H)-yl)-6-oxohexane-1,5-diyl)dicarbamate (S)-4-((2-((4-Cyanophenyl)amino)-6-(2,6-diaminohexanoyl)-5,6,7,8-tetrahydropyrido[4,3-d]pyrimidine-4-yl)oxy)-3,5-dimethylbenzonitrile 4-((7-(2-Chloroacetyl)-2-((4-cyanophenyl)amino)-6,7,8,9-tetrahydro-5H-pyrimido[4,5-d]azepine-4-yl)oxy)-3,5-dimethylbenzonitrile Methyl 4-(4-cyano-2,6-dimethylphenoxy)-2-((4-4-cyanophenyl) amino)-8,9-dihydro-5H-pyrimido[4,5-d]azepine-7(6H)-carboxylate 4-((2-((4-Cyanophenyl)amino)-7-(methylsulfonyl)-6,7,8,9-tetrahydro-5H-pyrimido[4,5-d]azepine-4-yl)oxy)-3,5-dimethylbenzonitrile 4-((2-((4-Cyanophenyl)amino)-6-(pyridine-4-ylmethyl)-5,6,7,8-tetrahydropyrido[4,3-d]pyrimidine-4-yl)oxy)-3,5-dimethylbenzonitrile 4-((2-((4-Cyanophenyl)amino)-6-(pyridine-3-ylmethyl)-5,6,7,8-tetrahydropyrido[4,3-d]pyrimidine-4-yl)oxy)-3,5-dimethylbenzonitrile 4-((2-((4-Cyanophenyl)amino)-6-(2-hydroxybenzyl)-5,6,7,8-tetrahydropyrido[4,3-d]pyrimidine-4-yl)oxy)-3,5-dimethylbenzonitrile 4-((2-((4-Cyanophenyl)amino)-6-(2-(prop-2-in-1-yloxy)benzyl)-5,6,7,8-tetrahydropyrido[4,3-d]pyrimidine-4-yl)oxy)-3,5-dimethylbenzonitrile 3-(4-(4-Cyano-2,6-dimethylphenoxy)-2-((4-cyanophenyl)amino)-8,9-dihydro-5H-pyrimido[4,5-d]azepine-7(6H)-yl)propanoic acid 4-((7-Allyl-2-((4-cyanophenyl)amino)-6,7,8,9-tetrahydro-5H-pyrimido[4,5-d]azepine-4-yl)oxy)-3,5-dimethylbenzonitrile 4-((7-Acetyl-2-((4-cyanophenyl)amino)-6,7,8,9-tetrahydro-5H-pyrimido[4,5-d]azepine-4-yl)oxy)-3,5-dimethylbenzonitrile 4-((7-(2-(1H-Imidazole-1-yl)acetyl)-2-((4-cyanophenyl)amino)-6,7,8,9-tetrahydro-5H-pyrimido[4,5-d]azepine-4-yl)oxy)-3,5-dimethylbenzonitrile 4-((2-((4-Cyanophenyl)amino)-7-(2-(methyl-1H-imidazole-1-yl)acetyl)-6,7,8,9-tetrahydro-5H-pyrimido[4,5-d]azepine-4-yl)oxy)-3,5-dimethylbenzonitrile 4-(4-Cyano-2,6-dimethylphenoxy)-2-[(4-cyanophenyl)amino]-5H,6H,7H,8H-pyrido[4,3-d]pyrimidine-6-sulfonamide Methyl 2-{2-[(4-cyanophenyl)amino]-4-(4-formyl-2,6-dimethylphenoxy)-5H,6H,7H,8H,9H-pyrimido [4,5-d]azepine-7-yl}-2-oxoacetate 4-(4-Cyano-2,6-dimethylphenoxy)-2-[(4-cyanophenyl)amino]-N-(oxane-4-yl)-4aH,5H,6H,7H,8H,8aH-pyrido[4,3-d]pyrimidine-6-carboxamide In another embodiment, the invention relates to a compound of the present invention, which comprises at least one isotope.

In another embodiment, the invention relates to a compound of the present invention in the form of:

a free base, or a pharmaceutically acceptable salt selected from a group, comprising salts of amino groups formed by inorganic acids, such as hydrochloric, hydrobromic, phosphoric, sulfuric and chloric acids, or formed by organic acids, such as acetic, oxalic, maleic, tartaric, succinic or malonic acids, or pharmaceutically acceptable salts: adipate, alginate, ascorbate, aspartate, benzene sulfonate, benzoate, bisulfate, borate, butyrate, camphorate, camphor sulfonate, citrate, cyclopentanepropionate, digluconate, dodecyl sulfate, ethane sulfonate, formate, fumarate, glucoheptonate, glycerophosphate, gluconate, hemisulfate, heptanoate, hexanoate, hydroiodide, 2-hydroxyethane sulfonate, lactobionate, lactate, laurate, lauryl sulfate, malate, maleate, malonate, methanesulfonate, 2-naphthalene sulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, or a pharmaceutically acceptable salt, containing alkaline and/or alkaline-earth metals, or nontoxic cations of ammonium, quaternary ammonium and amine, or a pharmaceutically acceptable salt obtained using counterions, such as halogenides, hydroxides, carboxylates, sulfates, phosphates, nitrates, lower alkyl sulfates and aryl sulfonates.

In another embodiment, the invention relates to a compound of the present invention for use as a reverse transcriptase inhibitor.

In another embodiment, the invention relates to a compound of the present invention for use as a pharmaceutical preparation, having anti-HIV antiviral activity.

In another embodiment, the invention relates to a compound of the present invention as described herein for obtaining a pharmaceutical preparation, having anti-HIV antiviral activity.

In another embodiment, the invention relates to a pharmaceutical composition, as described herein modulating the reverse transcriptase activity, comprising the compound of the present invention in a therapeutically effective amount and at least one carrier, excipient or diluent.

In another embodiment, the invention relates to a pharmaceutical composition as described herein for the treatment or prevention of HIV, comprising at least one compound of the present invention in a therapeutically effective amount and at least one carrier, excipient or diluent.

In another embodiment, the invention relates to a pharmaceutical composition as described herein, modulating the HIV reverse transcriptase activity, comprising the compound of the present invention in a therapeutically effective amount, and at least one compound, selected from a group, comprising HIV protease inhibitors, nucleoside reverse transcriptase inhibitors, non-nucleoside reverse transcriptase inhibitors, CCR5 antagonists and viral cell entry inhibitors.

In another embodiment, the invention relates to a pharmaceutical composition as described herein, modulating the HIV reverse transcriptase activity, wherein HIV reverse transcriptase has at least one mutation compared to Wild type HIV, comprising the compound of the present invention in a therapeutically effective amount.

In another embodiment, the invention relates to a pharmaceutical composition, modulating the HIV reverse transcriptase activity, wherein HIV reverse transcriptase has reduced sensitivity to the following drugs: Efavirenz, Nevirapine, Doravirine or Delavirdine, comprising the compound of the present invention in a therapeutically effective amount.

In another embodiment, the invention relates to a pharmaceutical composition for obtaining an agent for the treatment or prevention HIV, comprising at least one compound of the present invention in a therapeutically effective amount, and a pharmaceutically acceptable carrier.

In another embodiment, the invention relates to the use of compounds of the present invention for obtaining an agent for the treatment or prevention of HIV.

In another embodiment, the invention relates to the use of the composition of the present invention for obtaining an agent for the treatment or prevention of HIV.

In another embodiment, the invention relates to a method for the treatment or prevention of HIV, comprising the use of at least one compound of the present invention.

In another embodiment, the invention relates to a method for the treatment or prevention of HIV, comprising the use of the composition of the present invention.

In another embodiment, the invention relates to a method for the treatment or prevention of HIV infection, wherein a therapeutically effective amount of at least one compound of the present invention is administered to the subject as needed for such treatment.

In another embodiment, the invention relates to the abovementioned method for the treatment or prevention, wherein said therapeutically effective amount of compounds means a daily dose, which is approximately 0.1 to approximately 500 mg/kg body weight in parenteral infusion.

In another embodiment, the invention relates to the abovementioned method for the treatment or prevention, wherein daily dose may be administered as a single dose or 1-5 separate doses.

In another embodiment, the invention relates to a combination for the treatment or prevention of HIV-mediated diseases, comprising therapeutically effective amount of compounds of the present invention and at least one compound, selected from a group, comprising HIV protease inhibitors, nucleoside reverse transcriptase inhibitors, non-nucleoside reverse transcriptase inhibitors, CCR5 antagonists and viral cell entry inhibitors.

In another embodiment, the invention relates to a method for the treatment or prevention of HIV-mediated diseases, wherein a therapeutically effective amount of compounds of the present invention and at least one compound selected from a group, comprising HIV protease inhibitors, nucleoside reverse transcriptase inhibitors, non-nucleoside reverse transcriptase inhibitors, CCR5 antagonists, and viral cell entry inhibitors is administered to a subject in need of such treatment.

In another embodiment, the invention relates to a reverse transcriptase inhibition method in a body of an HIV infected subject, wherein a therapeutically effective amount of at least one compound of the present invention is administered to the subject as needed for such treatment.

In another embodiment, the invention relates to a method of obtaining a pharmaceutical composition of the present invention, comprising mixing of compounds of the present invention with pharmaceutically acceptable carriers.

The term "As mentioned above" means the widest definition of each group specified in section Summary of Invention or in the widest claim of the claims of invention or in the present specification. In other embodiments provided below, substituents are present in each variant, which optionally maintain the most general volume specified in section Summary of Invention or in the present specification.

Unless otherwise stated, technical and scientific terms used in the description of the present invention have meanings known to a specialist in the prior art, to which the invention refers. The description comprises references to different procedures and materials known to a skilled in the art. Standard document, wherein pharmacology common factors are considered, is monograph: Goodman and Gilman, The Pharmacological Basis of Therapeutics, 13 ed., McGraw Hill Companies Inc., New York (2017). In the context of this invention, any suitable materials and/or methods may be used known to a skilled in the art. However, the specification of the present invention contains description of preferable materials and methods. Materials, reagents, etc. mentioned in the specification and in examples, are commercial products, unless otherwise stated.

The term "Compound of the present invention" or "compound according to the invention" mentioned herein refers to at least one compound mentioned in the present invention, as well as to any combination of them, including double combination, triple combination, etc.

In the specification of the invention, for example, in any section of the application or in the invention claims, the terms "includes (include)" and "including" have conventional meaning. I.e. the terms approximately correspond to "containing at least" or "including at least" provisions. As for the method, the term "including" means that the method includes at least the mentioned stages. As for compounds or compositions, the term "including" means that a compound or composition includes at least the abovementioned features or components; however, it may also include additional features or components.

The term "approximately" used in the specification means approximately, about, around or roughly. The term "approximately" used in relation to number interval means that maximal and minimal values of the interval have the abovementioned values. In general, the term "approximately" is used to specify acceptable changes of the numerical value 20% higher and lower than the value specified.

It is entailed that numerical value interval used in the description specification means that the invention may be used at any value within the specified interval. Thus, a variable, which is discrete by nature, may have any integral value within the mentioned interval, including final values of the interval. Likewise, a variable, which is continuous by nature, may have any actual value within the interval specified, including final values of the interval. For example, a variable, which according to the specification have values between 0 and 2, may mean 0, 1 or 2, if this is a discrete value, and may have values of 0.0, 0.1, 0.01, 0.001, or any actual value, if this is a continuous variable.

If any group (for example, $R^1$) is contained in a fragment content or in any formula mentioned or in any compound described more than two times, and described compounds are used or claimed in this invention, then its value in each case is independent. Moreover, combinations of substituents and/or variables are allowed in such a case only if obtained compounds are stable compounds.

In one embodiment of the present invention, a compound of formula I is proposed, wherein $R^1$, $X^1$, $X^2$, $Y^1$ have the abovementioned values. The terms "abovementioned", "as mentioned above" and "said" mean variables included in the form of a reference in the widest definition of variables mentioned in section Summary of invention or in the widest claim of the invention specification.

In one more embodiment of the present invention, a compound is proposed, which represents free base or pharmaceutically acceptable salt compounds according to the present invention.

In another embodiment of the present invention, a method for the treatment of HIV infection or prevention of HIV infection is proposed, which consists of a subject in need for treatment being administered with a therapeutically effective amount of compounds of formula I, wherein $R^1$, $X^1$, $X^2$, $Y^1$ have the abovementioned values.

In one more embodiment of the present invention, a method for the treatment or prevention of HIV-mediated diseases is proposed, which consists of a subject in need for treatment being administered with a therapeutically effective amount of compounds of formula I, wherein $R^1$, $X^1$, $X^2$, $Y^1$ have the abovementioned values, and at least one compound selected from a group, comprising HIV protease inhibitors, nucleoside reverse transcriptase inhibitors, non-nucleoside reverse transcriptase inhibitors, CCR5 antagonists and viral cell entry inhibitors.

In another embodiment of the present invention, a method of inhibition of HIV reverse transcriptase in the body of a HIV infected subject is proposed, which consists in a subject in need for treatment being administered with a therapeutically effective amount of compounds of formula I, wherein $R^1$, $X^1$, $X^2$, $Y^1$ have the abovementioned values.

In another embodiment of the present invention, a method of inhibition of HIV reverse transcriptase in the body of a HIV infected subject is proposed, wherein HIV reverse transcriptase contains at least one mutation compared to Wild type HIV, which consists of a subject in need for treatment being administered with a therapeutically effective amount of compounds of formula I, wherein $R^1$, $X^1$, $X^2$, $Y^1$ have the abovementioned values.

In another embodiment of the present invention, a method of inhibition of HIV reverse transcriptase in the body of a HIV infected subject is proposed, wherein HIV reverse transcriptase has reduced sensitivity to Efavirenz, Nevirapine or Delavirdine products, which consists of a subject in need for treatment being administered with a therapeutically effective amount of compounds of formula I, wherein $R^1$, $X^1$, $X^2$, $Y^1$ have the abovementioned values.

In one embodiment of the present invention, a pharmaceutical composition is proposed, comprising the compound of formula I, wherein $R^1$, $X^1$, $X^2$, $Y^1$ have the abovementioned values, and at least one carrier, excipient or diluent.

The following definitions are used in this document, if not otherwise clearly stated. Moreover, unless otherwise stated, all inclusions of functional groups are selected independently, two inclusions may be both the same, and different.

The term "alkyl" on its own or as a part of another substituent refers to saturated hydrocarbon groups with linear or branched chain, including hydrocarbon groups, having the stated number of carbon atoms (i.e., $C_{1-6}$-alkyl assumes between one and six carbon atoms). Examples of alkyls include methyl, Ethyl, n-propyl, iso-propyl.

The term "alkynyl" on its own or as a part of another substituent refers to hydrocarbon groups, wherein at least one carbon-carbon bond is a triple bond, while the rest of bonds may be single, double or additional triple bonds, including hydrocarbon groups, between 2 and 6 carbon atoms. Examples of alkynyl groups include ethinyl, 1-propynyl, 2-propynyl, etc.

The term "alkenyl" on its own or as a part of another substituent refers to hydrocarbon groups, wherein at least one carbon-carbon bond is a double bond, while the rest of bonds may be either single bonds, or additional double bonds, including hydrocarbon groups, containing between 2 and 6 carbon atoms. Examples of alkenyl groups include ethenyl, 1-propenyl, 2-propenyl, 1-butenyl, 2-butenyl, 3-butenyl, 2-methyl-1-propenyl, 2-methyl-2-propenyl, etc.

The term "halogen" on its own or as a part of another term refers to atoms of fluorine, chlorine, bromine, or iodine.

The terms "carboxyl", "carboxy" or "hydroxycarbonyl" refer to —COOH group.

The terms "alkoxy" and "alkyloxy" on their own or in word combinations refer (if not otherwise stated) to aliphatic radicals of alkyl-O— type, wherein alkyl is determined above. Illustrative examples of alkoxy-groups include (but not limited to those listed) methoxy-, ethoxy-, propoxy-, isopropoxy-, butoxy-, isobutoxy-, tert-butoxy-, pentoxy-, isopentoxy-, neopentoxy-, tert-pentoxy-, hexoxy-, isohexoxy-, geptoxy, octoxy-group, etc. Preferable alkoxy-groups are methoxy- and ethoxy-group.

Monocyclic, bicyclic or tricyclic saturated carbocycle represents a cyclic system, consisting of 1, 2 or 3 cycles; wherein, the specified cyclic system consists of carbon atoms only, and the specified cyclic system contains single bonds only; monocyclic, bicyclic, or tricyclic partially saturated carbocycle represents cyclic system, consisting of 1, 2 or 3 cycles; wherein, the specified cyclic system consists of carbon atoms only and includes at least double bond, given that cyclic system is not an aromatic cyclic system; monocyclic, bicyclic, or tricyclic aromatic carbocycle represents aromatic cyclic system, consisting of 1, 2 or 3 cycles; wherein, the specified cyclic system consists of carbon atoms only; the term "aromatic" is well known to specialists in the prior art, and it means cyclic conjugated system, including 4n+2 electrons, i.e. 6, 10, 14 etc. π-electrons (Huckel's rule); monocyclic, bicyclic or tricyclic saturated heterocycle represents cyclic system, consisting of 1, 2 or 3 cycles and including at least one heteroatom selected from O, N or S; wherein, the specified cyclic system contains single bonds only; monocyclic, bicyclic, or tricyclic partially saturated heterocycle represents cyclic system, consisting of 1, 2 or 3 cycles and including at least one heteroatom selected from O, N or S, and at least one double bond, given that cyclic system is not an aromatic cyclic system; monocyclic, bicyclic, or tricyclic aromatic heterocycle represents aromatic cyclic system, consisting of 1, 2 or 3 cycles and including at least one heteroatom selected from O, N or S.

Specific examples of monocyclic, bicyclic or tricyclic saturated carbocycles are cyclopropyl, cyclobutyl, cyclopentyl, cyclohexyl, cycloheptyl, cyclooctyl, bicyclo[4,2,0]-octanyl, cyclononanyl, cyclodecanyl, decahydronaphthalenyl, tetradecahydroanthracenyl, etc. Preferable are cyclopropyl, cyclobutyl, cyclopentyl, cyclohexyl, cycloheptyl, more preferable are cyclopentyl, cyclohexyl, cycloheptyl.

Specific examples of monocyclic, bicyclic or tricyclic partially saturated carbocycles are cyclopropenyl, cyclobutenyl, cyclopenthenyl, cyclohexenyl, cycloheptenyl, cyclooctenyl, bicyclo[4,2,0]octenyl, cyclononenyl, cyclodecenyl, octahydronaphthalenyl, 1,2,3,4-tetrahydronaphthalenyl, 1,2,3,4,4a,9,9a,10-octahydroanthracenyl, etc.

Specific examples of monocyclic, bicyclic or tricyclic aromatic carbocycles are phenyl, naphthalenyl, anthracenyl. Phenyl is preferable.

Specific examples of monocyclic, bicyclic or tricyclic saturated heterocycles are tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiophorpholinyl, piperazinyl, trithianyl, decahydroquinolinyl, octahydroindolyl, etc. Preferable are tetrahydrofuranyl, pyrrolidinyl, dioxolanyl, imidazolidinyl, thiazolidinyl, dihydrooxazolyl, triazolidinyl, piperidinyl, dioxanyl, morpholinyl, thiomorpholinyl, piperazinyl. The most preferable are tetrahydrofuranyl, pyrrolidinyl, dioxolanyl, piperidinyl, dioxanyl, morpholinyl, thiomorpholinyl, piperazinyl.

Specific examples of monocyclic, bicyclic and tricyclic partially saturated heterocycles are pyrrolinyl, imidazolinyl, pyrazolinyl, 2,3-dihydrobenzofuranyl, 1,3-benzodioxolyl, 2,3-dihydro-1,4-benzodioxynyl, indolinyl, etc. Preferable are the following: pyrrolinyl, imidazolinyl, 2,3-dihydrobenzofuranyl, 1,3-benzodioxolyl, indolinyl.

Specific examples of monocyclic, bicyclic or tricyclic aromatic heterocycles are asetyl, oxetilidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolysinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolynyl, quinolizinyl, phthalazinyl, quinooxalinyl, quinazolinyl, naphtyridinyl, pteridinyl, benzopyranyl, pyrrolopyridyl, thienopyridyl, furopyridyl, isothiazolepyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazole pyrazinyl, thiazole pyrazinyl, isoxazole pyrazinyl, oxazole pyrazinyl, pyrazole pyrazinyl, imidazopyrazinyl, pyrrolo-pyrimidinyl, thienopyrimidinyl, furopyrimidinyl, isothiazole pyrimidinyl, thiazole pyrimidinyl, isoxazole pyrimidinyl, oxazole pyrimidinyl, pyrazole pyrimidinyl, imidazopyrimidinyl, pyrrole pyridazinyl, thienopyridazinyl, furopyridazinyl, isothiazole pyridazinyl, thiazole pyridazinyl, isoxazole pyridazinyl, oxazole pyridazinyl, pyrazole pyridazinyl, imidazopyridazinyl, oxadiazole opyridyl, thiadiazole pyridyl, triazole pyridyl, oxadiazole pyrazinyl, thiadiazole pyrazinyl, triazole pyrazinyl, oxadiazole pyrimidinyl, thiadiazole pyrimidinyl, triazole pyrimidinyl, oxadiazole pyridazinyl, thiadiazole pyridazinyl, triazole pyridazinyl, imidazooxazolyl, imidazothiazolyl, imidazoimidazolyl, isoxazole triazinyl, isothiazole triazinyl, pyrazole triazinyl, oxazole triazinyl, thiazole triazinyl, imidazotriazinyl, oxadiazole triazinyl, thiadiazole triazinyl, triazole triazinyl, carbazolyl, acridinyl, phenazinyl, phenothiazinyle, phenoxazinyl, etc.

Preferable aromatic heterocycles are monocyclic or bicyclic aromatic heterocycles. Monocyclic, bicyclic, or tricyclic aromatic heterocycles of interest are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, xinolynyl, isoxinolynyl, phthalazinyl, quinooxalinyl, quinazolinyl, benzopyranyl, pyrrole pyridyl, thienopyridyl, furopyridyl, isothiazole pyridyl, thiazole pyridyl, isoxazole pyridyl, oxazole pyridyl, pyrazole pyridyl, imidazopyridyl, pyrrolopyrazinyl, thienopyrazinyl, furopyrazinyl, isothiazole pyrazinyl, thiazole pyrazinyl, isoxazole pyrazinyl, oxazole pyrazinyl, pyrazole pyrazinyl, imidazopyrazinyl, pyrrolopyrimidinyl, thienopyrimidinyl, furopyrimidinyl, isothiazole pyrimidinyl, thiazole pyrimidinyl, isoxazole pyrimidinyl, oxazole pyrimidinyl, pyrazole pyrimidinyl, imidazopyrimidinyl, oxadiazole pyridyl, thiadiazole pyridyl, triazole pyridyl, oxadiazole pyrazinyl, thiadiazole pyrazinyl, triazole pyrazinyl, oxadiazole pyrimidinyl, thiadiazole pyrimidinyl, triazole pyrimidinyl, carbazolyl, acridinyl, phenothyazinyl, phenoxazinyl, etc.

The term “cycloalkyl” in this document refers to groups, having between 3 and 12 carbon atoms in mono- or polycyclic structure, including spirocycles. For purposes of illustration, cycloalkyls include, but are not limited to, the following radicals: cyclopropyl, cyclopentyl, cyclohexyl, bicyclo[2.2.2]octanyl, spiro[5.5]undecanyl, which, as in case with other aliphatic or heteroaliphatic or heterocyclic substituents, may be substituted.

“Heterocycle”, “heterocyclyl” or «heterocyclic» mean in this document non-aromatic mono- or polycyclic systems (saturated or partially non-saturated), having between three and twelve atoms, containing heteroatoms N, O or S. Heterocycle may by attached to the main moiety through nitrogen atom (N-heterocyclyl) or through carbon atom. Heterocycles may also be substituted. In particular, heterocycle may represent, but not limited to, azipidinyl, oxyranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, 1,1-dioxothiomorpholine-4-yl, azepanyl, diazepanyl, homopiperazinyl, oxazepanyl, 8-aza-bicyclo[3.2.1]octyl, quinuclidinyl, 8-oxa-3-aza-bicyclo[3.2.1]octyl, 9-azabicyclo[3.3.1]nonyl, 3-oxa-9-azabicyclo[3.3.1]nonyl, or 3-thia-9-azabicyclo[3.3.1]nonyl. Specific examples of heterocycles are also dihydrofuryl, imidazolinyl, dihydro-oxazolyl, tetrahydropyridinyl, dihydropyranyl, pyrrolidinyl, piperidinyl, piperazinyl, morpholinyl and 2-oxa-5-aza-bicyclo[2.2.1]heptyl. The term “cycloalkenyl” means in this document partially non-saturated cycloalkyl, containing between 5 and 12 carbon atoms, having between one and two double carbon-carbon bonds.

The term “aryl” in this document means groups, containing aromatic cycle, having between five and ten carbon atoms. An example of aryl cyclic groups is phenyl and naphtyl.

The term “heteroaryl”, “heteroaryl cycle”, as it is used herein, means a stable heterocyclic and polyheterocyclic aromatic fragment, having 5-10 atoms in a cycle. Heteroaryl group may be substituted or not substituted and may consist of one or several rings. Possible substituents include, among others, any from the abovementioned substituents. Examples of typical heteroaryl cycles are five- and six-membered monocyclic groups, such as thienyl, pyrrolyl, imidazolyl, pyrazolyl, pyridyl, pyrimidinyl, pyridazinyl, triazinyl, tetrazolyl, etc.; as well as polycyclic heterocyclic groups, such as benzo[b]thienyl, isobenzofuranyl, isoindolyl, benzimidazolyl, etc. The term "heteroaryl" may be used equivalently to "heteroaryl cycle" or "heteroaromatic".

Aryl group or heteroaryl group (including heteroaryl part of heteroaralkyls or heteroaralkoxy moieties, etc.) may contain one or several substituents. Examples of suitable substituent on unsaturated carbon atom of aryl or heteroaryl groups include, but are not limited to, halogen (F, Cl, Br or I), $C_{1-3}$-alkyl, —CN, —OH, —$C_{1-3}$-alkyl and others, as specified in this invention.

Carbocycles or heterocycles mentioned in the definition of $R^7$ or $R^{7a}$ may be attached to the rest of molecular of formula (I) through any suitable cyclic carbon atom or heteroatom if not otherwise specified. Thus, for example, if heterocycle represents imidazolyl, it may be 1-imidazolyl, 2-imidazolyl, 4-imidazolyl, etc., or, if carbocycle represents naphthalenyl, it may be 1-naphthalenyl, 2-naphthalenyl, etc.

If any of substituents (for example, $R^7$) at the same time is met in the same compound more than once, each from the definitions of such a substituent is independent.

The term "substituted" shall mean that one or more hydrogen atom at atom or group mentioned as "substituted" is substituted by any of the listed groups, provided that the atom mentioned has normal valency, or that valency of the group atom being substituted is not excessive, and that substitution results in a stable compound. The term "substituted or unsubstituted" means that this compound or substructure is either unsubstituted, or substituted, as defined in the application, by one or more substituents, as mentioned or as defined below.

O, or substituted or unsubstituted 4-9-membered heterocyclyl, containing 1 to 4 heteroatoms;

Another group, from which substituents may be selected, represents:

COO-isobutyl, $NH_2$, CN, $C_{1-4}$-alkoxy, 4-6-membered heteroaryl, containing 1 to 4 heteroatoms, independently selected from a group S, N and O (17, 18, 67, 45, 60), in addition, the abovementioned heteroaryl is unsubstituted or substituted with —OH, $C_{1-6}$-alkyl, O, or Rc; BOC, COOH, $R^c$, $C_{3-6}$-aryl, optionally substituted OH, O or $OCH_2C{\equiv}CH$, 4-6-membered heterocyclyl, containing 1-2 heteroatom selected from N and O, O, nitrogen atom, S—$C_{1-6}$-alkyl, halogen. This invention contains such only combinations of substituents and derivatives, which form stable or chemically possible compound. Stable or chemically possible compound is a compound, the stability of which is sufficient for its synthesis and analytical detection. Preferable compounds of the present invention are stable enough and do not degrade at the temperature up to 40° C. in the absence of chemically active conditions for at least one week.

Some compounds of the present invention may exist in tautomeric forms, and this invention includes such tautomeric forms of such compounds, unless otherwise stated.

For example, compounds of the present invention may exist in the form of tautomers 1-3, being in a state of dynamic balance. Under normal conditions, their separation is not possible, thus, pharmacological prosperities of compounds of the present invention represent a complex of effects of tautomers.

An example of tautomeric forms of compounds according to the invention represents:

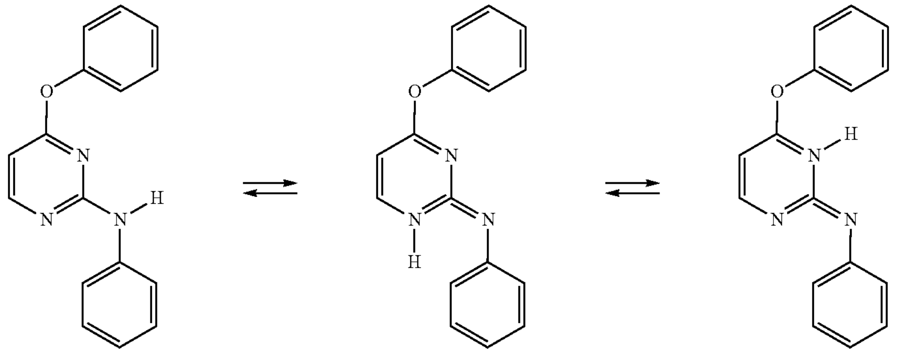

(1) (2) (3)

In this document, alkyl, alkenyl, alkynyl, alkylene, cycloalkyl, cycloalkenyl, heterocyclyl, aryl and heteroaryl groups, as well as other substructures, containing at least one hydrogen atom in their composition, may be substituted by one or more substituents:

—F, —Cl, —Br, —CN, —OH, —$NO_2$, —$NH_2$, —$CF_3$, —$CHF_2$, —$CH_2F$, —$C_1$-$C_4$-alkyl, —$C_2$-$C_4$-alkenyl, —$C_2$-$C_4$-alkynyl, —$C_3$-$C_9$-cycloalkyl, -4-9-membered-heterocyclyl attached through C- or N-atoms, -phenyl, -5-6-membered-heteroaryl attached through C- or N-atoms, —O—$R^z$, —$N(R^z)_2$, —$NR^z$—C(═O)—$R^z$, —$NR^z$—$S(═O)_2$—$R^z$, —S—$R^z$, —C(═O)—$R^z$, —C(═O)—$OR^z$, —C(═O)—$N(R^z)_2$, —O—C(═O)—$R^z$, —O—C(═O)—$(NR^z)_2$, —SO—$N(R^z)_2$, —$SO_2$—$R^z$, wherein each $R^z$ is independently selected and represents —H, —$C_1$-$C_6$-alkyl, —$C_3$-$C_9$-cycloalkyl, -5-6-membered heteroaryl, containing 1 to 4 heteroatoms, independently selected from N, S and/or If not otherwise stated, structures shown herein also assume all stereoisomers, i.e. R- and S-isomers for each asymmetric center. Moreover, some stereochemical isomers, likewise enantiomers and diastereomeric mixtures of these compounds, are also a subject of the present invention. Thus, this invention covers each diastereomer or enantiomer, significantly free from other isomers (>90%, preferably >95% molar purity), as well as the mixture of such isomers.

A specific isomer may be obtained by the separation of racemic mixture according to the standard procedure, for example, by obtaining diastereomeric salts by exposing to optically active acid or base followed by the separation of the mixture of diastereomers by crystallization with further isolation of optically active bases from these salts. Examples of such acids are tartaric, diacetyl tartaric, dibenzoyl tartaric, ditoluene tartaric and camphorsulfonic acid. Another procedure of separation of optic isomers consists in the use of chiral chromatographic column. Moreover, another method of separation includes synthesis of covalent diastereomeric molecules by the reaction of invention compounds with optically pure acid in an activated form or by optically pure isocyanate. Obtained diastereomers may be separated using general methods, for example, chromatography, distillation, crystallizations or sublimation, and then hydrolyzed to obtain enantiomerically pure compounds.

Optically active compounds of the present invention may be obtained using optically active initial materials. Such isomers may be in the form of free acid, free base, ester or salt.

This invention includes all pharmaceutically acceptable isotopically-labelled compounds according to this invention, wherein one or several atoms is substituted by atoms, having the same atomic number, but atomic weight or mass number different from those usually met in nature.

Examples of isotopes suitable for the inclusion into compounds according to the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Some isotopically-labelled compounds of the present invention, for example, those, which include radioactive isotope, are used in studies of distribution of the pharmaceutical preparation and/or substrate in tissues. In particular, for this purpose, radioactive isotopes are used, such as tritium, i.e. $^{3}H$, and carbon-14, i.e. $^{14}C$, considering that they are easy to administer, and their detection tools are available.

Substitution by more heavy isotopes, such as deuterium, i.e. $^{2}H$, may provide some therapeutic effects conditioned by metabolical stability, for example, by an increase in the half-life period in vivo or a decrease in dosage limits, and, consequently, may be preferable in some cases.

Isotopically-labelled compounds according to the invention may be obtained using general methods known to a skilled in the art, or by methods similar to those described in the attached examples of synthesis methods, when using appropriate isotopically-labelled reagents instead of unlabeled earlier used reagent.

Thus, this invention also refers to the use of compounds according to this invention for the diagnostics, including the distribution of the pharmaceutical preparation according to this invention or determination of targets, having affinity towards compounds of the present invention, in particular isotopically-labelled compounds according to this invention.

The term "wild type" used in the application specification means HIV virus strain, having dominant genotype present in normal population and resistant to the reverse transcriptase inhibitor. The term "wild type reverse transcriptase» used in the application specification means reverse transcriptase expressed by a wild type strain, which is sequenced and provided in SwissProt database under number P03366.

The term "reduced sensitivity" used in the application specification means an approximately 10-fold or more change in sensitivity of isolate of a specific virus strain or compared to the sensitivity, which is observed for a wild type virus under similar experimental conditions.

Compounds according to the present invention are obtained using methods shown in the schemes provided and described in section Implementation of invention. Starting materials and reagents, which are used in obtaining of the mentioned compounds, are commercial reagents supplied by firms, for example, Acros Organics, Alfa Aesar, Lancaster, Merck and Sigma-Aldrich, and others, or they are obtained using known methods according to procedures, described in literature, such as Fieser and Fieser, Reagents for Organic Synthesis, Wiley & Sons: New York, T.T. 1-21, R. C. LaRock, Comprehensive Organic Transformations, 2 ed., Wiley-VCH, New York (1999), Comprehensive Organic Synthesis, B. Trost and I. Fleming (Eds.), T.T. 1-9 Pergamon, Oxford (1991), Comprehensive Geterocyclic Chemistry, A. R. Katritzky and C. W. Rees (Eds) Pergamon, Oxford, T.T. 1-9 (1984), Comprehensive Geterocyclic Chemistry II, A. R. Katritzky and C. W. Rees (Eds), Pergamon, Oxford, T.T. 1-11 (1986) and Organic Synthesis, Wiley & Sons: New York, T.T. 1-40 (1991), as well as provided in databases, such as SciFinder and Reaxis, but not limited to them. The following reaction schemes only illustrate some methods of synthesis of compounds according to this invention, and different modifications of these reaction schemes may be developed and proposed by a skilled in the art with a reference to materials of this application.

Starting materials and intermediate compounds in the mentioned reaction schemes may be obtained and, if necessary, purified using appropriate methods, including, with no limitation of those listed, filtration, distillation, crystallization, chromatography, etc. Such materials may be characterized by appropriate methods, including physical constants and spectral data.

Unless otherwise stated, reactions provided in the application specification were preferably conducted in inert gas atmosphere at atmosphere pressure at the temperature of between approximately −78° C. and approximately 150° C., more preferably between approximately 0° C. and approximately 125° C., and the most preferably usually at room temperature, for example, at approximately 20° C.

Some compounds in the shown schemes are provided with the inclusion of generalized substituents; however, it is quite obvious for a specialist that nature of groups R may vary according to the structure of different compounds according to this invention. Moreover, reaction conditions are typical, and alternative conditions are also well known. It is assumed that the reaction sequence in the following examples does not limit the volume of the invention mentioned above in claims of the invention.

Pharmaceutically acceptable solvates according to the invention include solvates, where solvent may be isotopically substituted, for example, $D_2O$, d6-acetone, d6-DMSO.

The term "solvate" refers to an association or complex from one or several molecules of the solvent and compounds according to the invention. Examples of solvents, forming solvates, include, but not limited to them, water, isopropanol, ethanol, methanol, DMSO, ethylacetate, acetic acid and ethanolamine.

The term "hydrate" refers to the complex, where solvent molecules are water.

Compounds of the present invention may exist in a free form or, if necessary, in the form of pharmaceutically acceptable salts or other derivatives. The term "pharmaceutically acceptable salt" used herein refers to such salts, which, within the conducted medical conclusion, are suitable for the use in contact with human and animal tissues without excessive toxicity, irritation, allergic reaction, etc., and are consistent with a reasonable benefit/risk ratio. Pharmaceutically acceptable salts of amins, carboxylic acids, phosphonates and other types of compounds are well known in medicine. Salts may be obtained in situ in the process of isolation or purification of invention compounds, as well as may be obtained separately, by interaction of free acid or free base invention compounds with a suitable base or acid, respectively. Salt of amino groups formed by inorganic acids, such as hydrochloric, hydrobromic, phosphoric, sulfuric and chloric acids, or by organic acids, such as acetic, oxalic, maleic, tartaric, succinic or malonic acids, or obtained by other methods used in this area, for example, with ion exchange, may be examples of pharmaceutically acceptable, non-toxic acid salts. Other pharmaceutically acceptable salts are as follows: adipate, alginate, ascorbate, aspartate, benzene sulfonate, benzoate, bisulfate, borate, butyrate, camphorate, camphor sulfonate, citrate, cyclopentanepropionate, digluconate, dodecyl sulfate, ethane sulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalene sulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate and similar. Typical salts of alkaline and alkali-earth metals contain sodium, lithium, potassium, calcium, magnesium, etc. Moreover, pharmaceutically acceptable salts may contain, if necessary, nontoxic cations of ammonium, quaternary ammonium and amine, obtained using counterions, such as halogenides, hydroxides, carboxylates, sulfates, phosphates, nitrates, lower alkyl sulfates and aryl sulfonates.

Compounds of the present invention may exist in the form of pharmaceutically acceptable esters. The term "pharmaceutically acceptable esters" refers to derivatives of compounds of the present invention, wherein carboxyl group is converted to ester. Lower alkyl, lower hydroxyalkyl, lower-alkoxy-lower-alkyl, amino-lower-alkyl, mono- or di-lower-alkyl-amino-lower-alkyl, morpholine-lower-alkyl, pyrrolidine-lower-alkyl, piperidine-lower-alkyl, piperazine-lower-alkyl, lower-alkyl-piperazine-lower-alkyl and arylalkyl esters are examples of suitable esters. Specific esters are as follows: methyl, ethyl, propyl, butyl and benzyl esters. Moreover, the term "pharmaceutically acceptable esters" covers compounds of the present invention, wherein hydroxy groups are converted into respective esters by organic or inorganic acids, such as nitric acid, sulfuric acid, phosphoric acid, citric acid, formic acid, maleic acid, acetic acid, succinic acid, tartaric acid, methanesulfonic acid, p-toluenesulfonic acid and similar, which are non-toxic for living organisms.

If one of the starting materials or compounds of the present invention contains one or more functional groups, which are not stable or are reactive under the reaction conditions of one or several reaction stages, respective protection groups (as described, for example, in "Protective Groups in Organic Chemistry" by T. W. Greene and P. G. M. Wutts, 3rd Ed., 1999, Wiley, New York) may by introduced before the critical stage using methods well known in this area. Such protective groups may be eliminated at the later stage of the synthesis using standard methods described in literature. Examples of protective groups are as follows: tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

Compounds of the present invention may contain several asymmetrical centers and may be present in the form of optically pure enantiomers, enantiomer mixtures, such as, for example, racemates, diastereoisomer mixtures, diastereoisomer racemates or diastereoisomer racemate mixtures.

"Asymmetric carbon atom" is defined as carbon atom with four different substituents. According to Cahn-Ingold-Prelog rules, asymmetric carbon atom may be of R- or S-configuration.

Another embodiment of the present invention relates to pharmaceutical compositions or pharmaceutical preparations, containing compounds for the invention and therapeutically inert carrier, diluent or excipient, as well as methods for use of compounds according to the invention to obtain such compositions and pharmaceutical preparations. In one variant, compounds of the present invention may be prepared by stirring at room temperature, corresponding pH and at a desirable grade, with physiologically acceptable carriers, for example, carriers, which are non-toxic for recipients in doses and concentrations used, in galenic formulation. Specific use and concentration of compound mostly affect the pH of the composition, but preferably it may vary in the range of about 3 to about 8. In another embodiment, compounds of the present invention are sterile. Compound may be stored, for example, in a solid or amorphous composition, in the form of lyophilized preparation or in the form of water solution.

Compositions are prepared, dosed and administered according to good medical practice. Factors considered in this context include a specific disorder to be managed, specific mammal to be treated, clinical condition of specific patient, cause of the disorder, agent site of delivery, method of administration, dosage regimen and other factors familiar to clinicians.

Compounds according to the invention can be administered by any appropriate route, including orally, locally (including transbuccally and sublingually), rectally, vaginally, transdermally, parenterally, subcutaneously, intraperitoneally, intrapulmonary, intradermally, intrathecally, epidurally and intranasally. Parenteral infusions include intramuscular, intravenous, intra-arterial, intraperitoneal or subcutaneous administration.

Compounds according to this invention can be administered in any suitable pharmaceutical form, for example, tablets, powders, capsules, solutions, dispersions, suspensions, syrups, sprays, suppositories, gels, emulsions, patches, etc. Such compositions may contain general for pharmaceutical preparations ingredients, for example, diluents, carries, pH modifiers, sweeteners, excipients and other active ingredients.

Typical preparation is obtained by mixing the compound for the present invention and carrier or excipient. Acceptable carriers and excipients are well known to specialists in the field of the present invention and are well described, for example, in Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. Compositions may also include one or more buffers, stabilizing agents, superficially active substances, wetting agents, lubricating agents, emulsifiers, suspending agents, preservatives, antioxidants, opaquing agents, glidants, processing additives, colorants, sweeteners, flavorings, fragrances, diluents and other known additives, providing elegant presentation of the product (for example, compounds according to this invention or its pharmaceutical composition) or helping in the manufacture of the pharmaceutical product (for example, pharmaceutical preparation).

Thus, this invention also refers to: a compound of the present invention for use as therapeutically active substance; for use as a reverse transcriptase inhibitor; or as a pharmaceutical preparation having anti-HIV antiviral activity.

Pharmaceutical composition, containing a compound according to the present invention and therapeutically inert carrier;

- Use of compounds according to the present invention for the treatment or prevention of HIV;
- Pharmaceutical composition, having activity towards HIV reverse transcriptase, including a compound according to this invention in a therapeutically effective amount, and at least one compound selected from a group, comprising HIV protease inhibitors, nucleoside reverse transcriptase inhibitors, non-nucleoside reverse transcriptase inhibitors, CCR5 antagonists and viral cell entry inhibitors;
- Use of compounds according to this invention for obtaining a pharmaceutical preparation for the treatment or prevention of HIV;
- Compound of the present invention for the treatment or prevention of HIV; and
- Method for the treatment or prevention of HIV, which includes administration of an effective amount of compounds of the present invention to a patient in need thereof.

Modification of compounds for the invention for raising their solubility in water or other carrier is reached by using simple enough techniques (obtaining of salts, etherification, etc.), which are well known to skilled in the art. Moreover, a specialist may change the route of administration and the treatment course with a specific compound to regulate pharmacokinetics of compounds for the invention and to achieve maximum therapeutic effect for the patient.

The term “therapeutically effective amount” used in the application description means an amount necessary to decrease the intensity of disease symptoms in a patient. The level of the development of HIV infection is established by measuring viral load (RNA) or T-cells level. The dose may be adjusted according to individual requirements in each particular case. The dose may be adjusted in a wide range depending on many factors, such as, severity of the disease being managed, age and relative health condition of the subject, use of other pharmaceutical preparations by the patient, route of administration and dosage form, experience and qualification of the physician. In case of oral administration, suitable daily dose is between approximately 0.01 and approximately 100 mg/kg of body weight, when treated with one pharmaceutical preparation and/or in combination therapy. Preferable daily dose is between approximately 0.1 and approximately 500 mg/kg of body weight, more preferably between 0.1 and 100 mg/kg of body weight and more preferably between 1.0 and approximately 10 mg/kg body weight. Thus, for administering to the patient with a body weight of 70 kg, the dose is between approximately 7 mg and approximately 0.7 g per day. Daily dose may be administered as a single dose or as 1-5 divided doses. Usually, the treatment is started with administration of doses, not exceeding the optimal dose. Then, the dose is gradually increased to achieve optimal action for a particular patient. A specialist in the mentioned diseases without any experiments, based on his/her own experience and specification of the present invention, may determine a therapeutically effective number of compounds according to this invention necessary to manage this disease in a particular patient.

Active compound for the invention or its salt may be administered in combination with other antiviral agent, such as nucleoside reverse transcriptase inhibitor or HIV protease inhibitor. In case of administration of an active compound or its derivative or salts in combination with another antiviral agent, activity of the combination may exceed the activity of initial compounds. In case of combination therapy, such an administration may be conducted simultaneously with or sequentially with administration of nucleosides derivatives. Consequently, the term “simultaneous administration” used in the application specification includes administration of agents simultaneously or at different times. Two or more agents may be administered simultaneously as part of one formulation, containing two or more active ingredients; or two or more formulations, each containing one active ingredient, may be administered almost simultaneously.

It is assumed that references to treatment include prevention, as well as treatment of conditions observed. Moreover, the term “treatment of HIV infection” used in the application specification also includes treatment or prevention of the disease or condition associated or mediated by HIV infection, or its clinical symptoms.

Pharmaceutical preparations preferably represent standard pharmaceutical forms. In such a form, the product is divided into standard doses, containing appropriate amounts of the active ingredient. A standard pharmaceutical form may be a packed product, moreover, the packaging contains discrete amounts of the product, such as, packed tablets, capsules, and powders in bottles or ampules. Moreover, a standard dose may be a capsule, tablet, starch capsule or cake, or may be a packaging, containing a specific amount of any of the specified dosage forms.

BEST MODE FOR CARRYING OUT THE INVENTION

The invention is illustrated by the following examples, not limiting their volume.

The examples and products mentioned below are provided with a purpose of explaining the summary of the invention and supporting its practical use.

EXAMPLES

General Procedure for Substitution of Sulfogroups by the Activated Amine
(Reaction XIX)

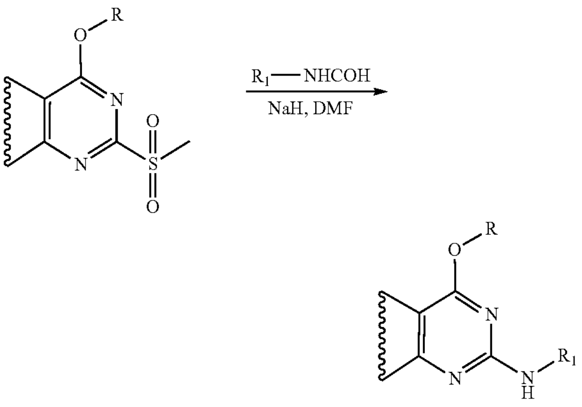

Add NaH (7 mmol, 1.8 eq.) to the formamide solution (3.9 mmol, 1 eq.) in dimethylformamide (15 ml) at the temperature of 0° C. Mix the reaction mixture at room temperature for 20 minutes. Then again cool the mixture to 0° C. and add sulfone to it (3.9 mmol, 1.0 eq.). Mix the reaction mixture for 8 hours, then boil out organic solvent, add water to the residue (pH=9). Filter the residue formed and wash with water. Dissolve the residue in methylene chloride and conduct purification by chromatography using Hex:EA (1:1) as eluent.

General Procedure for Alkylation of Substituted Tetrahydropyrimidines Derivatives (Reaction XX)

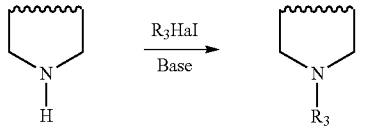

Transfer pyrimidine in the form of a free base (1 mmol, 1 eq.) and alkylbromide (1.1 mmol) into a 50 ml round-bottomed flask equipped with an effective reflux condenser with a chlorocalcium tube. Boil the mixture, until all the mass is solidified. Hydrobromide of the target product is formed. At the end of reaction, cool the flask and pour in portions (while cooling to avoid significant heating) 1 g caustic soda solution into 20 ml of water. Determine the extracted product in a separation funnel, add chlorous, wash the organic phase with water, dry over anhydrous sodium sulfate. Remove the organic solvent at under pressure, and purify the residue by chromatography using Hex:EA (1:3) as eluent.

Example 1

Synthesis of 4-((7-benzyl-4-(2,6-dimethylphenoxy)-5,6,7,8-tetrahydropyrido[3,4-d]pyrimidine-2-yl) amino)benzonitrile

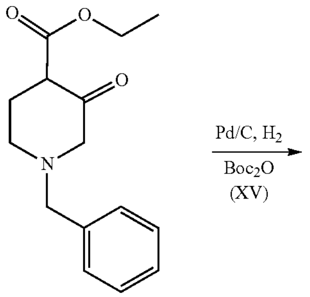

26

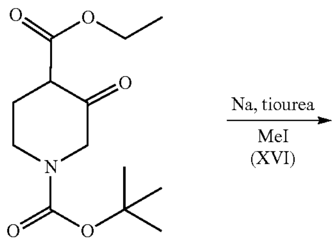

27

-continued

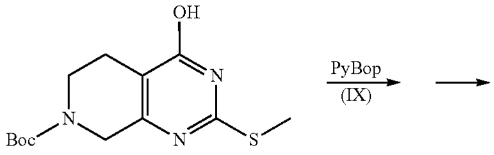

28

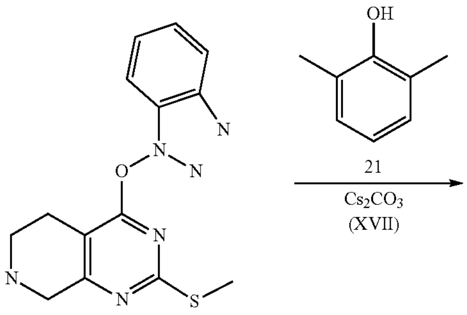

29

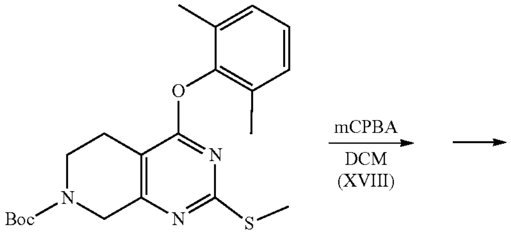

30

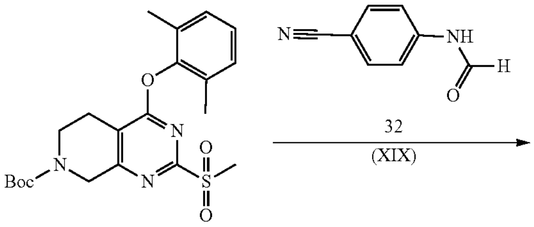

31

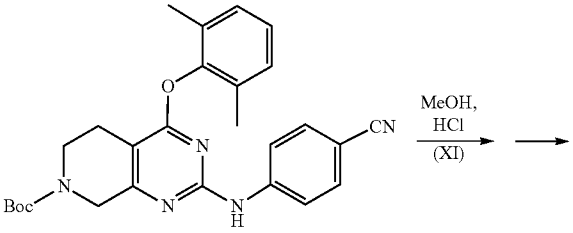

33

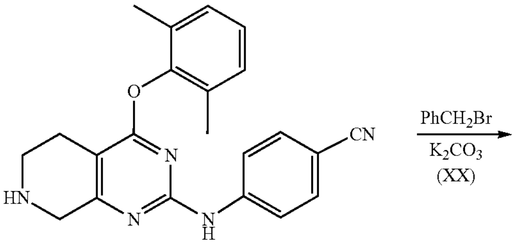

34

-continued

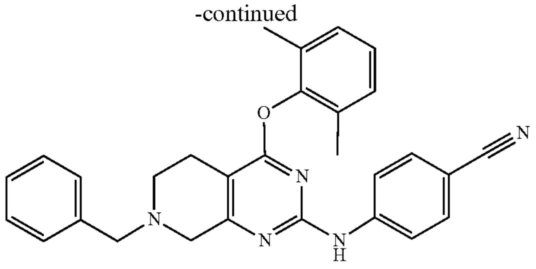

BB 0273459

1-(Tert-butyl) 4-ethyl 3-oxopiperidine-1,4-dicarboxylate (27)

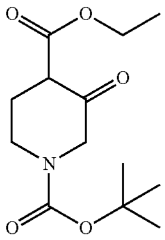 [SMILES: CCOC(=O)C1CCN(C(=O)OC(C)(C)C)CC1=O]

Dissolve hydrochloride 26 (59.6 g, 0.2 mole, 1 eq.) in ethanole (400 ml) and add triethylamine (27.8 ml, 0.2 mole, 1 eq.), mix for 5 minutes. Then add 5% Pd/C (5 g) to the reaction mass. Degas the reaction mixture and conduct the reaction of debenzylation in hydrogen environment. Stir the reaction mixture for 3 days, then add $Boc_2O$ (43.6 g, 0.2 mole, 1 eq.). Stir the reaction mixture for three hours, then pass through a layer of silt, add cold water (250 ml) and dichloromethane (500 ml). Separate the organic layer, wash twice with water (2×150 ml), dry over anhydrous sodium sulfate, filter the drying agent, and remove the organic solvent on a rotary evaporator at under pressure. Purify the residue by column chromatography using Hex:EA (3:1) as eluent. Rf=0.6.

Weight=20 g

Yield=52%

Tert-butyl 4-hydroxy-2-(methylthio)-5,8-dihydro-pyrido[3,4-d]pyrimidine-7(6H)-carboxylate (28)

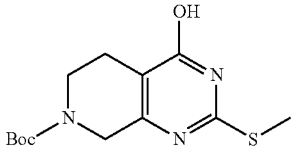 [SMILES: CSc1nc(O)c2c(n1)CN(C(=O)OC(C)(C)C)CC2]

To sodium ethoxide solution obtained by dissolution of Na (1.95 r, 81 mmol, 3.0 eq.) in absolute ethanole (100 ml), add thiourea (3.22 g, 42 mmol, 1.5 eq.) and ketoester (27) (7.67 g, 28.2 mmol, 1.0 eq.). The reaction mixture was boiled for 8 hours, then the mixture was cooled to the room temperature and added to it dropwise from a dropping funnel while stirring MeI (1.76 ml, 28.2 mmol, 1 eq.). After adding of alkylating reagent, the mixture was mixed at the room temperature for 1 hour. The reaction mixture was boiled, the residue was dissolved in water. During acidification of water solution with citric acid to pH 3-4, precipitation occurred, which was filtered, washed sequentially with water, hexane, ethylacetate, ester.

Weight=7.8 g

Yield=85%

Tert-butyl 4-((1H-benzo[d][1,2,3]triazole-1-yl)oxy)-2-(methylthio)-5,8-dihydropyrido[3,4-d]pyrimidine-7(6H)-carboxylate (29)

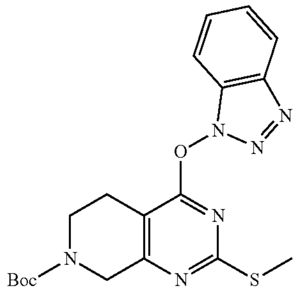 [SMILES: CSc1nc2c(c(On3nnc4ccccc43)n1)CCN(C(=O)OC(C)(C)C)C2]

Dissolve pyrimidine 28 (5.68 g, 19.1 mmol, 1 eq.) in 80 ml of dimethylformamide, then add triethylamine (TEA) (2.66 ml, 19.1 mmol, 1 eq.) and, in 5 minutes, add benzotriazole-1-yl-oxytripyrrolidinephosphonium hexafluorophosphate (PyBop) (9.9 g, 19.1 mmol, 1 eq.). Stir the reaction mixture for 5 hours, then pour into ethylacetate, and wash the organic phase with sodium hydrocarbonate saturated solution. Boil out the organic layer and purify by column chromatography using Hex:EA (3:1) as eluent.

Weight=4.6 g

Yield=68%.

Tert-butyl 4-(4-cyano-2,6-dimethylphenoxy)-2-(methylthio)-5,8-dihydropyrido[3,4-d]pyrimidine-7(6H)-carboxylate (30)

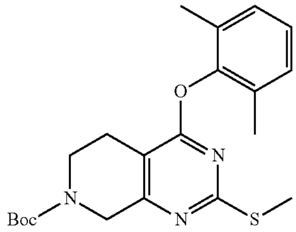 [SMILES: CSc1nc2c(c(Oc3c(C)cccc3C)n1)CCN(C(=O)OC(C)(C)C)C2]

Dissolve pyrimidine 29 (4.1 g, 8.5 mmol, 1 eq.) in dimethylformamide (50 ml), then add phenol 21 (1.24 g, 8.5 mmol, 1 eq.) and cesium carbonate (2.76 g, 8.5 mmol, 1 eq.). Mix the reaction mixture for 8 hours, then pour into ethylacetate and wash with water. Boil out the organic layer and purify by column chromatography using Hex:EA (3:1) as eluent.

Weight=3.2 g

Yield=85%.

LCMS (M+H)=402

Tert-butyl 4-(4-cyano-2,6-dimethylphenoxy)-2-(methylsulfonyl)-5,8-dihydro-pyrido[3,4-d]pyrimidine-7(6H)-carboxylate (31)

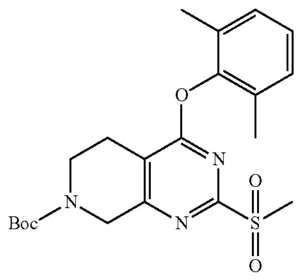 [SMILES: Cc1cccc(C)c1Oc1nc(S(C)(=O)=O)nc2c1CCN(C(=O)OC(C)(C)C)C2]

To pyrimidine 30 (3.0 g, 7 mmol, 1 eq.) solution in dichloromethane (50 ml) at 0° C., add m-chloroperbenzoic acid (mCPBA) (3.8 g, 21.1 mmol, 3 eq.). Stir the reaction mixture for 24 hours. Then to stop the reaction, add to the mixture saturated water solution of $NaHCO_3$. Extract the obtained product with dichloromethane. Boil out the organic phase on a rotary evaporator and purify by column chromatography using Hex:EA (1:1) as eluent.

Weight=2.2 g

Yield=54%

$^1$H NMR (400 MHz, DMSO-$d_6$, δ, ppm): 1.46 (s, 9H), 2.11 (s, 6H), 2.98 (t, J=5.4 Hz, 2H), 3.12 (s, 3H), 3.76 (t, J=5.5 Hz, 2H), 4.72 (broadened singlet, 2H), 7.72-7.78 (m, 3H)

LCMS (M+H)=434

Tert-butyl 2-((4-cyanophenyl)amino)-4-(2,6-dimethylphenoxy)-5,8-dihydropyrido [3,4-d]pyrimidine-7 (6H)-carboxylate (32)

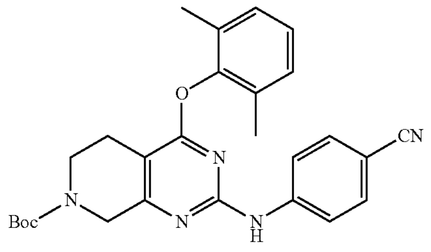 [SMILES: Cc1cccc(C)c1Oc1nc(Nc2ccc(C#N)cc2)nc2c1CCN(C(=O)OC(C)(C)C)C2]

To formamide 32 (0.51 g, 3.9 mmol, 1 eq.) solution in dimethylformamide (15 ml), add NaH (0.28 g, 7 mmol, 1.8 eq.) at the temperature of 0° C. Stir the reaction mixture at the room temperature for 20 minutes. Then cool down the mixture to 0° C. again and add sulfone 31 (1.8 g, 3.9 mmol, 1.0 eq.) to it. Stir the reaction mixture for 8 hours, then boil out the organic solvent, add water to the residue (pH=9). Filter the obtained residue and wash with water. Dissolve the residue in dichloromethane and purify by chromatography using Hex:EA (1:1) as eluent.

Weight=520 mg

Yield=42%

4-(((4-(2,6-Dimethylphenoxy)-5,6,7,8-tetrahydro-pyrido[3,4-d]pyrimidine-2-yl)amino)-benzonitrile hydrochloride (33)

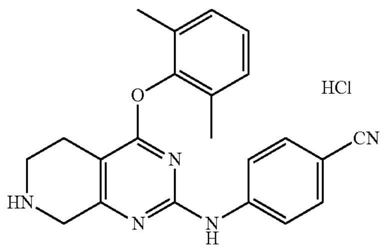 [SMILES: Cc1cccc(C)c1Oc1nc(Nc2ccc(C#N)cc2)nc2c1CCNC2 ; Cl]

Dissolve pyrimidine 32 (500 Mr) in methanole saturated with hydrogen chloride, mix for an hour, boil out the organic solvent, recrystallize the precipitate formed from ethanol.

Weight=500 mg

Yield=96%

4-(((7-Benzyl-4-(2,6-dimethylphenoxy)-5,6,7,8-tetrahydropyrido[3,4-d]pyrimidine-2-yl)amino)methyl) benzonitrile (BB 0273459)

Transfer pyrimidine 20 in the form of a free base (500 mg, 1 mmol, 1 eq.) and

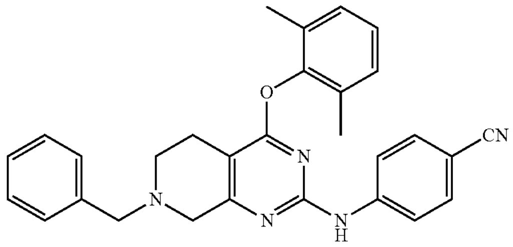 [SMILES: Cc1cccc(C)c1Oc1nc(Nc2ccc(C#N)cc2)nc2c1CCN(Cc1ccccc1)C2]

benzylbromide (205.5 mg, 1.1 mmol) into a 100 ml round-bottomed flask equipped with an effective reflux condenser with a calcium chloride tube. Boil the mixture, until all the mass is solidified. Hydrobromide of target N-benzyl pyrimidine is formed. At the end of reaction, cool the flask and pour in portions (while cooling to avoid significant heating) 1 g caustic soda in 20 ml of water solution. Separate the product extracted in a separation funnel, add chlorous, wash the organic phase with water, dry over anhydrous sodium sulfate. Remove the organic solvent at under pressure, purify the residue by chromatography, using Hex:EA (1:3) as eluent.

Weight=300 mg

Yield=58%

BB 0273459

1H NMR (400 MHz, DMSO-d6, δ, ppm): 1.95-2.13 (m, 6H), 2.78 (broadened singlet, 2H), 3.43 (broadened singlet, 2H), 3.47-3.57 (m, 2H), 3.64-3.79 (m, 2H), 7.19-7.46 (m, 12H)

LCMS m/z (M+H): 462.

Example 2
Synthesis of 4-((2-((4-cyanophenyl)amino)-7-methyl-5,6,7,8-tetrahydropyrido[3,4-d]pyrimidine-4-yl)oxy)-3,5-dimethylbenzonitrile
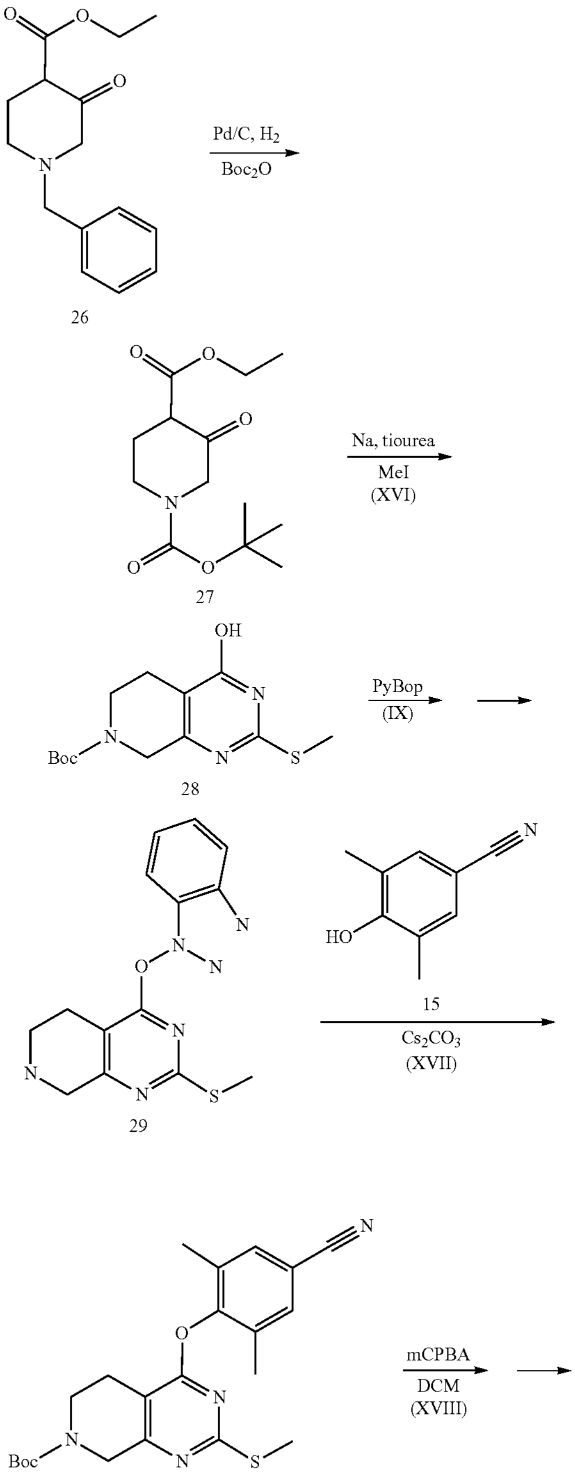
26, 27, 28, 29, 56
-continued
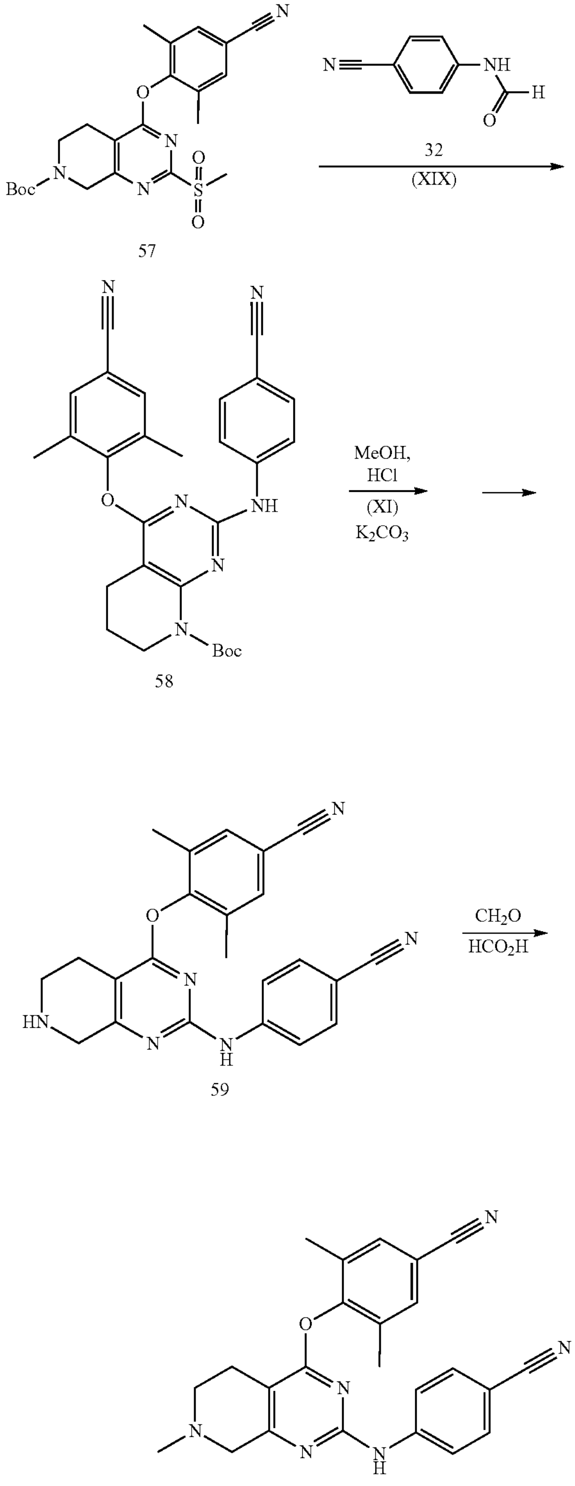
57, 58, 59
BB 0273774
BB 0273774
$^1H$ NMR (400 MHz, $CDCl_3$, δ, ppm): 1.26 (s, 3H), 2.18 (s, 6H), 2.20-2.22 (m, 2H), 3.12-3.15 (m, 2H), 7.22 (d, J=8.2 Hz, 2H), 7.35 (d, J=8.4 Hz, 2H), 7.55 (s, 2H).
Weight Yield—4.5 mg (8%)
LCMS m/z (M+H): 411.

Example 3
Synthesis of 4-((4-(4-Formyl-2,6-dimethylphenoxy)-7-methyl-5,6,7,8-tetrahydro[3,4-d]pyrimidine-2-yl)amino)benzonitrile
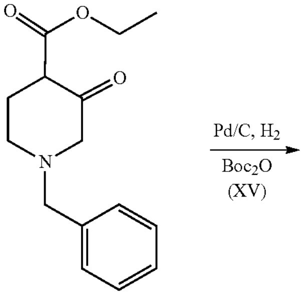
26
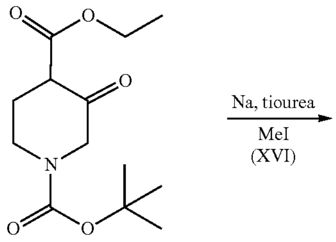
27
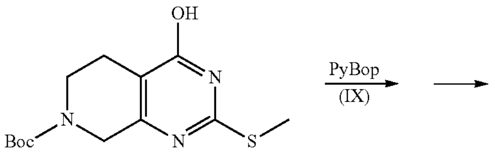
28
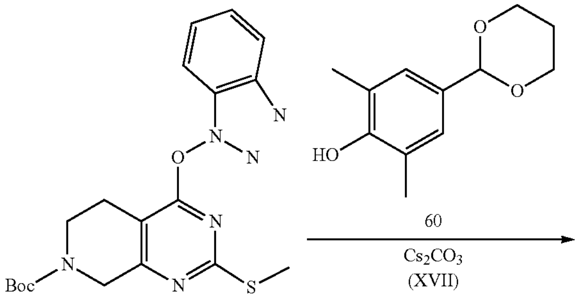
29
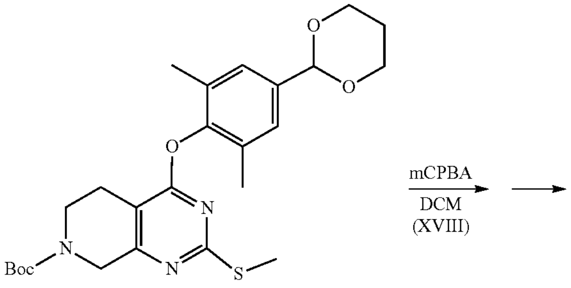
61
-continued
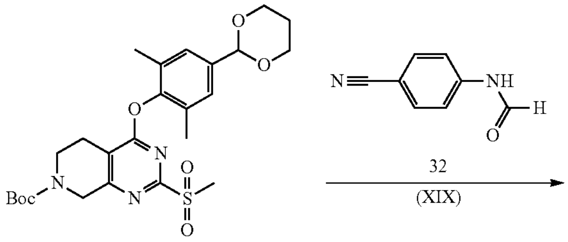
62
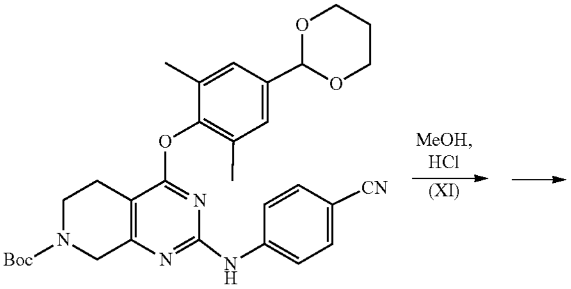
63
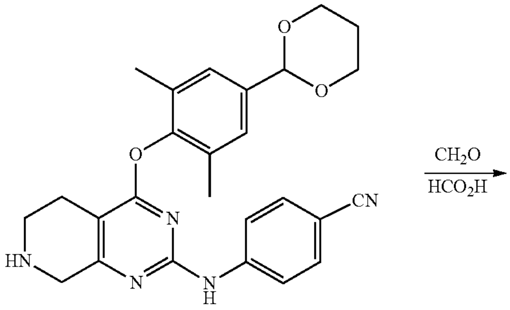
64
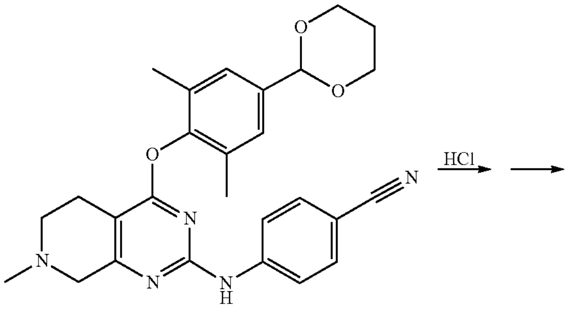
65
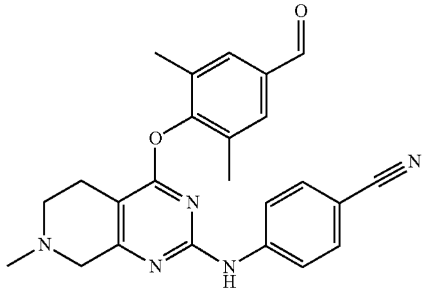
BB 0273775

BB 0273775
$^1$H NMR (400 MHz, $CDCl_3$, δ, ppm): 1.26 (s, 3H), 2.18-2.20 (m, 2H), 2.23 (s, 6H), 3.14-3.18 (m, 2H), 3.74-3.78 (m, 2H), 7.20 (d, J=8.4 Hz, 2H), 7.28 (d, J=8.4 Hz, 2H), 7.76 (s, 2H), 10.07 (s, 1H).
Weight Yield—8.2 mg (12%)
LCMS m/z (M+H): 413
Example 4
Synthesis of tert-butyl 4-(4-(1,3-dioxolane-2-yl)-2,6-dimethylphenoxy)-2-((4-cyanophenyl)amino)-8,9-dihydro-5H-pyrimido[4,5-d]azepine-7(6H)-carboxylate
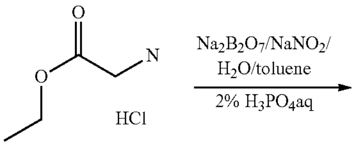
49
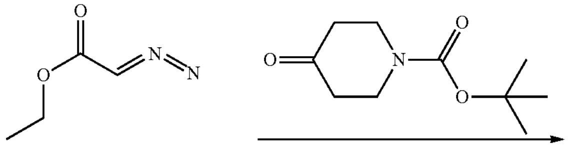
50
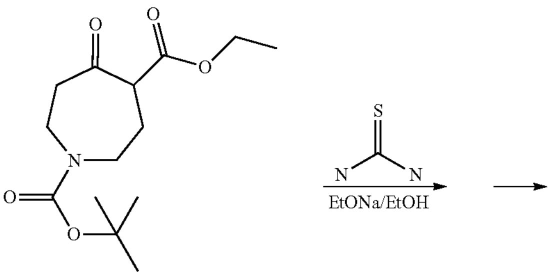
51
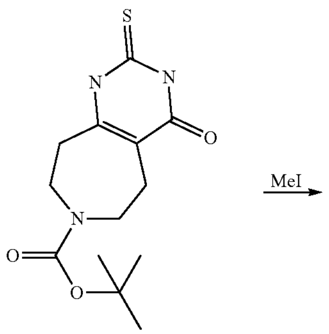
52
-continued
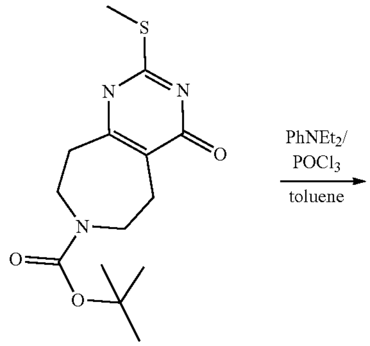
53
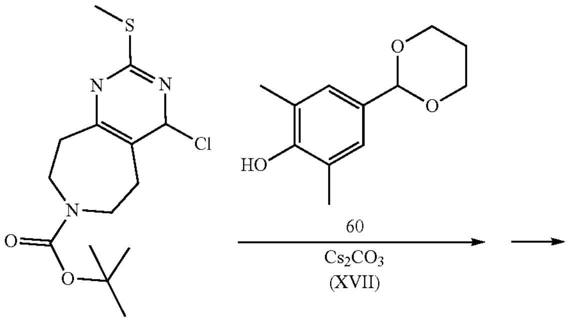
54
60
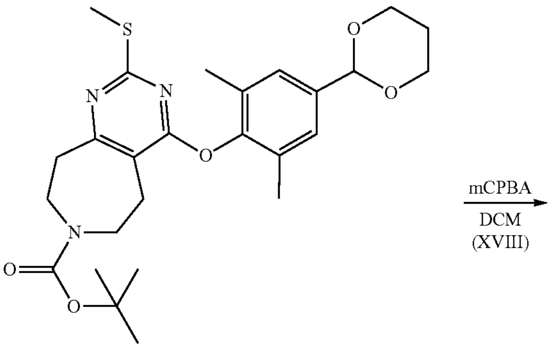
BB 0273228
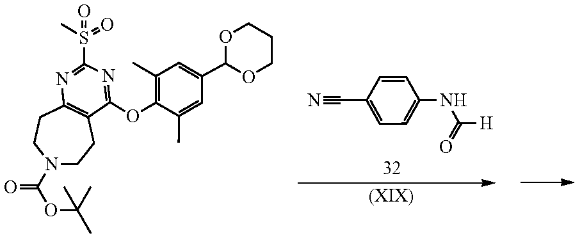
66
32

-continued
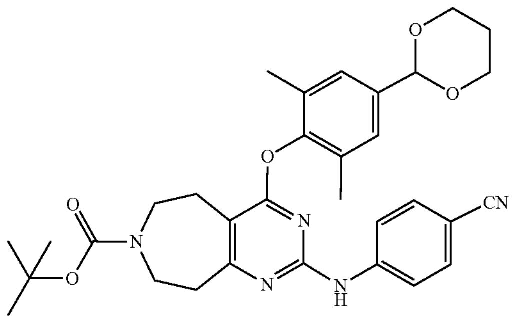
BB 0273892
BB 0273892
$^1$H NMR (400 MHz, $CDCl_3$, δ, ppm): 1.51 (s, 10H), 2.09 (s, 6H), 2.20-2.42 (m, 1H), 2.94-3.18 (m, 4H), 3.66 (broadened singlet, 4H), 4.06 (t, J=12.3 Hz, 2H), 4.36 (dd., J=10.97 Hz, 4.86 Hz, 2H), 5.55 (s, 1H), 7.08 (s, 1H), 7.16 (d, J=8.56 Hz, 2H), 7.30 (s, 2H), 7.41 (d, J=8.74 Hz, 2H),
Weight Yield—0.0043 g (12%)
LCMS m/z (M+H): 572.
Example 5
Synthesis of tert-butyl 2-((4-cyanophenyl)amino)-4-(4-formyl-2,6-dimethylphenyoxy)-8,9-dihydro-5H-pyrimido[4,5-d]azepine-7(6H)-carboxylate
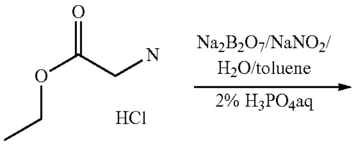
49
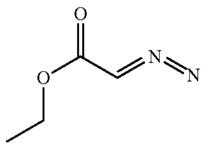
50
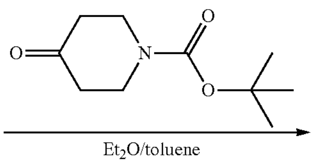
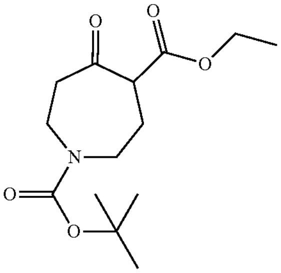
51
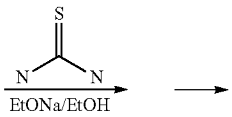
-continued
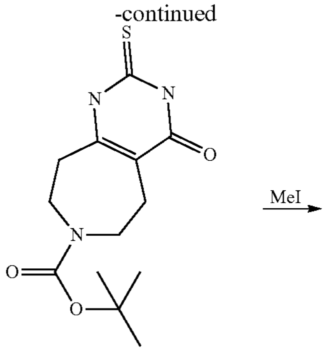
52
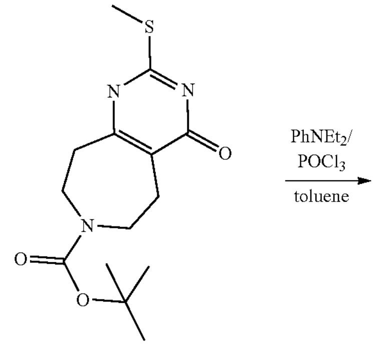
53
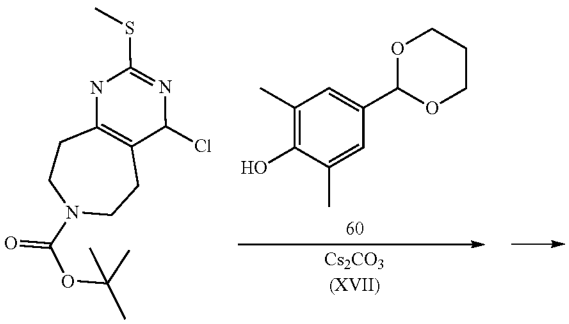
60
54
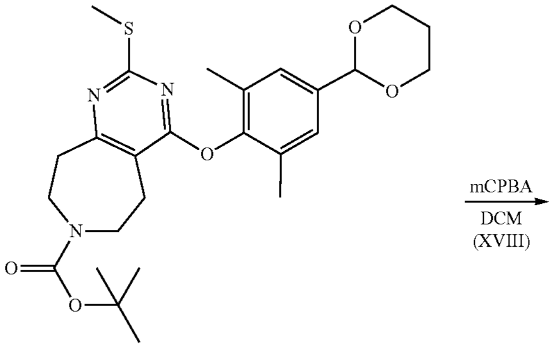
BB 0273228

-continued
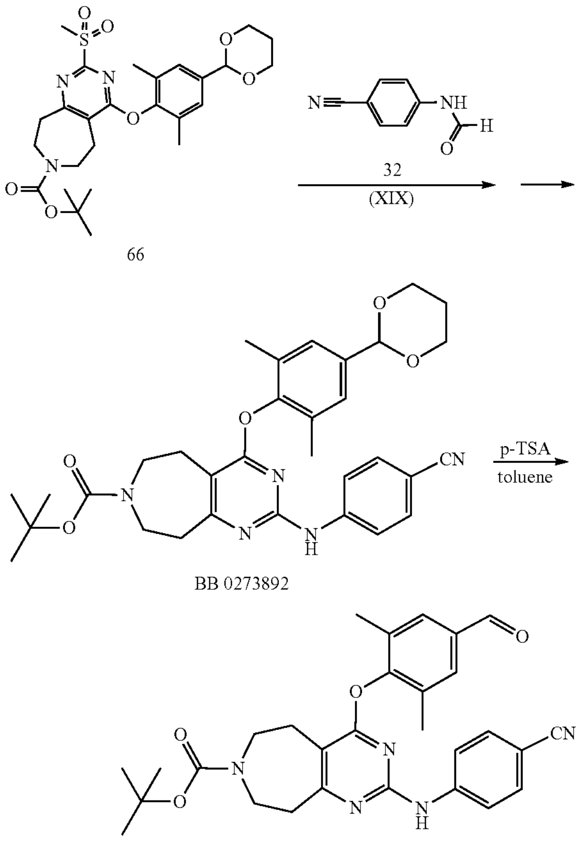
66
BB 0273892
BB 0273943
BB 0273943
$^1$H NMR (400 MHz, $CDCl_3$, δ, ppm): 1.51 (s, 9H), 2.19 (s, 6H), 3.09 (broadened singlet, 4H), 3.68 (broadened singlet, 4H), 7.12 (broadened singlet, 1H), 7.30 (s, 4H), 7.70 (s, 2H), 10.02 (s, 1H).
Weight Yield—0.056 g (12%)
LCMS m/z (M+H): 514.
Example 6
Synthesis of tert-butyl 4-(4-cyano-2,6-dimethylphenoxy)-2-((4-cyanophenyl)amino)-7,8-dihydropyrido[4,3-d]pyrimidine-6(5H)-carboxylate
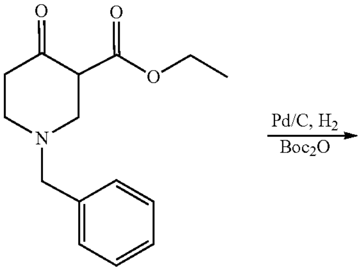
11
-continued
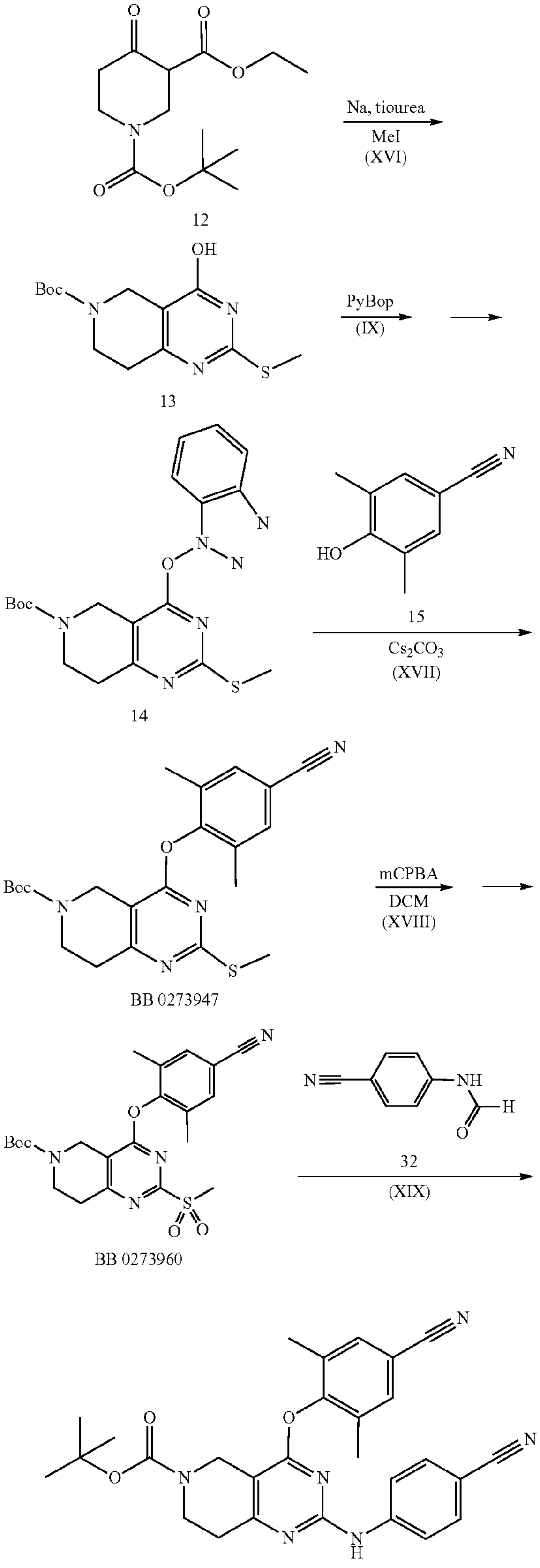
12
13
14
BB 0273947
BB 0273960
BB 0273961

BB 0273961
$^1$H NMR (400 MHz, $CDCl_3$, δ, ppm): 1.53 (s, 9H), 2.16 (s, 6H), 2.82-2.89 (m, 2H), 3.81 (t, J=5.6 Hz, 2H), 4.62 (broadened singlet, 2H), 7.39 (d, J=8.8 Hz, 4H), 7.48 (s, 2H).
Weight Yield—2.87 g (46%)
LCMS m/z (M+H): 497.
Example 7
Synthesis of 4-((2-((4-cyanophenyl)amino)-5,6,7,8-tetrahydropyrido[4,3-d]pyrimidine-4-yl)oxy)-3,5-dimethylbenzonitrile
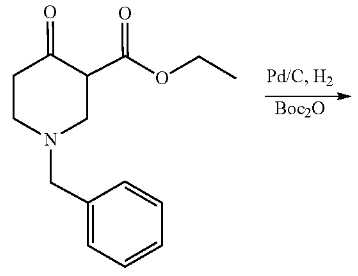
11
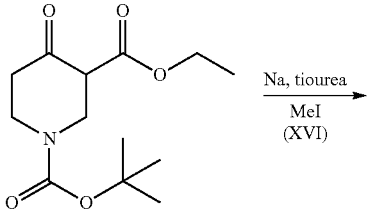
12
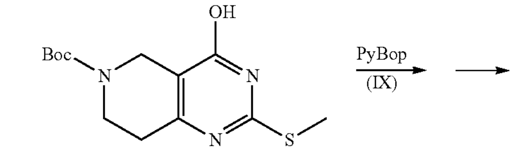
13
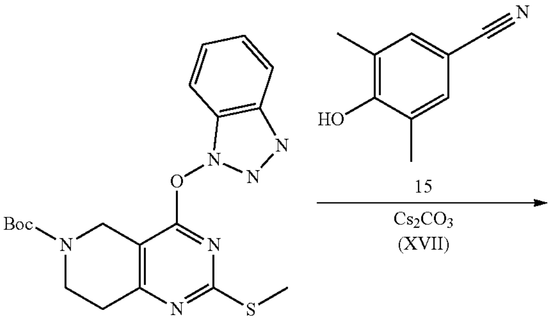
14
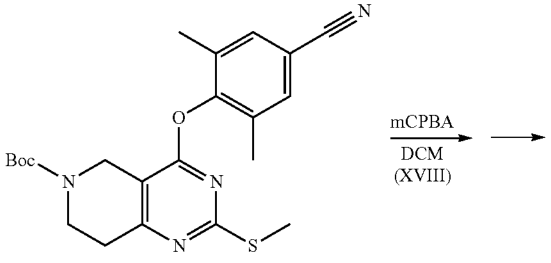
BB 0273947
-continued
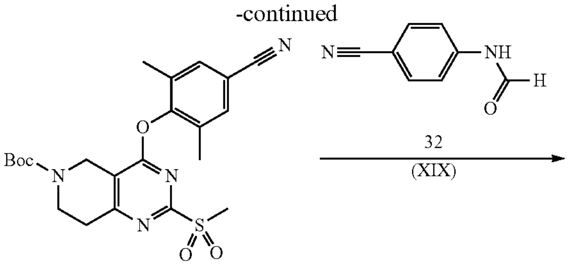
BB 0273960
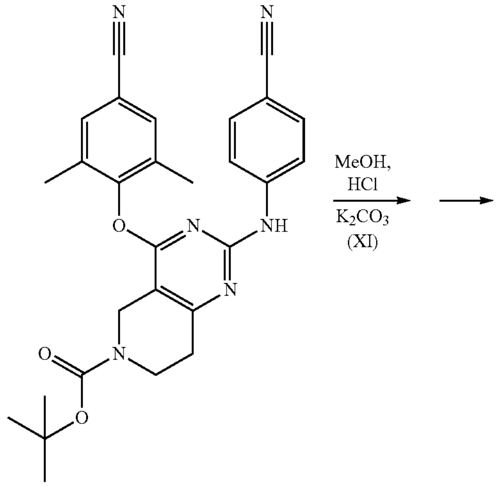
BB 0273961
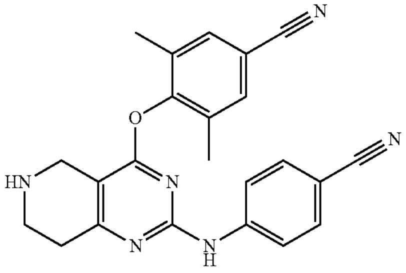
BB 0273963
BB 0273963
$^1$H NMR (400 MHz, DMSO-$d_6$, δ, ppm): 2.11 (s, 6H), 3.02 (t, J=5.8 Hz, 2H), 3.50 (d, J=5.2 Hz, 2H), 4.31 (broadened singlet, 2H), 7.47 (broadened singlet, 4H), 7.79 (s, 2H).
Weight Yield—2.08 g (96%)
LCMS m/z (M+H): 397.

Example 8
Synthesis of 4-((2-((4-cyanophenyl)amino)-6-(methylsulfonyl)-5,6,7,8-tetrahydropyrido[4,3-d]pyrimidine-4-yl)oxy)-3,5-dimethylbenzonitrile
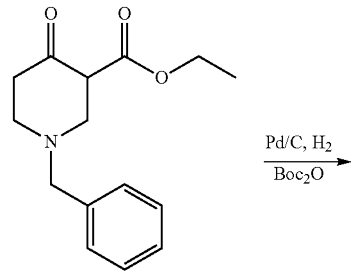
11
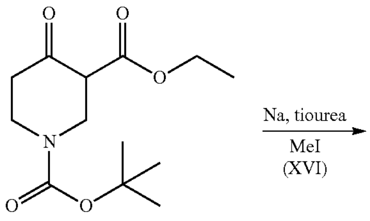
12
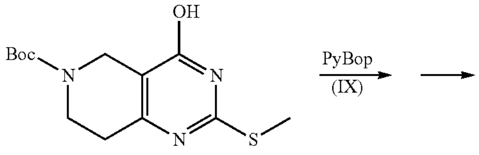
13
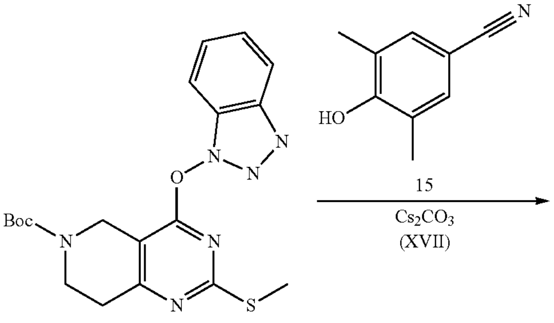
14
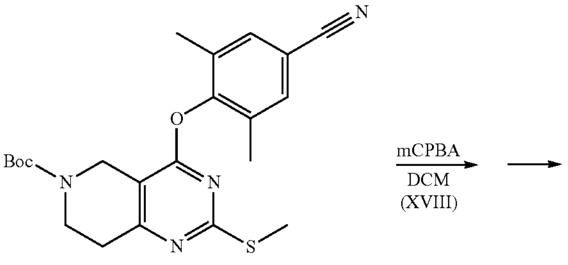
BB 0273947
-continued
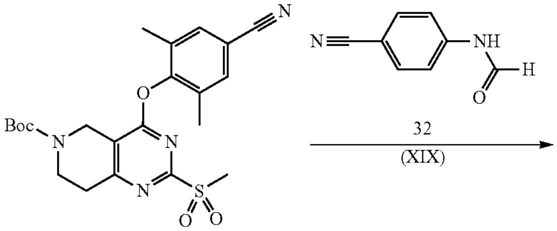
BB 0273960
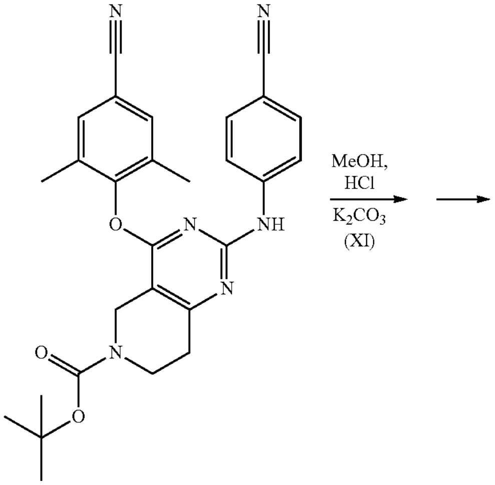
BB 0273961
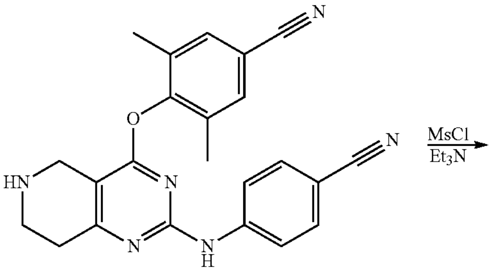
BB 0273963
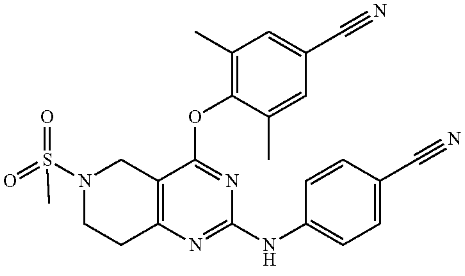
BB 0273964
BB 0273964
$^1H$ NMR (400 MHz, $CDCl_3$, δ, ppm): 2.16 (s, 6H), 2.98 (s, 3H), 3.04 (t, J=5.8 Hz, 2H), 3.67-3.72 (m, 2H), 4.50 (s, 2H), 7.34-7.40 (m, 2H), 7.41-7.45 (m, 2H), 7.49 (s, 2H)
Weight Yield—0.072 g (84%)
LCMS m/z (M+H): 475.

Example 9
Synthesis of ethyl 4-(4-cyano-2,6-dimethylphenoxy)-2-((4-cyanophenyl)amino)-7,8-dihydropyrido[4,3-d]pyrimidine-6(5H)-carboxylate
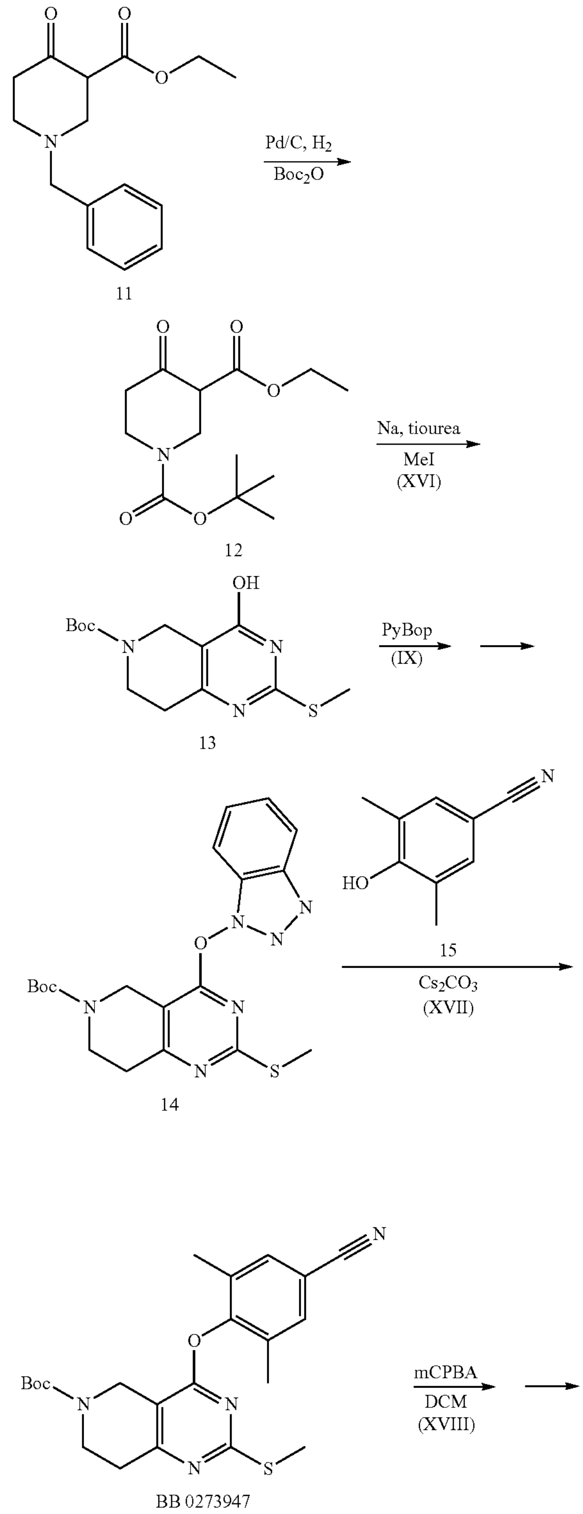
-continued
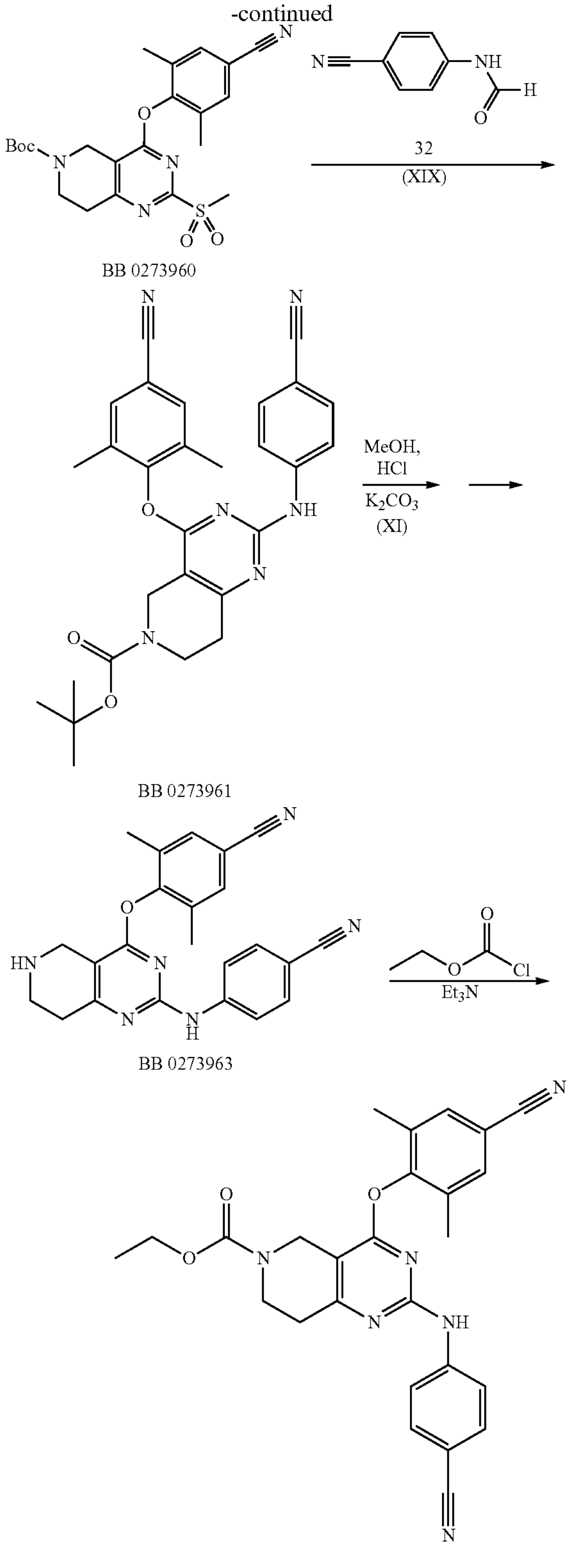
BB 0273965
$^1$H NMR (400 MHz, $CDCl_3$, δ, ppm): 1.33 (t, J=7.1 Hz, 3H), 2.17 (s, 6H), 2.89 (t, J=5.5 Hz, 2H), 3.86 (t, J=5.7 Hz, 2H), 4.24 (kv., J=7.1 Hz, 2H), 4.67 (s, 2H), 7.39 (d, J=8.9 Hz, 4H), 7.49 (s, 2H)
Weight Yield—0.056 g (56%)
LCMS m/z (M+H): 468.

Example 10
Synthesis of (E)-3-(4-((7-(tert-butoxycarbonyl)-2-((4-cyanophenyl)amino)-6,7,8,9-tetrahydro-5H-pyrimido[4,5-d]azepine-4-yl)oxy)-3,5-dimethylphenyl) acrylic acid
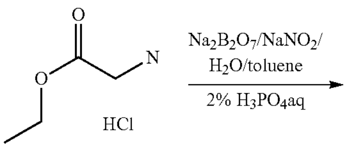
49
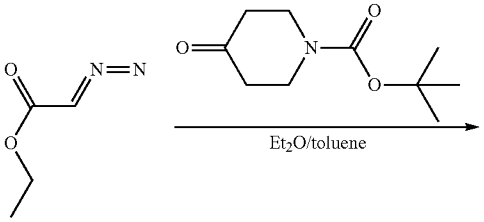
50
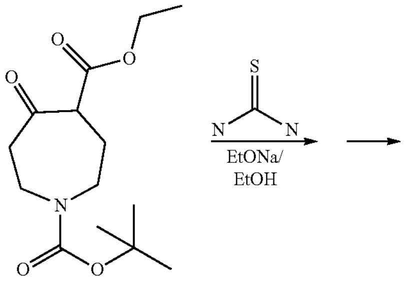
51
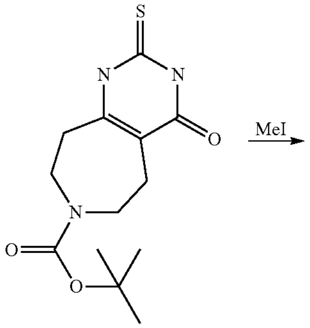
52
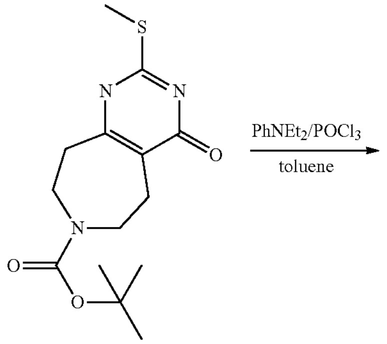
53
-continued
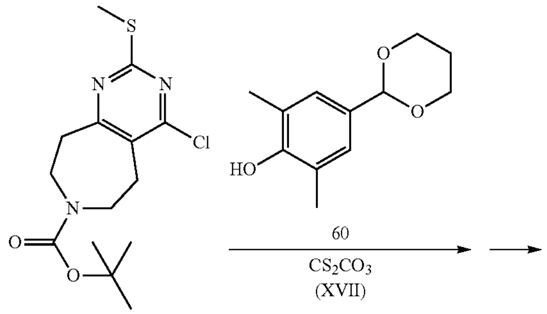
54
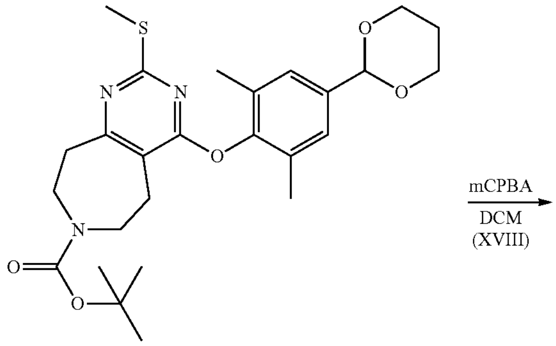
BB 0273228
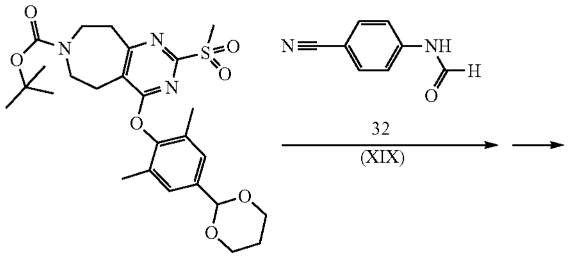
66
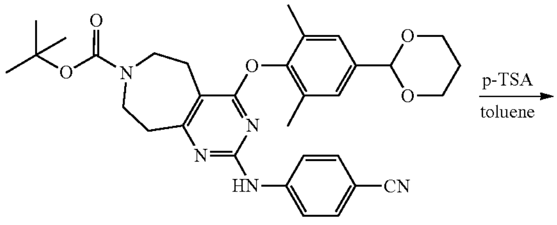
BB 0273892
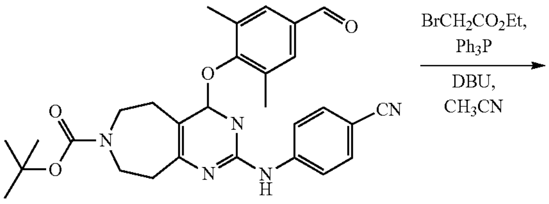
BB 0273943

-continued
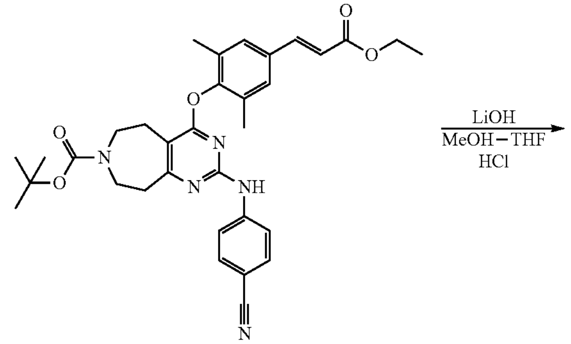
67
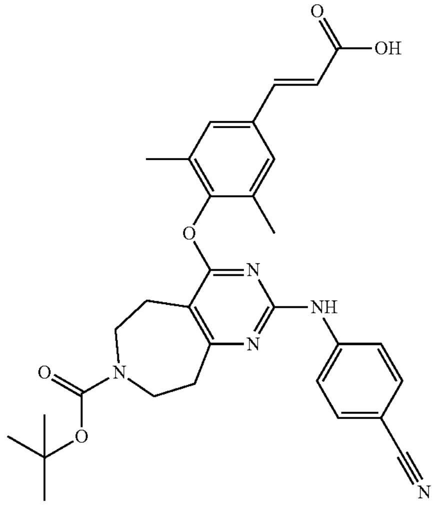
BB 0273969
BB 0273969
$^1$H NMR (400 MHz, DMSO-$d_6$, δ, ppm): 1.40 (broadened singlet, 9H), 2.07 (s, 6H), 3.02 (broadened singlet, 4H), 3.59 (broadened singlet, 4H), 6.56 (d, J=16.0 Hz, 1H), 7.27-7.39 (m, 2H), 7.40-7.52 (m, 2H), 7.53-7.67 (m, 2H), 9.95-10.09 (m, 1H).
Example 11
Synthesis of tert-butyl 4-(4-cyano-2,6-dimethylphenoxy)-2-((4-cyanophenyl)amino)-8,9-dihydro-5H-pyrimido[4,5-d]azepine-7(6H)-carboxylate
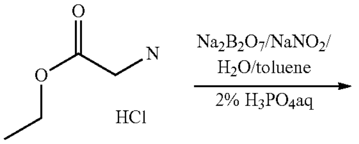
49
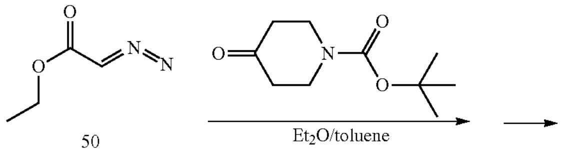
50
-continued
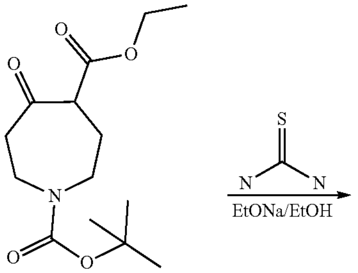
51
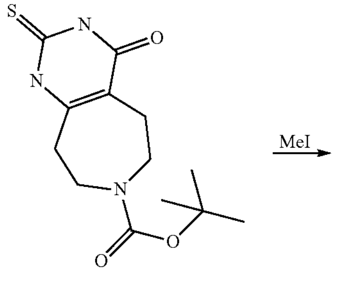
52
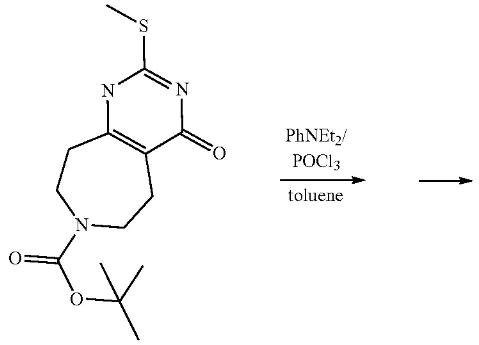
53
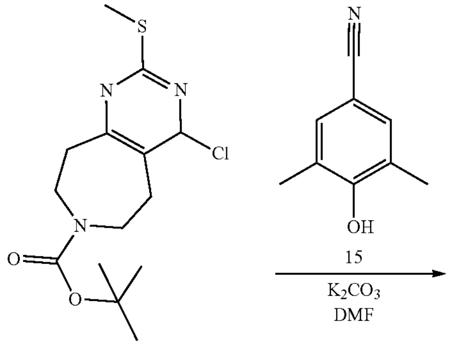
54

-continued
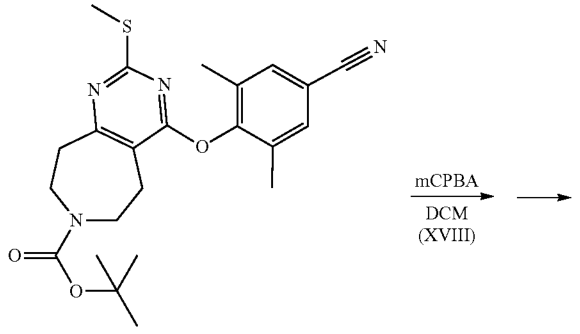
BB 0273957
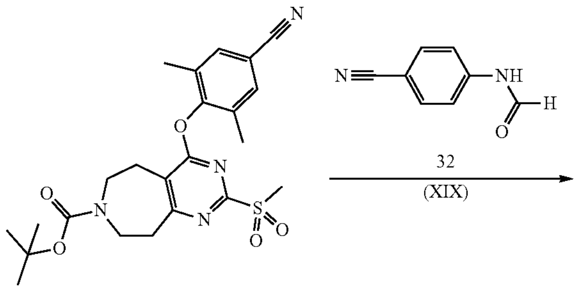
BB 0273968
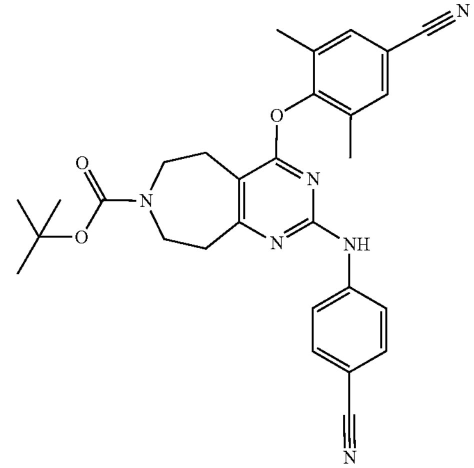
BB 0273972
BB 0273972
$^1$H NMR (400 MHz, $CDCl_3$, δ, ppm): 1.51 (s, 9H), 2.14 (s, 6H), 3.06-3.10 (m, 4H), 3.65-3.68 (m, 4H), 7.07 (broadened singlet, 1H), 7.29-7.35 (m, 2H), 7.36-7.42 (m, 2H), 7.48 (s, 2H),
Weight Yield—0.462 g (24%)
LCMS m/z (M+H): 511.
Example 12
Synthesis of 4-((2-((4-cyanophenyl)amino)-6,7,8,9-tetrahydro-5H-pyrimido[4,5-d]azepine-4-yl)oxy)-3,5-dimethylbenzonitrile dihydrochloride
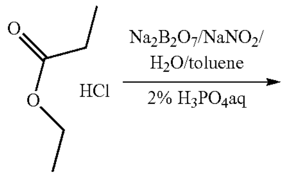
49
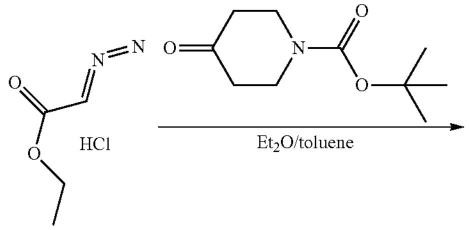
50
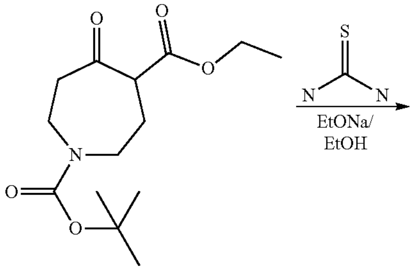
51
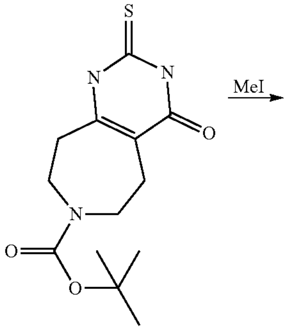
52
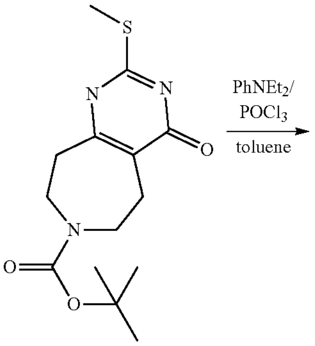
53

-continued
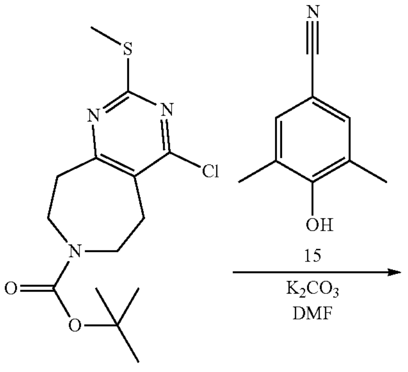
54
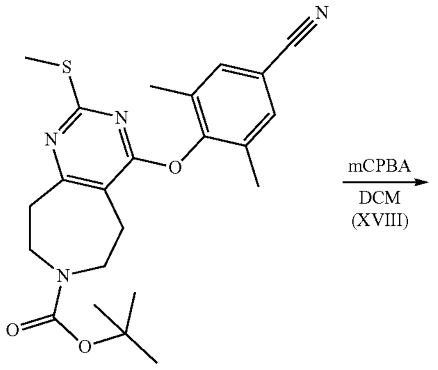
BB 0273957
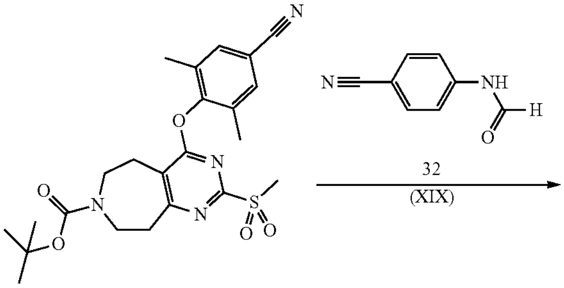
BB 0273968
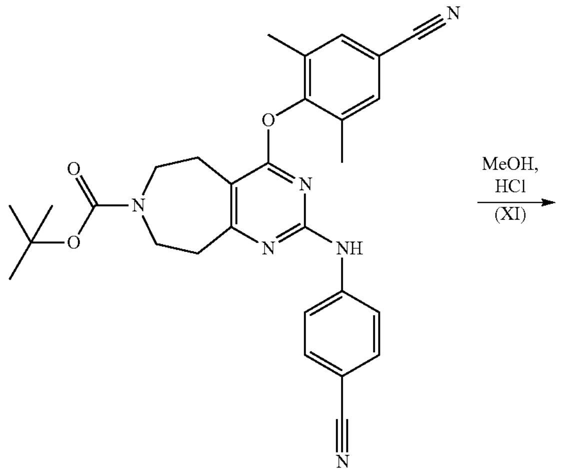
BB 0273972
-continued
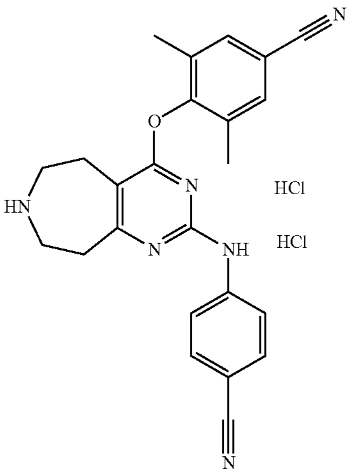
BB 0273976
BB 0273976
$^1H$ NMR (400 MHz, DMSO-$d_6$, δ, ppm): 2.11 (s, 6H), 3.14-3.45 (m, 8H), 7.43 (s, 4H), 7.78 (s, 2H), 9.79 (broadened singlet, 2H), 10.12 (broadened singlet, 1H),
Weight Yield—0.237 g (92%)
LCMS m/z (M+H): 411.
Synthesis of tert-butyl 2-((4-cyanophenyl)amino)-4-(4-(2-cyanovinyl)-2,6-dimethylphenoxy)-8,9-dihydro-5H-pyrimido[4,5-d]azepine-7(6H)-carboxylate
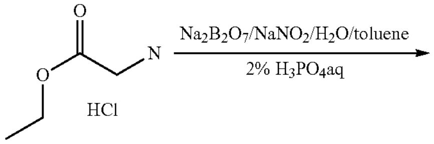
49
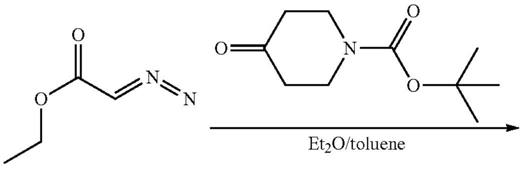
50
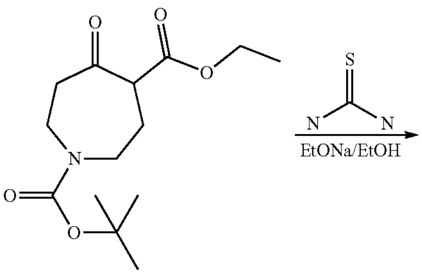
51

-continued
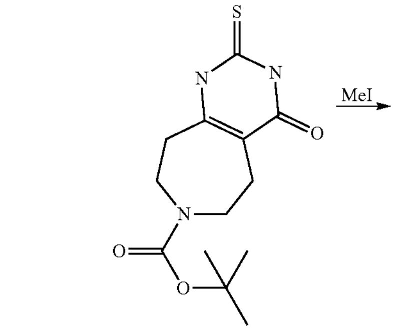
52
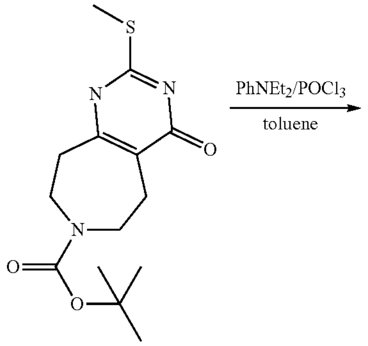
53
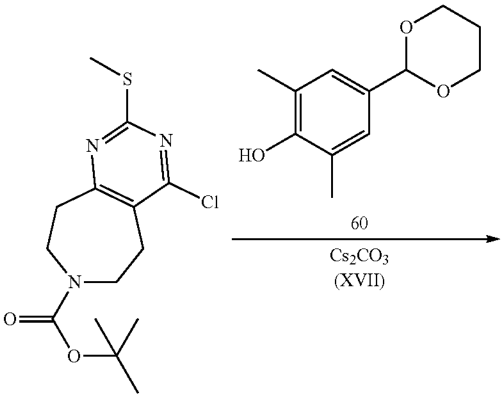
54
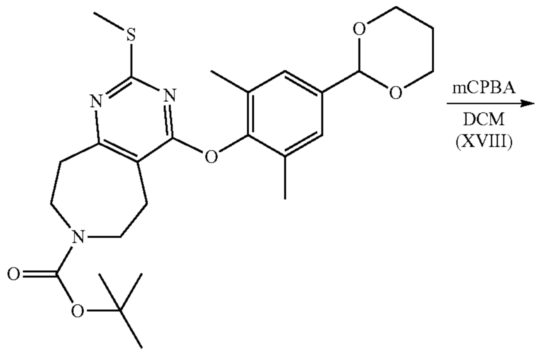
BB 0273228
-continued
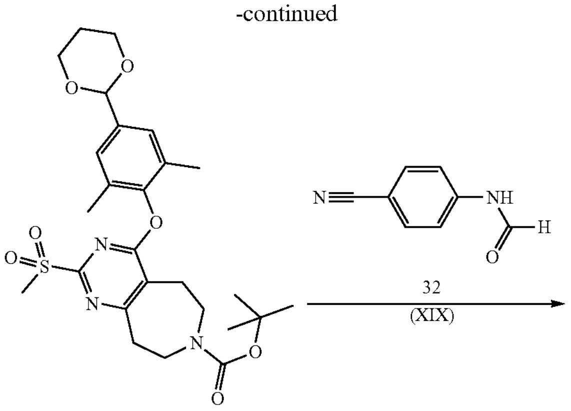
66
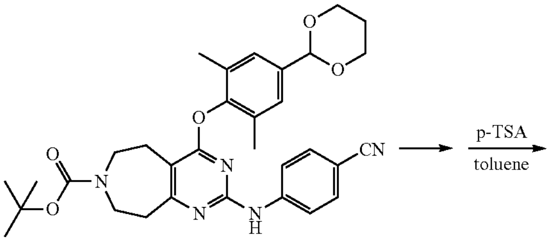
BB 0273892
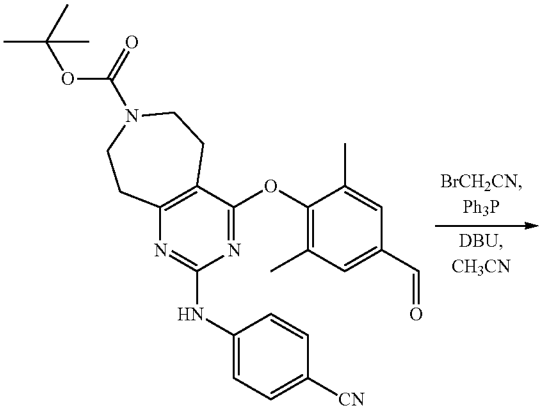
BB 0273943
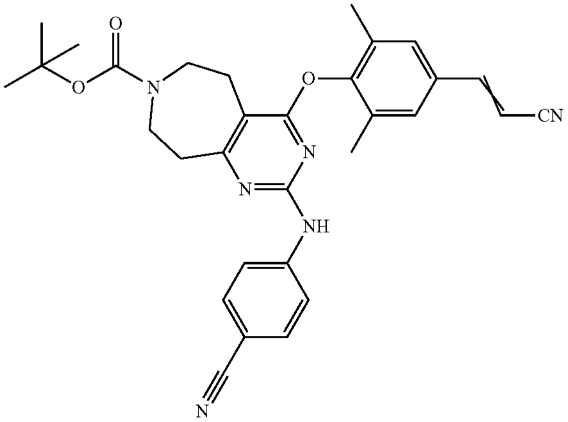
BB 0274009

BB 0274009
$^1$H NMR (400 MHz, $CDCl_3$, δ, ppm): 1.51 (s, 9H), 2.10-2.17 (m, 6H), 3.08 (broadened singlet, 4H), 3.67 (broadened singlet, 4H), 5.90-5.46 (m, 1H), 7.63-7.04 (m, 8H),
Weight Yield—0.06 g (8%)
LCMS m/z (M+H): 537.
Example 13
Synthesis of 4-((2-((4-cyanophenyl)amino)-7-picolynoyl-6,7,8,9-tetrahydro-5H-pyrimido[4,5-d]azepine-4-yl)oxy)-3,5-dimethylbenzonitrile
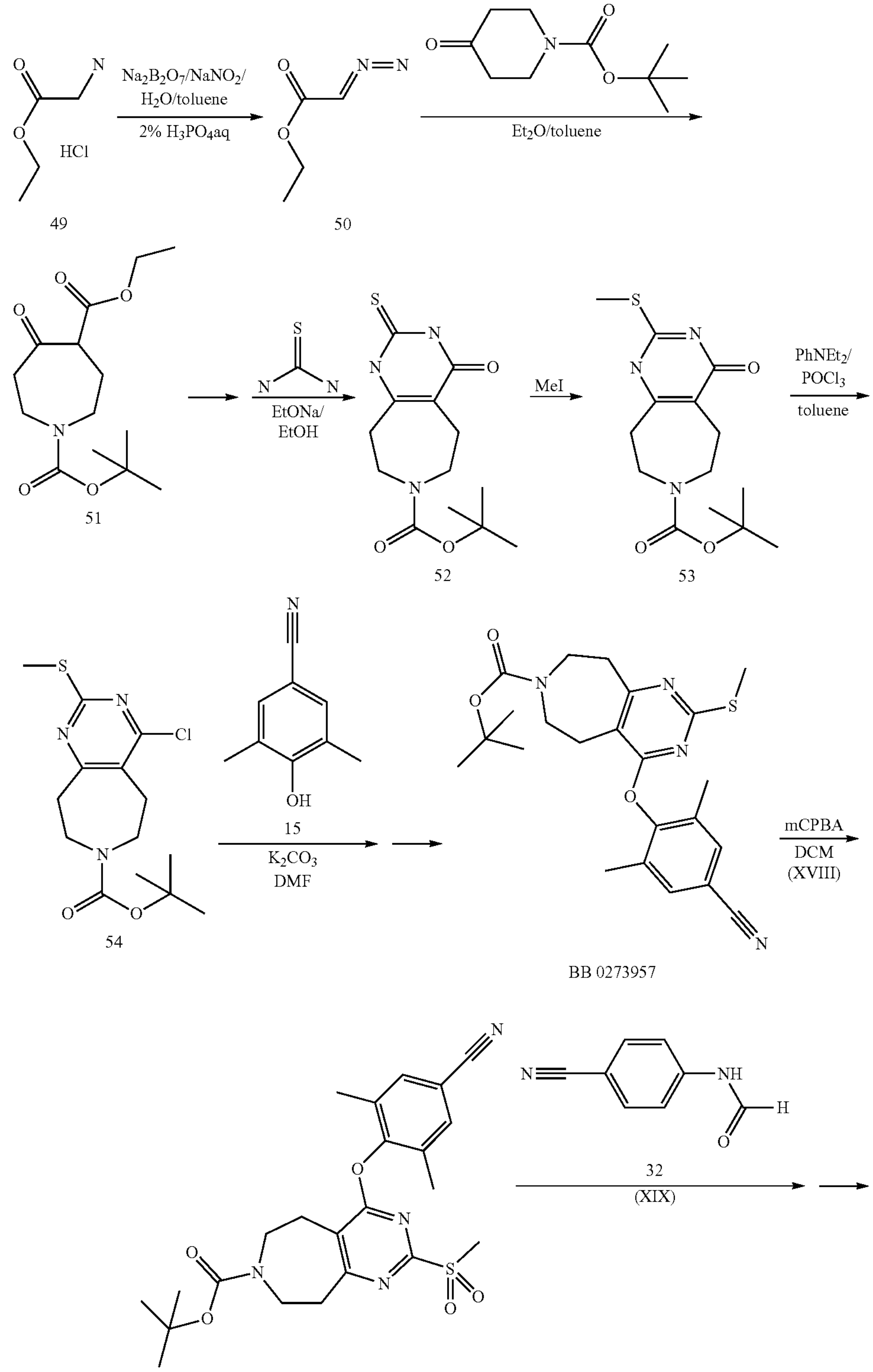
49, 50, 51, 52, 53, 54, 15, BB 0273957, 32, BB 0273968

-continued
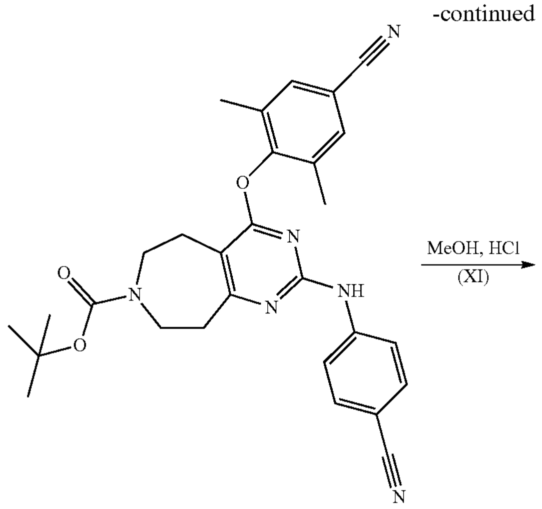
BB 0273972
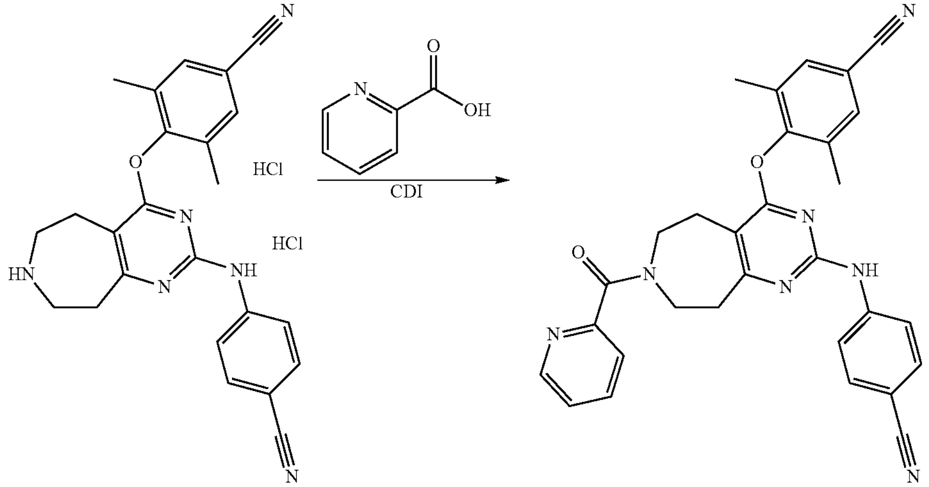
BB 0273976 BB 0274010
BB 0274010
$^1$H NMR (400 MHz, DMSO-$d_6$, δ, ppm): 2.01-2.08 (m, 3H), 2.12 (s, 3H), 3.08 (d, J=2.4 Hz, 2H), 3.17 (d, J=3.7 Hz, 2H), 3.63 (broadened singlet, 2H), 3.83-3.97 (m, 2H), 7.42 (d, J=7.8 Hz, 4H), 7.50 (t, J=5.8 Hz, 1H), 7.59 (d, J=7.7 Hz, 1H), 7.78 (d, J=13.8 Hz, 2H), 7.90-8.00 (m, 1H), 8.62 (d, J=4.3 Hz, 1H), 10.09 (broadened singlet, 1H),
Weight Yield—0.072 g (29%)
LCMS m/z (M+H): 516.
Example 14
Synthesis of 4-((2-((4-cyanophenyl)amino)-7-isonicotinoyl-6,7,8,9-tetrahydro-5H-pyrimido[4,5-d]azepine-4-yl)oxy)-3,5-dimethylbenzonitrile
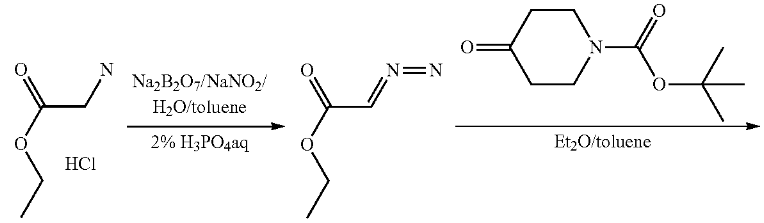
49 50

-continued
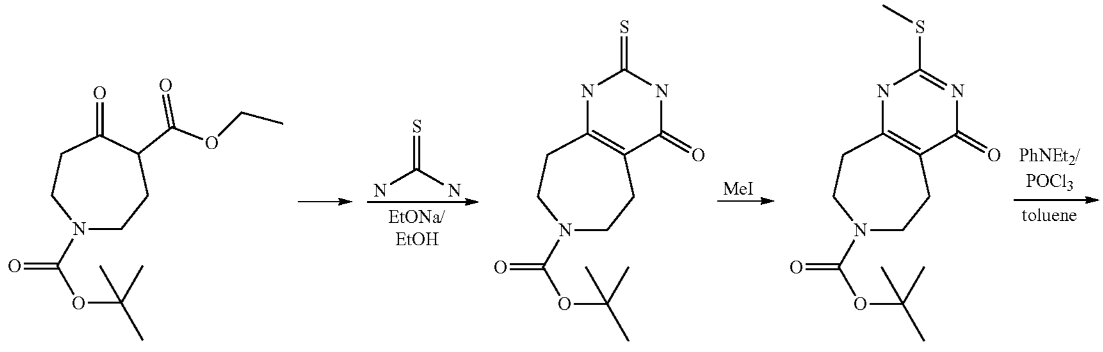
51 52 53
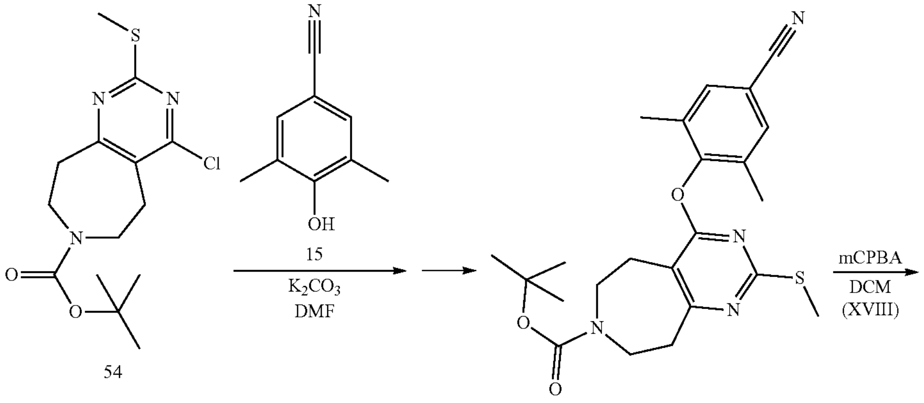
54
BB 0273957
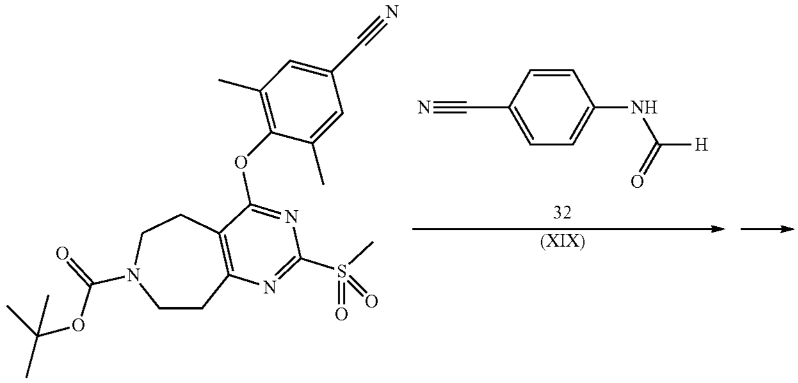
BB 0273968

-continued
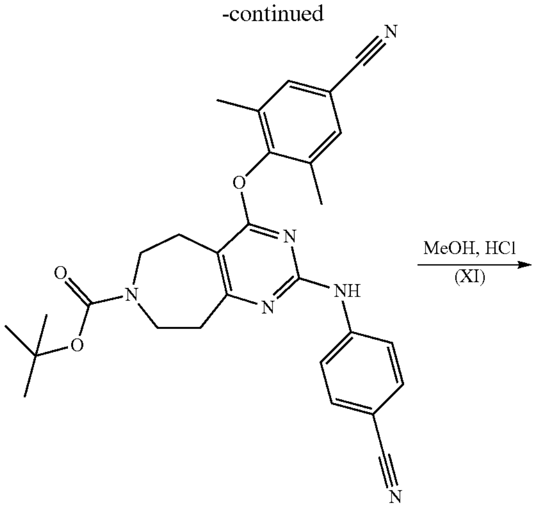
BB 0273972
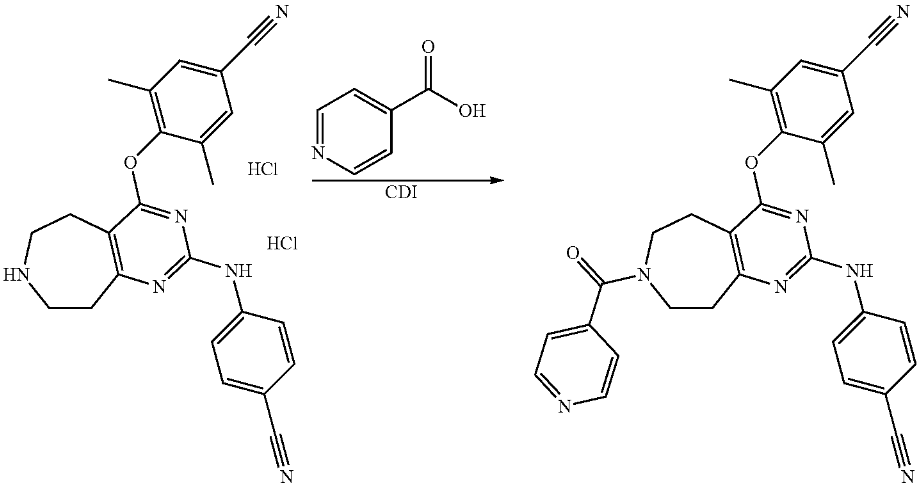
BB 0273976 BB 0274011
BB 0274011
$^1H$ NMR (400 MHz, DMSO-$d_6$, δ, ppm): 2.05 (s, 3H), 2.12 (s, 3H), 3.05 (broadened singlet, 2H), 3.12-3.24 (m, 2H), 3.51 (broadened singlet, 2H), 3.82-3.96 (m, 2H), 7.32-7.51 (m, 6H), 7.78 (d, J=14.6 Hz, 2H), 8.69 (d, J=4.8 Hz, 2H), 10.10 (d, J=4.0 Hz, 1H).
Weight Yield—0.067 g (32%)
LCMS m/z (M+H): 516.
Example 15
Synthesis of 4-((2-((4-cyanophenyl)amino)-7-nicotinoyl-6,7,8,9-tetrahydro-5H-pyrimido[4,5-d]azepine-4-yl)oxy)-3,5-dimethylbenzonitrile
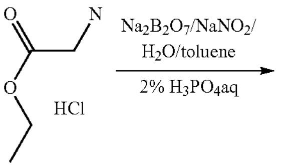
49
-continued
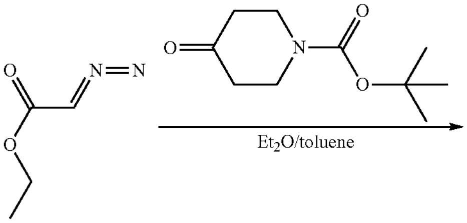
50
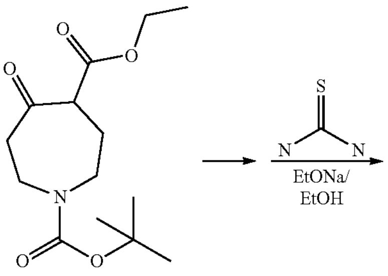
51

-continued
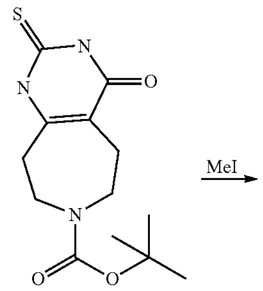
52
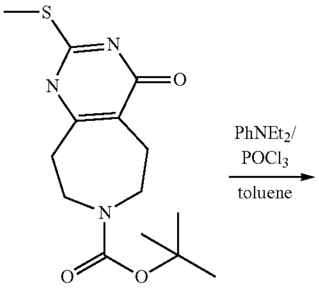
53
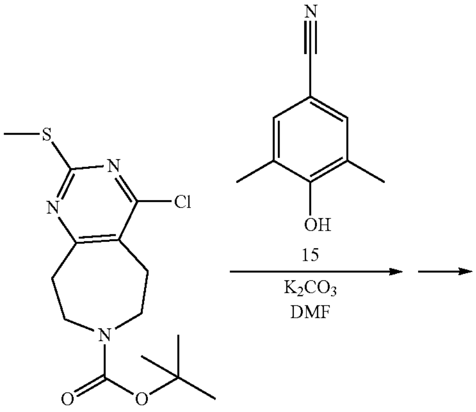
54
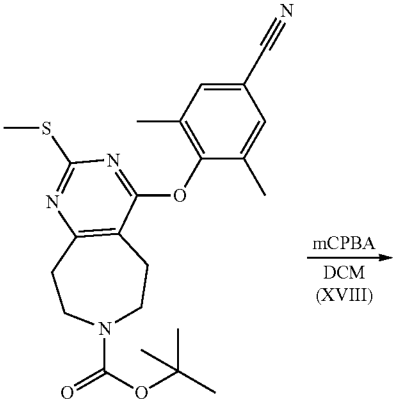
BB 0273957
-continued
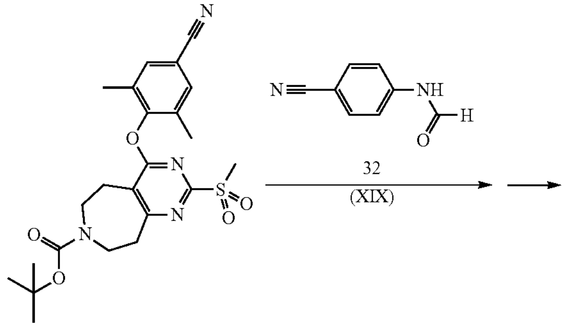
BB 0273968
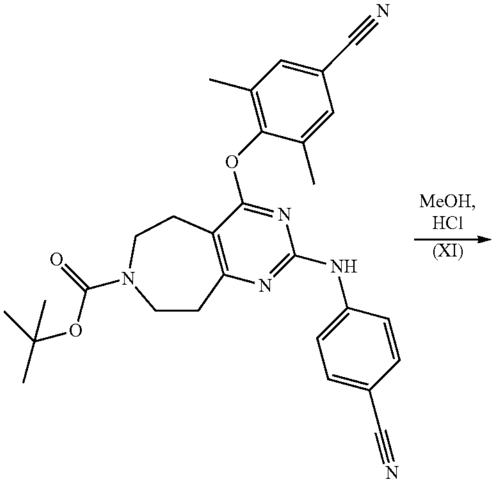
BB 0273972
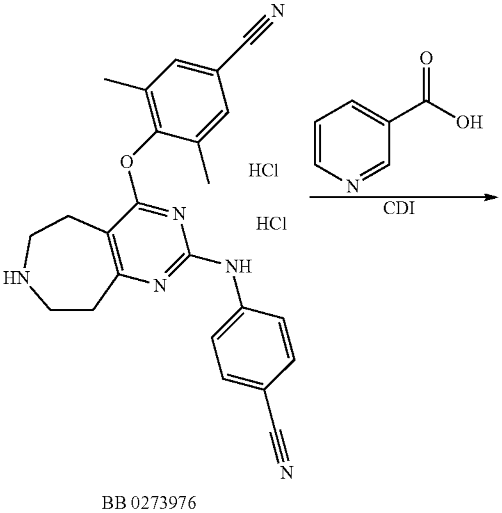
BB 0273976

-continued
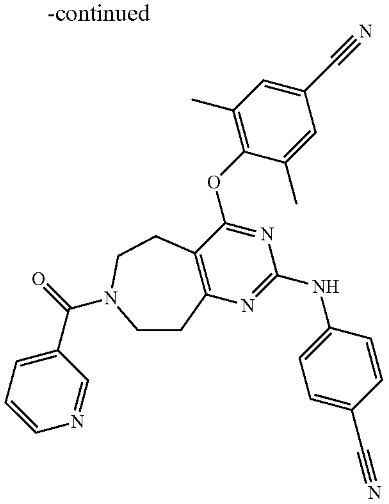
BB 0274012
BB 0274012
$^1$H NMR (400 MHz, DMSO-$d_6$ δ, ppm): 2.04 (s, 3H), 2.12 (broadened singlet, 3H), 3.06 (broadened singlet, 2H), 3.19 (broadened singlet, 2H), 3.58 (broadened singlet, 2H), 3.90 (broadened singlet, 2H), 7.41 (d, J=11.6 Hz, 4H), 7.50 (dd, J=7.5, 5.0 Hz, 1H), 7.77 (d, J=14.4 Hz, 2H), 7.87 (d, J=6.7 Hz, 1H), 8.60-8.71 (m, 2H), 10.10 (broadened singlet, 1H).
Weight Yield—0.055 g (30%)
LCMS m/z (M+H): 516.
Example 16
Synthesis of 4-((2-((4-cyanophenyl)amino)-7-(pyridine-2-ylmethyl)-6,7,8,9-tetrahydro-5H-pyrimido[4,5-d]azepine-4-yl)oxy)-3,5-dimethylbenzonitrile
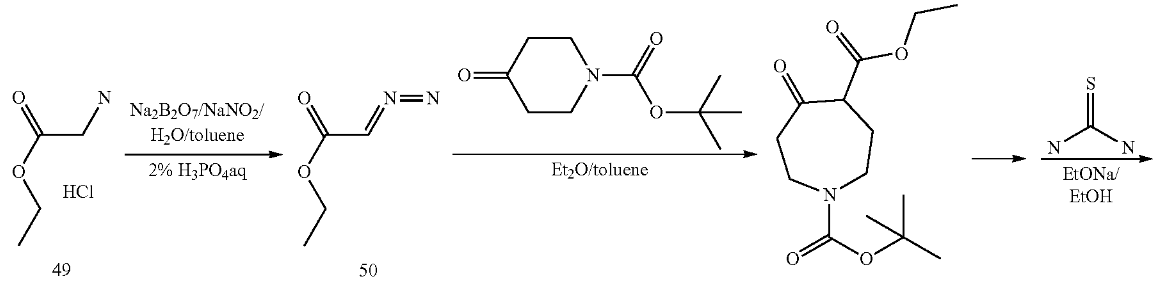
49
50
51
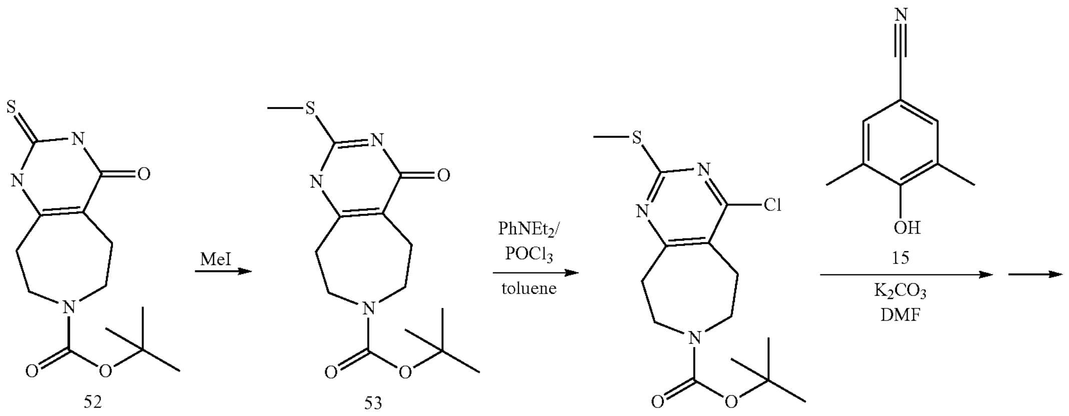
52
53
54

-continued
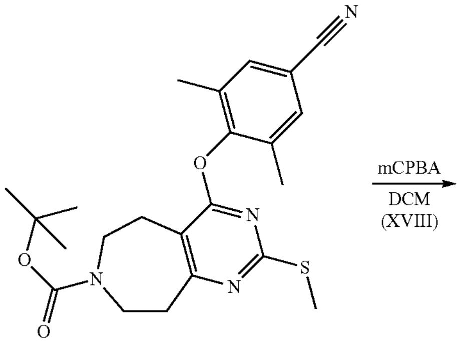
BB 0273957
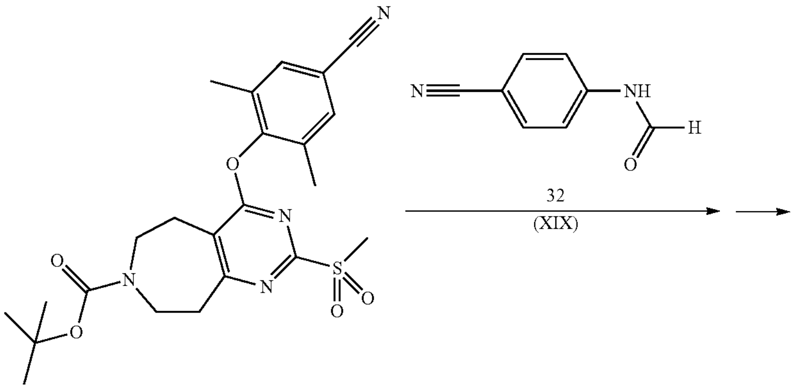
BB 0273968
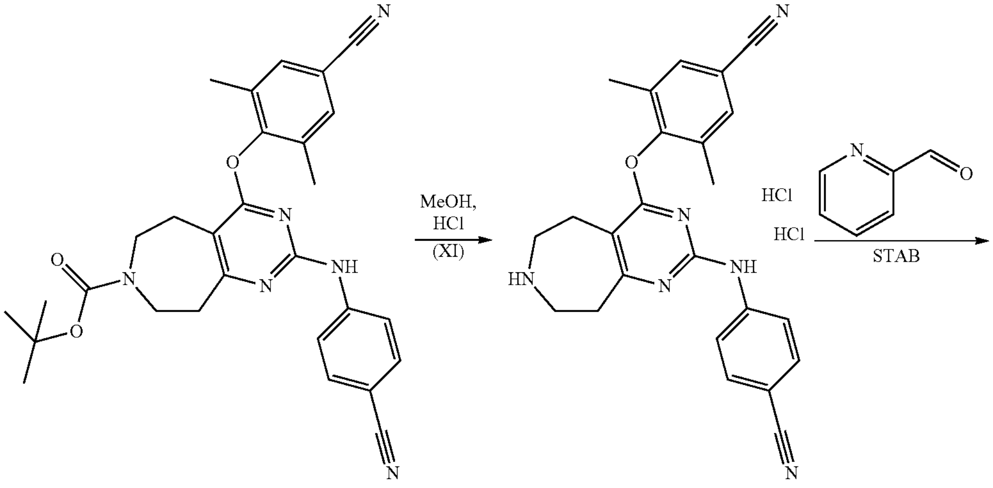
BB 0273972
BB 0273976

-continued
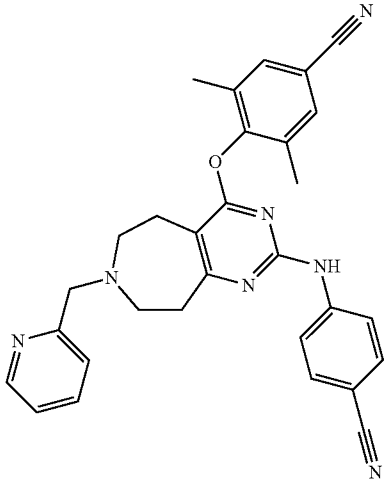
BB 0274014
BB 0274014
$^1$H NMR (400 MHz, DMSO-$d_6$, δ, ppm): 2.08 (s, 6H), 2.72 (d, J=7.5 Hz, 4H), 3.01 (d, J=8.5 Hz, 4H), 3.80 (s, 2H), 7.27 (dd, J=6.7, 5.2 Hz, 1H), 7.40 (s, 4H), 7.54 (d, J=7.8 Hz, 1H), 7.72-7.84 (m, 3H), 8.50 (d, J=4.2 Hz, 1H), 10.04 (s, 1H).
Weight Yield—0.106 g (78%)
LCMS m/z (M+H): 502.
Example 17
Synthesis of 4-((2-((4-cyanophenyl)amino)-7-(pyridine-3-ylmethyl)-6,7,8,9-tetrahydro-5H-pyrimido[4,5-d]azepine-4-yl)oxy)-3,5-dimethylbenzonitrile
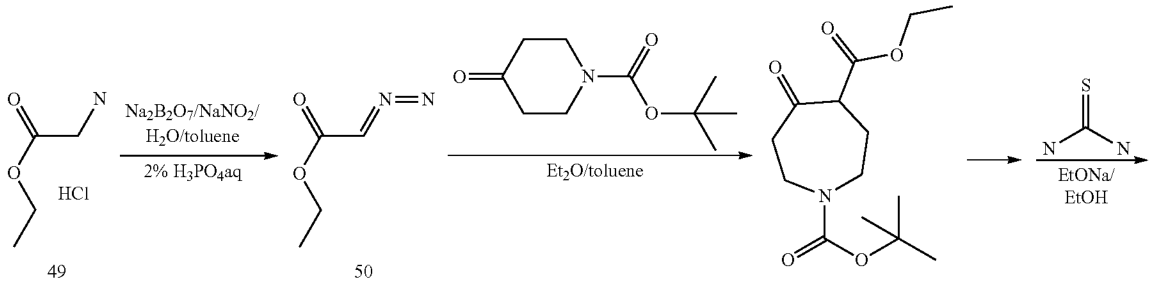
49 50 51
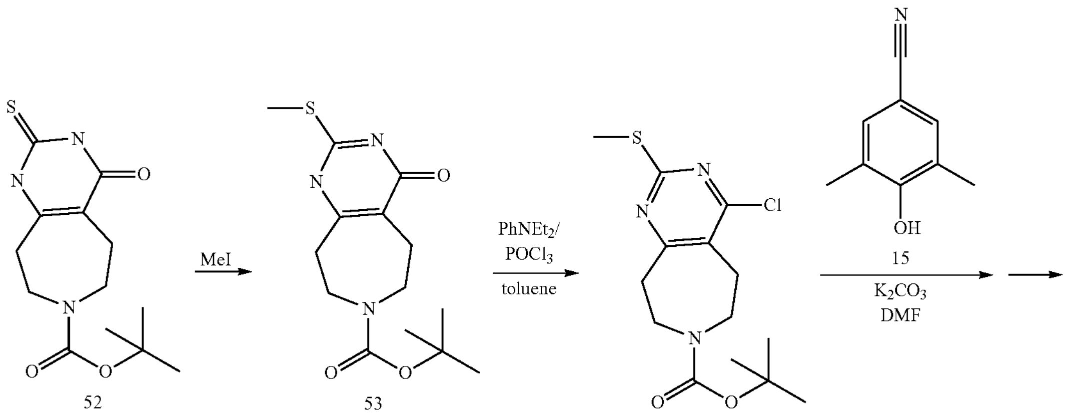
52 53 54

-continued
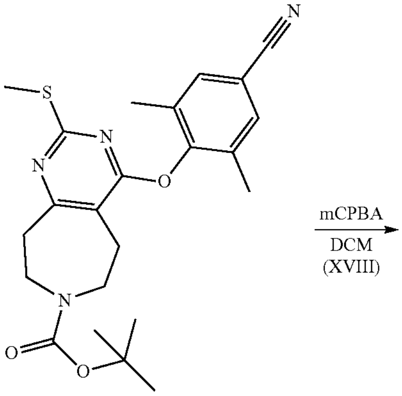
BB 0273957
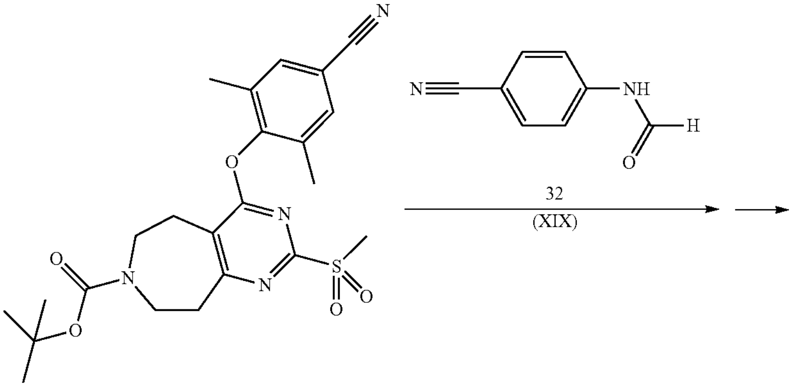
BB 0273968
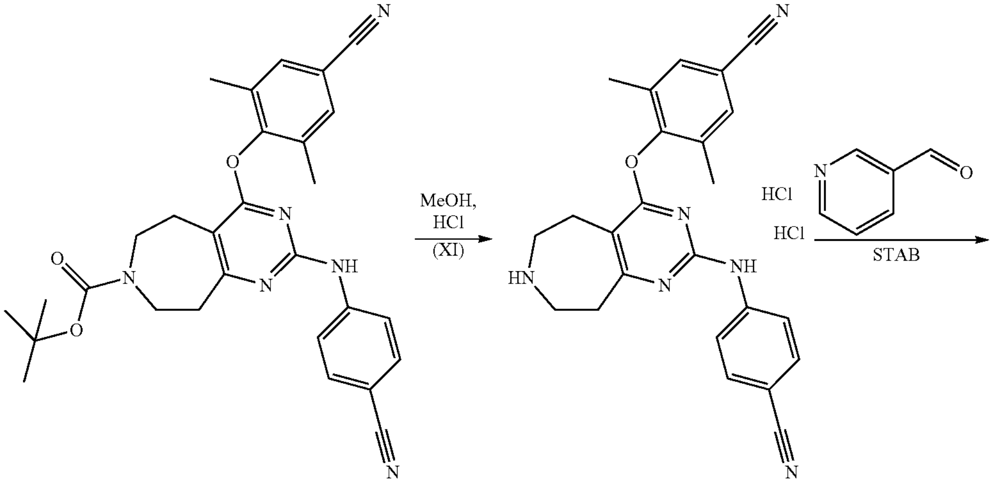
BB 0273972
BB 0273976

-continued
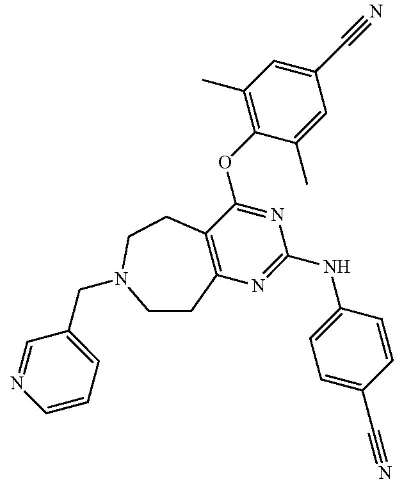
BB 0274015
BB 0274015
$^1H$ NMR (400 MHz, DMSO-$d_6$, δ, ppm): 2.08 (s, 6H), 2.67 (d, J=6.3 Hz, 4H), 3.00 (dd, J=6.3, 2.6 Hz, 4H), 3.71 (s, 2H), 7.33-7.46 (m, 5H), 7.71-7.82 (m, 3H), 8.48 (dd, J=4.7, 1.5 Hz, 1H), 8.56 (d, J=1.5 Hz, 1H), 10.04 (s, 1H).
Weight Yield—0.090 g (64%)
LCMS m/z (M+H): 502.
Example 18
Synthesis of 4-((2-((4-cyanophenyl)amino)-7-(pyridine-4-ylmethyl)-6,7,8,9-tetrahydro-5H-pyrimido[4,5-d]azepine-4-yl)oxy)-3,5-dimethylbenzonitrile
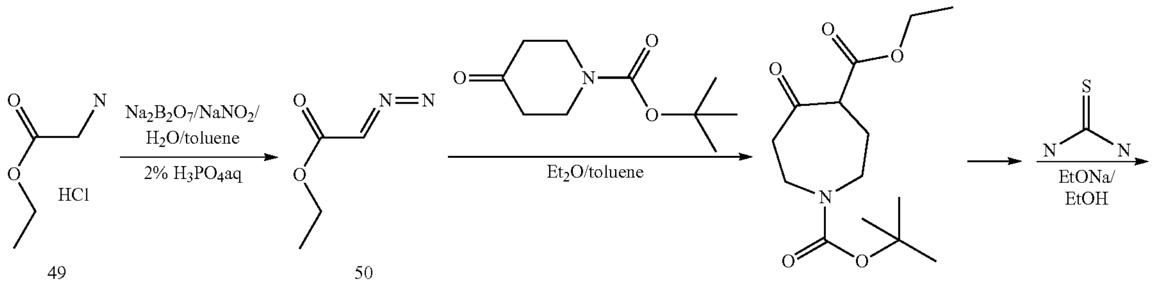
49 50 51
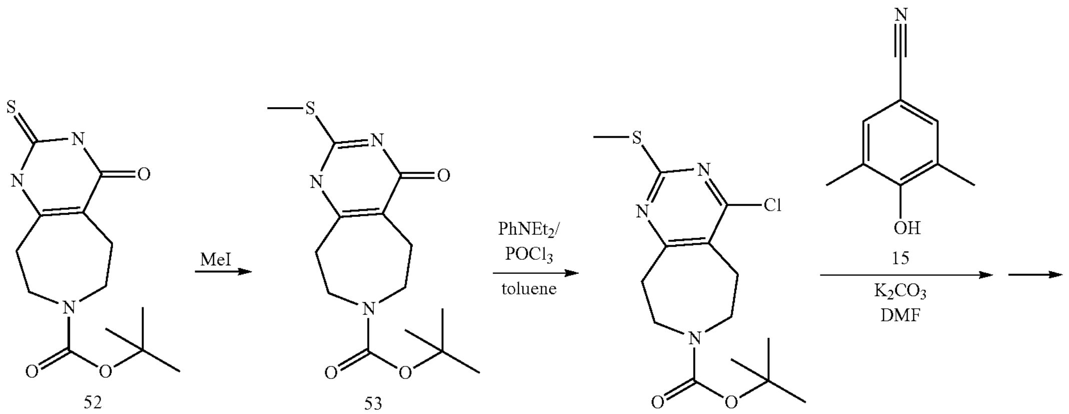
52 53 54 15

-continued
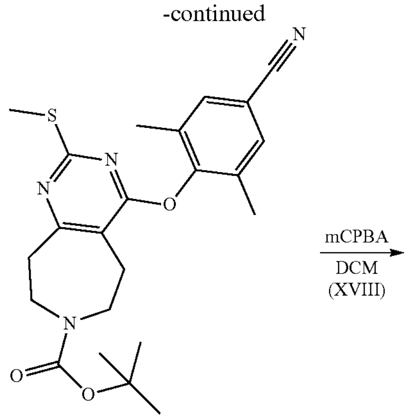
BB 0273957
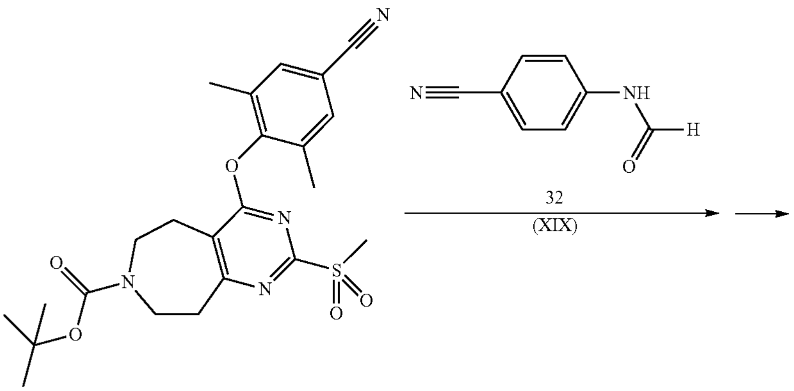
BB 0273968
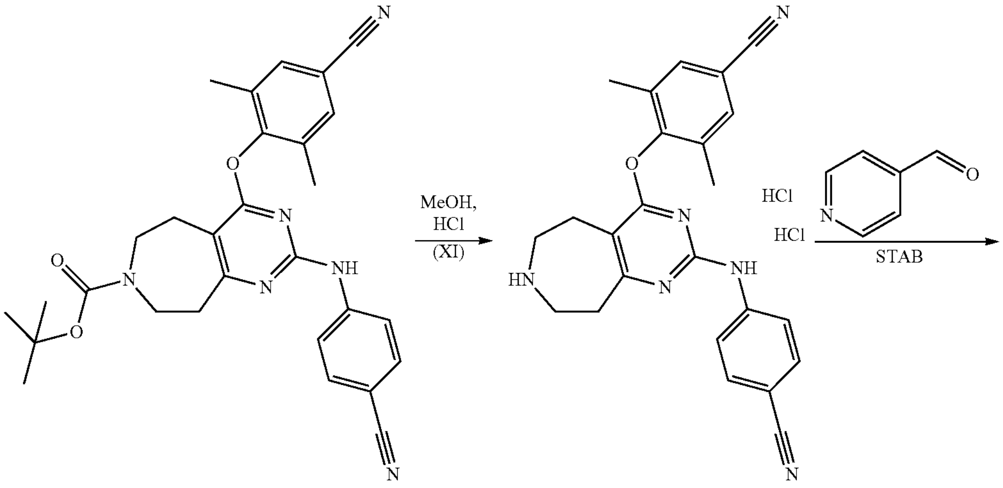
BB 0273972
BB 0273976

-continued
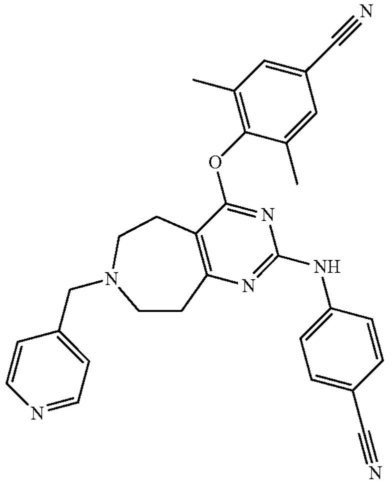
BB 0274016
BB 0274016
$^{1}H$ NMR (400 MHz, DMSO-$d_6$, δ, ppm): 2.09 (s, 6H), 2.68 (d, J=5.8 Hz, 4H), 3.02 (d, J=6.2 Hz, 4H), 3.72 (s, 2H), 7.33-7.46 (m, 6H), 7.78 (s, 2H), 8.54 (d, J=5.6, 2H), 10.04 (s, 1H).
Weight Yield—0.095 g (66%)
LCMS m/z (M+H): 502.
Synthesis of 4-((2-((4-cyanophenyl)amino)-6,7,8,9-tetrahydro-5H-pyrimido[4,5-d]azepine-4-yl)oxy)-3,5-dimethylbenzonitrile
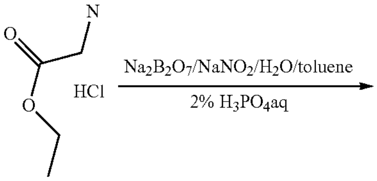
49
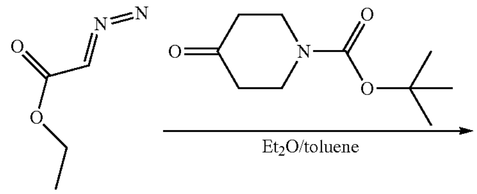
50
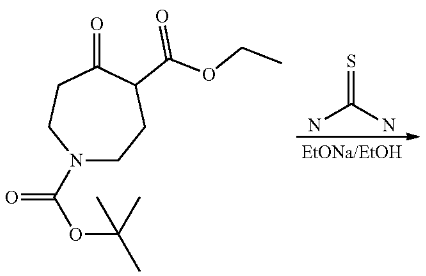
51
-continued
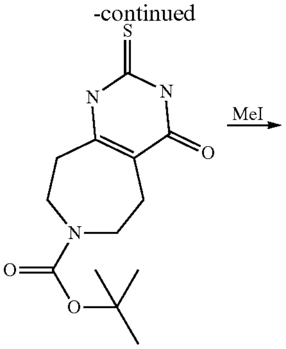
52
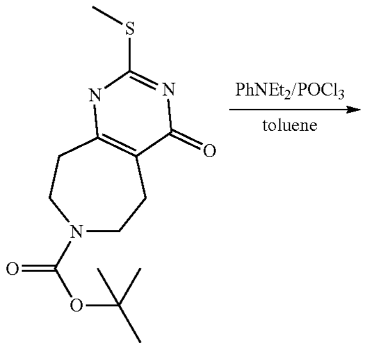
53

-continued
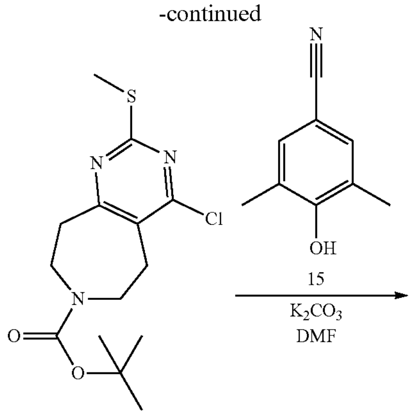
54
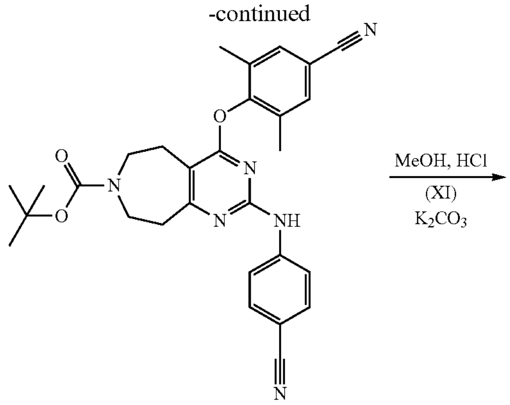
BB 0273972
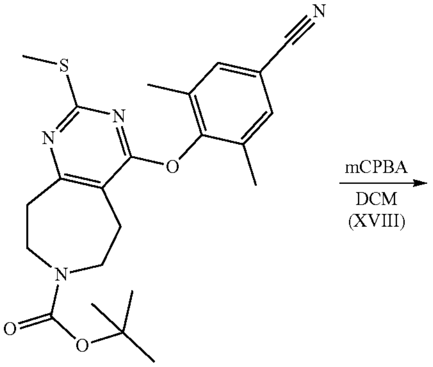
BB 0273957
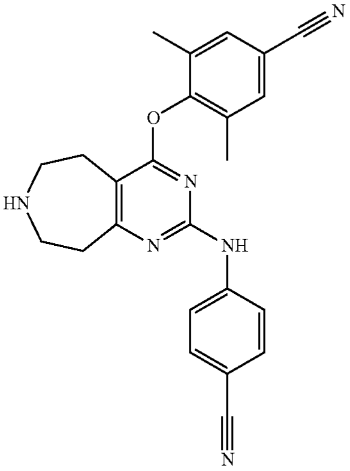
BB 0274021
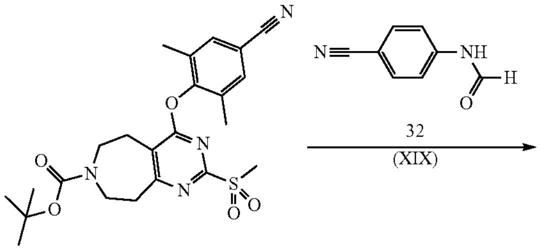
BB 0273968
BB 0274021
$^1$H NMR (400 MHz, DMSO-$d_6$, δ, ppm): 2.09 (broadened singlet, 6H), 2.73-3.08 (m, 8H), 7.41 (broadened singlet, 4H), 7.77 (broadened singlet, 2H), 9.99 (broadened singlet, 1H),
Weight Yield—0.174 g (96%)
LCMS m/z (M+H): 411
Example 19
Synthesis of tert-butyl 4-(4-(4-cyano-2,6-dimethylphenoxy)-2-((4-cyanophenyl)amino)-6,7,8,9-tetrahydro-5H-pyrimido[4,5-d]asein-7-carbonyl)piperidine-1-carboxylate
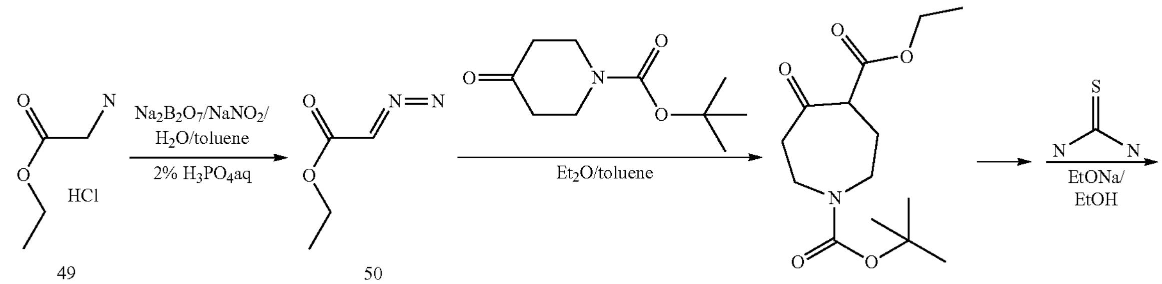
49
50
51

-continued
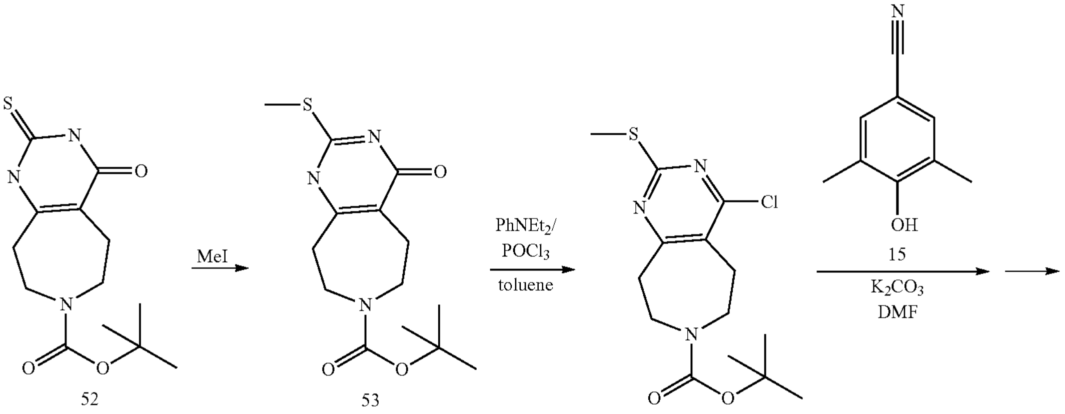
52 53 54 15
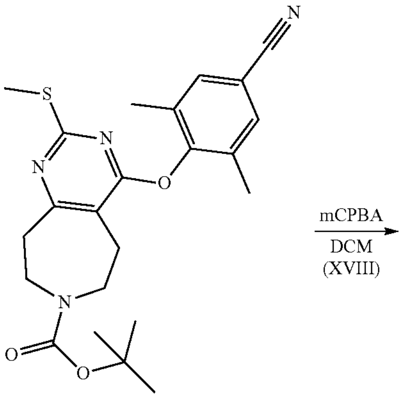
BB 0273957
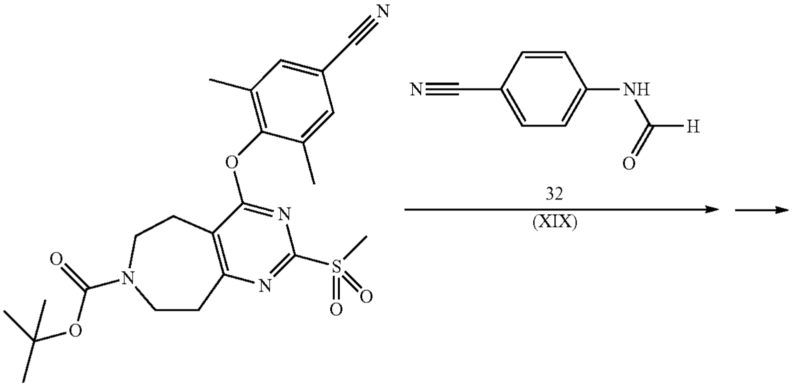
32
BB 0273968

-continued
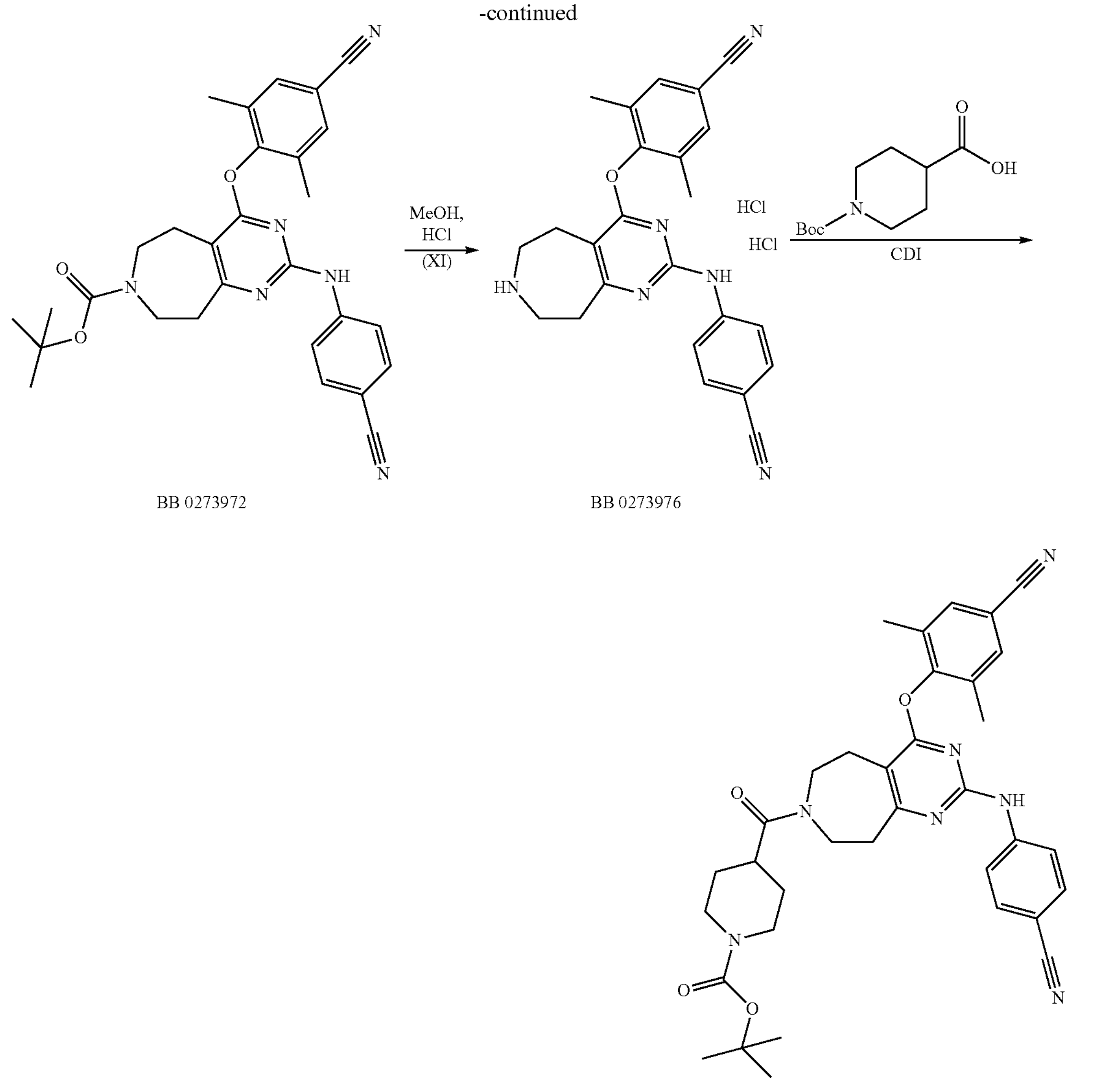
BB 0273972
BB 0273976
BB 0274025
BB 0274025
$^1$H NMR (400 MHz, $CDCl_3$, δ, ppm): 1.47 (s, 9H), 1.64-1.90 (m, 5H), 2.14 (d, J=1.6 Hz, 6H), 2.64-2.89 (m, 3H), 3.03-3.22 (m, 4H), 3.70-3.91 (m, 4H), 4.05-4.34 (m, 2H), 7.05-7.16 (m, 1H), 7.33 (t, J=8.4 Hz, 2H), 7.36-7.42 (m, 2H), 7.48 (d, J=4.5 Hz, 2H).
Weight Yield—0.230 g (55%)
LCMS m/z (M+H): 622.
Synthesis of 4-((2-((4-cyanophenyl)amino)-7-(piperidine-4-carbonyl)-6,7,8,9-tetrahydro-5H-pyrimido[4,5-d]azepine-4-yl)oxy)-3,5-dimethylbenzonitrile dihydrochloride
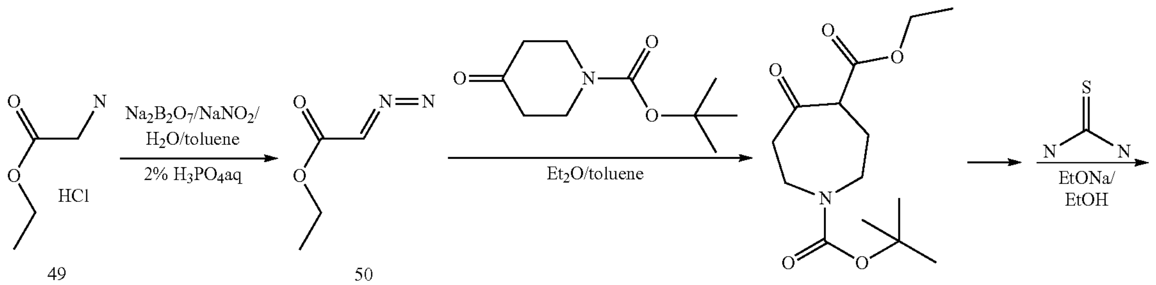
49
50
51

-continued
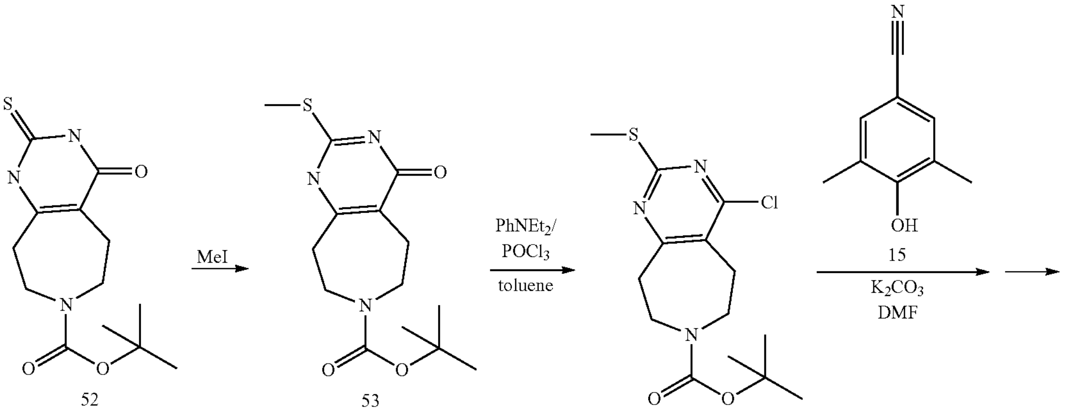
52 53 54
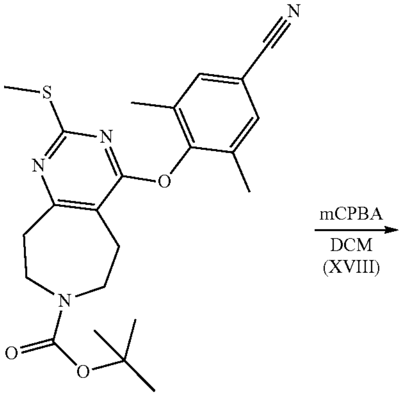
BB 0273957
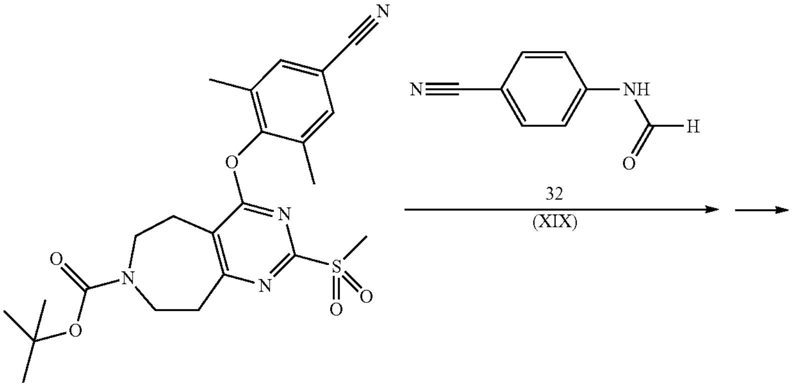
BB 0273968

-continued

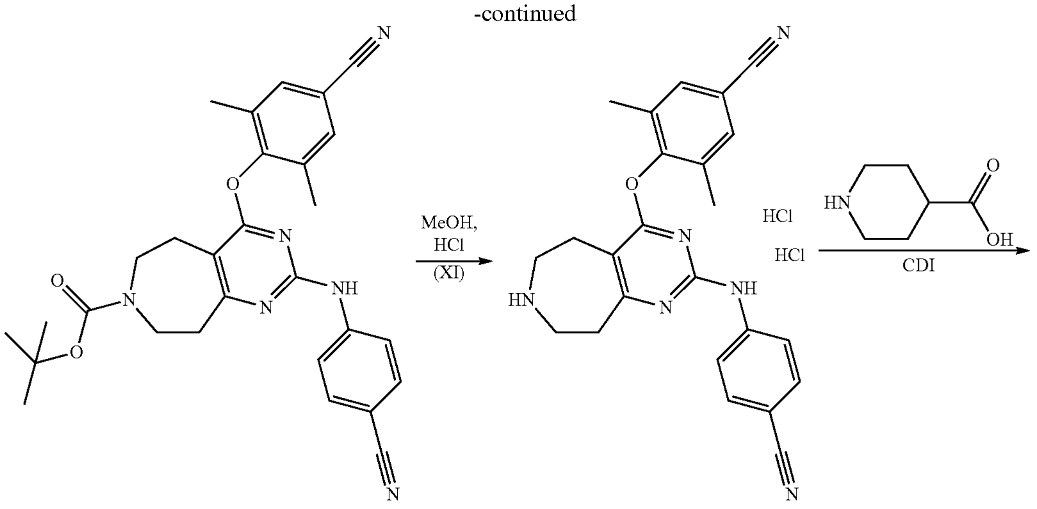

BB 0273972

BB 0273976

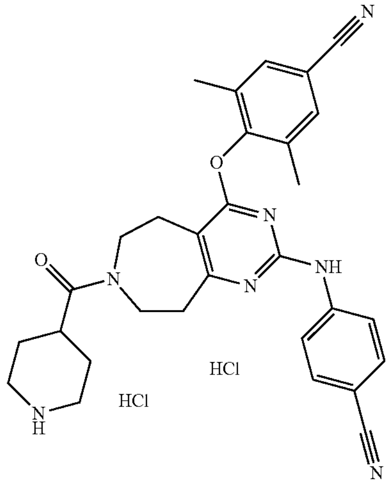

BB 0274026

BB 0274026

$^1$H NMR (400 MHz, DMSO-$d_6$, δ, ppm): 1.78 (broadened singlet, 4H), 2.09 (broadened singlet, 6H), 2.81-3.16 (m, 7H), 3.23 (broadened singlet, 2H), 3.62-3.90 (m, 4H), 7.41 (broadened singlet, 4H), 7.78 (broadened singlet, 2H), 8.86 (broadened singlet, 1H), 9.27 (broadened singlet, 1H), 10.08 (broadened singlet, 1H).

Weight Yield—0.090 g (80%)

LCMS m/z (M+H): 522.

Example 20

Synthesis of tert-butyl 4-(4-(4-cyano-2,6-dimethylphenoxy)-2-((4-cyanophenyl)amino)-8,9-dihydro-5H-pyrimido[4,5-d]azepine-7(6H)-yl)piperidine-1-carboxylate

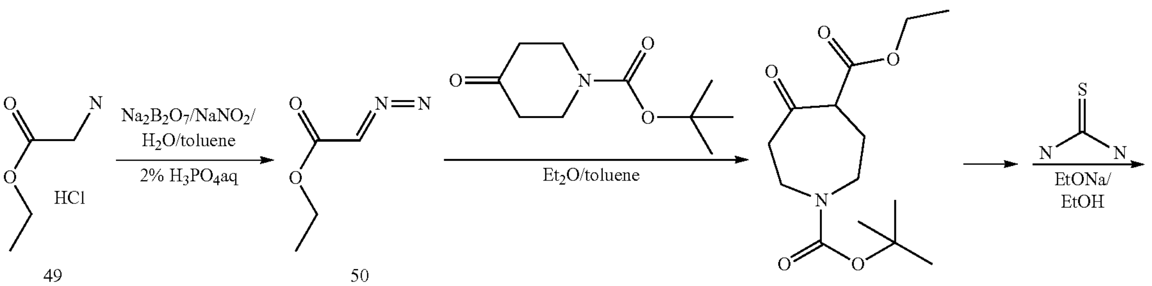

49

50

51

-continued
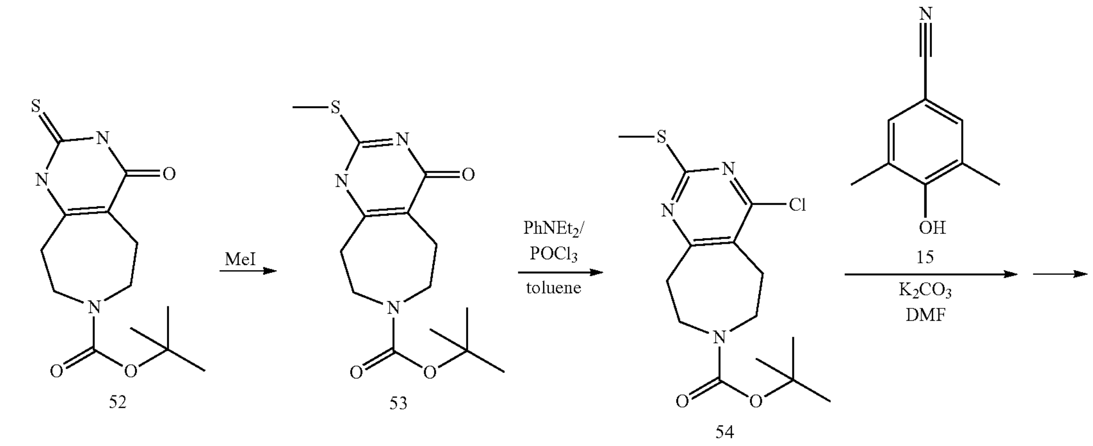
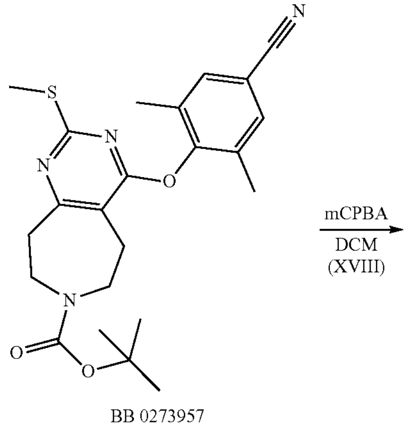
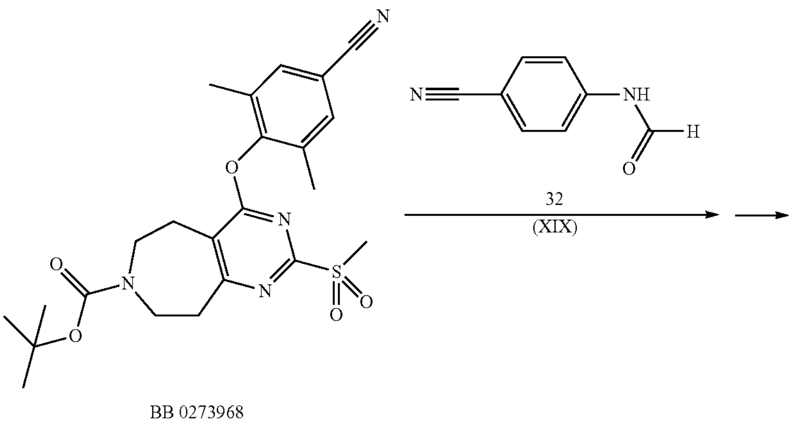

-continued
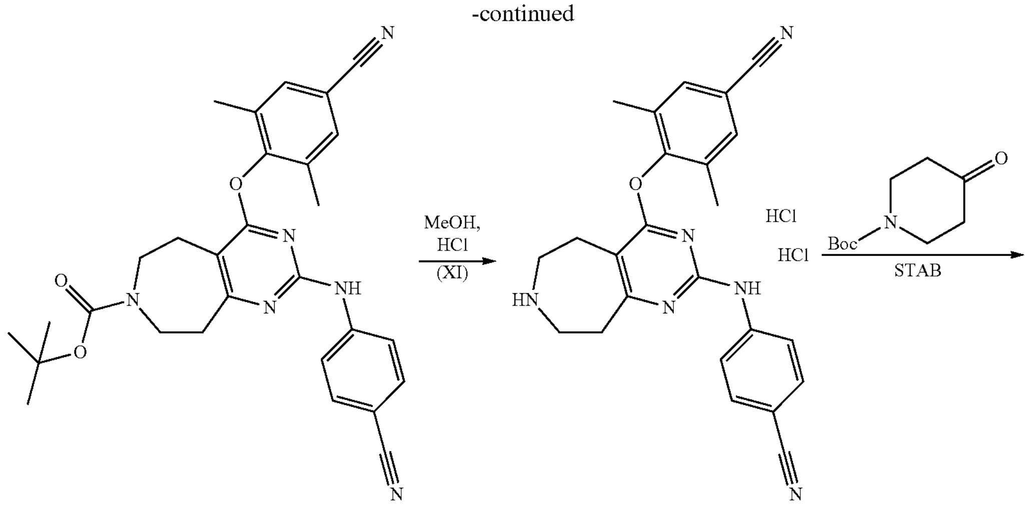
BB 0273972 BB 0273976
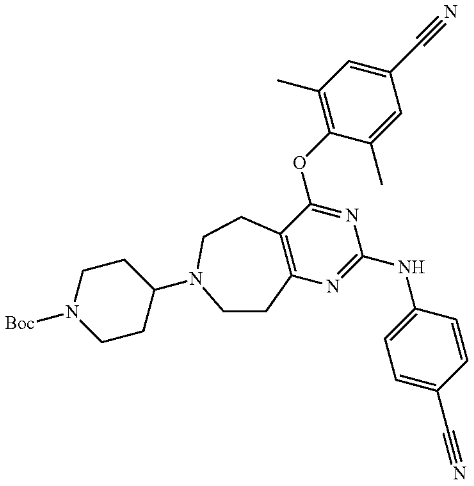
bb 0274027
BB 0274027
$^1$H NMR (400 MHz, DMSO-$d_6$, δ, ppm): 1.26-1.46 (m, 11H), 1.68 (d, J=11.0 Hz, 2H), 2.08 (s, 6H), 2.58-2.83 (m, 7H), 2.94 (broadened singlet, 4H), 3.91-4.08 (m, 2H), 7.41 (s, 4H), 7.78 (s, 2H), 10.01 (s, 1H).
Weight Yield—0.203 g (82%)
LCMS m/z (M+H): 594.
Example 21
Synthesis of 4-((2-((4-cyanophenyl)amino)-7-(piperidine-4-yl)-6,7,8,9-tetrahydro-5H-pyrimido[4,5-d]azepine-4-yl)oxy)-3,5-dimethylbenzonitrile trihydrochloride
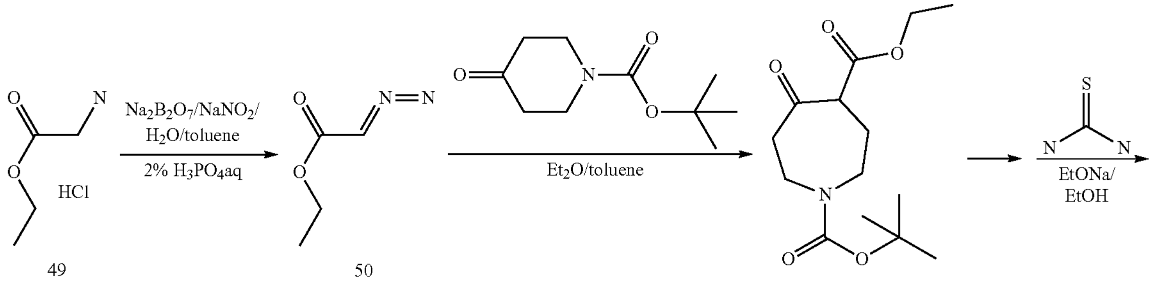
49 50 51

-continued
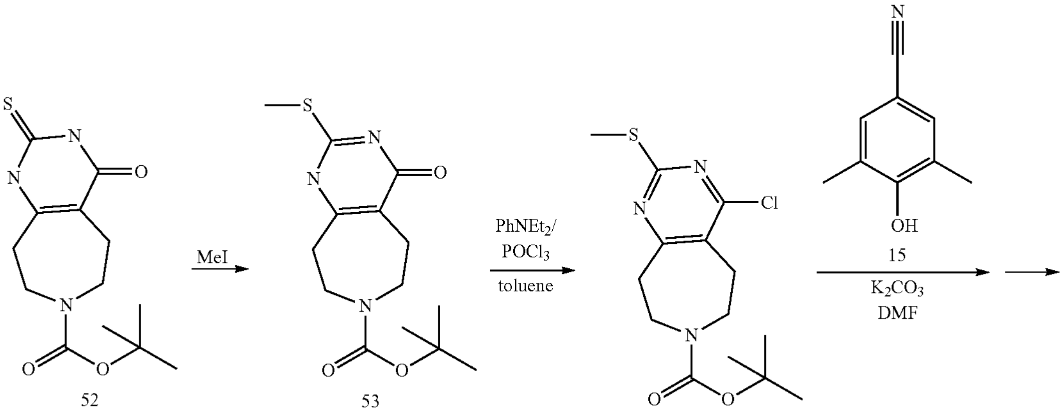
52 53 54
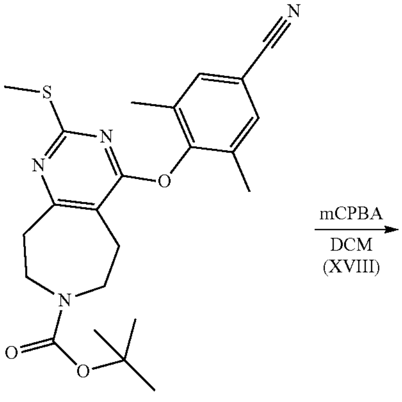
BB 0273957
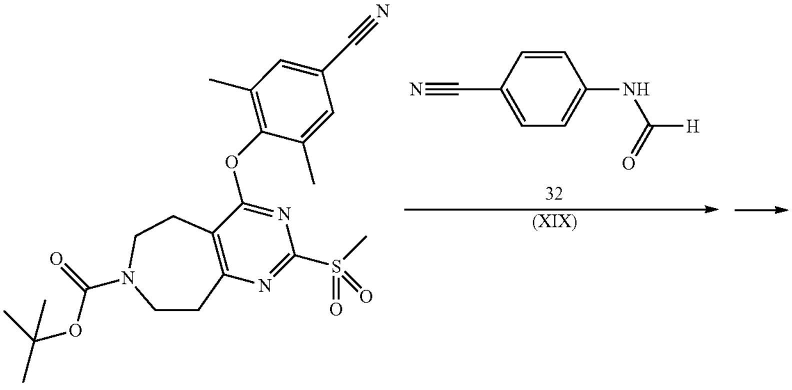
BB 0273968

-continued
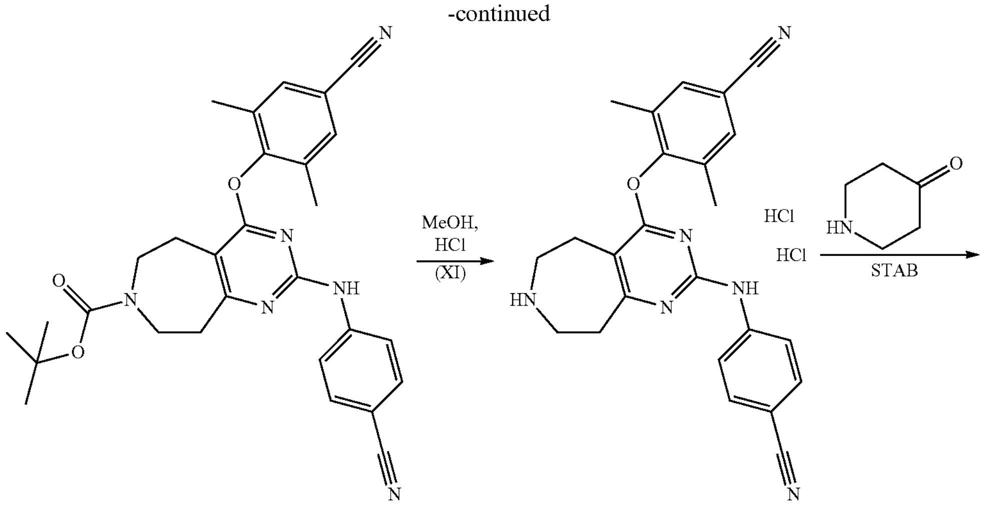
BB 0273972
BB 0273976
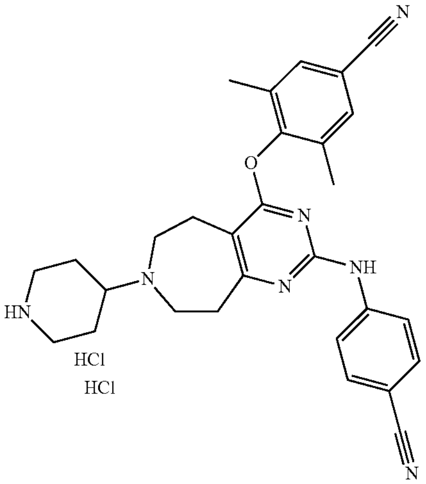
BB 0274028
BB 0274028
$^1$H NMR (400 MHz, DMSO-$d_6$, δ, ppm): 1.97-2.19 (m, 8H), 2.35 (d, J=11.9 Hz, 2H), 2.94 (kv, J=11.1 Hz, 2H), 3.09 (dd, J=16.5, 6.54 Hz, 1H), 3.24-3.36 (m, 1H), 3.37-3.53 (m, 5H), 3.58-3.70 (m, 2H), 3.71-3.87 (m, 2H), 7.44 (s, 4H), 7.79 (s, 2H), 9.25 (d, J=10.2 Hz, 1H), 9.40 (d, J=9.1 Hz, 1H), 10.14 (broadened singlet, 1H), 12.13 (broadened singlet, 1H).
Weight Yield—0.182 g (87%)
LCMS m/z (M+H): 494.

Example 22
Synthesis of 4-((6-(2-aminoacetyl)-2-((4-cyanophenyl)amino)-5,6,7,8-tetrahydropyrido[4,3-d]pyrimidine-4-yl)oxy)-3,5-dimethylbenzonitrile
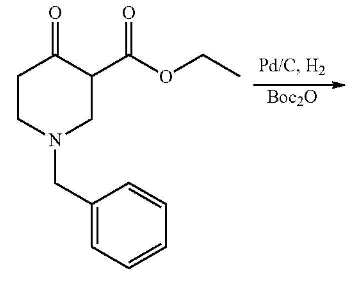
11
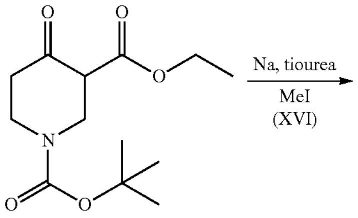
12
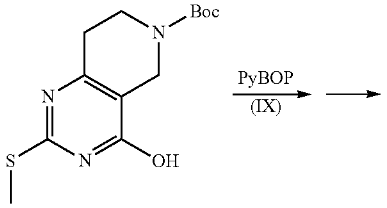
13
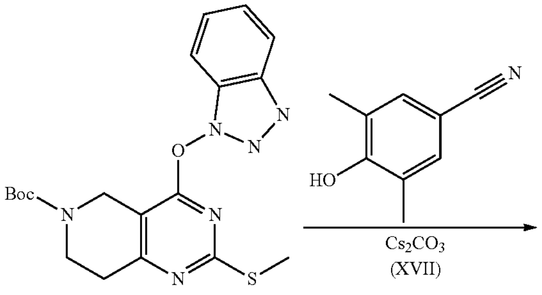
14
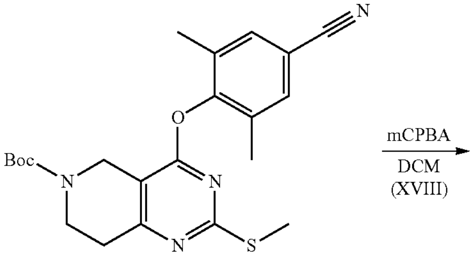
BB 0273947
-continued
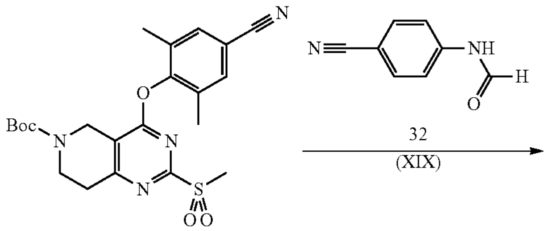
BB 0273960
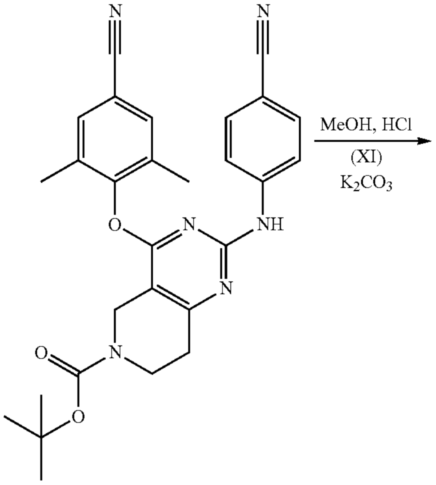
BB 0273961
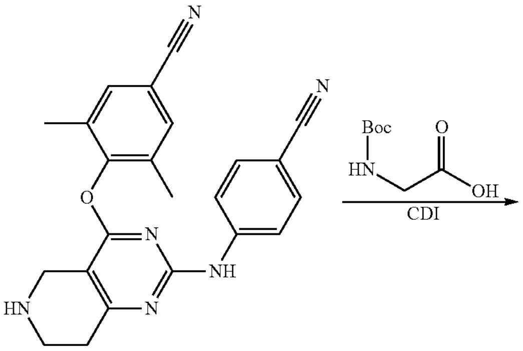
BB 0273963
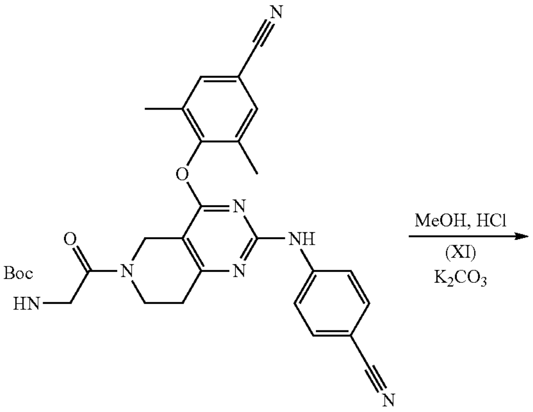
68

-continued
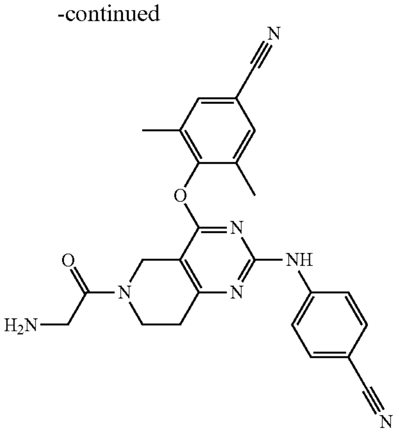
BB 0274051
BB 0274051
$^1$H NMR (400 MHz, $CDCl_3$, δ, ppm): 2.18 (s, 6H), 2.82-3.11 (m, 2H), 3.56-3.88 (m, 2H), 3.90-4.27 (m, 2H), 4.49-4.87 (m, 2H), 7.41 (s, 4H), 7.49 (s, 2H).
Weight Yield—0.029 g (26%)
LCMS m/z (M+H): 453
Example 23
Synthesis of 4-((2-((4-cyanophenyl)amino)-6-(2-(3-hydroxyazetidine-1-yl)acetyl)-5,6,7,8-tetrahydropyrido[4,3-d]pyrimidine-4-yl)oxy)-3,5-dimethylbenzonitrile
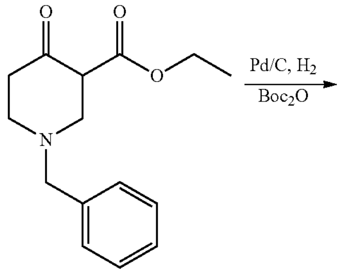
11
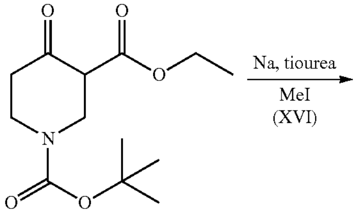
12
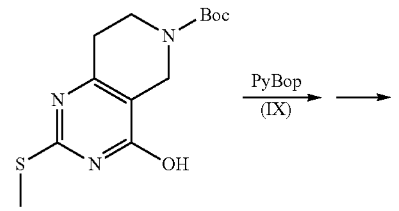
13
-continued
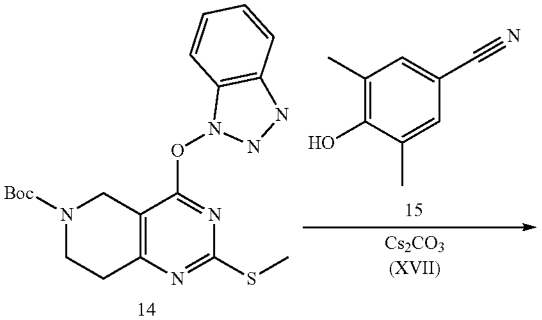
14
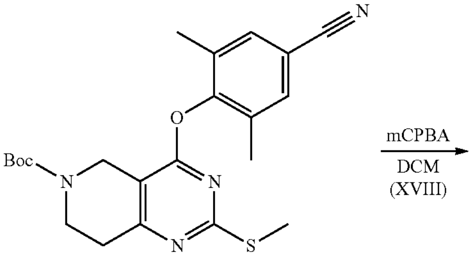
BB 0273947
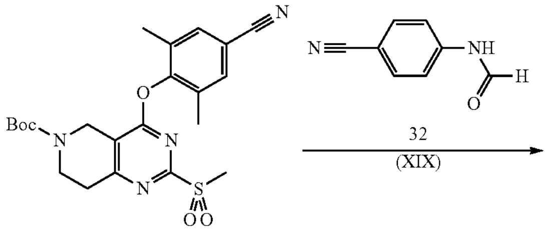
BB 0273960
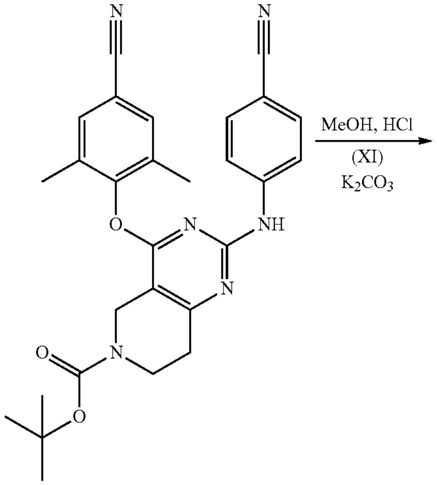
BB 0273961
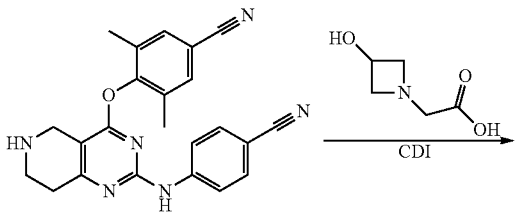
BB 0273963

-continued
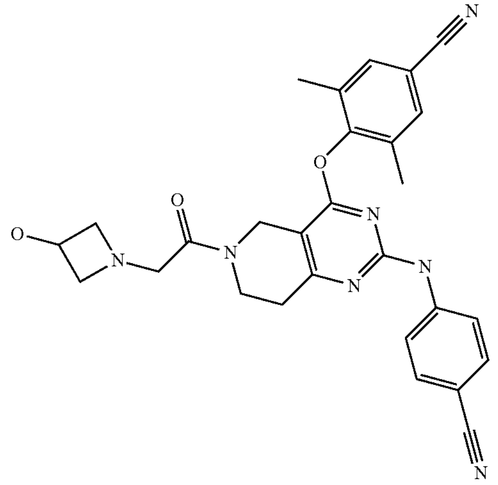
BB 0274052
BB 0274052
$^1$H NMR (400 MHz, $CDCl_3$, δ, ppm): 1.90 (broadened singlet, 1H), 2.34 (broadened singlet, 1H), 2.57-2.69 (m, 2H), 3.12-3.28 (m, 2H), 3.43-3.55 (m, 2H), 3.57-3.74 (m, 2H), 3.94-4.24 (m, 1H), 4.31-4.54 M, 2H), 4.65-4.88 (m, 1H), 7.05 (d, J=7.5 Hz, 2H), 7.19 (d, J=7.1 Hz, 2H), 7.26 (s, 2H).
Weight Yield—0.005 g (12%)
LCMS m/z (M+H): 510
Example 24
Synthesis of tert-butyl-2-(4-(4-cyano-2,6-dimethylphenoxy)-2-((cyanophenyl)amino)-6,7,8,9-tetrahydro-5H-pyrimido[4,5-d]azepine-7-carbonyl)pyrrolidine-1-carboxylate
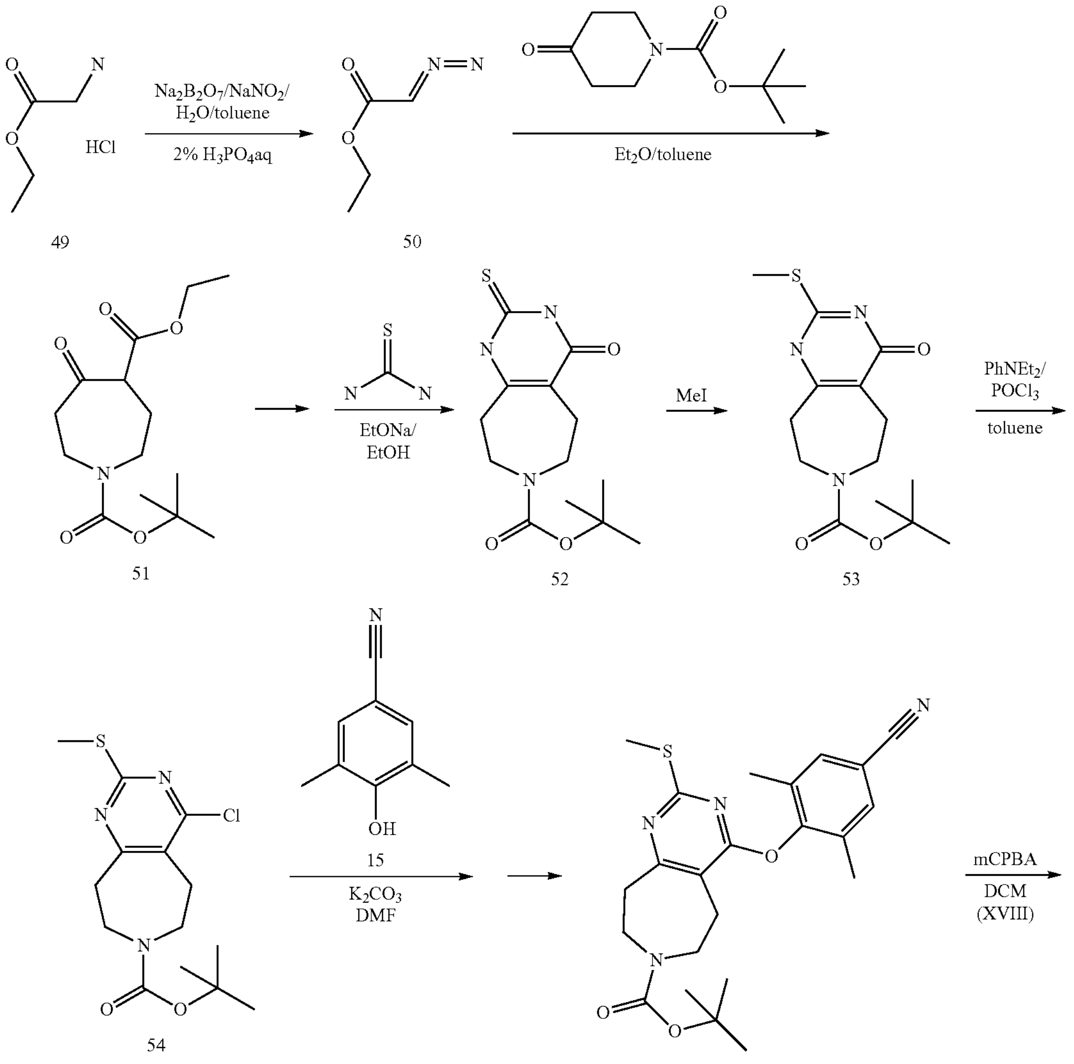
49, 50, 51, 52, 53, 54, 15
BB 0273957

-continued
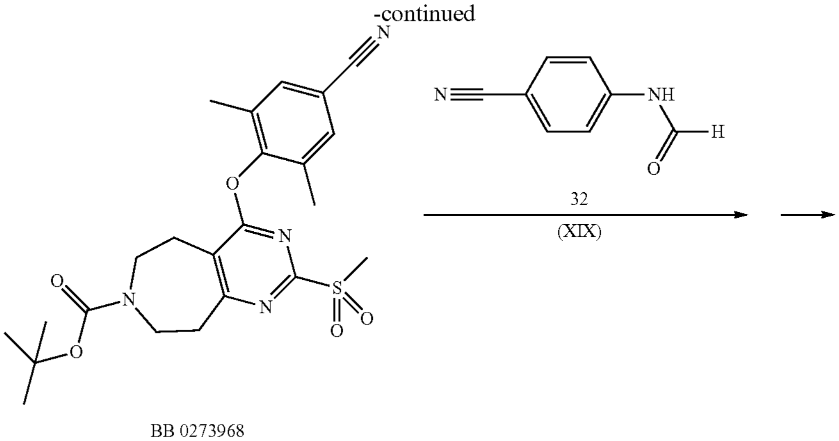
BB 0273968
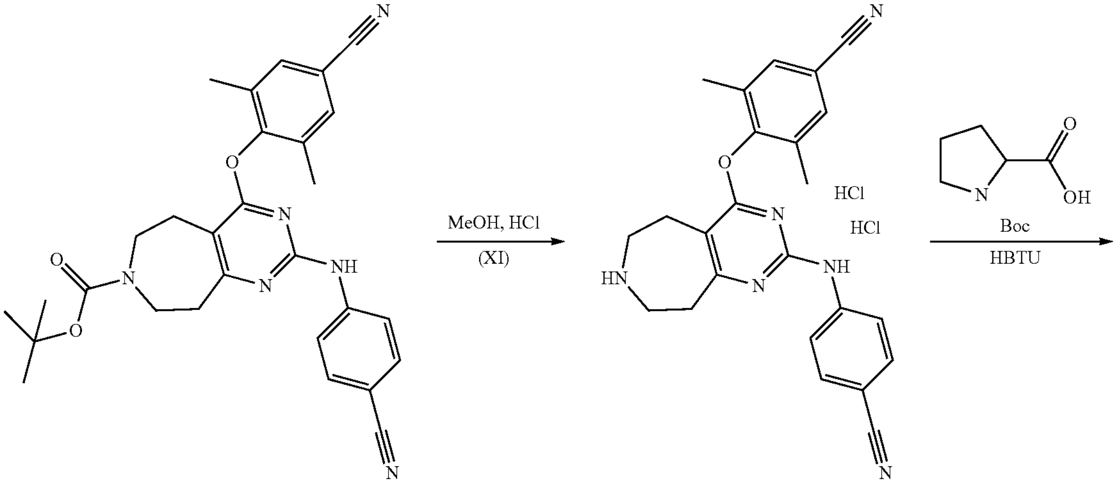
BB 0273972
BB 0273976
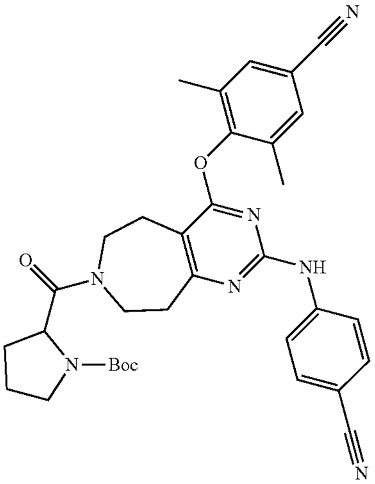
BB 0274063
BB 0274063
$^1$H NMR (400 MHz, DMSO-$d_6$, δ, ppm): 1.25 (broadened singlet, 9H), 1.36 (s, 3H), 1.59-1.91 (m, 3H), 2.02-2.14 (m, 6H), 2.14-2.33 (m, 1H), 2.74-3.33 (m, 5H), 3.36-4.06 (m, 5H), 4.58-4.78 (m, 1H), 7.41 (broadened singlet, 4H), 7.78 (broadened singlet, 2H), 9.96-10.16 (m, 1H).
Weight Yield—0.128 g (57%)
LCMS m/z (M+H): 608.

Example 25
Synthesis of (R)-tert-butyl-2-(4-(4-cyano-2,6-dimethylphenoxy)-2-((cyanophenyl)amino)-6,7,8,9-tetrahydro-5H-pyrimido[4,5-d]azepine-7-carbonyl)pyrrolidine-1-carboxylate
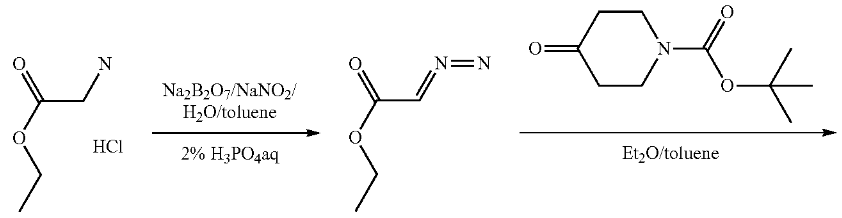
49 50
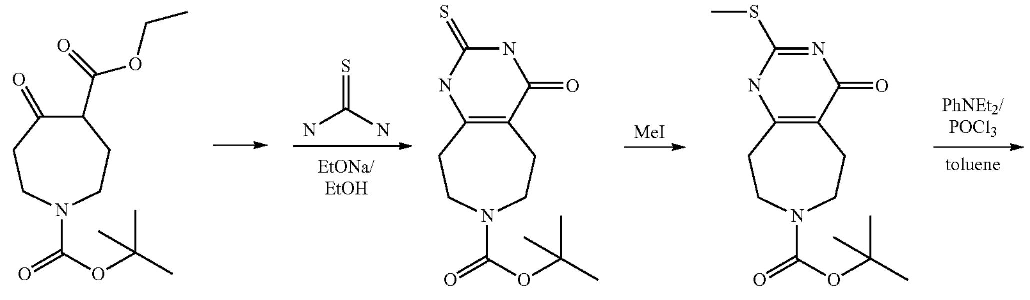
51 52 53
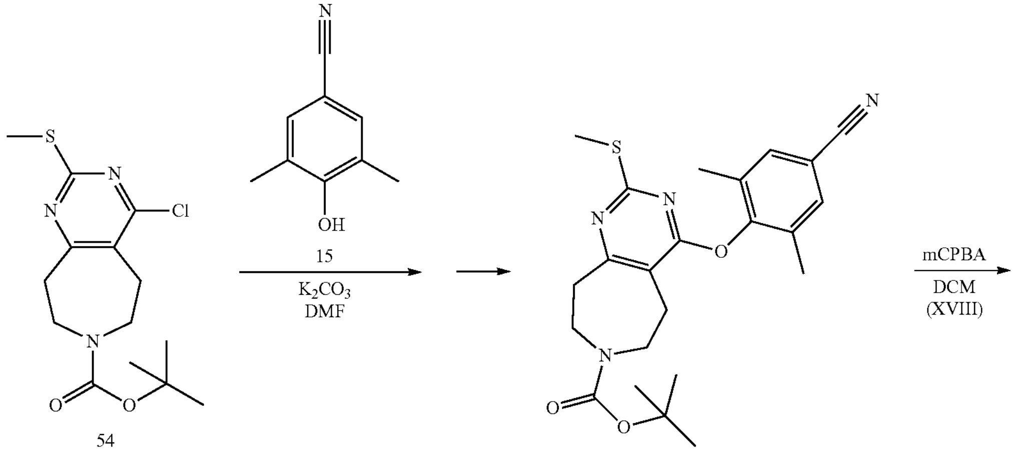
54
BB 0273957
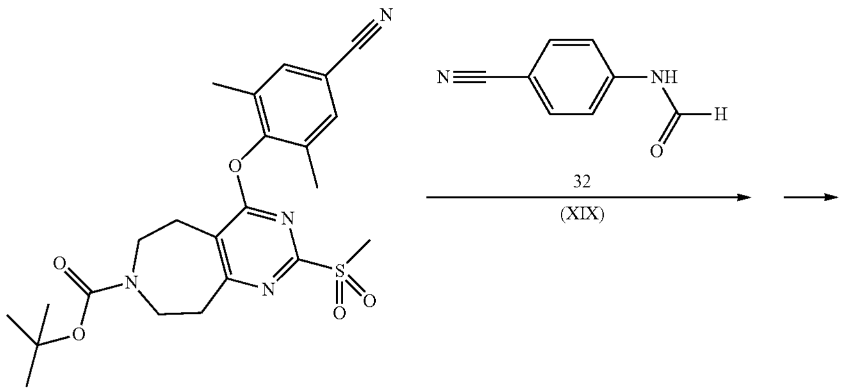
BB 0273968

-continued
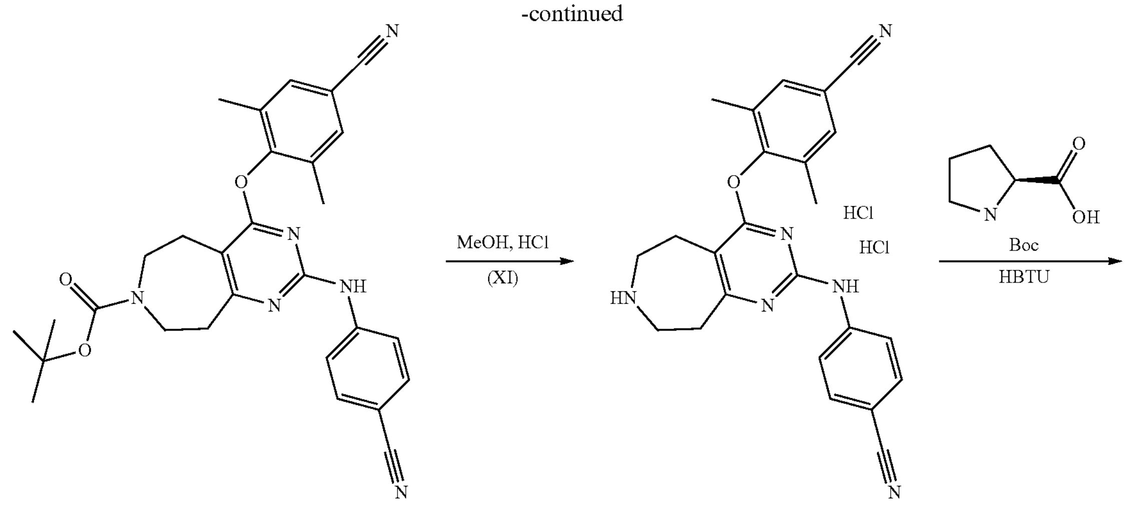
BB 0273972
BB 0273976
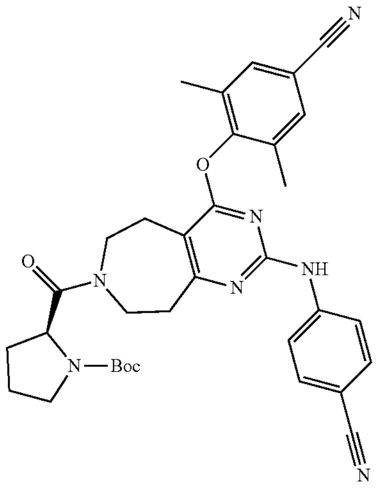
BB 0274064
BB 0274064
$^1$H NMR (400 MHz, DMSO-$d_6$, δ, ppm): 1.25 (broadened singlet, 6H), 1.36 (s, 3H), 1.58-1.91 (m, 3H), 2.02-2.15 (m, 6H), 2.15-2.34 (m, 1H), 2.76-3.32 (m, 5H), 3.36-4.05 (m, 5H), 4.54-4.79 (m, 1H), 7.41 (broadened singlet, 4H), 7.78 (d, J=2.4 Hz, 2H), 9.97-10.17 (m, 1H).
Weight Yield—0.103 g (52%)
LCMS m/z (M+H): 608.
Example 26
Synthesis of (S)-tert-butyl-2-(4-(4-cyano-2,6-dimethylphenoxy)-2-((cyanophenyl)amino)-6,7,8,9-tetrahydro-5H-pyrimido[4,5-d]azepine-7-carbonyl)pyrrolidine-1-carboxylate
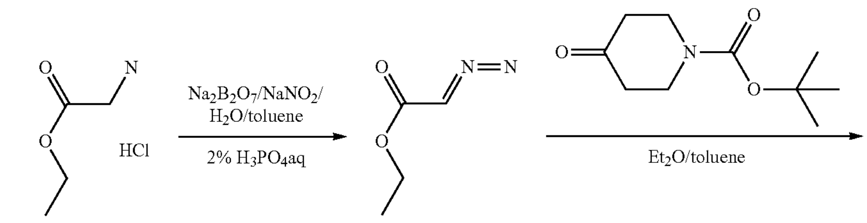
49
50

-continued
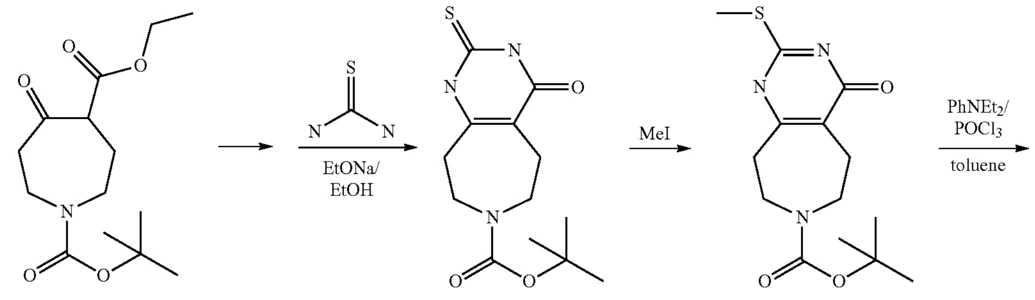
51 52 53
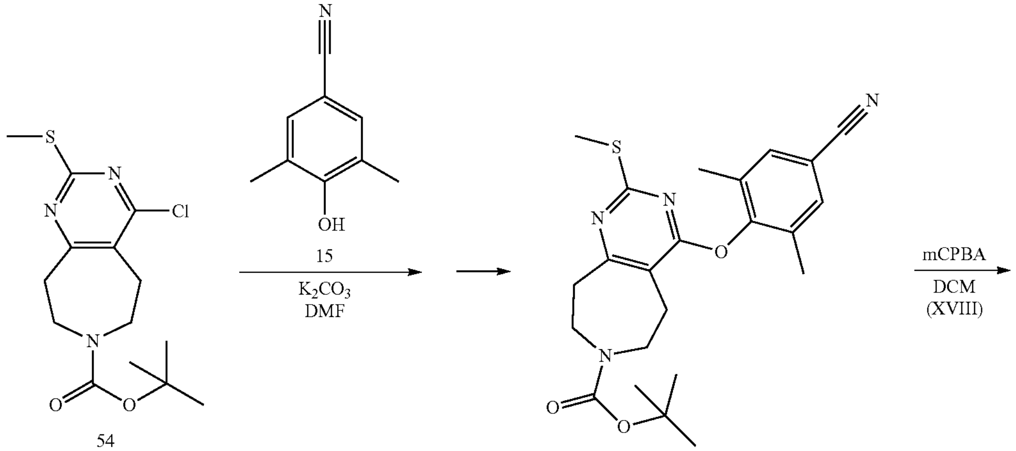
54
BB 0273957
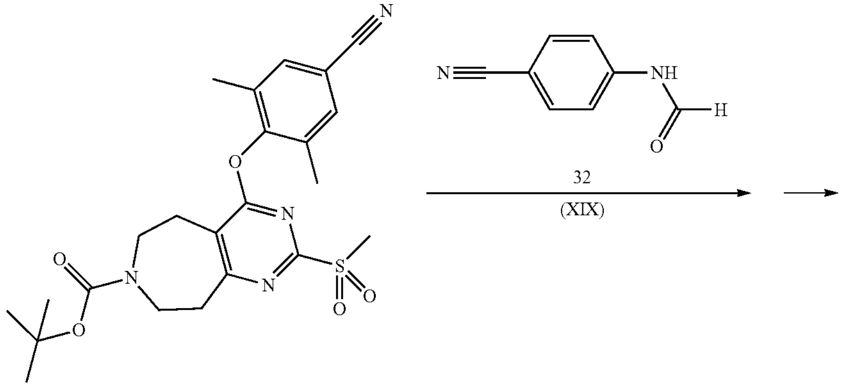
BB 0273968

-continued
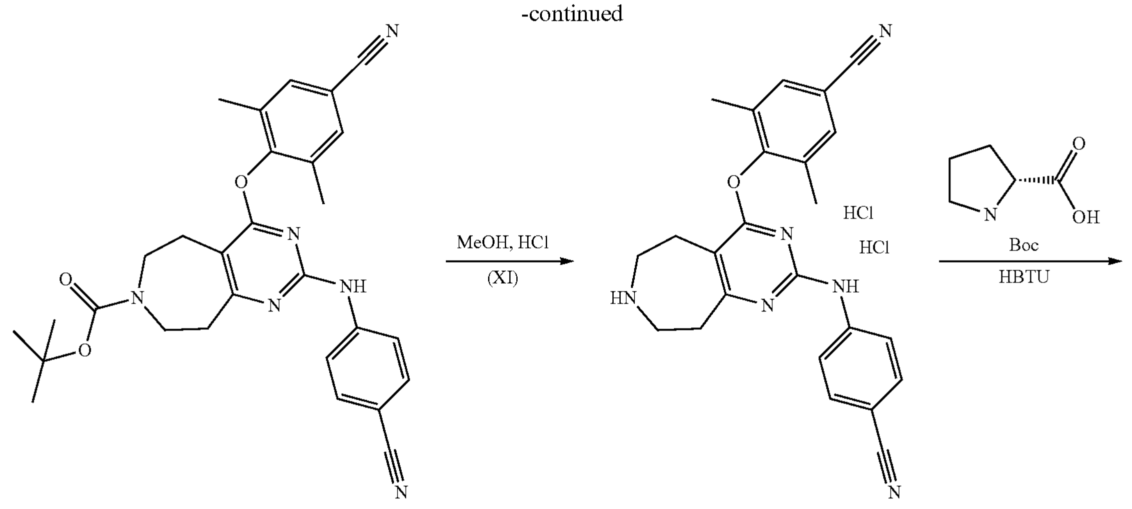
BB 0273972
BB 0273976
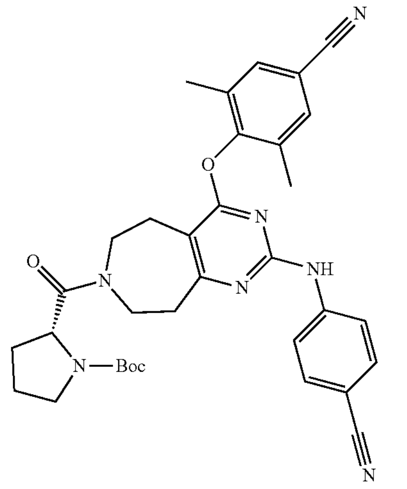
BB 0274065
BB 0274065
$^1$H NMR (400 MHz, DMO-$d_6$, δ, ppm): 1.25 (broadened singlet, 6H), 1.36 (s, 3H), 1.58-1.92 (m, 3H), 2.03-2.14 (m, 6H), 2.14-2.34 (m, 1H), 2.79-3.33 (m, 5H), 3.35-4.03 (m, 5H), 4.53-4.78 (m, 1H), 7.41 (broadened singlet, 4H), 7.77 (broadened singlet, 2H), 9.93-10.16 (m, 1H).
Weight Yield—0.098 g (50%)
LCMS m/z (M+H): 608
Example 27
Synthesis of 4-((2-((4-cyanophenyl)amino)-7-(tetrahydro-2H-pyran-4-yl)-6,7,8,9-tetrahydro-5H-pyrimido[4,5-d]azepine-4-yl)oxy)-3,5-dimethylbenzonitrile
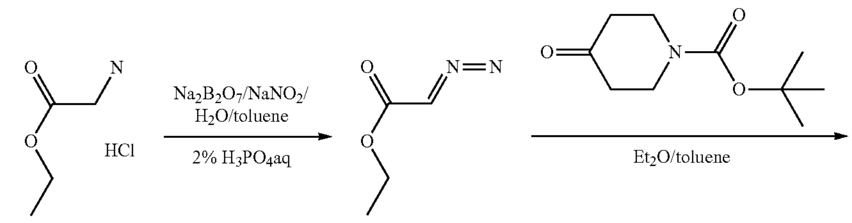
49
50

-continued
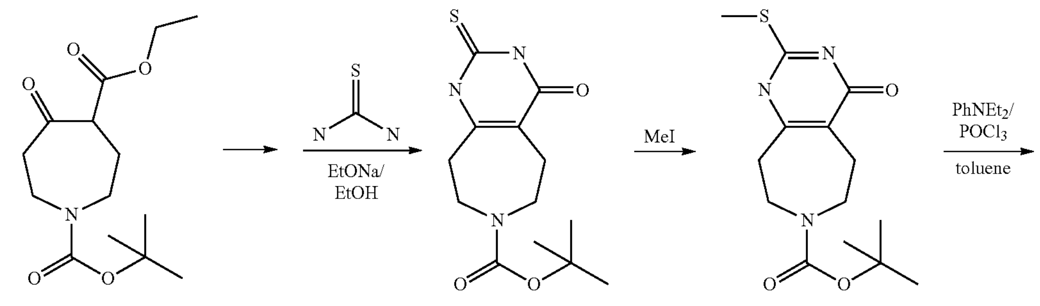
51 52 53
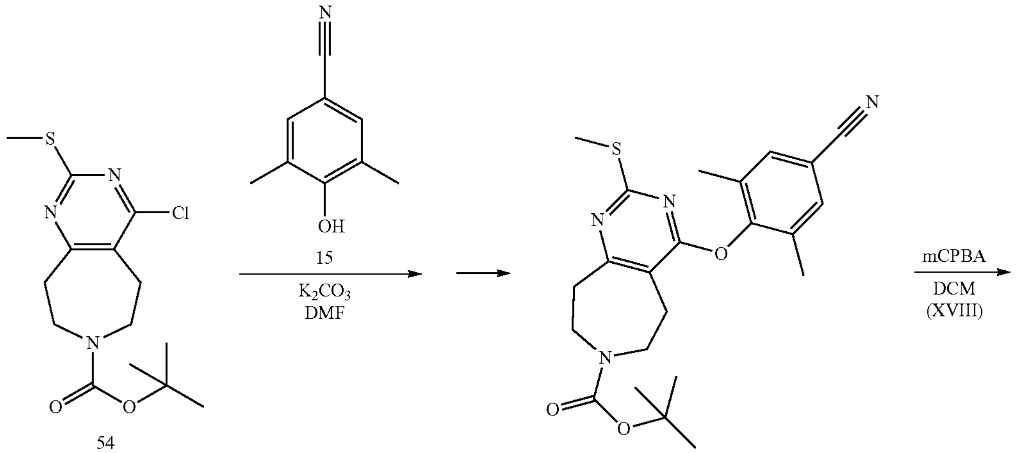
54
BB 0273957
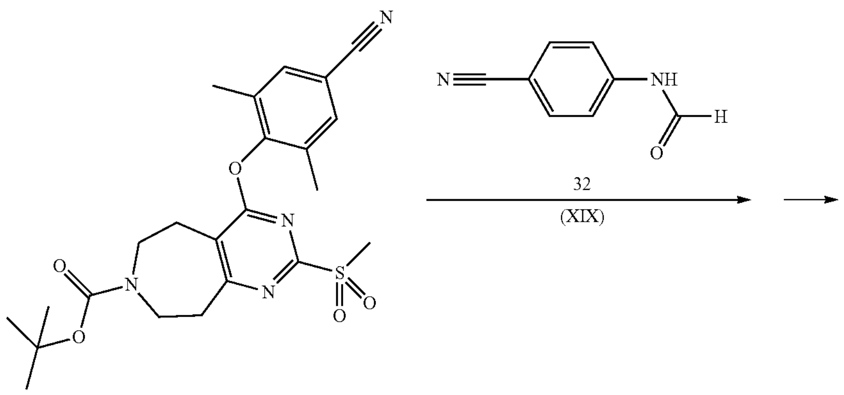
BB 0273968

-continued
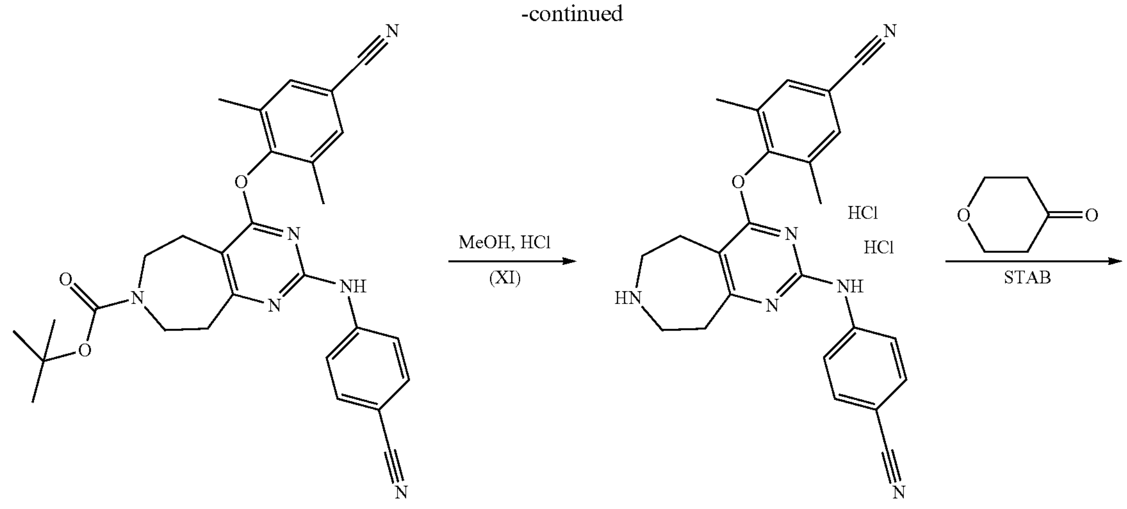
BB 0273972
BB 0273976
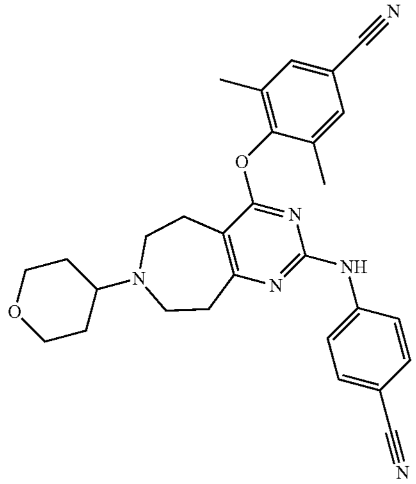
BB 0274072
BB 0274072
$^1$H NMR (400 MHz, DMSO-$d_6$, δ, ppm): 1.40-1.74 (m, 4H), 2.09 (s, 6H), 2.77 (broadened singlet, 4H), 2.97 (broadened singlet, 4H), 3.19-3.46 (m, 3H), 3.81-3.96 (m, 2H), 7.41 (s, 4H), 7.78 (s, 2H), 10.00 (broadened singlet, 1H).
Weight Yield—0.096 g (82%)
LCMS m/z (M+H): 495
Example 28
Synthesis of 4-((2-((4-cyanophenyl)amino)-7-(5-methylfuran-2-yl)methyl)-6,7,8,9-tetrahydro-5H-pyrimido[4,5-d]azepine-4-yl)oxy)-3,5-dimethylbenzonitrile
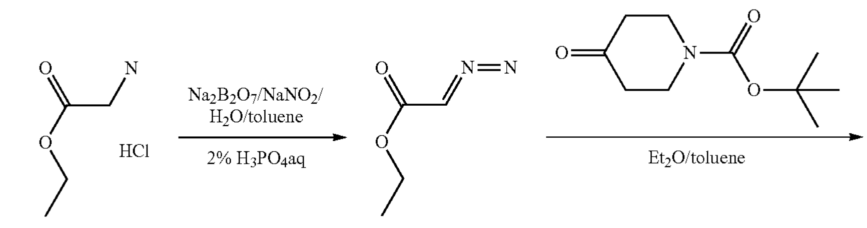
49
50

-continued
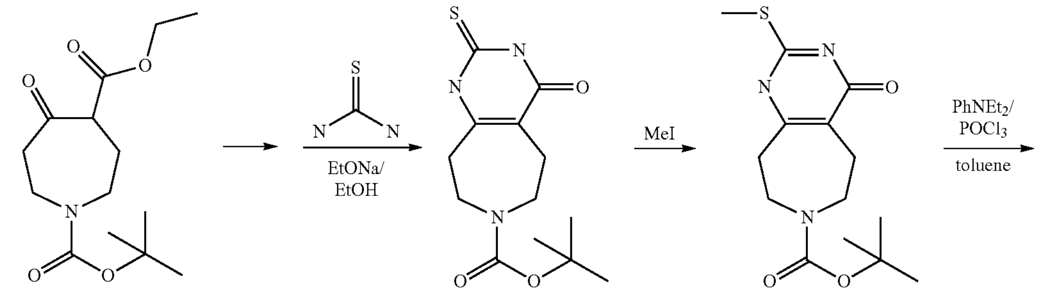
51 52 53
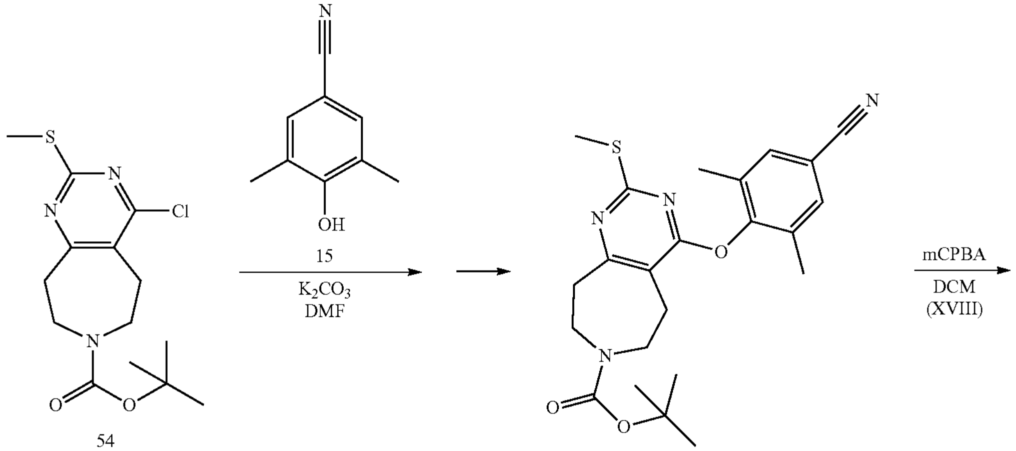
54
BB 0273957
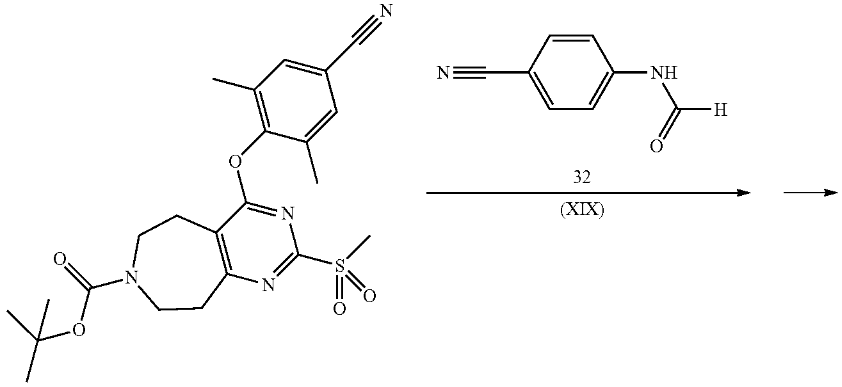
BB 0273968

-continued
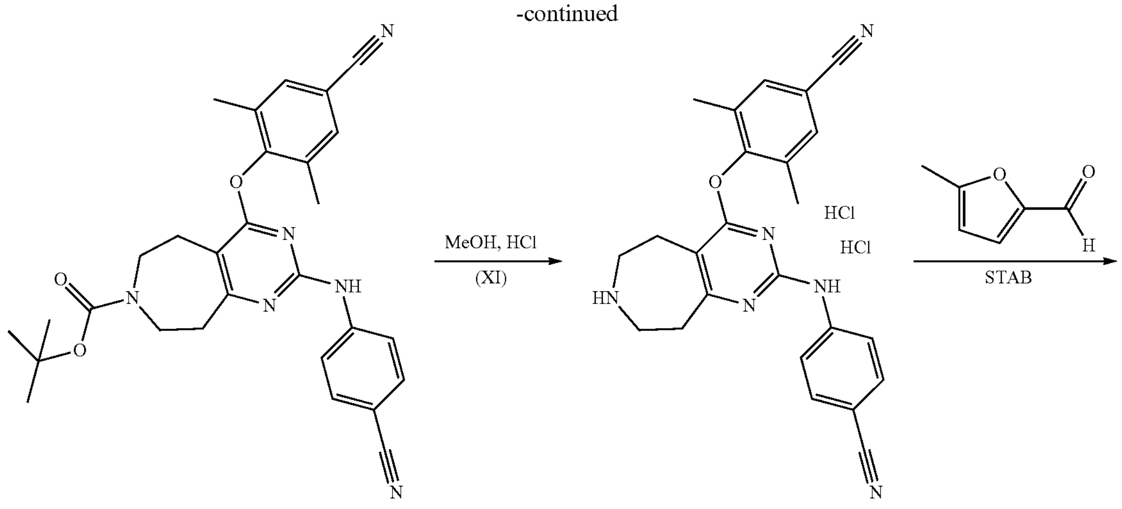
BB 0273972
BB 0273976
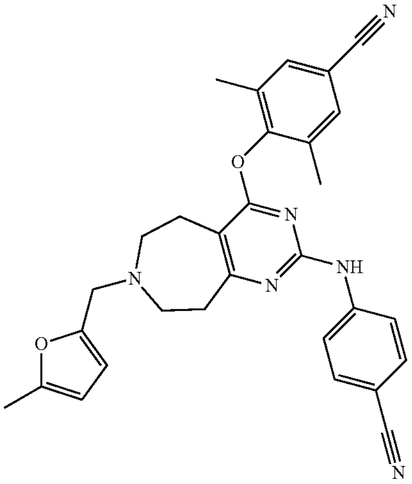
BB 0274073
BB 0274073
$^1$H NMR (400 MHz, $CDCl_3$, δ, ppm): 2.14 (s, 6H), 2.30 (s, 3H), 2.64-2.82 (m, 4H), 3.08 (d, J=6.7 Hz, 4H), 3.68 (s, 2H), 5.92 (broadened singlet, 1H), 6.11 (d, J=2.8 Hz, 1H), 7.14 (s, 1H), 7.24-7.33 (m, 2H), 7.34-7.41 (m, 2H), 7.47 (m, 2H).
Weight Yield—0.038 g (44%)
LCMS m/z (M+H): 505
Example 29
Synthesis of 4-((2-((4-cyanophenyl)amino)-7-(1-methyl-1H-pyrrol-2-yl)methyl)-6,7,8,9-tetrahydro-5H-pyrimido[4,5-d]azepine-4-yl)oxy)-3,5-dimethyl-benzonitrile
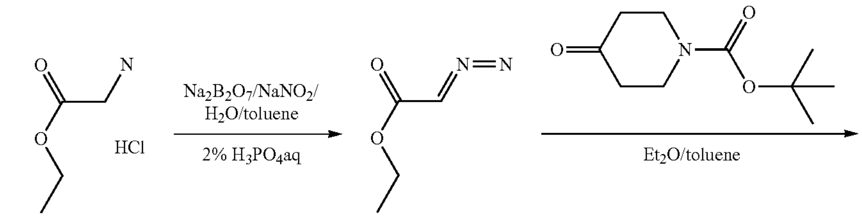
49
50

-continued
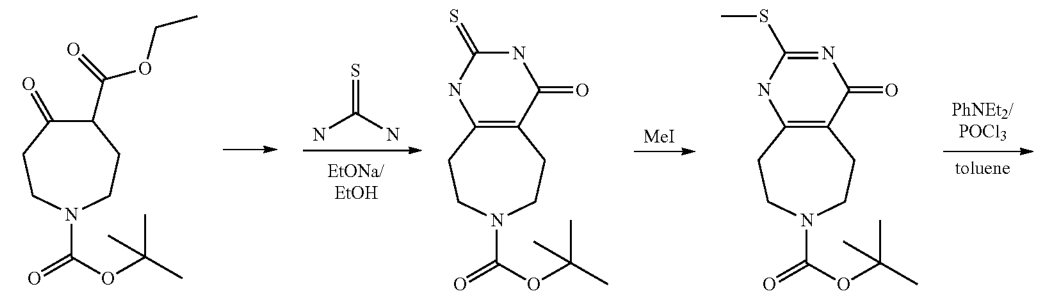
51
52
53
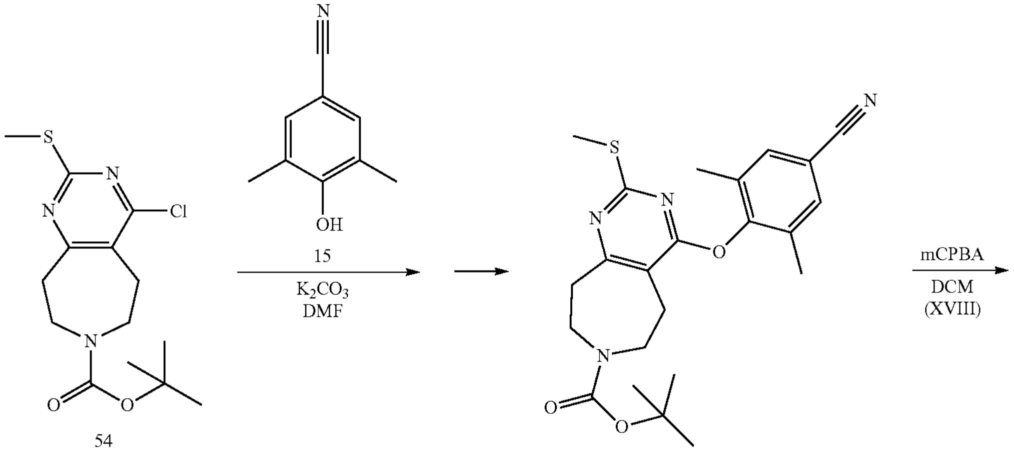
15
54
BB 0273957
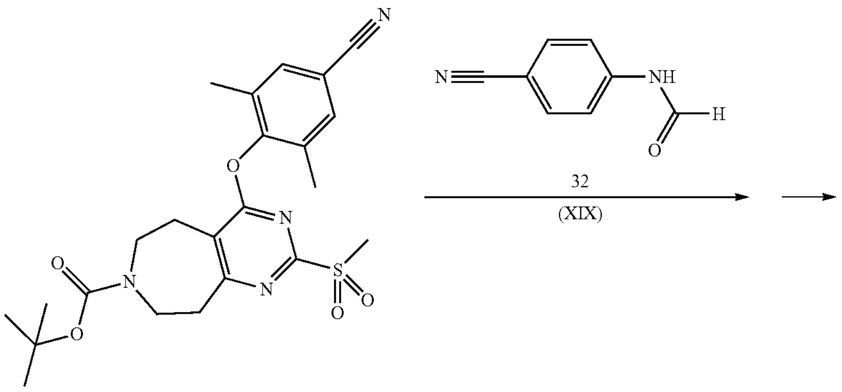
32
BB 0273968

-continued
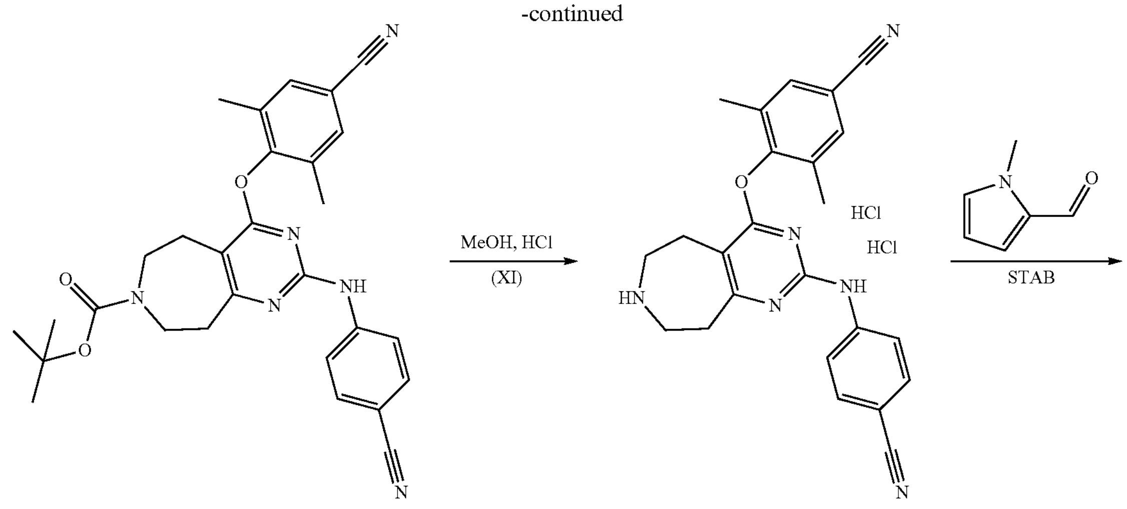
BB 0273972
BB 0273976
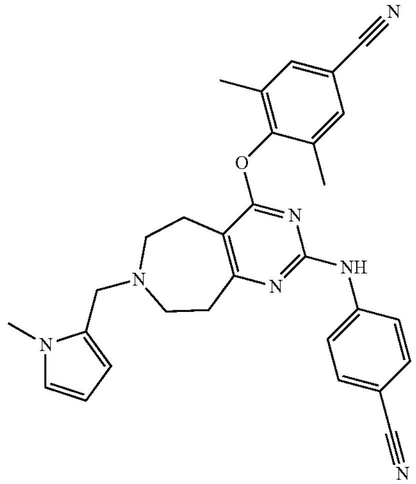
BB 0274074
BB 0274074
$^1$H NMR (400 MHz, $CDCl_3$, δ, ppm): 2.15 (s, 6H), 2.68 (dd, J=12.2 Hz, 10.3 Hz, 4H), 2.94-3.14 (m, 4H), 3.59 (s, 2H), 3.74 (s, 3H), 6.00-6.05 (m, 1H), 6.07 (t, J=3.0 Hz, 1H), 6.61-6.70 (m, 1H), 7.12 (s, 1H), 7.24-7.33 (m, 2H), 7.34-7.42 (m, 2H), 7.48 (s, 2H).
Weight Yield—0.152 g (38%)
LCMS m/z (M+H): 504
Example 30
Synthesis of 4-((2-((4-cyanophenyl)amino)-7-(4-hydroxybenzyl)-6,7,8,9-tetrahydro-5H-pyrimido[4,5-d]azepine-4-yl)oxy)-3,5-dimethylbenzonitrile
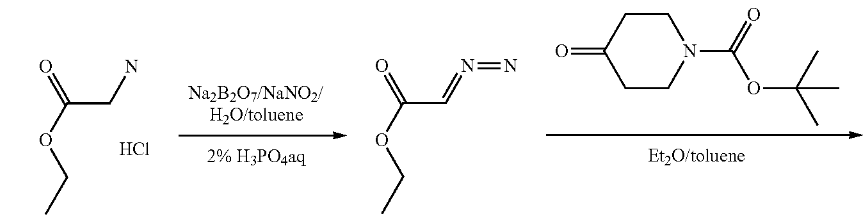
49
50

-continued
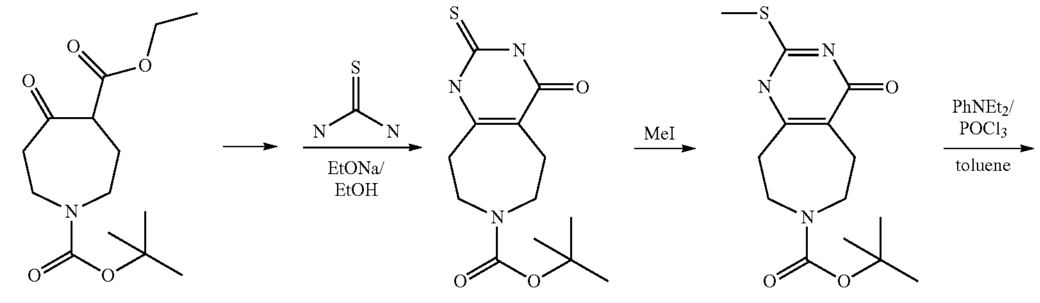
51 52 53
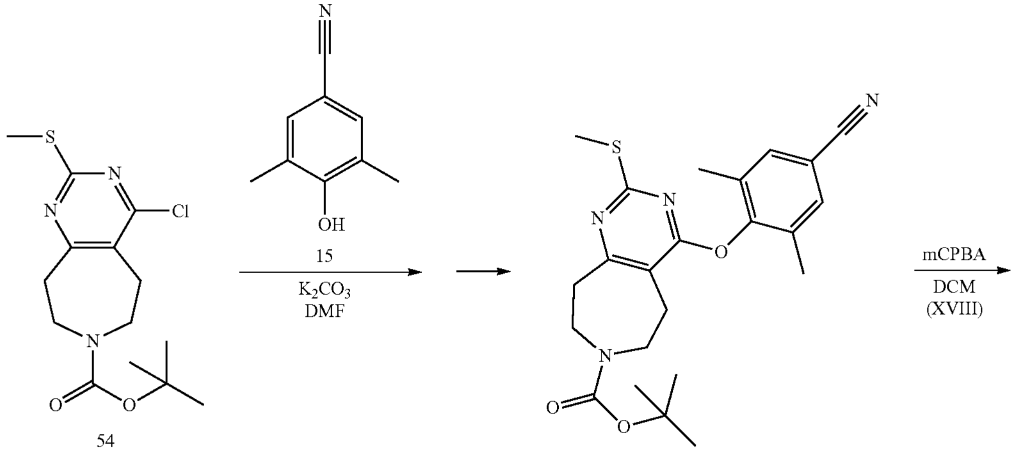
54
BB 0273957
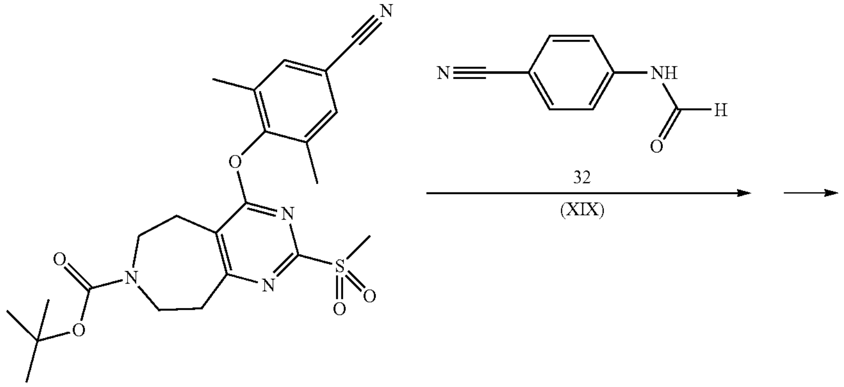
BB 0273968

-continued
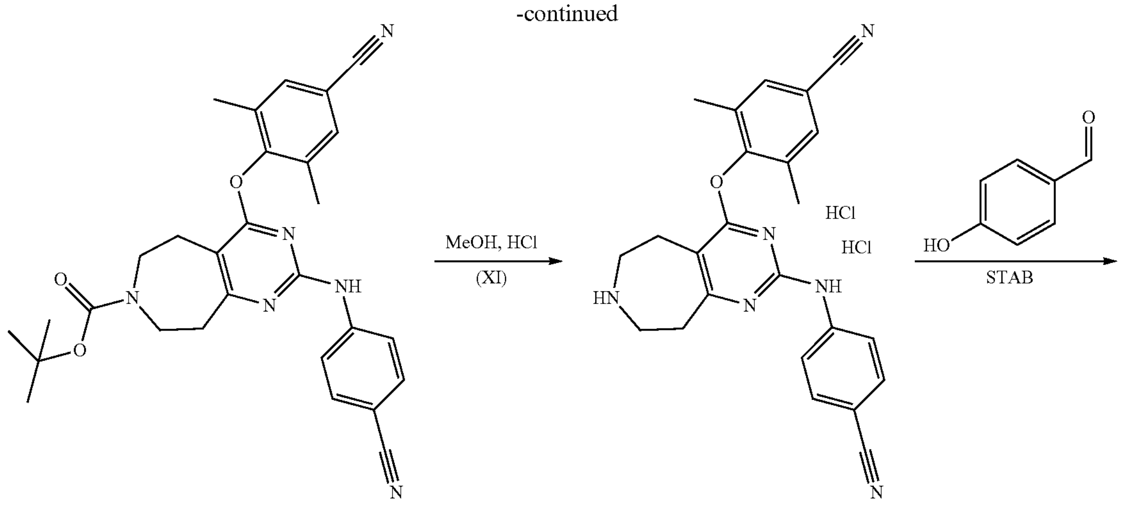
BB 0273972
BB 0273976
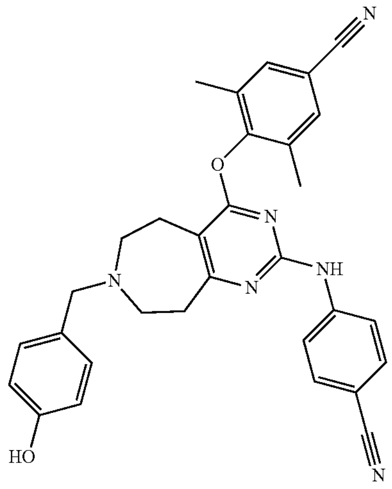
BB 0274075
BB 0274075
$^1$H NMR (400 MHz, DMSO-$d_6$, δ, ppm): 2.08 (s, 6H), 2.62 (broadened singlet, 4H), 2.98 (broadened singlet, 4H), 3.53 (broadened singlet, 2H), 6.72 (d, J=8.3 Hz, 2H), 7.14 (d, J=8.0 Hz, 2H), 7.40 (s, 4H), 7.77 (s, 2H), 9.30 (broadened singlet, 1H), 10.03 (s, 1H).
Weight Yield—0.042 g (24%)
LCMS m/z (M+H): 517
Example 31
Synthesis of 4-((2-((4-cyanophenyl)amino)-7-(1-methoxypropane-2-yl)-6,7,8,9-tetrahydro-5H-pyrimido[4,5-d]azepine-4-yl)oxy)-3,5-dimethylbenzonitrile
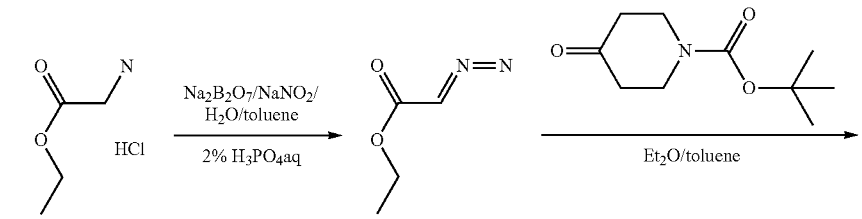
49
50

-continued
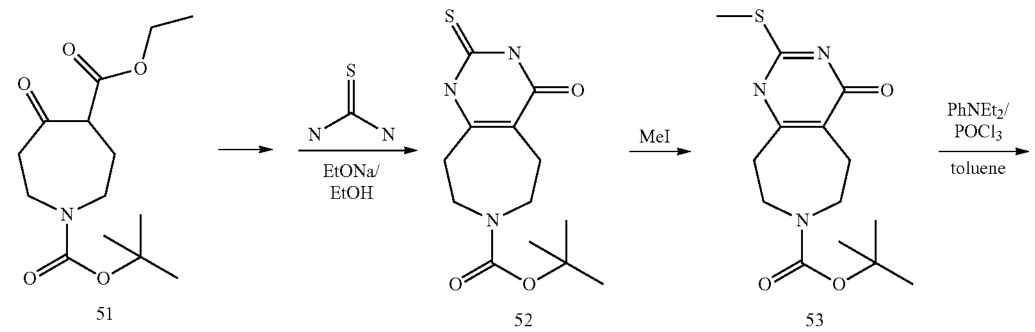
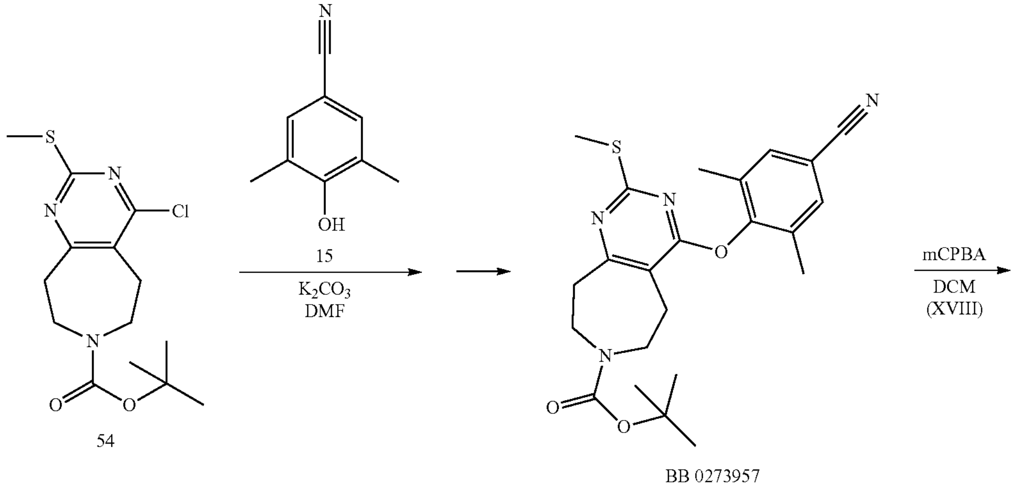
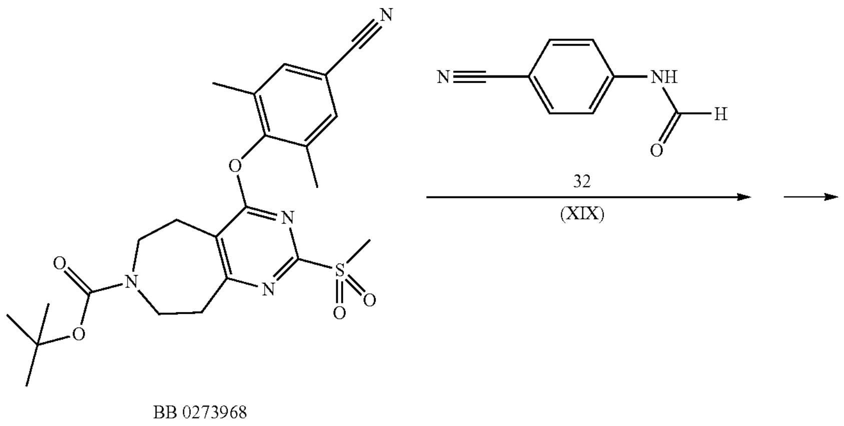

-continued
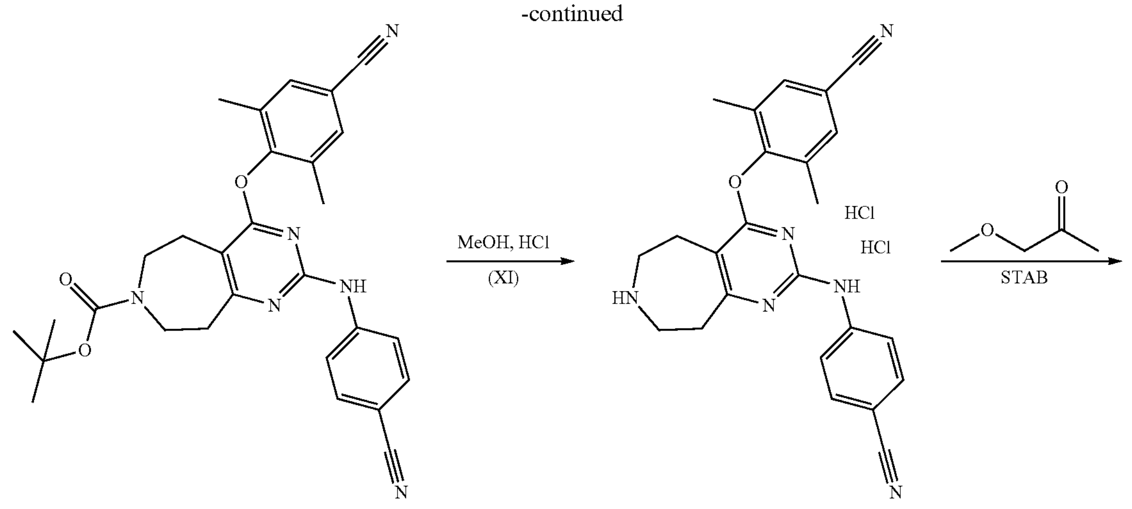
BB 0273972 BB 0273976
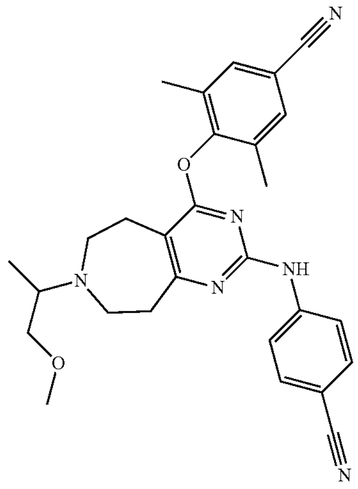
BB 0274080
BB 0274080
$^1$H NMR (400 MHz, $CDCl_3$, δ, ppm): 1.06 (d, J=5.8 Hz, 3H), 2.04-2.27 (m, 6H), 2.81 (broadened singlet, 4H), 3.04 (broadened singlet, 5H), 3.32 (broadened singlet, 1H), 3.36 (broadened singlet, 3H), 3.51 (d, J=6.7 Hz, 1H), 7.14 (broadened singlet, 1H), 7.24-7.33 (m, 2H), 7.36 (d, J=7.90 Hz, 2H), 7.47 (broadened singlet, 2H).
Weight Yield—0.128 g (48%)
LCMS m/z (M+H): 483
Example 32
Synthesis of 4-((7-(cyanomethyl)-2-((4-cyanophenyl)amino)-6,7,8,9-tetrahydro-5H-pyrimido[4,5-d]azepine-4-yl)oxy)-3,5-dimethylbenzonitrile
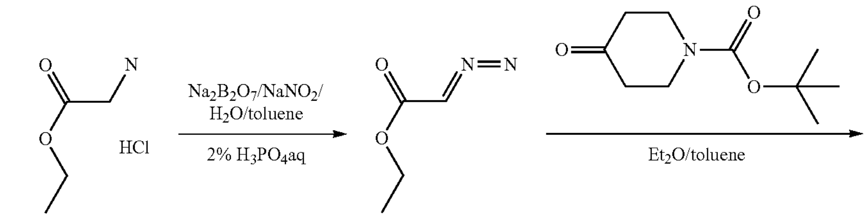
49 50

-continued
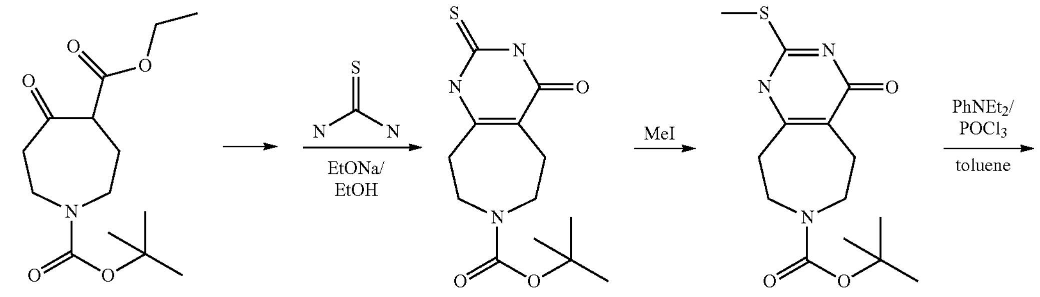
51 52 53
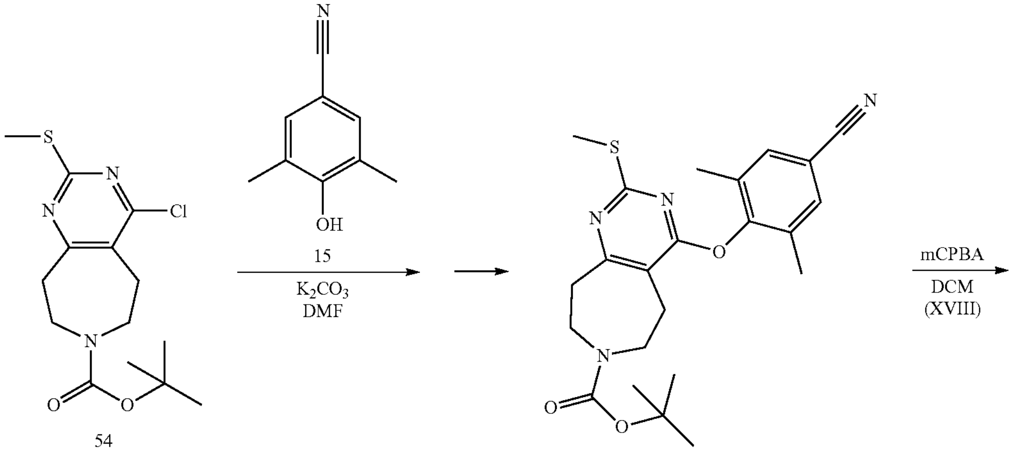
54
BB 0273957
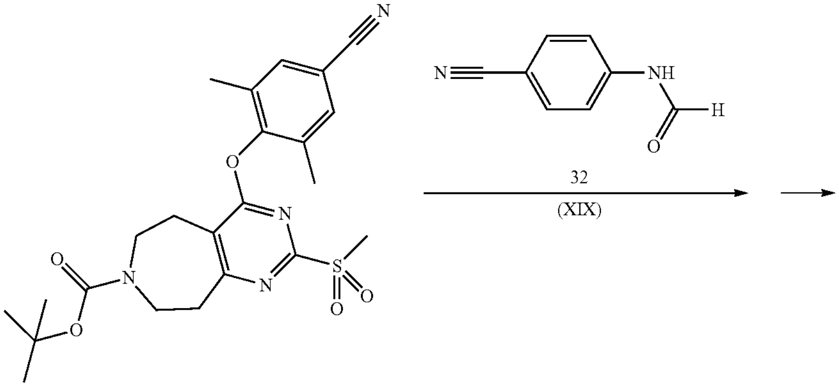
BB 0273968

-continued
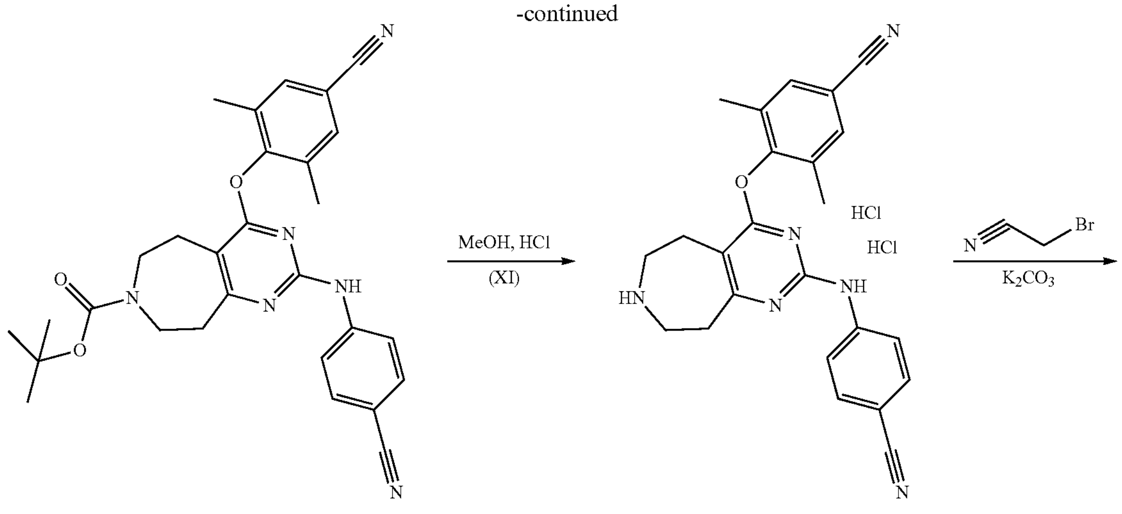
BB 0273972
BB 0273976
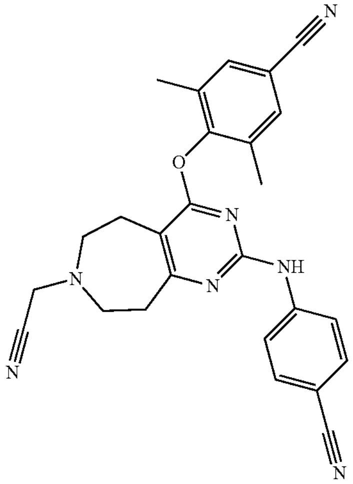
BB 0274095
BB 0274095
$^1$H NMR (400 MHz, DMSO-$d_6$, δ, ppm): 2.10 (s, 6H), 2.72 (broadened singlet, 4H), 3.03 (broadened singlet, 4H), 3.89 (s, 2H), 7.42 (broadened singlet, 4H), 7.78 (s, 2H), 10.05 (broadened singlet, 1H).
Weight Yield—0.042 g (24%)
LCMS m/z (M+H): 450

Example 33
Synthesis of tert-butyl 2-(4-(4-cyano-2,6-dimethylphenoxy)-2-((4-cyanophenyl)amino)-5,6,7,8-tetrahydropyrido[4,3-d]pyrimidine-6-carbonyl)pyrrolidine-1-carboxylate
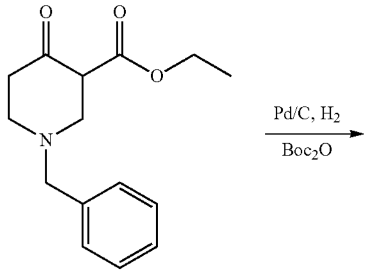
11
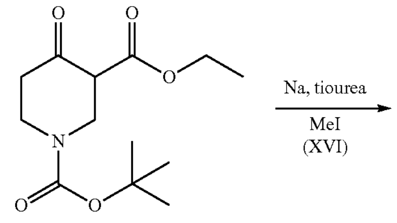
12
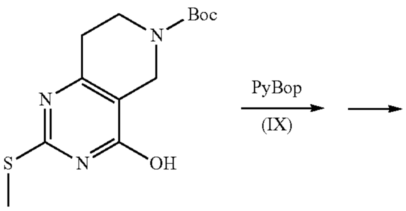
13
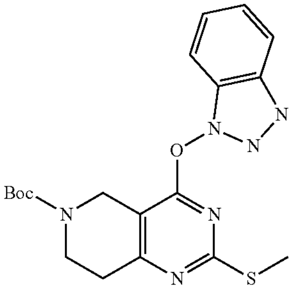
14
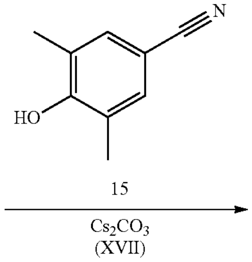
15
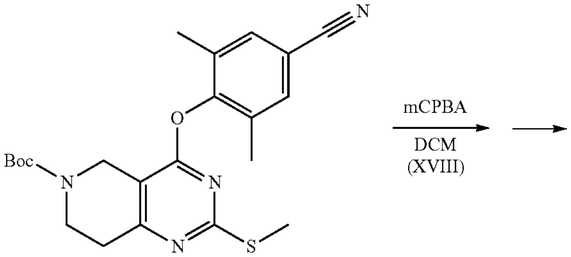
BB 0273947
-continued
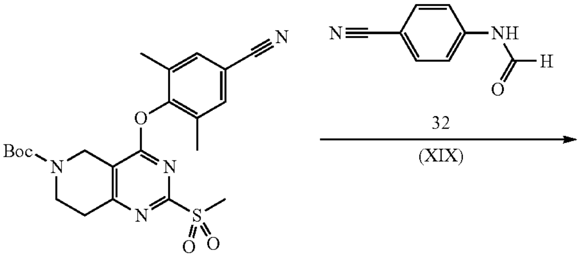
32
BB 0273960
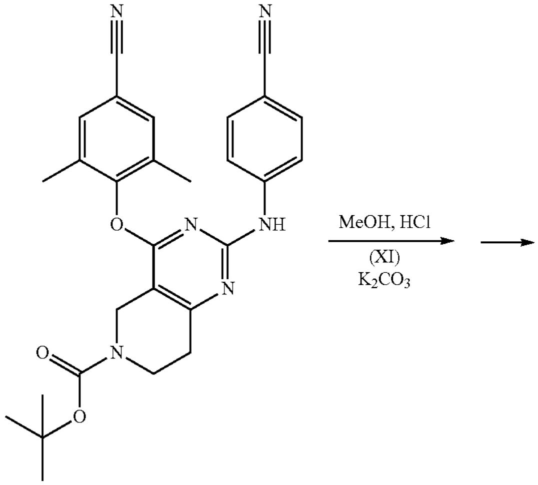
BB 0273961
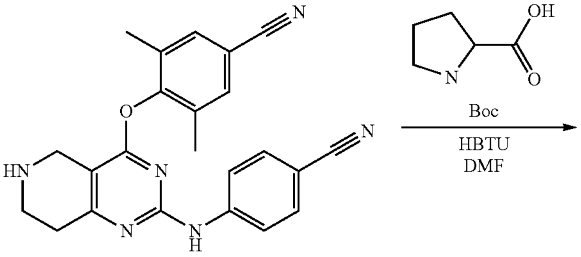
BB 0273963
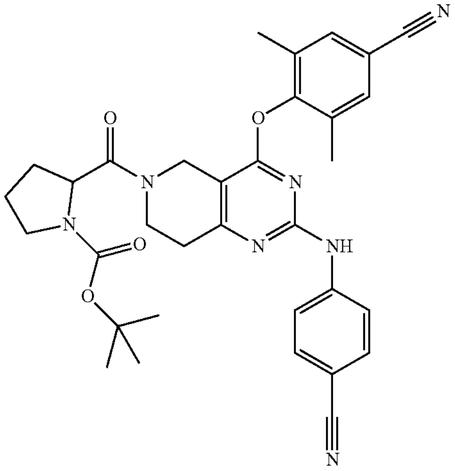
BB 0274097

BB 0274097
$^1$H NMR (400 MHz, $CDCl_3$, 6, ppm): 1.40-1.48 (m, 9H), 2.18 (s, 6H), 2.80-3.09 (m, 2H), 3.64-4.00 (m, 2H), 4.59-4.92 (m, 2H), 5.25-5.63 (m, 1H), 7.34-7.44 (m, 4H), 7.48 (s, 2H).
Weight Yield—0.068 g (67%)
LCMS m/z (M+H): 494 (M-Boc).
Example 34
Synthesis of 4-((2-((4-cyanophenyl)amino)-6-(pyrrolidine-2-carbonyl)-5,6,7,8-tetrahydropyrido[4,3-d]pyrimidine-4-yl)oxy)-3,5-dimethylbenzonitrile
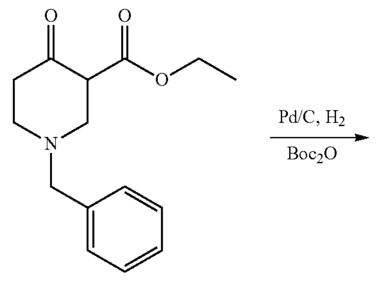
11
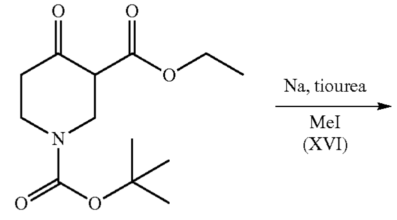
12
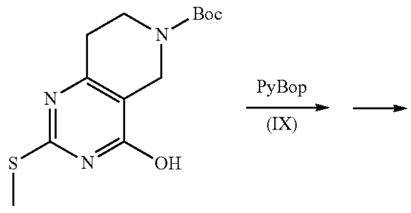
13
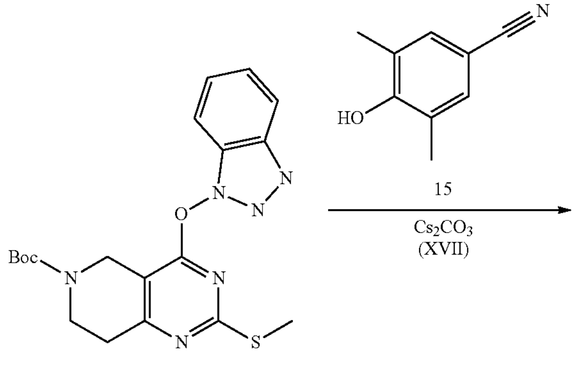
14
-continued
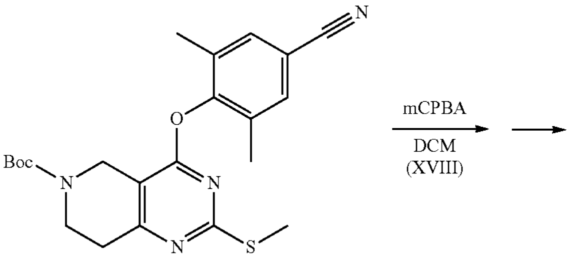
BB 0273947
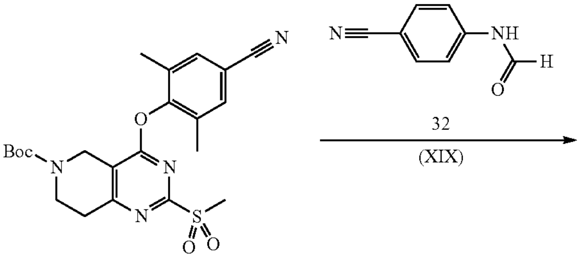
BB 0273960
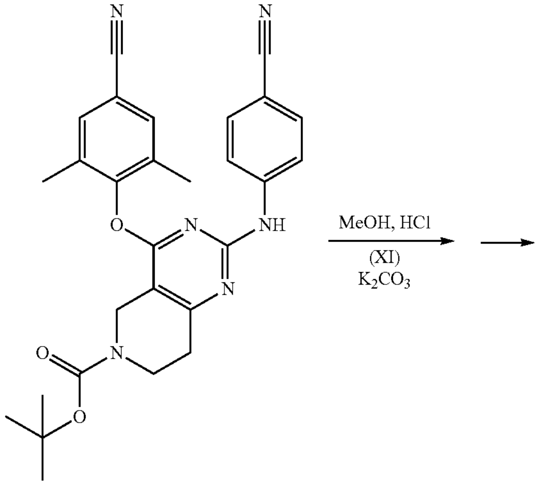
BB 0273961
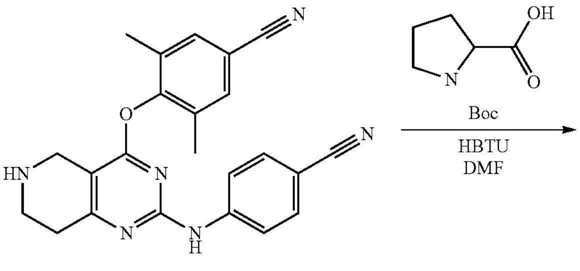
BB 0273963

-continued
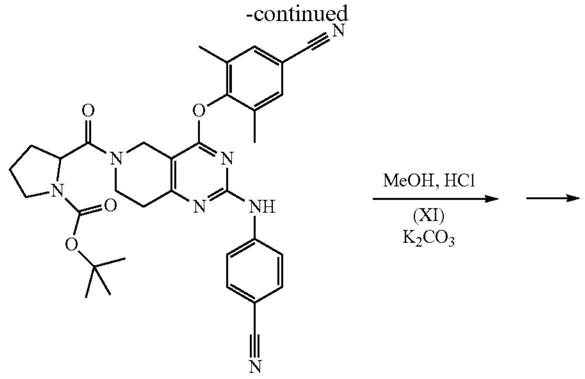
BB 0274097
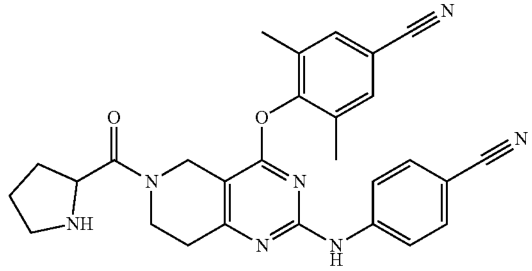
BB 0274098
BB 0274098
$^1$H NMR (400 MHz, DMSO-$d_6$, δ, ppm): 1.91 (broadened singlet, 3H), 2.07-2.17 (m, 6H), 2.78-2.98 (m, 2H), 3.10-3.32 (m, 2H), 3.90 (broadened singlet, 2H), 4.50-4.85 (m, 3H), 7.46 (broadened singlet, 4H), 7.79 (s, 2H), 8.35-8.63 (m, 1H), 10.12 (broadened singlet, 2H).
Weight Yield—0.032 g (88%)
LCMS m/z (M+H): 494
Example 35
Synthesis of 4-((6-(azetidine-3-carbonyl)-2-((4-cyanophenyl)amino)-5,6,7,8-tetrahydropyrido[4,3-d]pyrimidine-4-yl)oxy)-3,5-dimethylbenzonitrile
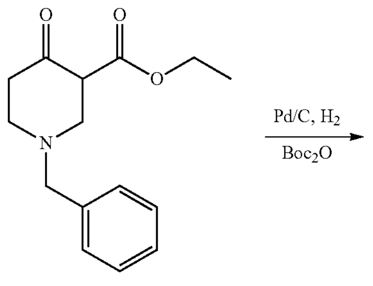
11
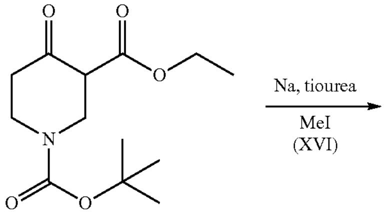
12
-continued
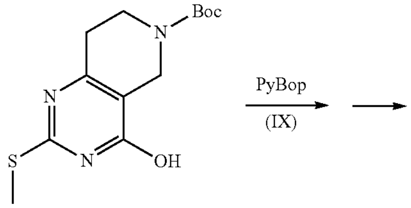
13
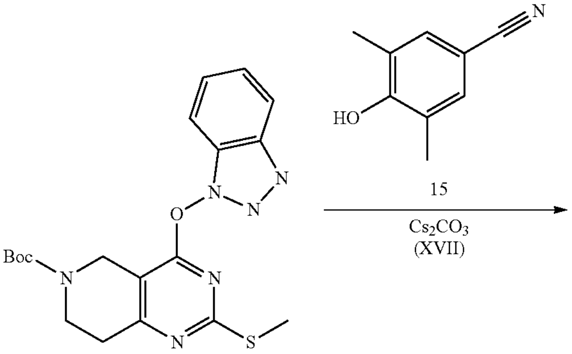
14
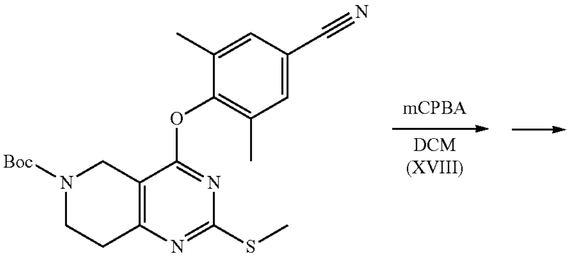
BB 0273947
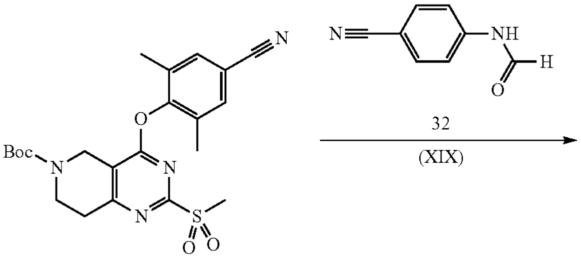
BB 0273960

-continued
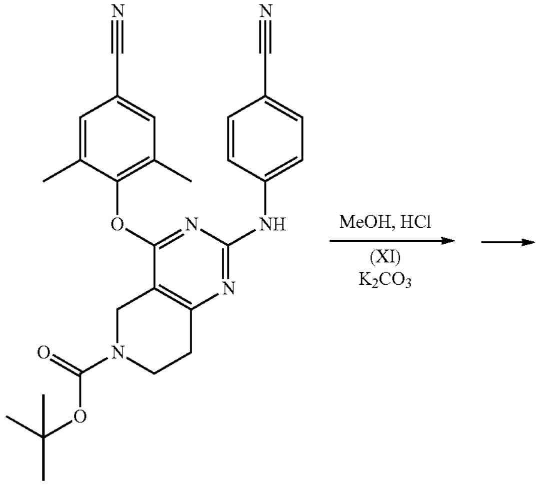
BB 0273961
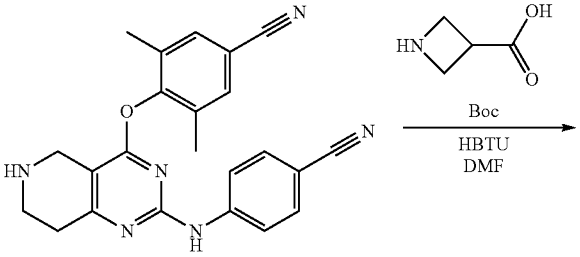
BB 0273963
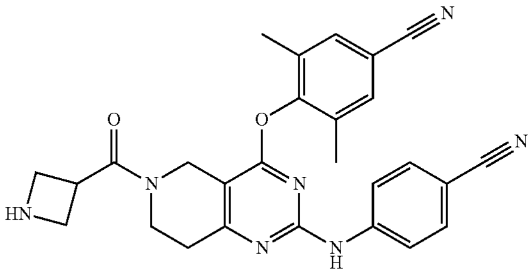
BB 0274099
BB 0274099
$^1$H NMR (400 MHz, DMSO-$d_6$, δ, ppm): 2.10 (s, 6H), 2.73-2.91 (m, 2H), 3.00-3.56 (m, 1H), 3.65 (s, 2H), 4.05-4.09 (m, 2H), 4.25-4.31 (m, 2H), 4.68 (s, 2H), 7.46 (broadened singlet, 4H), 7.79 (s, 2H).
Weight Yield—0.075 g (52%)
LCMS m/z (M+H): 480
Example 36
Synthesis of 4-((2-((4-cyanophenyl)amino)-6-(pyrazine-2-carbonyl)-5,6,7,8-tetrahydropyrido[4,3-d]pyrimidine-4-yl)oxy)-3,5-dimethylbenzonitrile
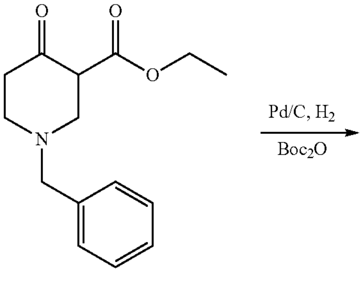
11
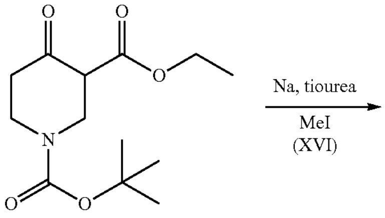
12
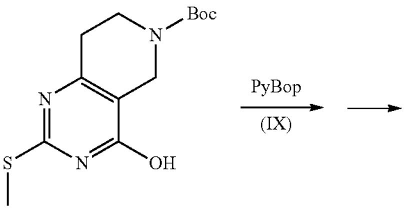
13
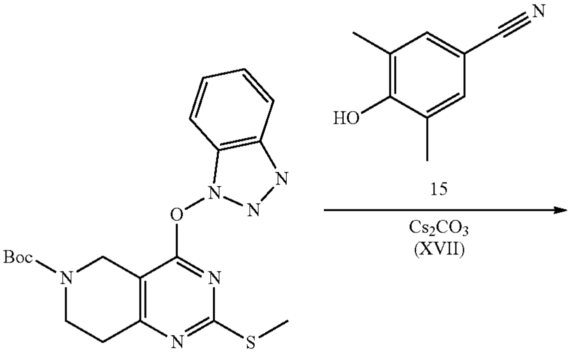
14
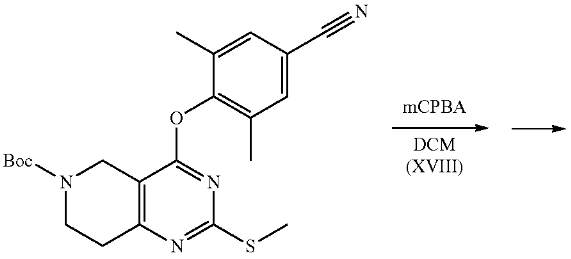
BB 0273947

-continued
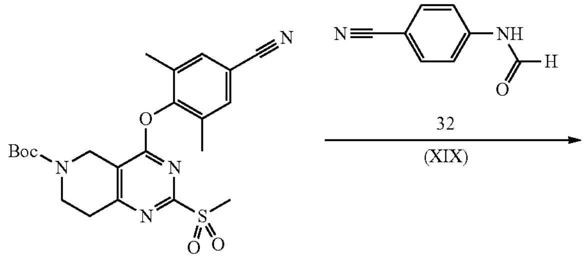
BB 0273960
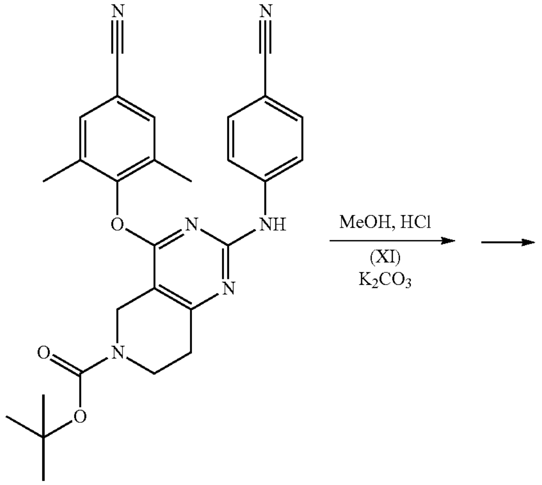
BB 0273961
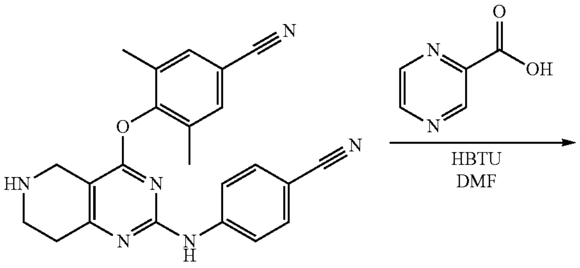
BB 0273963
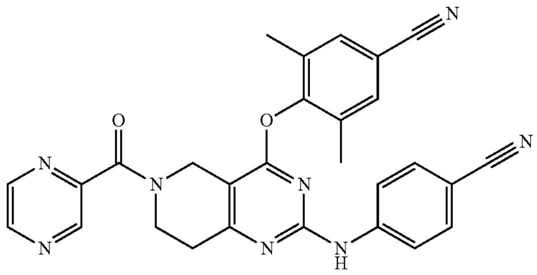
BB 0274100
BB 0274100
$^1$H NMR (400 MHz, DMSO-$d_6$, δ, ppm): 2.19 (s, 6H), 3.00-3.14 (m, 2H), 3.73-4.31 (m, 2H), 4.84-5.05 (m, 2H), 7.32-7.60 (m, 9H).
Weight Yield—0.012 g (20%)
LCMS m/z (M+H): 503
Example 37
Synthesis of (S)-tert-butyl (1-(4-(4-cyano-2,6-dimethylphenoxy)-2-((4-cyanophenyl)amino)-7,8-dihydropyrido[4,3-d]pyrimidine-6(5H)-yl)-1-oxopropane-2-yl)carbamate
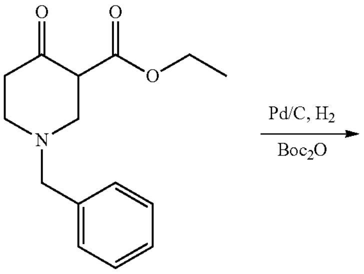
11
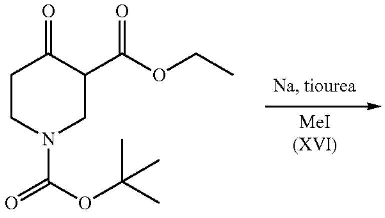
12
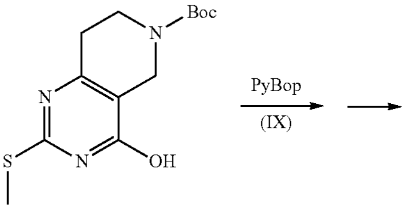
13
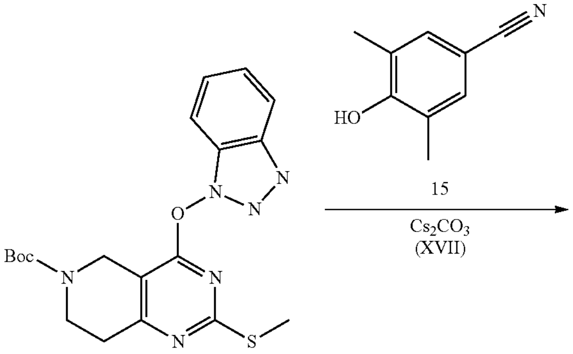
14
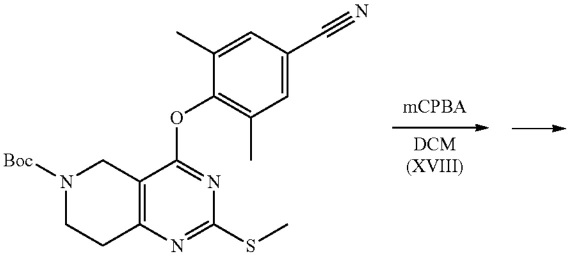
BB 0273947

-continued
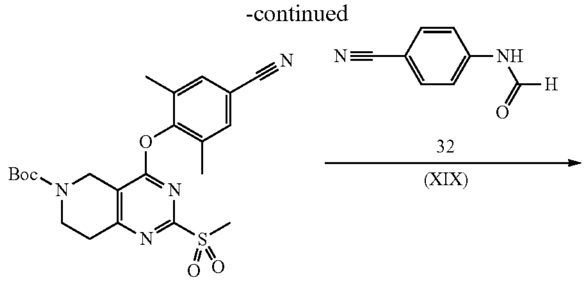
BB 0273960
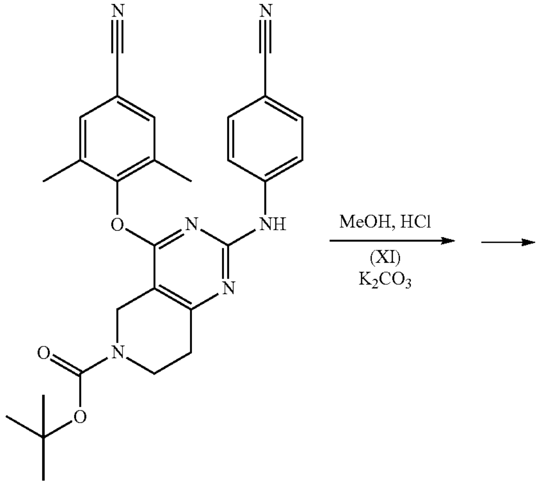
BB 0273961
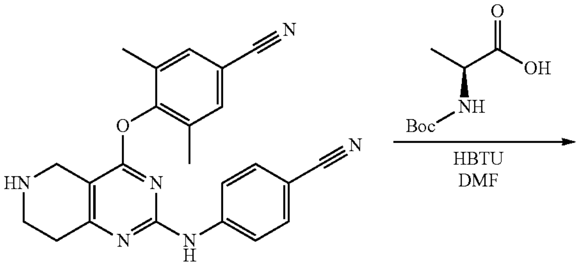
BB 0273963
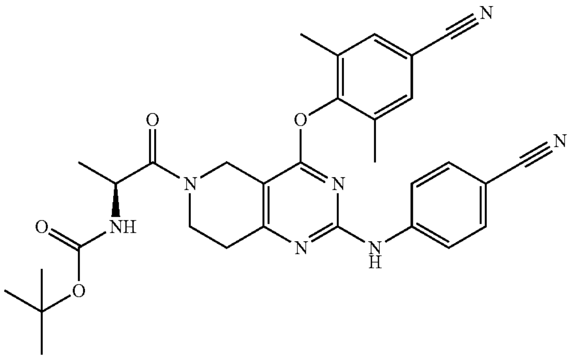
BB 0274101
BB 0274101
$^1$H NMR (400 MHz, DMSO-$d_6$, δ, ppm): 1.35-1.49 (m, 9H), 1.61 (s, 3H), 2.17 (s, 6H), 2.55-2.86 (m, 1H), 3.07 (broadened singlet, 2H), 3.62-4.07 (m, 2H), 4.56 (s, 2H), 4.94-5.57 (m, 2H), 7.35 (broadened singlet, 2H), 7.39-7.44 (m, 2H), 7.48 (s, 2H).
Weight Yield—0.075 g (52%)
LCMS m/z (M+H): 468 (M-Boc).
Example 38
Synthesis of (S)-4-((6-(2-aminopropanoyl)-2-((4-cyanophenyl)amino)-5,6,7,8-tetrahydropyrido[4,3-d]pyrimidine-4-yl)oxy)-3,5-dimethylbenzonitrile
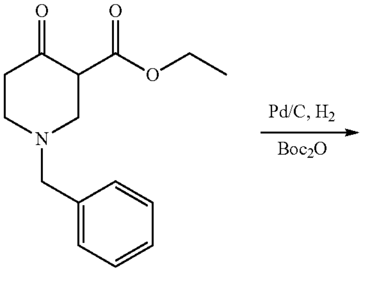
11
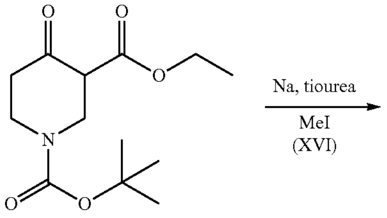
12
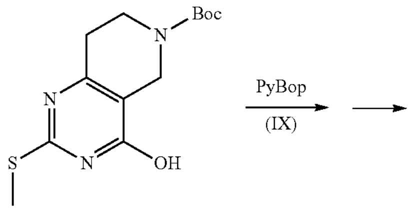
13
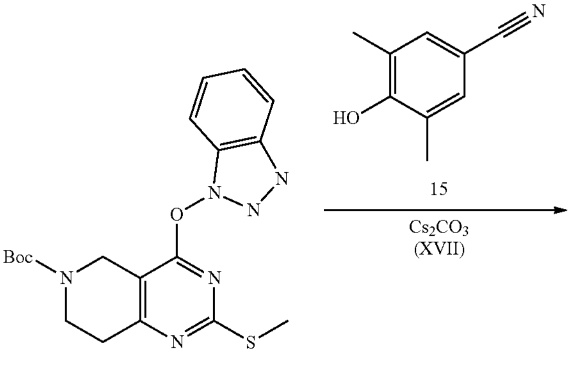
14
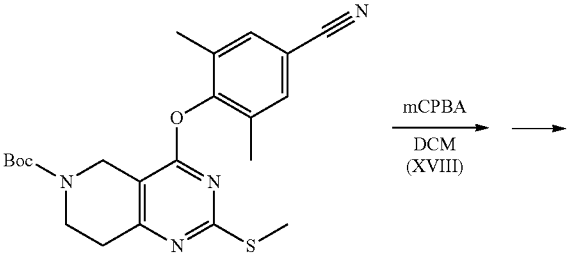
BB 0273947

-continued
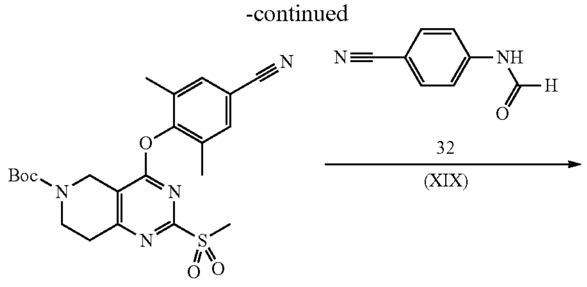
BB 0273960
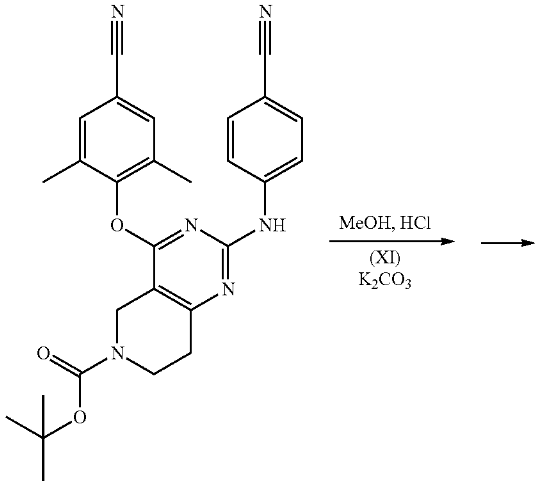
BB 0273961
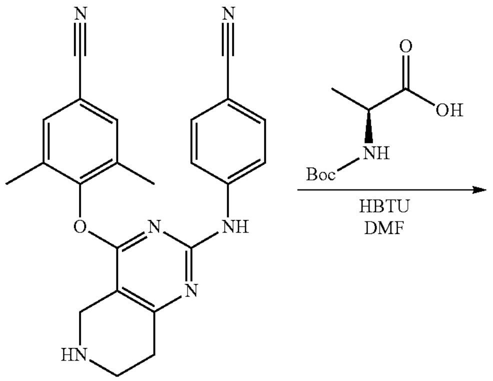
BB 0273963
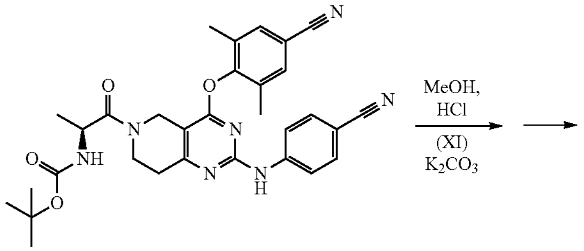
BB 0274101
-continued
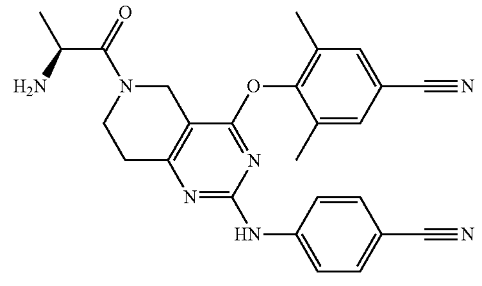
BB 0274102
BB 0274102
$^1$H NMR (400 MHz, DMSO-$d_6$, δ, ppm): 1.28-1.44 (m, 3H), 2.11 (s, 6H), 2.74-2.84 (m, 1H), 3.73-4.03 (m, 2H), 4.49-4.61 (m, 2H), 4.71-4.77 (m, 2H), 7.46 (broadened singlet, 4H), 7.79 (s, 2H), 7.94 (s, 1H), 8.33 (broadened singlet, 2H).
Weight Yield—0.0233 g (88%)
LCMS m/z (M+H): 468.
Example 39
Synthesis of (S)-tert-butyl (1-(4-(4-cyano-2,6-dimethylphenoxy)-2-((4-cyanophenyl)amino)-7,8-dihydropyrido[4,3-d]pyrimidine-6(5H)-yl)-1-oxo-3-phenylpropane-2-yl)carbamate
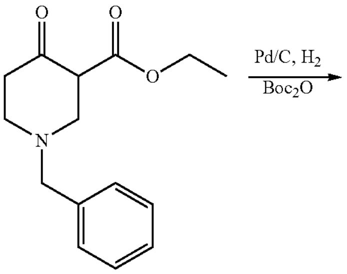
11
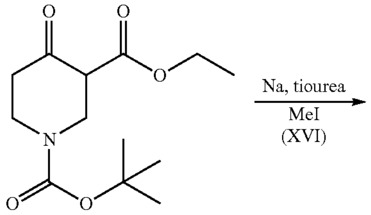
12
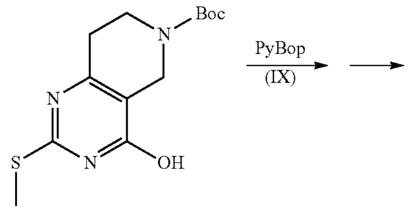
13

-continued
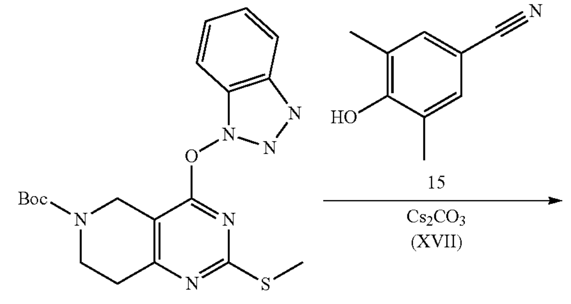
14
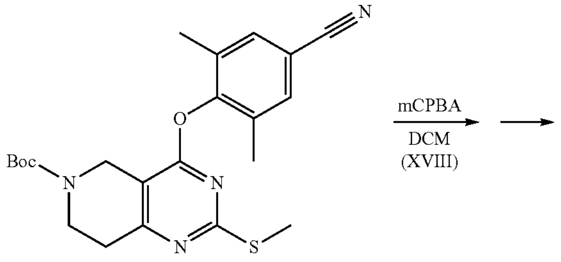
BB 0273947
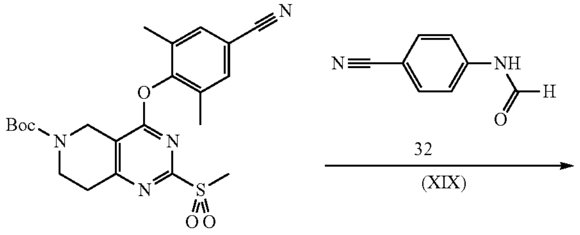
BB 0273960
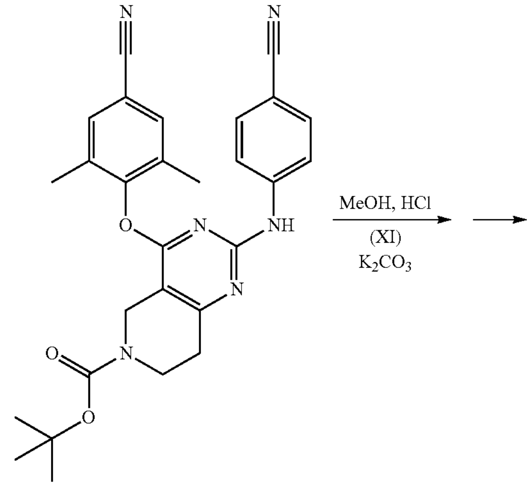
BB 0273961
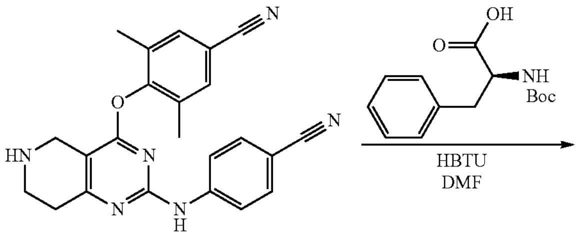
BB 0273963
-continued
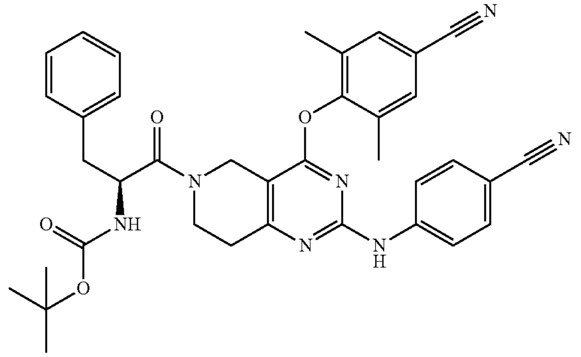
BB 0274103
BB 0274103
$^{1}$H NMR (400 MHz, DMSO-$d_6$, δ, ppm): 1.41-1.51 (m, 9H), 2.15-2.20 (m, 6H), 2.83-2.96 (m, 2H), 3.38-4.01 (m, 6H), 4.47-4.96 (m, 4H), 6.90-7.14 (m, 2H), 7.41 (broadened singlet, 6H), 7.50 (m, 3H).
Weight Yield—0.082 g (63%)
LCMS m/z (M+H): 544 (M-Boc).
Example 40
Synthesis of (S)-4-((6-(2-amino-3-phenylpropanoyl)-2-((4-cyanophenyl)amino)-5,6,7,8-tetrahydropyrido[4,3-d]pyrimidine-4-yl)oxy)-3,5-dimethylbenzonitrile
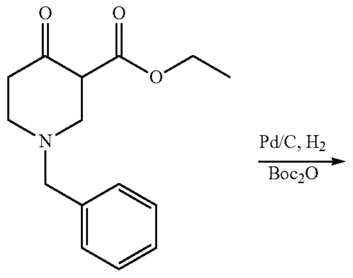
11
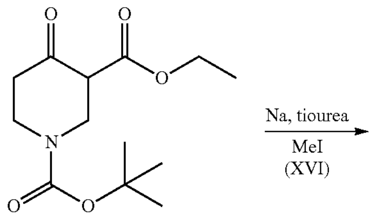
12
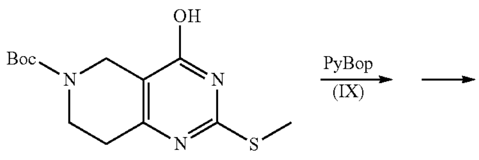
13

-continued
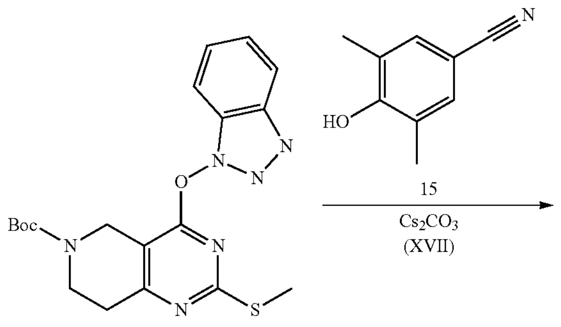
14
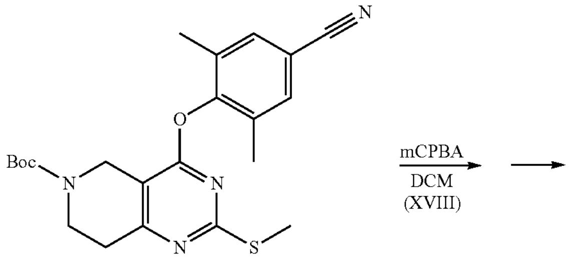
BB 0273947
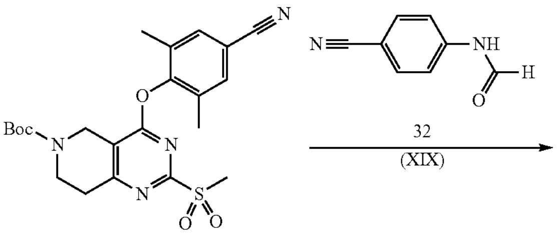
BB 0273960
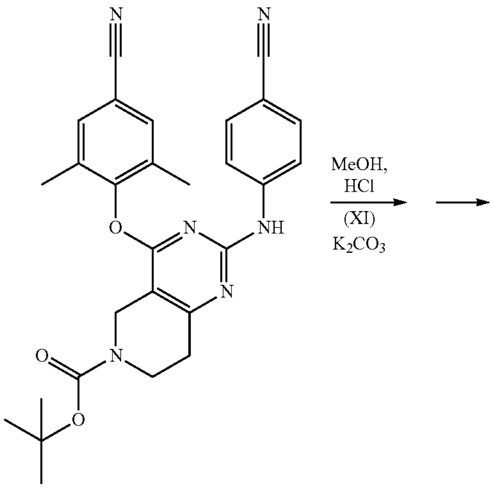
BB 0273961
-continued
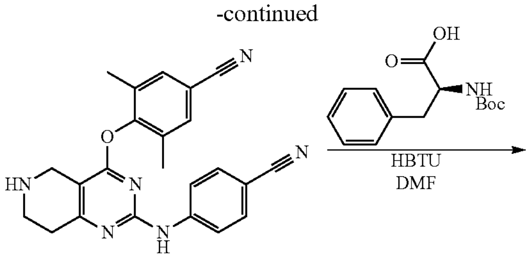
BB 0273963
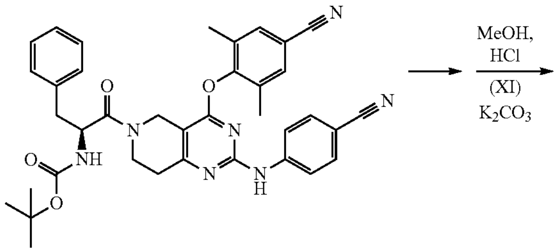
BB 0274103
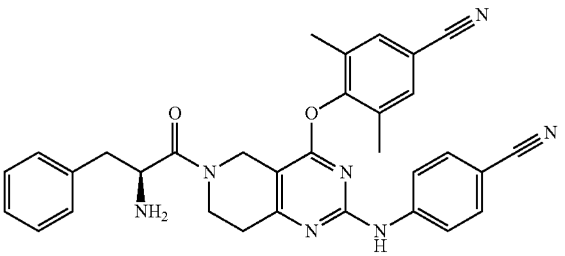
BB 0274111
BB 0274111
$^1$H NMR (400 MHz, DMSO-$d_6$, δ, ppm): 2.09 (broadened singlet, 6H), 2.59-2.82 (m, 1H), 3.15 (broadened singlet, 2H), 3.33-3.60 (m, 1H), 3.67-4.08 (m, 1H), 4.40-4.56 (m, 2H), 4.79 (broadened singlet, 2H), 7.26 (m, 5H), 7.43 (broadened singlet, 4H), 7.79 (broadened singlet, 2H), 8.46 (broadened singlet, 2H), 10.10 (broadened singlet, 1H).
Weight Yield—0.078 g (86%)
LCMS m/z (M+H): 544.

Example 41
Synthesis of 4-((2-((4-cyanophenyl)amino)-7-(2-morpholinoEthyl)-6,7,8,9-tetrahydro-5H-pyrimido[4,5-d]azepine-4-yl)oxy)-3,5-dimethylbenzonitrile
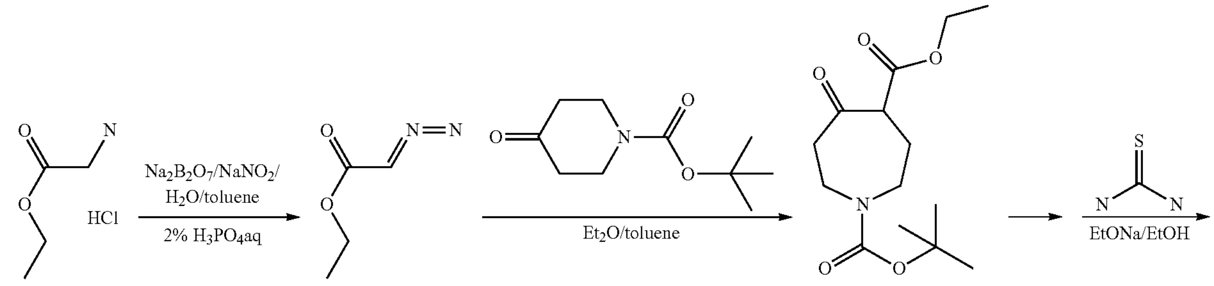
49 50 51
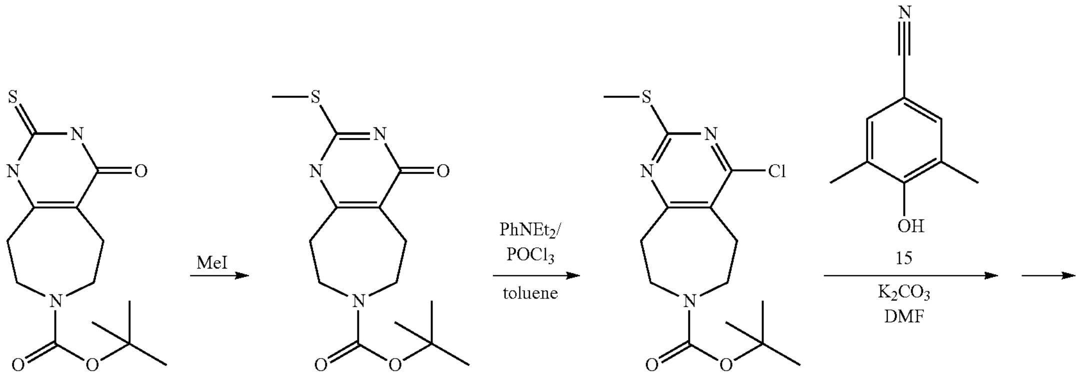
52 53 54
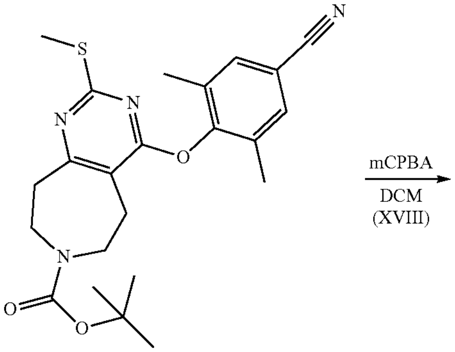
BB 0273957
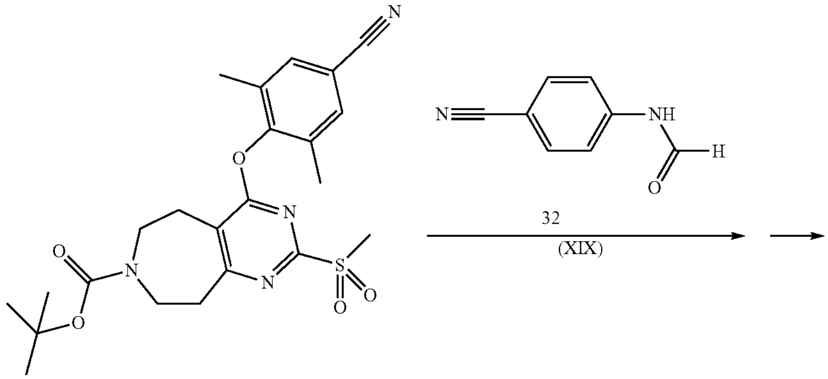
BB 0273972

-continued
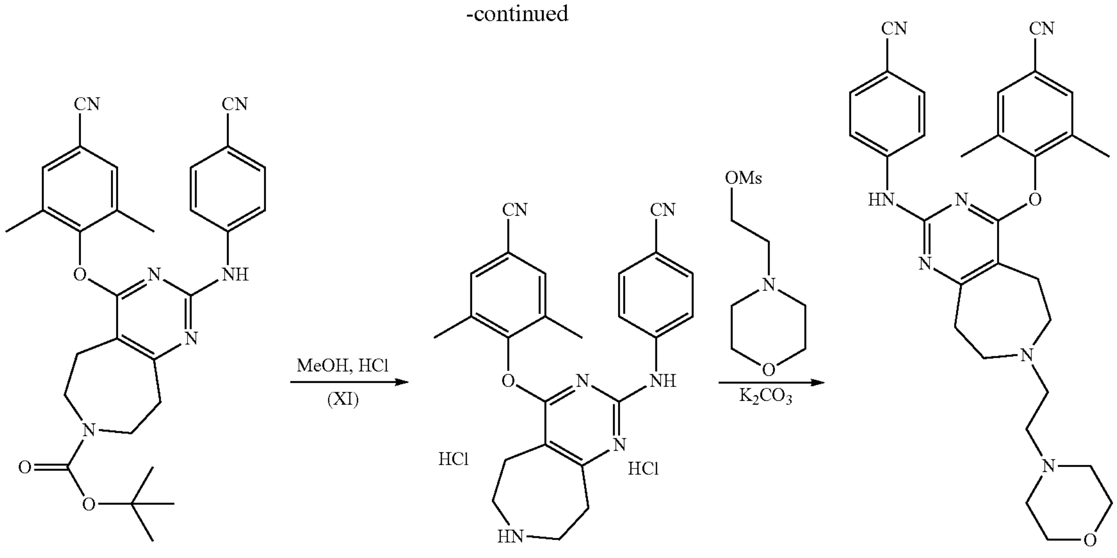
BB 0273972 BB 0274118 BB 0274118
BB 0274118
$^1$H NMR (400 MHz, $CDCl_3$, δ, ppm): 2.14 (s, 6H), 2.52 (broadened singlet, 4H), 2.58 (t, J=6.90 Hz, 2H), 2.70-2.86 (m, 6H), 3.00-3.12 (m, 4H), 3.73 (t, J=4.5, 4H), 7.09 (s, 1H), 7.28-7.33 (m, 2H), 7.34-7.40 (m, 2H), 7.48 (s, 2H).
Weight Yield—0.014 g (24%)
LCMS m/z (M+H): 524
Example 42
Synthesis of (R)-tert-butyl (1-(4-(4-cyano-2,6-dimethylphenoxy)-2-((4-cyanophenyl)amino)-7,8-dihydropyrido[4,3-d]pyrimidine-6(5H)-yl)-3-hydroxy-1-oxopropane-2-yl)carbamate
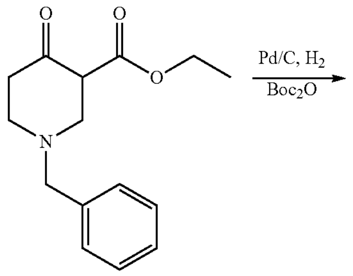
11
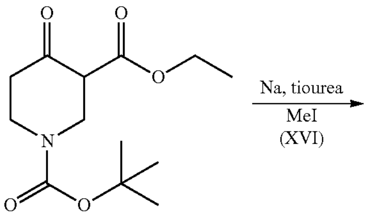
12
-continued
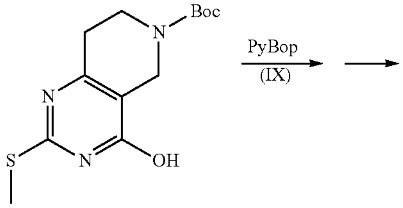
13
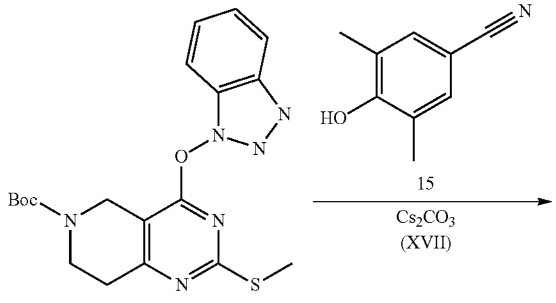
14
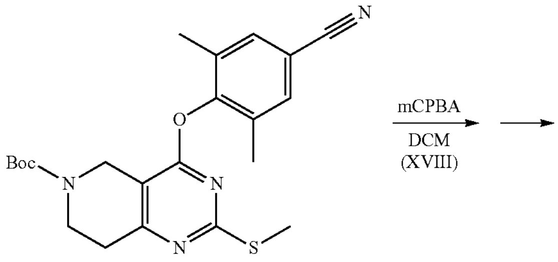
BB 0273947

-continued
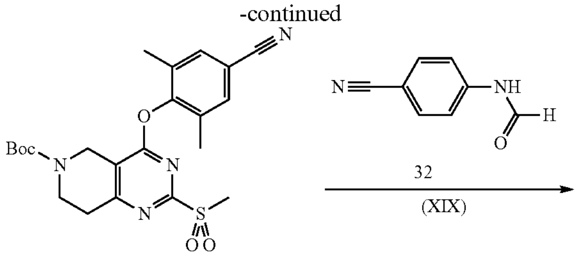
BB 0273960
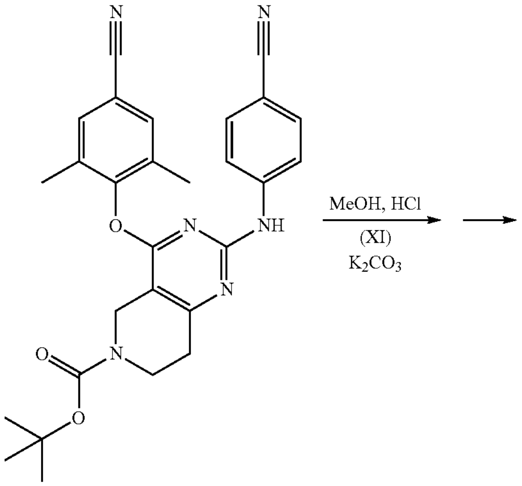
BB 0273961
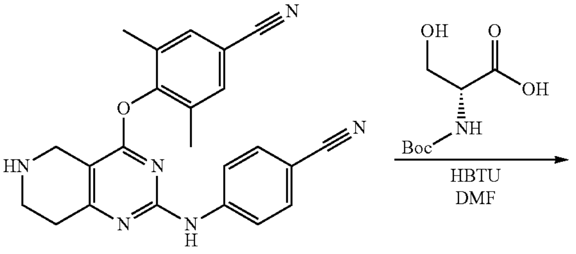
BB 0273963
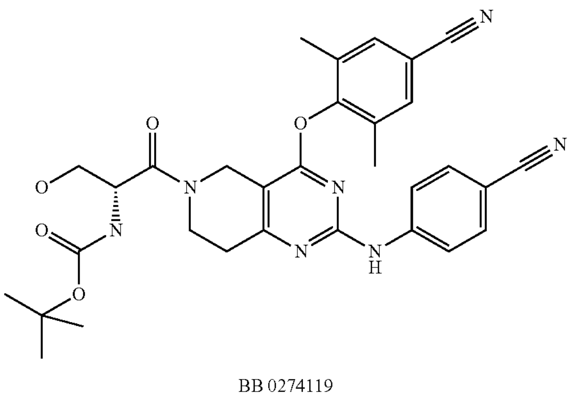
BB 0274119
BB 0274119
$^1$H NMR (400 MHz, $CDCl_3$, δ, ppm): 1.45 (s, 9H), 2.17 (s, 6H), 3.71-4.17 (m, 4H), 4.59-5.03 (m, 3H), 5.37-5.77 (m, 1H), 7.31-7.45 (m, 4H), 7.49 (s, 2H).
Weight Yield—0.011 g (42%)
LCMS m/z (M+H): 484 (M-Boc).
Example 43
Synthesis of tert-butyl (1-(4-(4-cyano-2,6-dimethylphenoxy)-2-((4-cyanophenyl)amino)-7,8-dihydropyrido[4,3-d]pyrimidine-6(5H)-yl)-4-(methylthio)-1-oxobutane-2-yl)carbamate
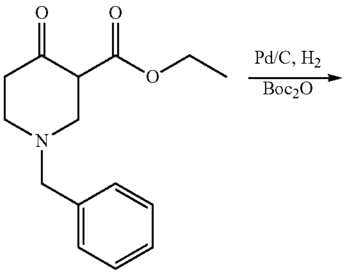
11
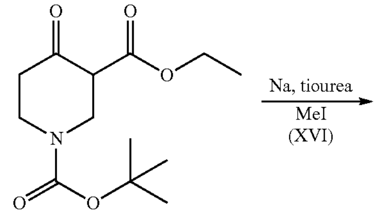
12
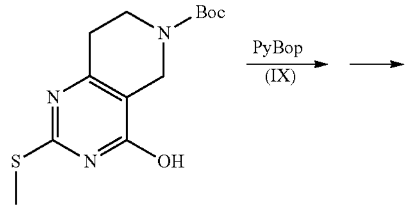
13
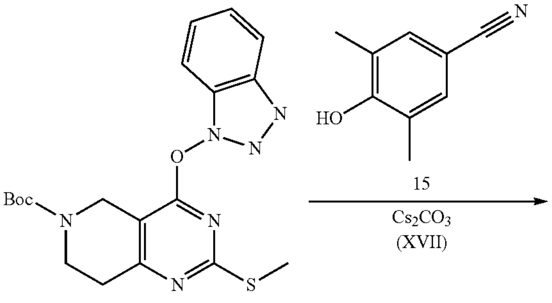
14
15
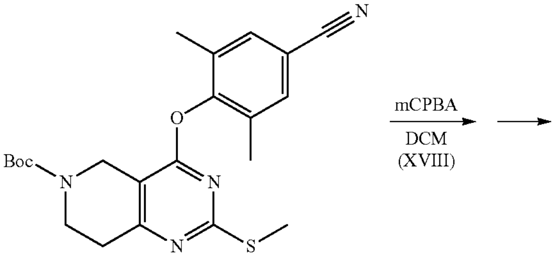
BB 0273947

-continued
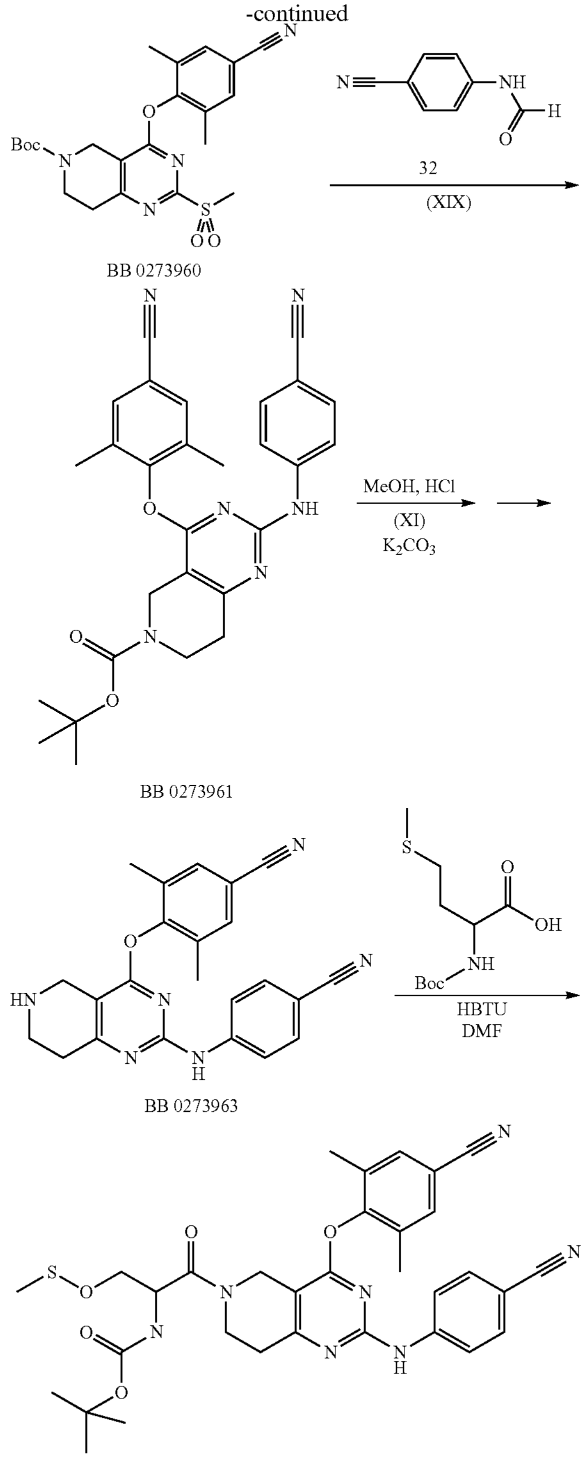
BB 0273960
BB 0273961
BB 0273963
BB 0274120
BB 0274120
$^1$H NMR (400 MHz, $CDCl_3$, δ, ppm): 1.43 (broadened singlet, 10H), 2.07 (s, 3H), 2.11-2.23 (m, 6H), 2.45-2.68 (m, 2H), 3.72-4.14 (m, 2H), 4.47-4.73 (m, 1H), 4.80-5.02 (m, 2H), 5.23-5.52 (m, 1H), 7.39 (d, J=4.6 Hz, 4H), 7.48 (broadened singlet, 2H), 8.01 (s, 2H).
Weight Yield—0.089 g (55%)
LCMS m/z (M+H): 528 (M-Boc).
Example 44
Synthesis of 4-((6-(2-amino-3-(1H-pyrazole-4-yl)propanoyl)-2-((4-cyanophenyl)amino)-5,6,7,8-tetrahydropyrido[4,3-d]pyrimidine-4-yl)oxy)-3,5-dimethylbenzonitrile
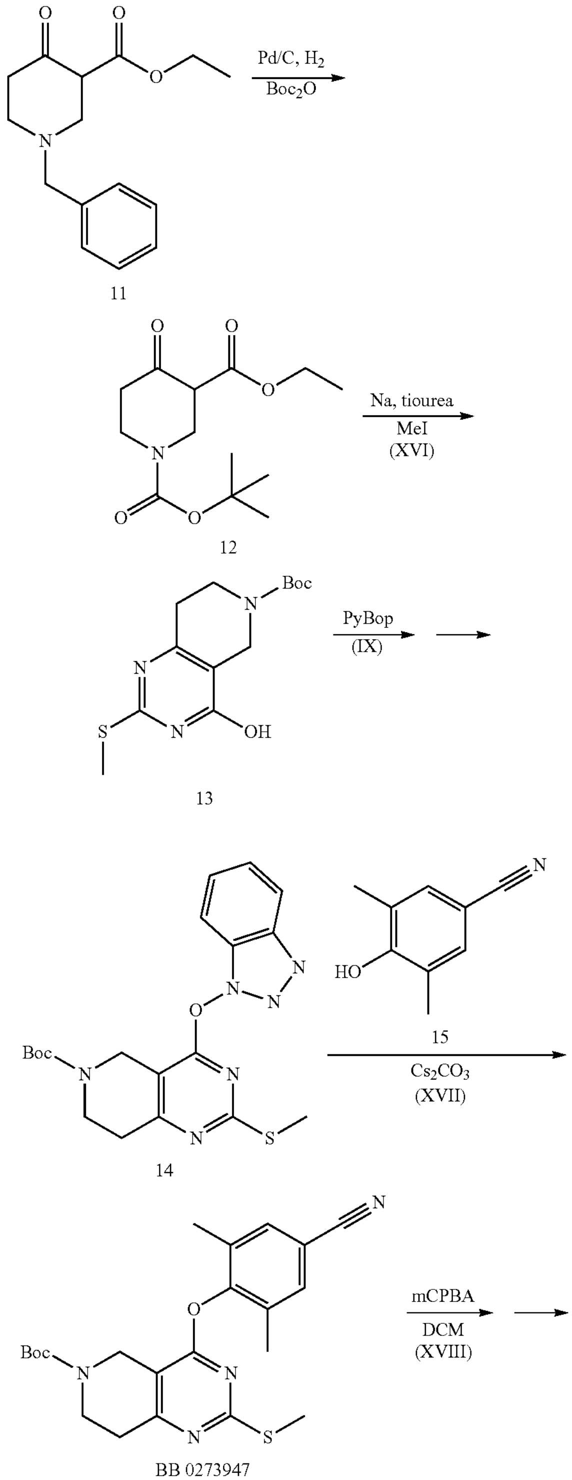
11
12
13
14
BB 0273947

-continued
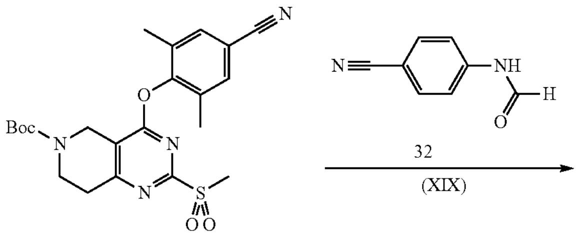
BB 0273960
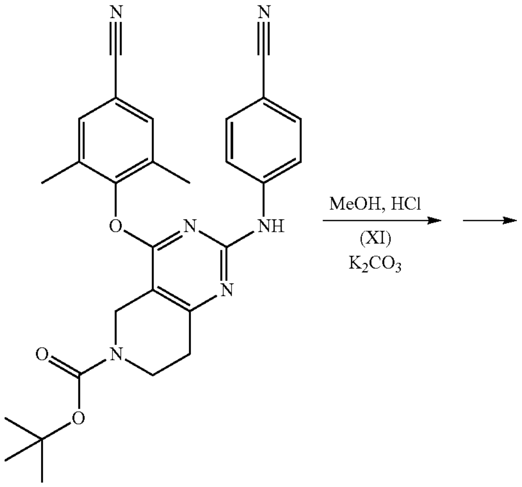
BB 0273961
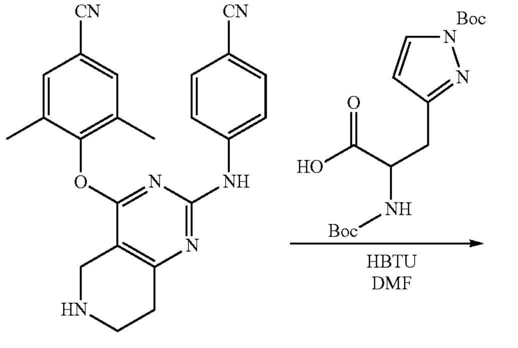
BB 0273963
-continued
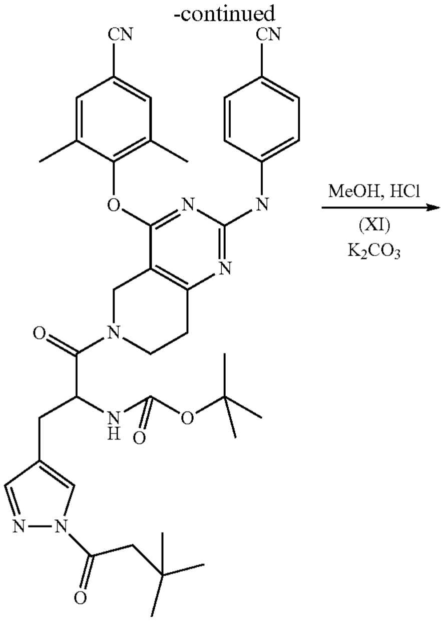
BB 0274122
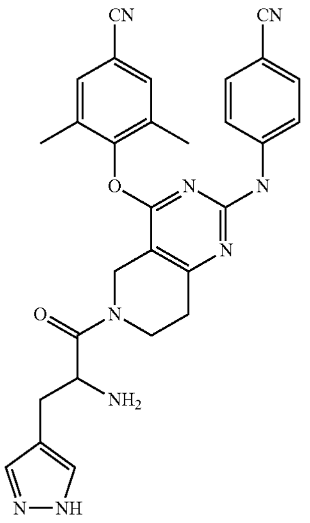
BB 0274121
BB 0274121
$^1$H NMR (400 MHz, DMSO-$d_6$, δ, ppm): 2.11 (broadened singlet, 6H), 2.60-3.01 (m, 2H), 3.05-3.42 (m, 2H), 3.84-4.29 (m, 3H), 4.51-4.64 (m, 1H), 4.77-5.00 (m, 2H), 7.46 (s, 4H), 7.80 (s, 2H), 8.44 (broadened singlet, 2H), 9.13 (s, 1H), 10.05 (broadened singlet, 1H).
Weight Yield—0.005 g (8%)
LCMS m/z (M+H): 534

Example 45
Synthesis of tert-butyl 4-(2-((tert-butoxycarbonyl) amino)-3-(4-(4-cyano-2,6-dimethylphenoxy)-2-((4-cyanophenyl)amino)-7,8-dihydropyrido[4,3-d]pyrimidine-6(5H)-yl)-3-oxopropyl)-1H-pyrazole-1-carboxylate
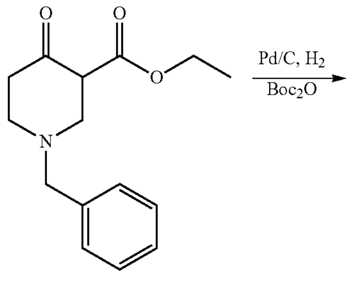
11
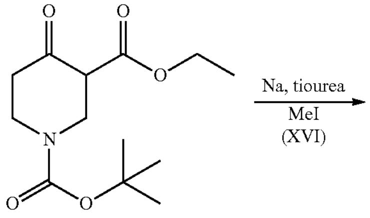
12
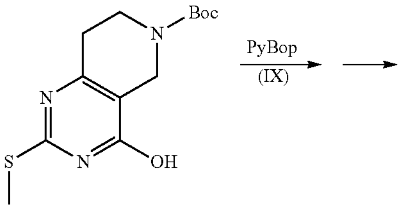
13
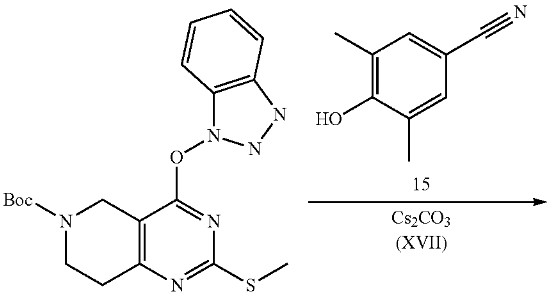
14
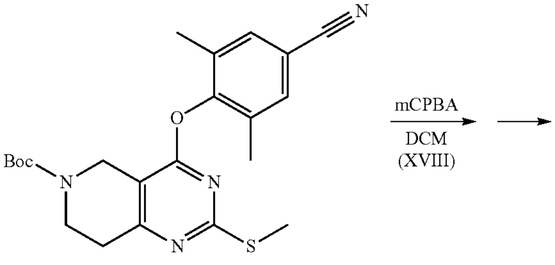
BB 0273947
-continued
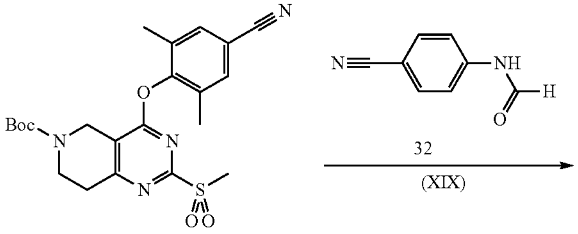
BB 0273960
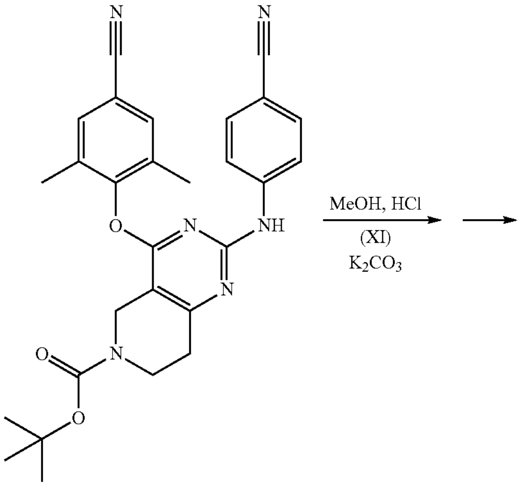
BB 0273961
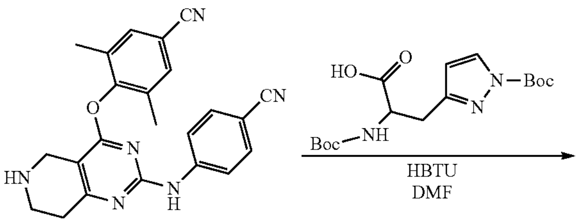
BB 0273963
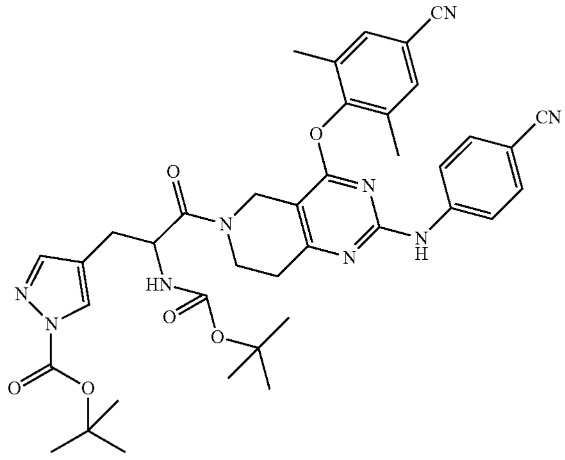
BB 0274122

BB 0274122
$^1$H NMR (400 MHz, $CDCl_3$, δ, ppm): 1.36-1.48 (m, 9H), 1.50-1.65 (m, 9H), 2.15 (s, 6H), 3.02-3.21 (m, 1H), 3.61-3.95 (m, 1H), 4.01-4.28 (m, 1H), 4.45-4.69 (m, 1H), 4.75-4.84 (m, 1H), 4.88-5.01 (m, 1H), 5.04-5.18 (m, 1H), 5.42-5.58 (m, 1H), 7.14 (s, 1H), 7.20 (s, 1H), 7.35-7.44 (m, 4H), 7.48 (s, 2H).
Weight Yield—0.032 g (33%)
LCMS m/z (M+H): 534 (M−2Boc)
Example 46
Synthesis of (R)-4-((6-(2-amino-3-hydroxypropanoyl)-2-((4-cyanophenyl)amino)-5,6,7,8-tetrahydropyrido[4,3-d]pyrimidine-4-yl)oxy)-3,5-dimethylbenzonitrile
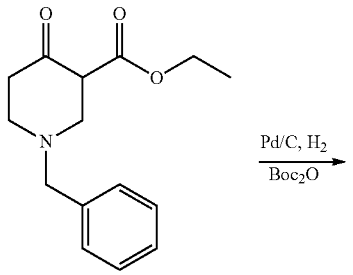
11
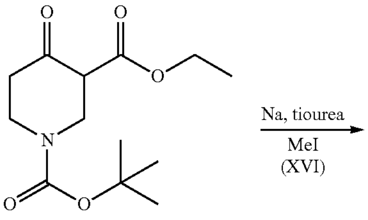
12
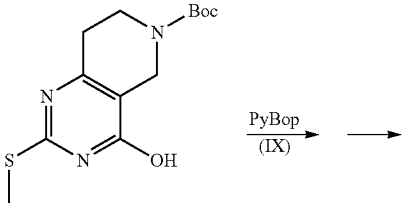
13
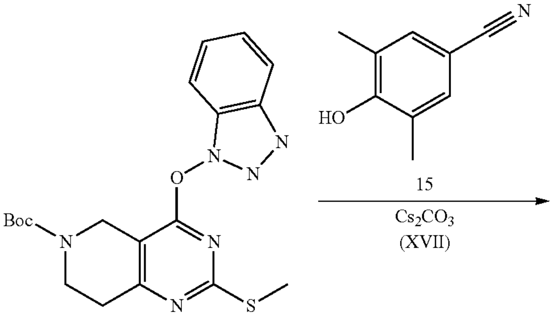
14
-continued
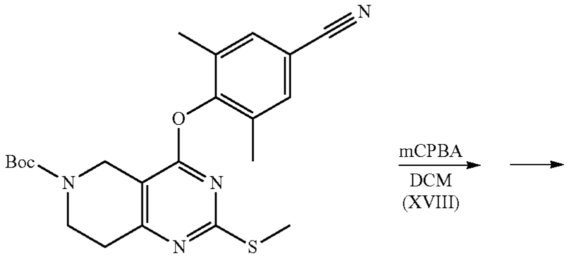
BB 0273947
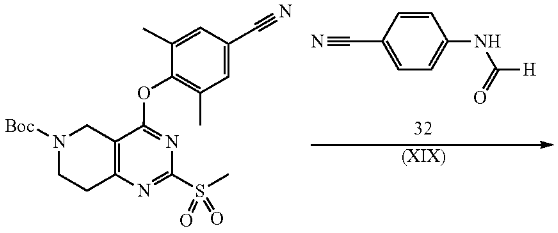
BB 0273960
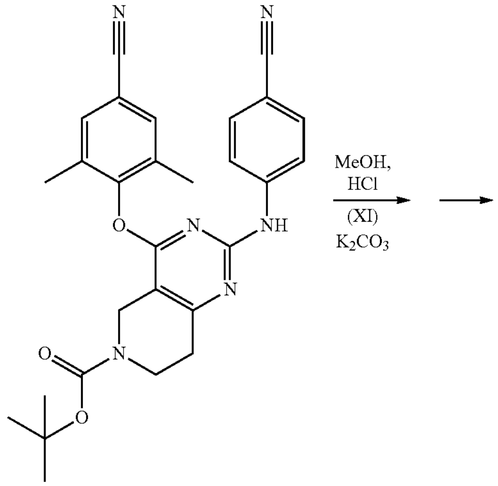
BB 0273961
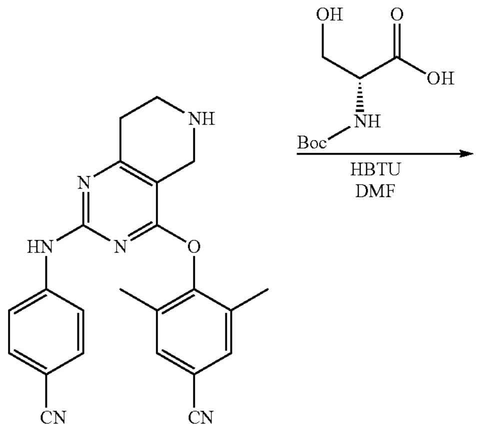
BB 0273963

-continued
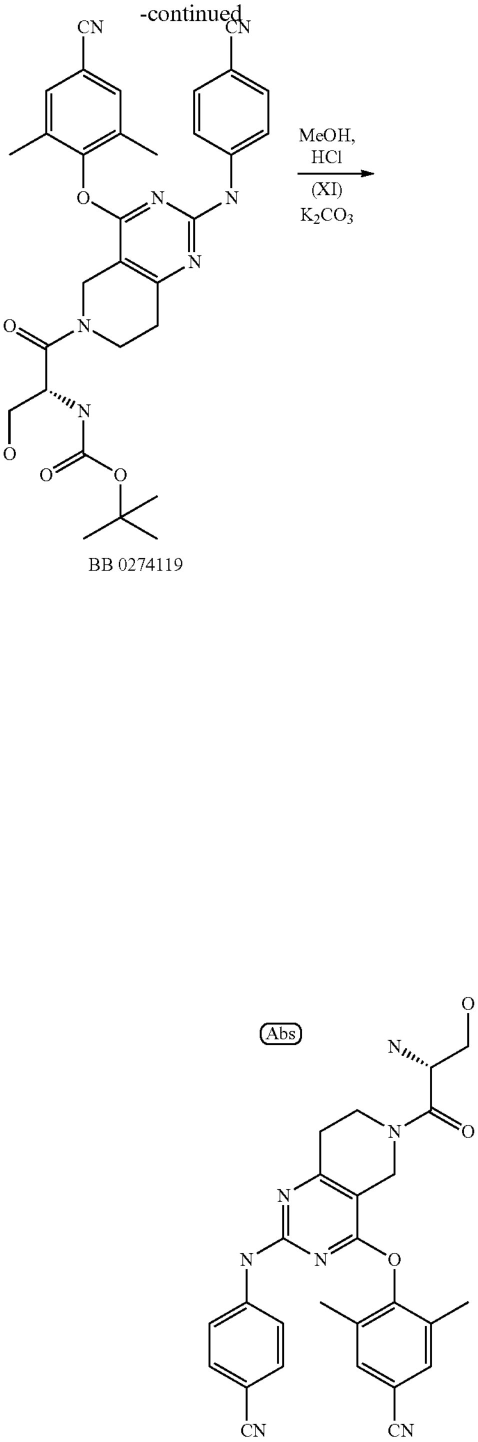
BB 0274119
BB 0274123
BB 0274123
$^1H$ NMR (400 MHz, DMSO-$d_6$, δ, ppm): 2.13 (s, 6H), 2.71-3.01 (m, 2H), 3.74 (broadened singlet, 2H), 3.95 (broadened singlet, 2H), 4.52-4.68 (m, 2H), 4.80 (broadened singlet, 2H), 7.46 (broadened singlet, 4H), 7.79 (s, 2H), 8.30 (broadened singlet, 3H).
Weight Yield—0.008 g (85%)
LCMS m/z (M+H): 484
Synthesis of (S)-tert-butyl (1-(4-(4-cyano-2,6-dimethylphenoxy)-2-((4-cyanophenyl)amino)-7,8-dihydropyrido[4,3-d]pyrimidine-6(5H)-yl)-3-(4-hydroxyphenyl)-1-oxopropane-2-yl)carbamate
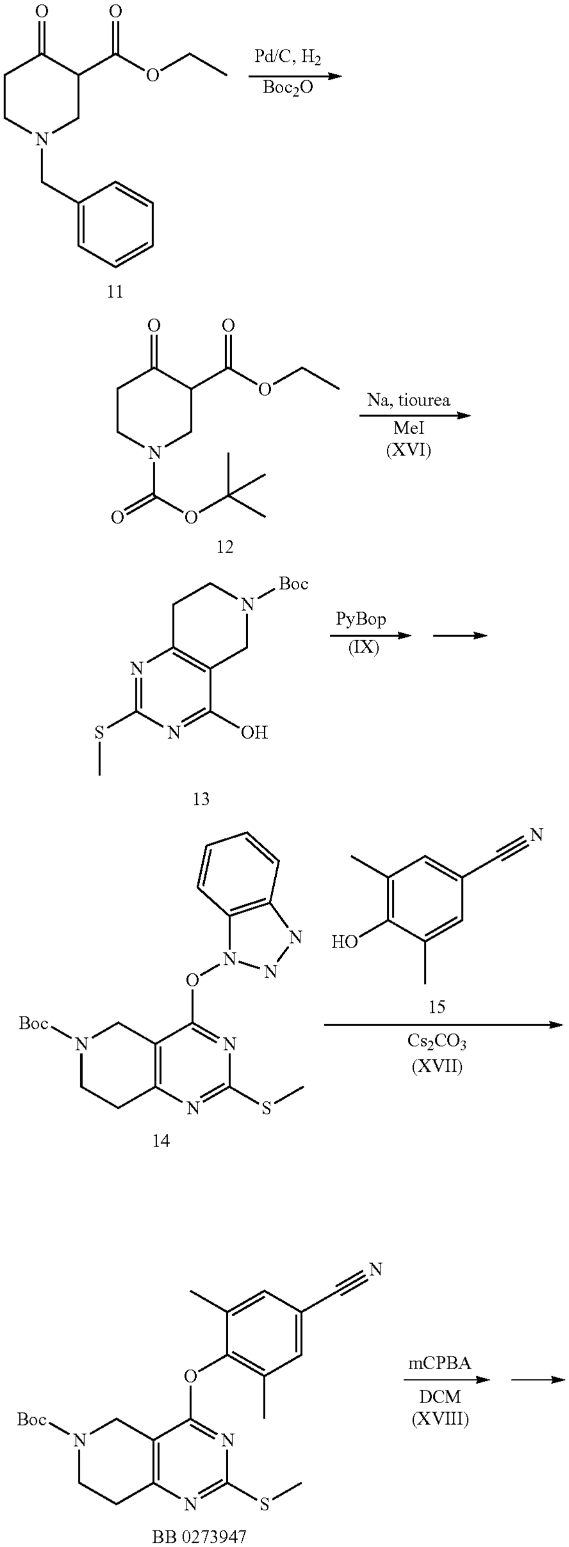
11
12
13
14
15
BB 0273947

-continued
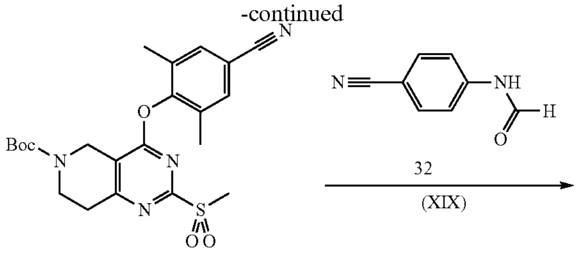
BB 0273960
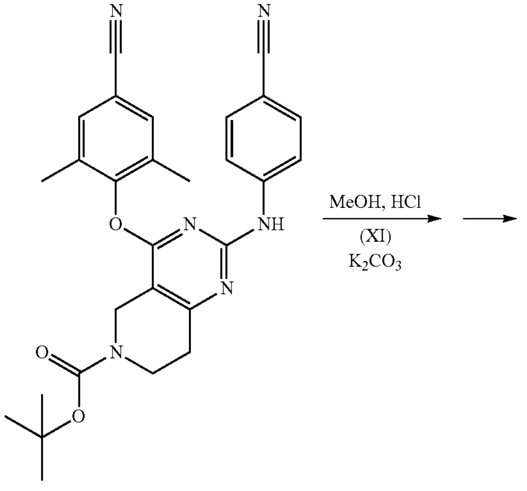
BB 0273961
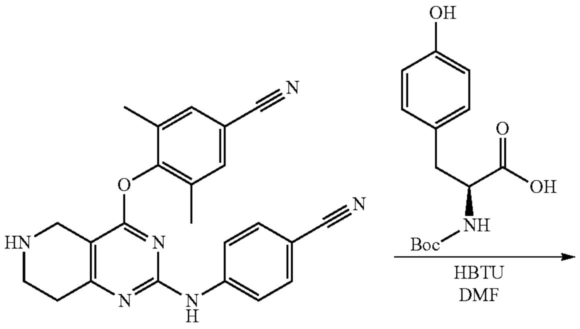
BB 0273963
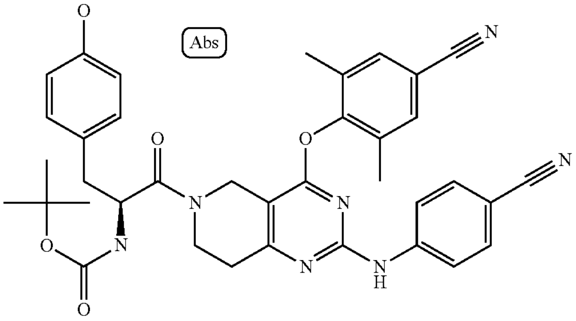
BB 0274124
BB 0274124
$^1$H NMR (400 MHz, $CDCl_3$, δ, ppm): 1.43 (d, J=6.9 Hz, 9H), 2.17 (broadened singlet, 6H), 2.61-2.85 (m, 2H), 3.03-3.45 (m, 1H), 3.56-3.80 (m, 1H), 3.92-4.22 (m, 1H), 4.37-4.64 (m, 1H), 4.69-5.02 (m, 2H), 5.36-5.53 (m, 1H), 6.59-6.75 (m, 2H), 6.97-7.10 (m, 2H), 7.35 (d, J=15.5 Hz, 4H), 7.48 (s, 2H).
Weight Yield—0.055 g (40%)
LCMS m/z (M+H): 560 (M−Boc).
Example 47
Synthesis of (S)-4-((6-(2-amino-3-(4-hydroxyphenyl)propanoyl)-2-((4-cyanophenyl)amino)-5,6,7,8-tetrahydropyrido[4,3-d]pyrimidine-4-yl)oxy)-3,5-dimethylbenzonitrile
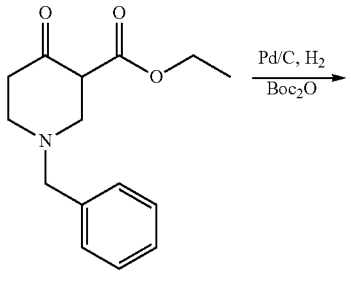
11
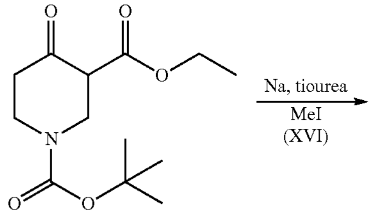
12
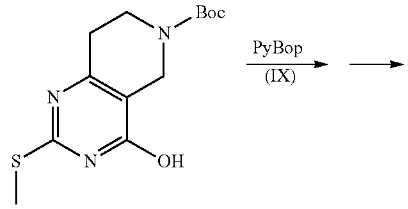
13
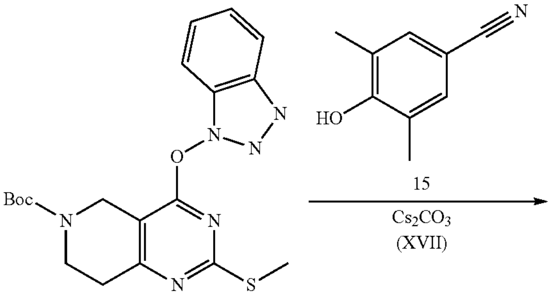
14
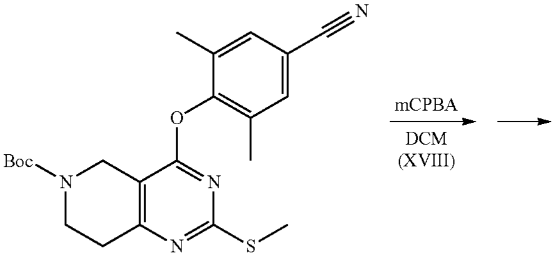
BB 0273947

-continued
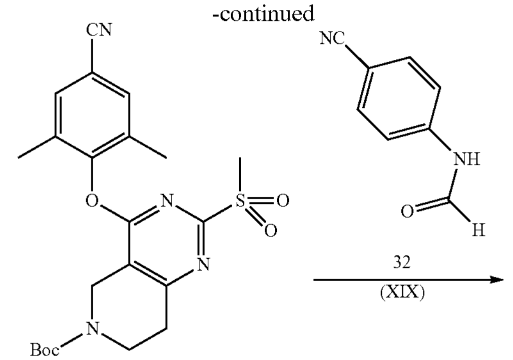
BB 0273960
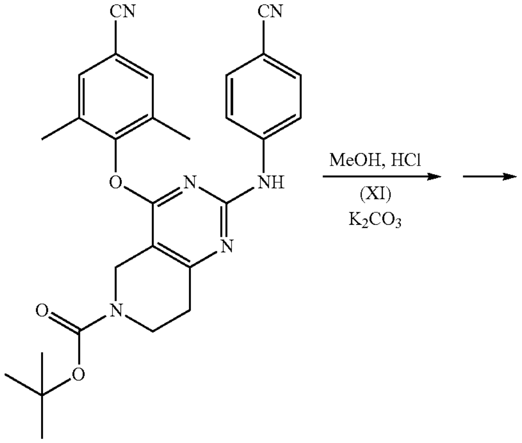
BB 0273961
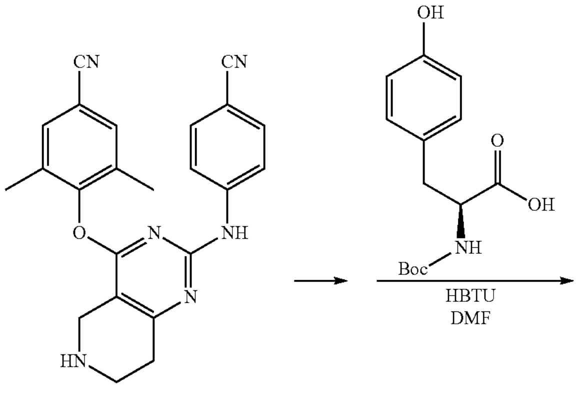
BB 0273963
-continued
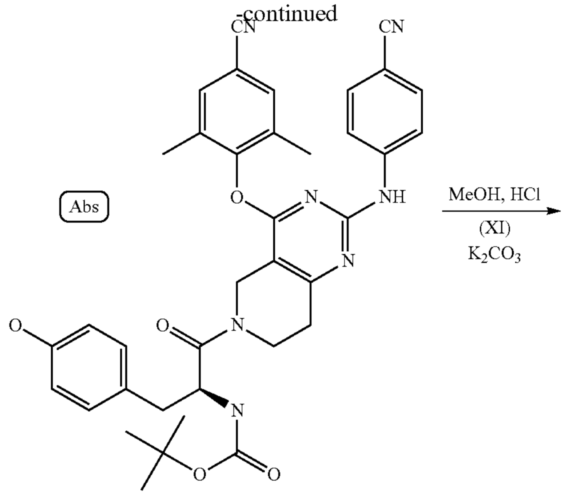
BB 0274124
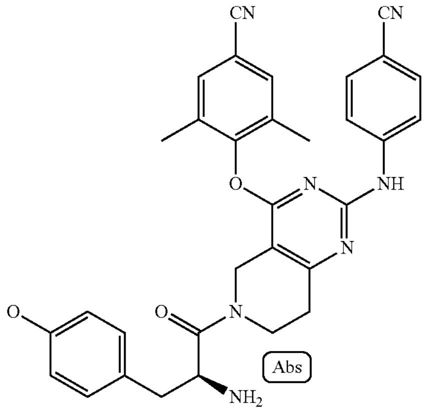
BB 0274125
BB 0274125
$^1$H NMR (400 MHz, DMSO-$d_6$, δ, ppm): 2.09 (broadened singlet, 6H), 2.59-2.82 (m, 1H), 3.15 (broadened singlet, 2H), 3.33-3.60 (m, 1H), 3.67-4.08 (m, 1H), 4.40-4.56 (m, 2H), 4.79 (broadened singlet, 2H), 7.26 (m, 5H), 7.43 (broadened singlet, 4H), 7.79 (broadened singlet, 2H), 8.46 (broadened singlet, 2H), 10.10 (broadened singlet, 1H).
Weight Yield—0.048 g (90%)
LCMS m/z (M+H): 560

Example 48
Synthesis of (R)-tert-butyl (1-(4-(4-cyano-2,6-dimethylphenoxy)-2-((4-cyanophenyl)amino)-7,8-dihydropyrido[4,3-d]pyrimidine-6(5H)-yl)-3-methyl-1-oxobutane-2-yl)carbamate
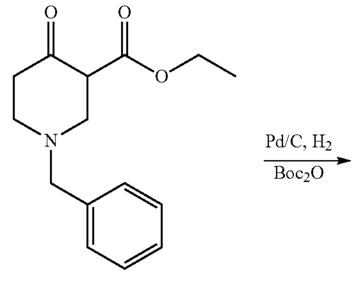
11
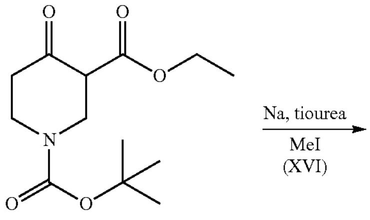
12
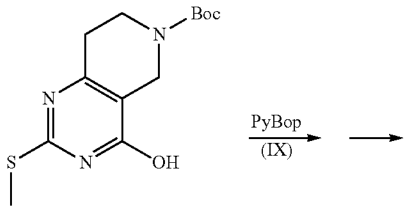
13
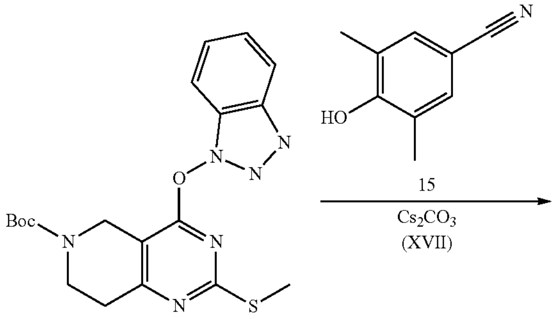
14
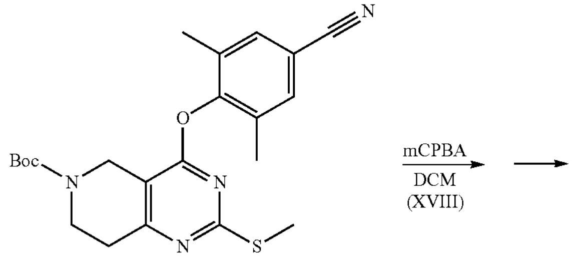
BB 0273947
-continued
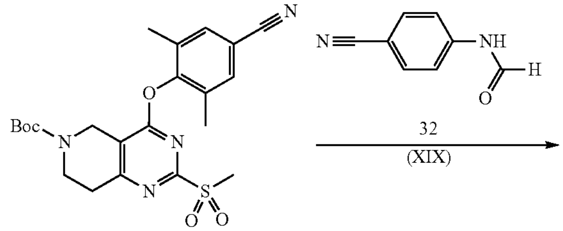
BB 0273960
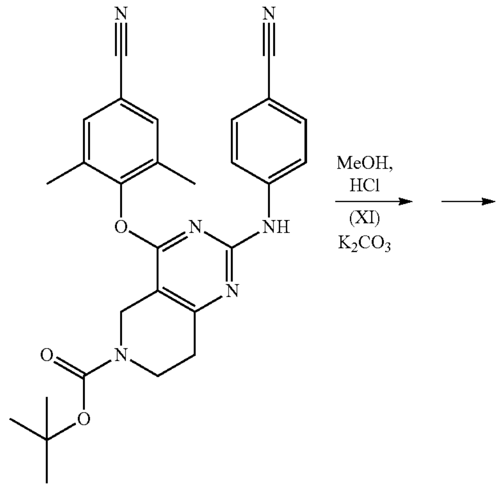
BB 0273961
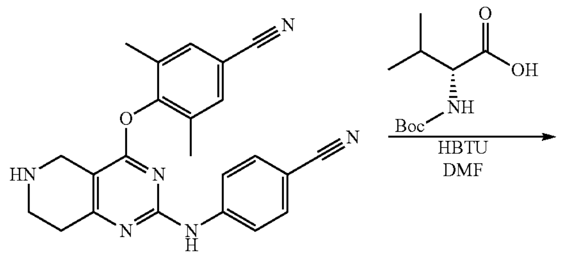
BB 0273963
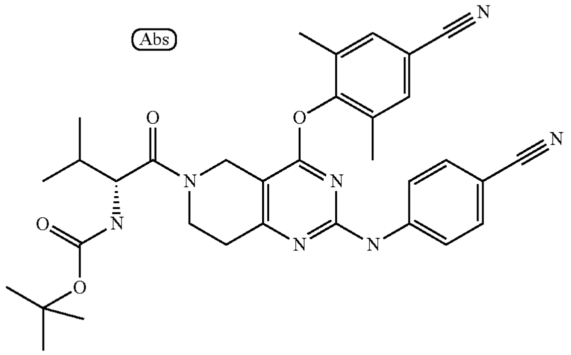
BB 0274126
BB 0274126
$^1$H NMR (400 MHz, DMSO-$d_6$, δ, ppm): 0.90-1.07 (m, 6H), 1.38-1.47 (m, 9H), 1.79-2.08 (m, 1H), 2.12-2.25 (m, 6H), 2.98-3.27 (m, 1H), 3.76-4.07 (m, 2H), 4.44-4.73 (m, 2H), 5.22-5.53 (m, 1H), 7.33-7.44 (m, 4H), 7.48 (s, 2H).
Weight Yield—0.042 g (52%)
LCMS m/z (M+H): 496 (M-Boc).

Example 49
Synthesis of (R)-4-((6-(2-amino-3-methylbutanoyl)-2-((4-cyanophenyl)amino)-5,6,7,8-tetrahydropyrido[4,3-d]pyrimidine-4-yl)oxy)-3,5-dimethylbenzonitrile
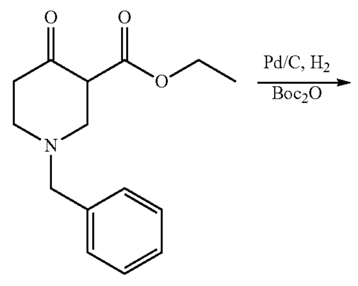
11
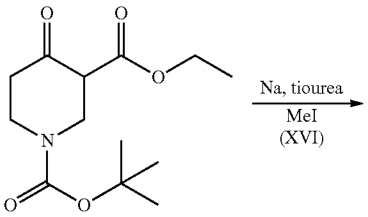
12
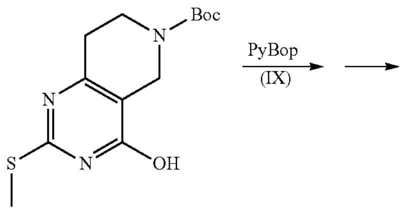
13
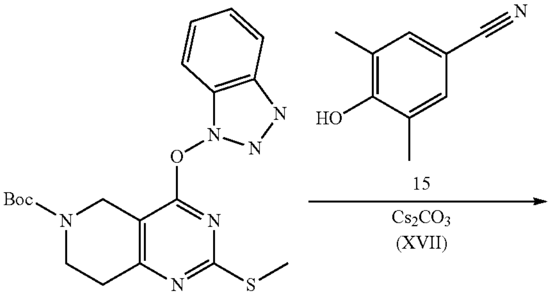
14
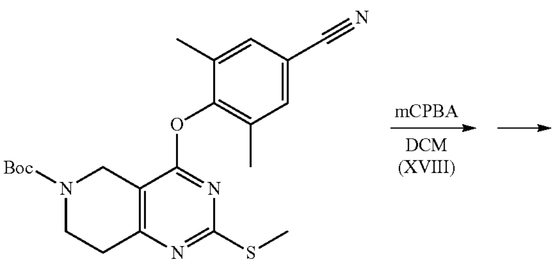
BB 0273947
-continued
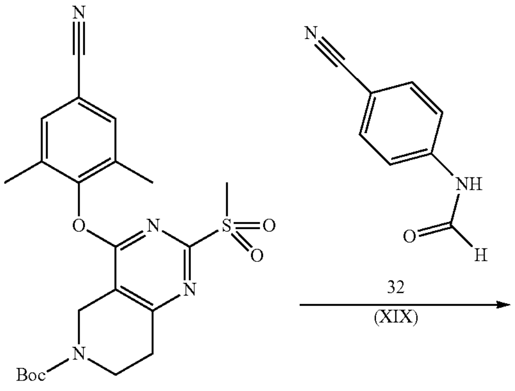
BB 0273960
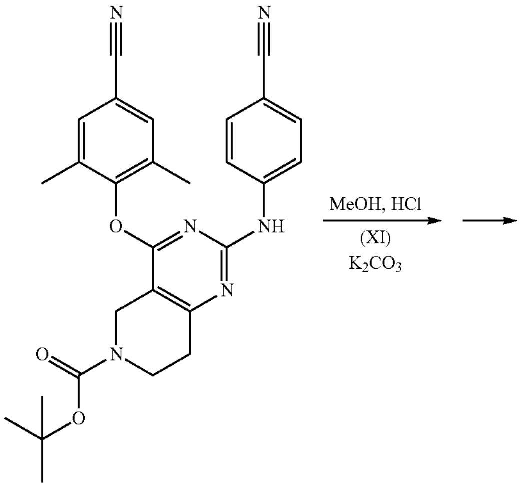
BB 0273961
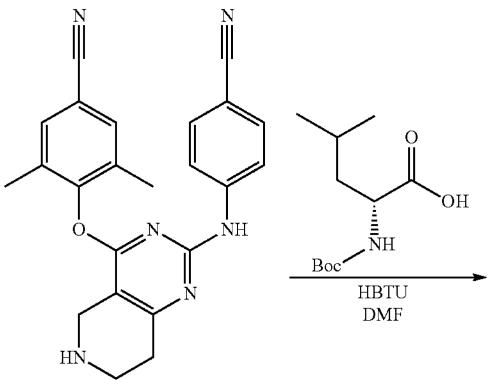
BB 0273963

-continued
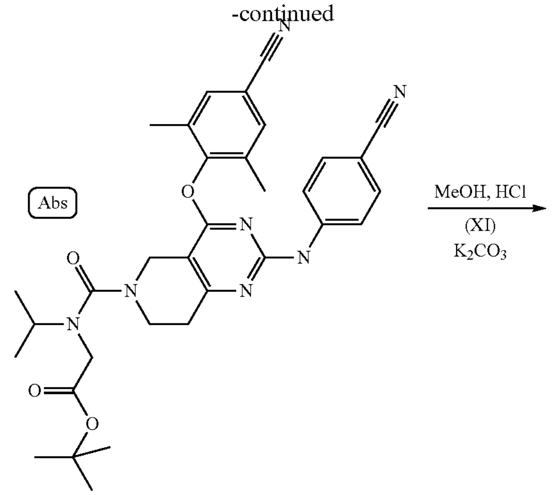
BB 0274126
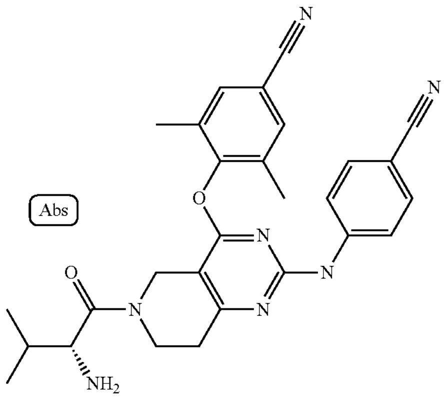
BB 0274127
BB 0274127
$^1H$ NMR (400 MHz, $CDCl_3$, δ, ppm): 1.36-1.48 (m, 2H), 1.53-1.86 (m, 4H), 2.08-2.22 (s, 6H), 3.02-3.29 (m, 2H), 3.75-4.08 (m, 2H), 4.51-5.06 (m, 4H), 5.30 (s, 1H), 7.31-7.45 (m, 4H), 7.48 (s, 2H).
Weight Yield—0.038 g (92%)
LCMS m/z (M+H): 496
Example 50
Synthesis of (S)-tert-butyl (1-(4-(4-cyano-2,6-dimethylphenoxy)-2-((4-cyanophenyl)amino)-7,8-dihydropyrido[4,3-d]pyrimidine-6(5H)-yl)-4-methyl-1-oxopentane-2-yl)carbamate
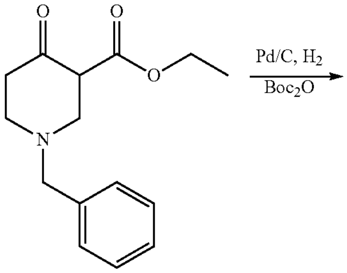
11
-continued
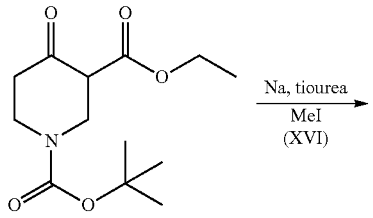
12
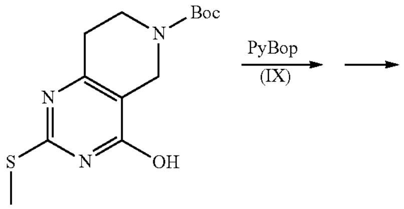
13
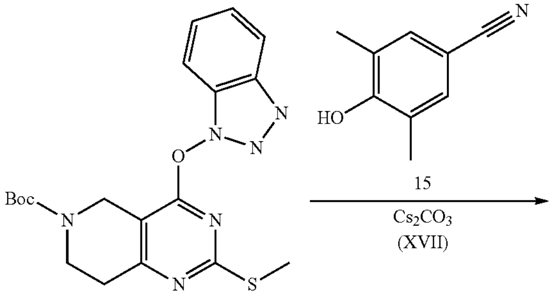
14
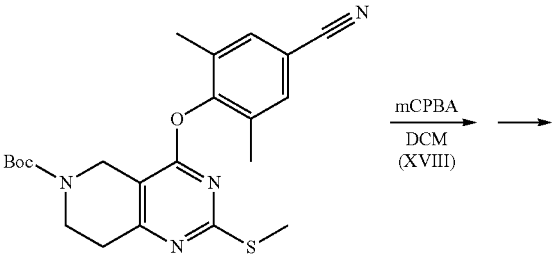
BB 0273947
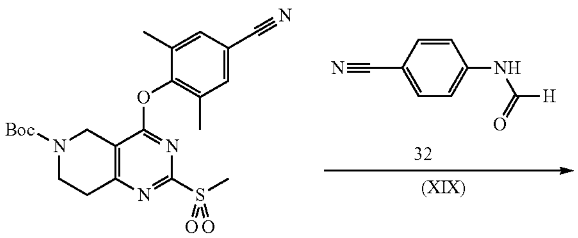
BB 0273960

-continued
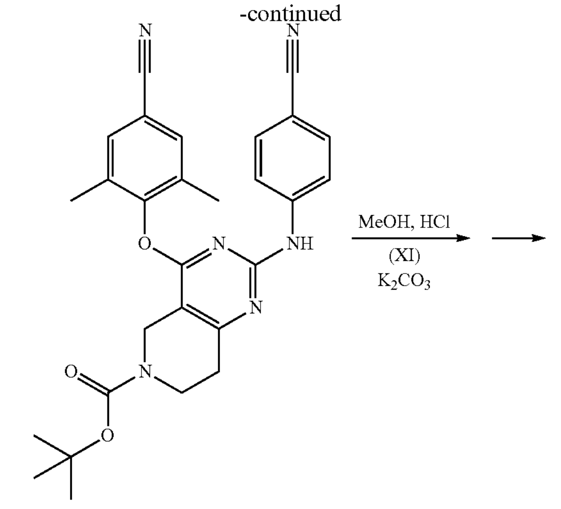
BB 0273961
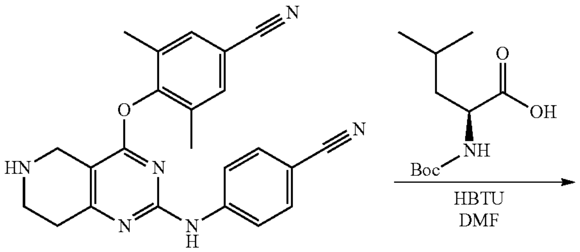
BB 0273963
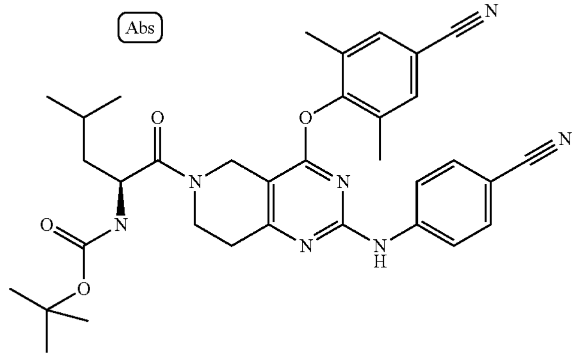
BB 0274128
BB 0274128
$^1H$ NMR (400 MHz, $CDCl_3$, δ, ppm): 0.88-1.13 (m, 6H), 1.35-1.48 (m, 9H), 1.58 (d, J=1.4 Hz, 2H), 2.16 (s, 6H), 2.99-3.26 (m, 1H), 3.72-4.27 (m, 2H), 4.64-4.98 (m, 3H), 5.30 (s, 1H), 7.33-7.45 (m, 4H), 7.45-7.56 (m, 2H).
Weight Yield—0.064 g (56%)
LCMS m/z (M+H): 510 (M-Boc
Example 51
Synthesis of (S)-4-((6-(2-amino-4-methylpentanoyl)-2-((4-cyanophenyl)amino)-5,6,7,8-tetrahydropyrido[4,3-d]pyrimidine-4-yl)oxy)-3,5-dimethylbenzonitrile
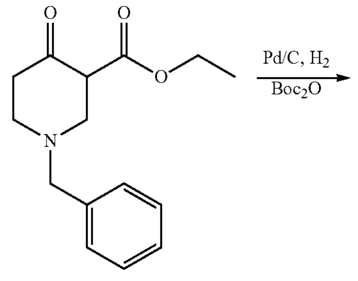
11
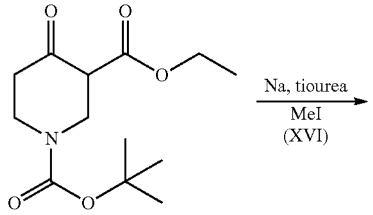
12
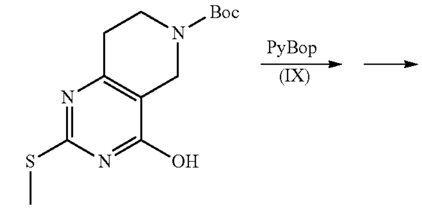
13
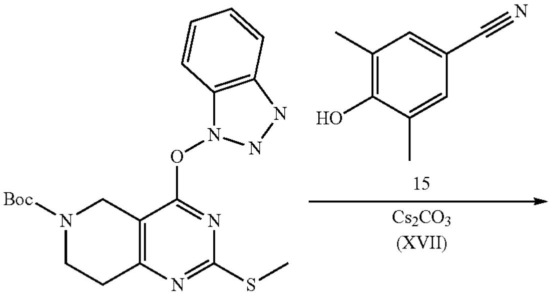
14
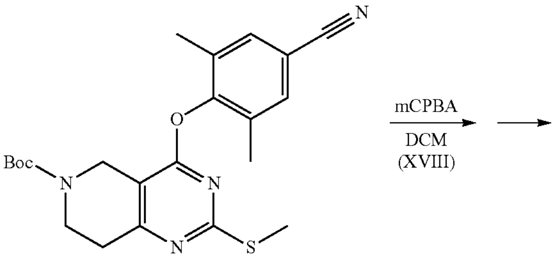
BB 0273947

-continued
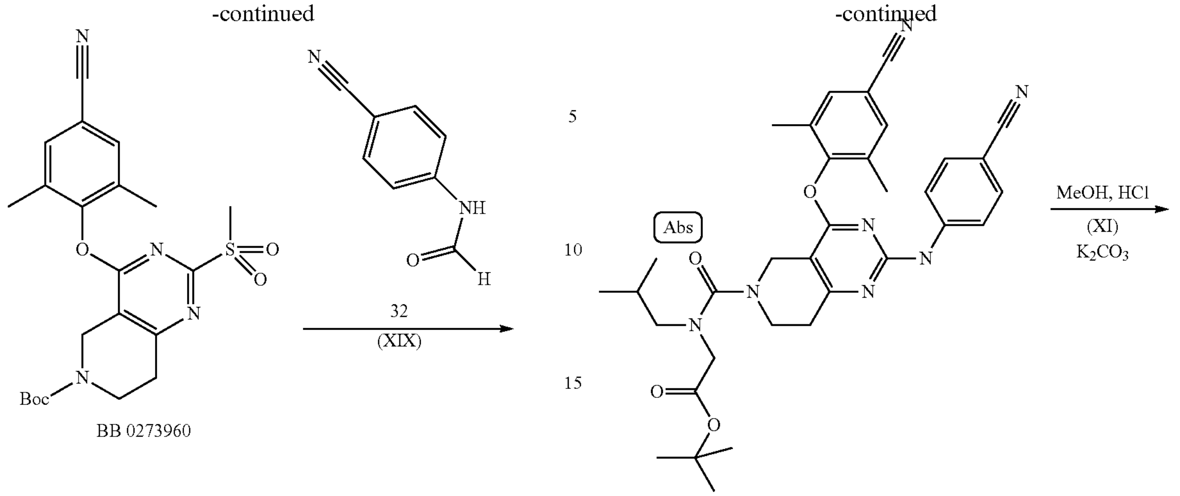
BB 0273960
BB 0274128
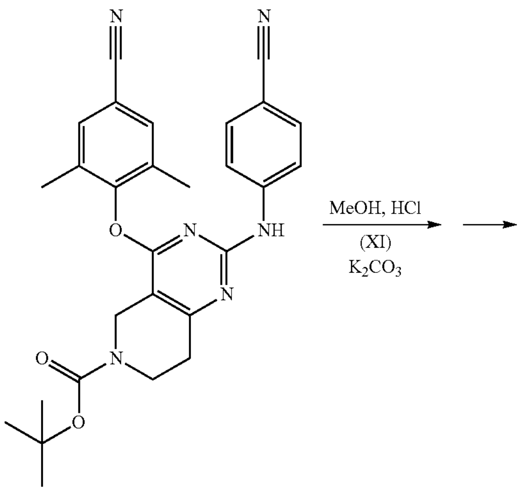
BB 0273961
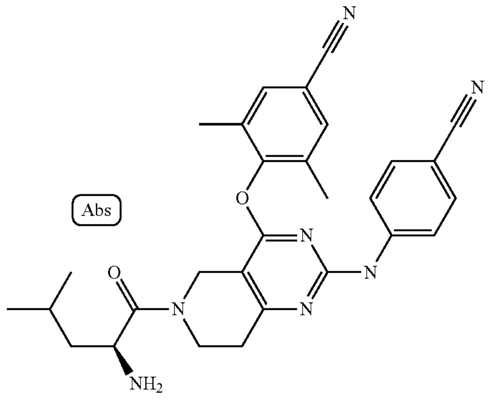
BB 0274129
BB 0274129
$^1$H NMR (400 MHz, DMSO-$d_6$, δ, ppm): 0.82-0.99 (m, 6H), 1.49-1.86 (m, 3H), 2.12 (s, 6H), 2.71-3.11 (m, 2H), 3.65-4.11 (m, 2H), 4.70 (s, 2H), 7.46 (broadened singlet, 4H), 7.79 (s, 2H), 8.28 (broadened singlet, 2H)
Weight Yield—0.060 g (90%)
LCMS m/z (M+H): 510
Example 52
Synthesis of (S)-di-tert-butyl (6-(4-(4-cyano-2,6-dimethylphenoxy)-2-((4-cyanophenyl)amino)-7,8-dihydropyrido[4,3-d]pyrimidine-6(5H)-yl)-6-oxo-hexane-1,5-diyl)dicarbamate
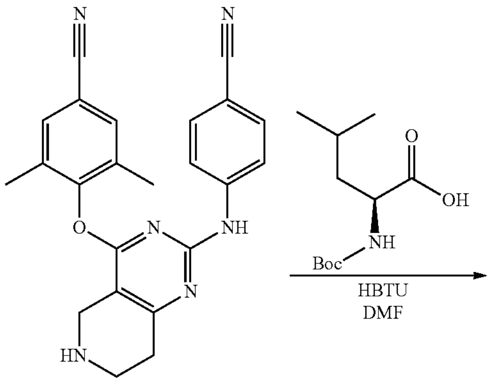
BB 0273963
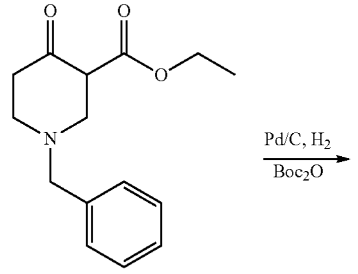
11

-continued
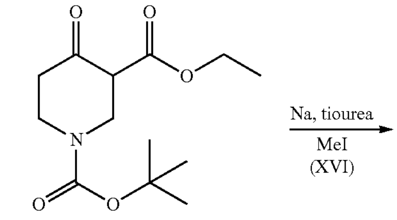
12
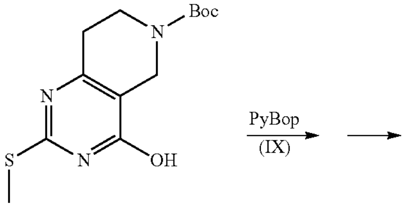
13
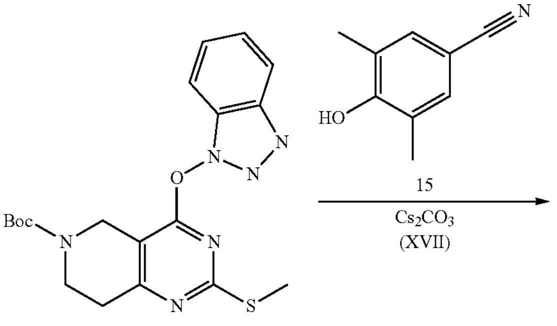
14
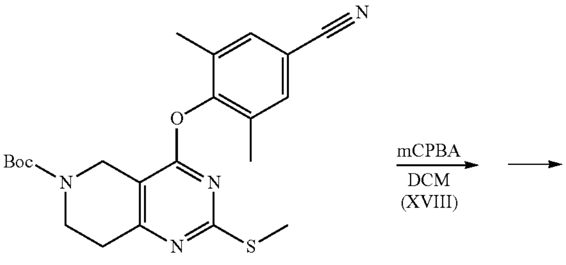
BB 0273947
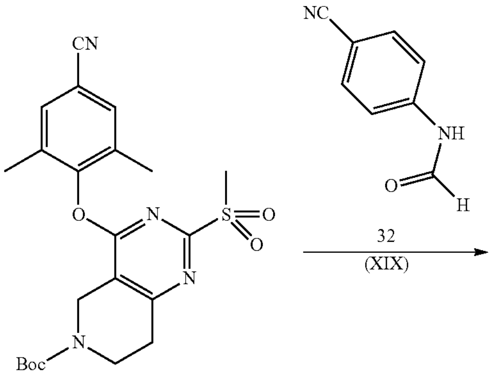
BB 0273960
-continued
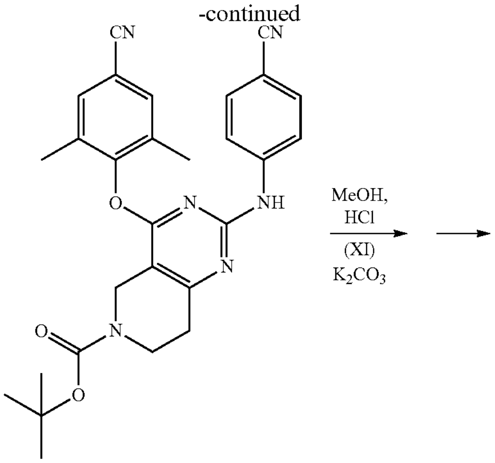
BB 0273961
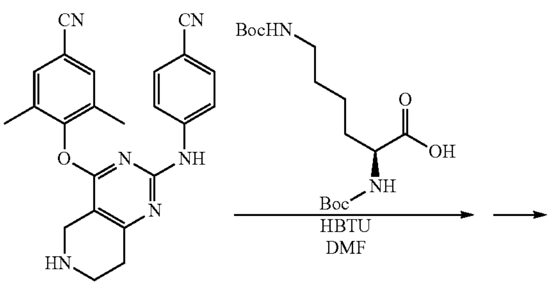
BB 0273963
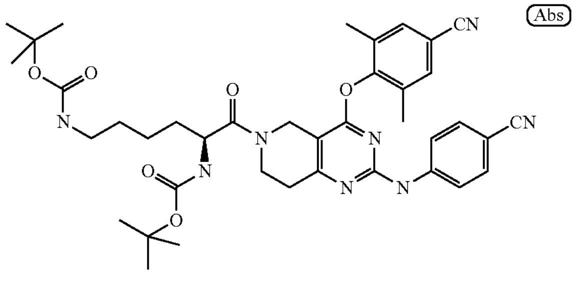
BB 0274130
BB 0274130
$^1$H NMR (400 MHz, DMSO-$d_6$, δ, ppm): 1.22-1.76 (m, 22H), 1.70-1.87 (m, 2H), 2.13 (s, 6H), 2.62-2.80 (m, 2H), 2.84-3.12 (m, 2H), 3.75-3.88 (m, 2H), 4.50-4.60 (m, 2H), 7.46 (broadened singlet, 4H), 7.80 (s, 2H), 8.02-8.14 (m, 2H), 8.34-8.38 (m, 3H).
Weight Yield—0.022 g (18%)
LCMS m/z (M+H): 525 (M-2Boc)

Example 53
Synthesis of (S)-4-((2-((4-cyanophenyl)amino)-6-(2,6-diaminohexanoyl)-5,6,7,8-tetrahydropyrido[4,3-d]pyrimidine-4-yl)oxy)-3,5-dimethylbenzonitrile
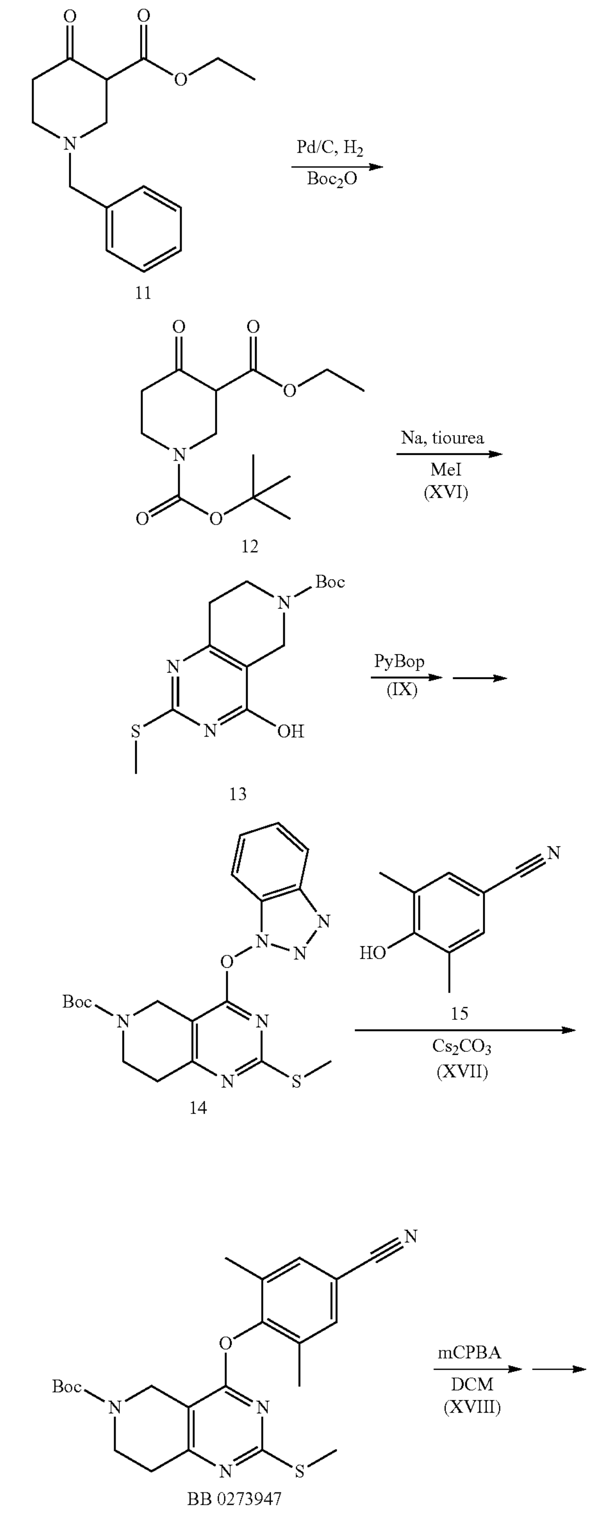
-continued
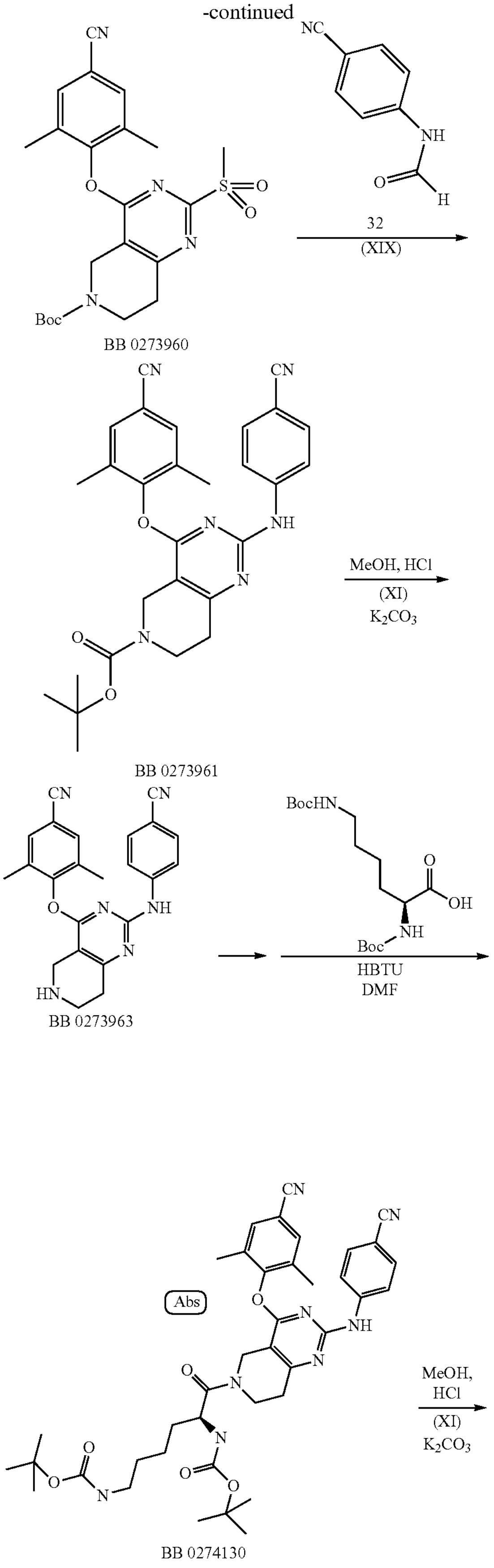

-continued
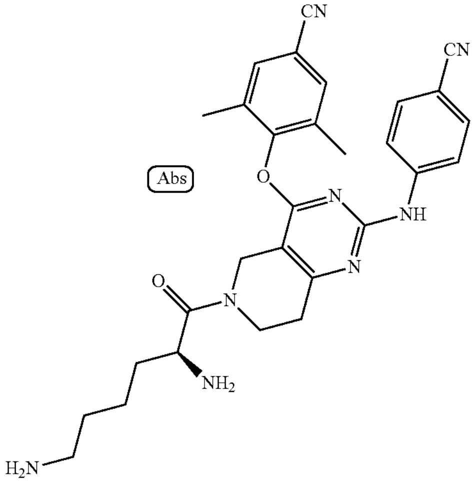
BB 0274131
BB 0274131
$^1H$ NMR (400 MHz, DMSO-$d_6$, δ, ppm): 1.30-1.66 (m, 4H), 1.71-1.85 (m, 2H), 2.12 (s, 6H), 2.63-2.79 (m, 2H), 2.85-3.09 (m, 2H), 3.77-4.04 (m, 2H), 4.53-4.59 (m, 2H), 7.46 (broadened singlet, 4H), 7.79 (s, 2H), 8.01-8.14 (m, 3H), 8.36-8.40 (m, 3H)
Weight Yield—0.018 g (85%)
LCMS m/z (M+H): 525
Example 54
Synthesis of (S)-4-((6-(2-amino-4-(methylthio)butanoyl)-2-((4-cyanophenyl)amino)-5,6,7,8-tetrahydropyrido[4,3-d]pyrimidine-4-yl)oxy)-3,5-dimethylbenzonitrile
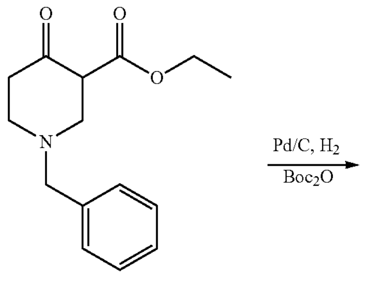
11
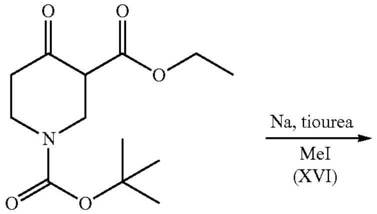
12
-continued
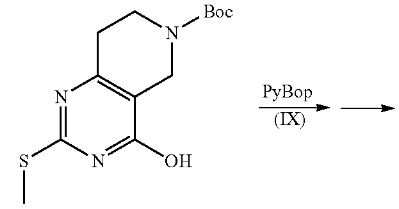
13
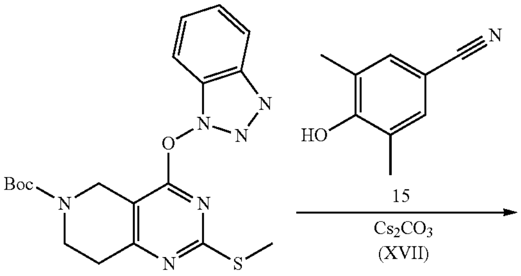
14
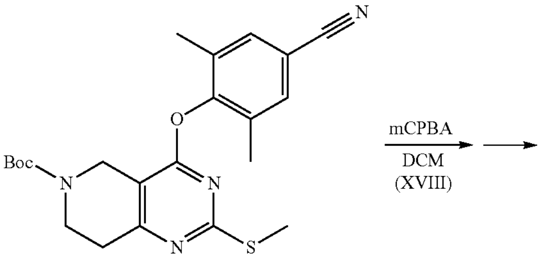
BB 0273947
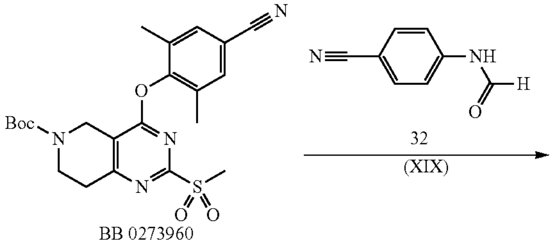
BB 0273960
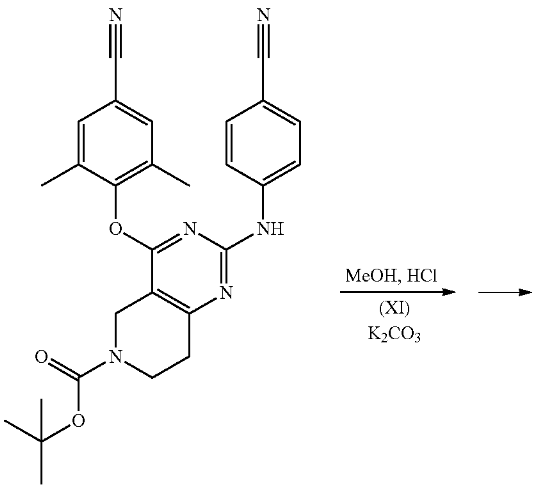
BB 0273961

-continued
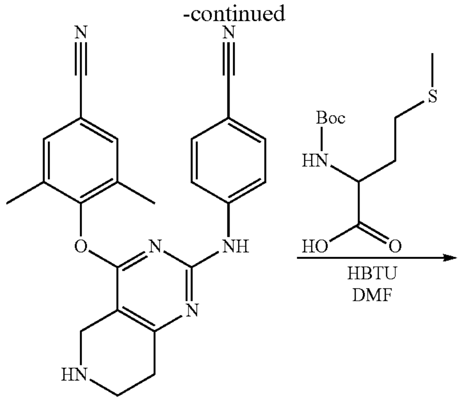
BB 0273963
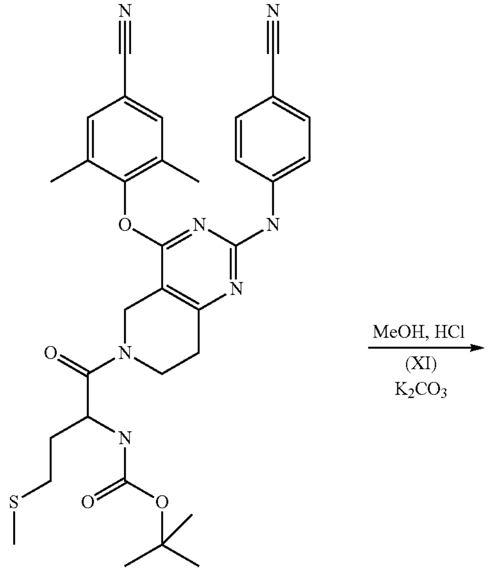
BB 0274120
-continued
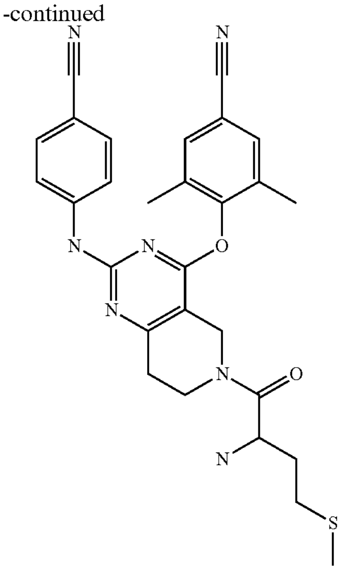
BB 0274132
BB 0274132
$^1$H NMR (400 MHz, DMSO-$d_6$, δ, ppm): 2.08 (s, 3H), 2.15 (broadened singlet, 6H), 2.51-2.73 (m, 2H), 2.80-3.07 (m, 2H), 3.79-4.08 (m, 2H), 4.47-4.57 (m, 2H), 4.81-5.01 (m, 2H), 7.46 (broadened singlet, 4H), 7.79 (s, 2H), 8.40 (broadened singlet, 2H)
Weight Yield—0.076 g (82%)
LCMS m/z (M+H): 528
Example 55
Synthesis of 4-((7-(2-chloroacetyl)-2-((4-cyanophenyl)amino)-6,7,8,9-tetrahydro-5H-pyrimido[4,5-d]azepine-4-yl)oxy)-3,5-dimethylbenzonitrile
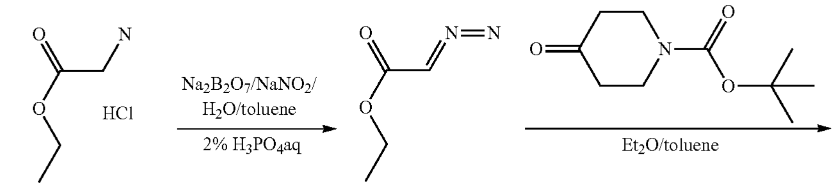
49 50
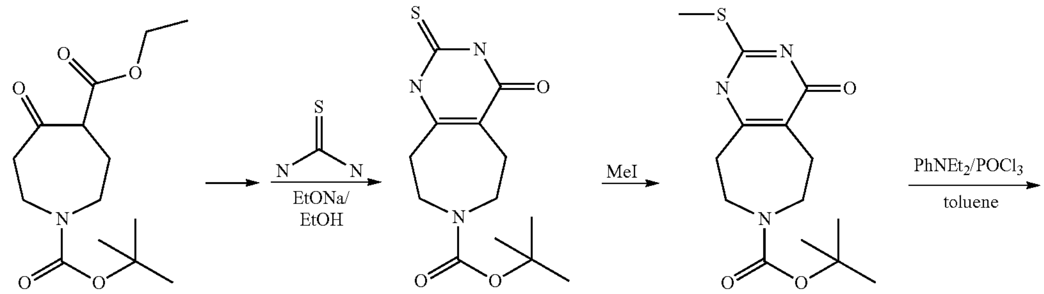
51 52 53

-continued
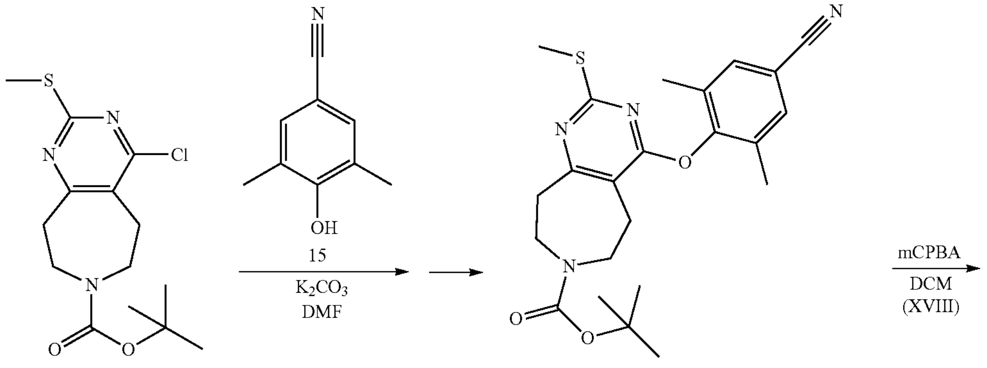
54
BB 0273957
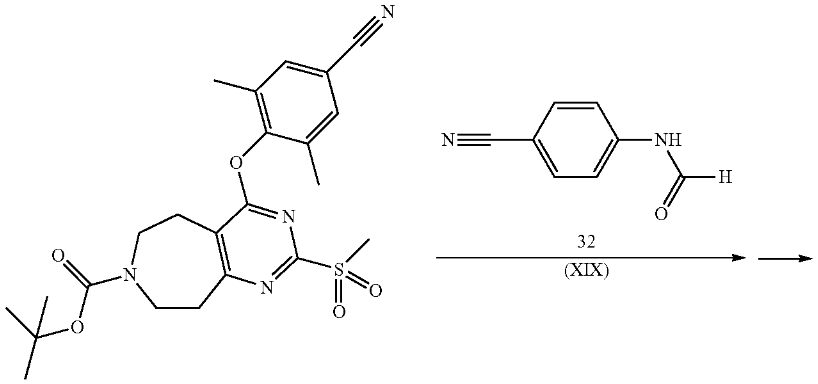
BB 0273968
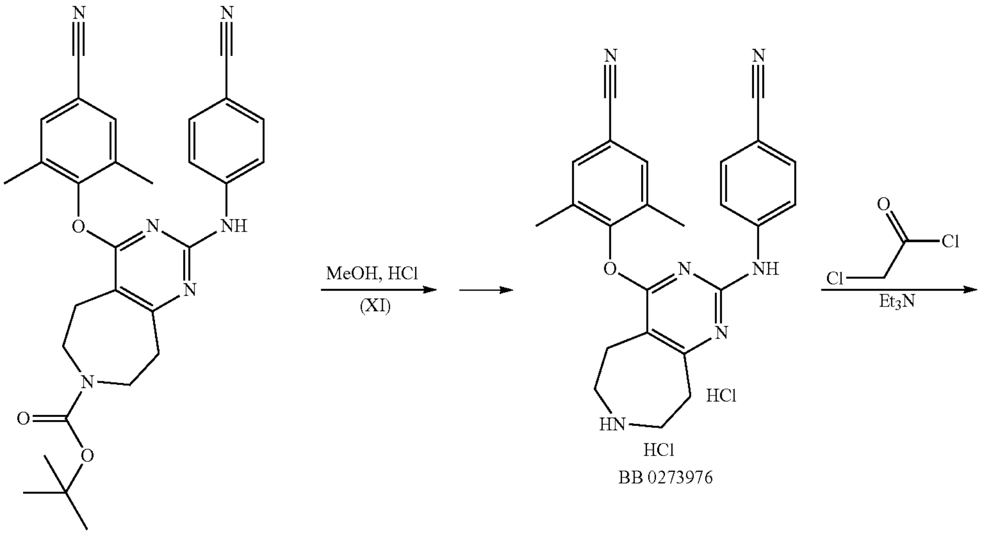
BB 0273976
BB 0273972

-continued
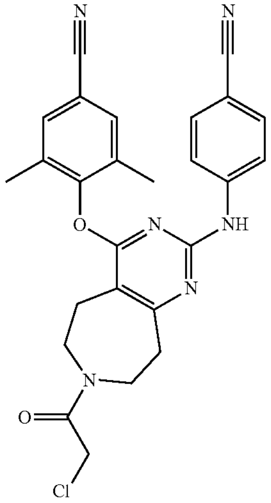
BB 0274133
BB 0274133
$^{1}H$ NMR (400 MHz, DMSO-$d_6$, δ, ppm): 2.10 (s, 6H), 3.02 (broadened singlet, 2H), 3.13 (broadened singlet, 2H), 3.75 (broadened singlet, 4H), 4.49 (broadened singlet, 2H), 7.42 (broadened singlet, 4H), 7.78 (broadened singlet, 2H), 10.06 (broadened singlet, 1H).
Weight Yield—0.045 g (57%)
LCMS m/z (M+H): 487
Example 56
Synthesis of methyl 4-(4-cyano-2,6-dimethylphenoxy)-2-((4-4-cyanophenyl) amino)-8,9-dihydro-5H-pyrimido[4,5-d]azepine-7(6H)-carboxylate
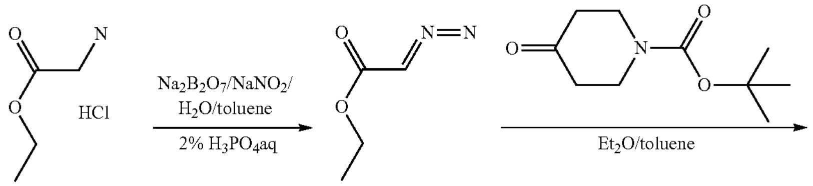
49 50
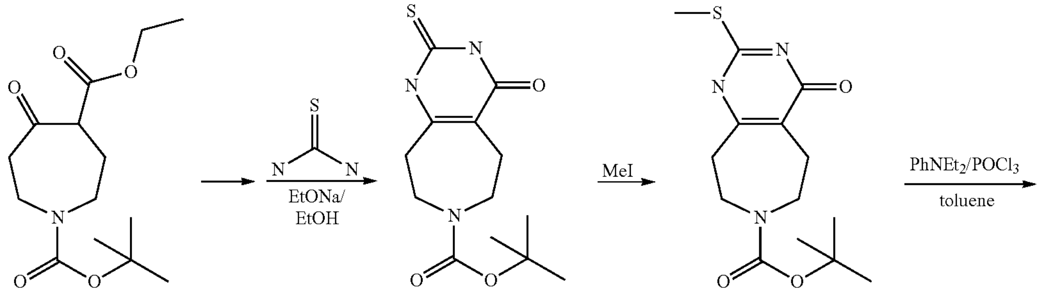
51 52 53

-continued
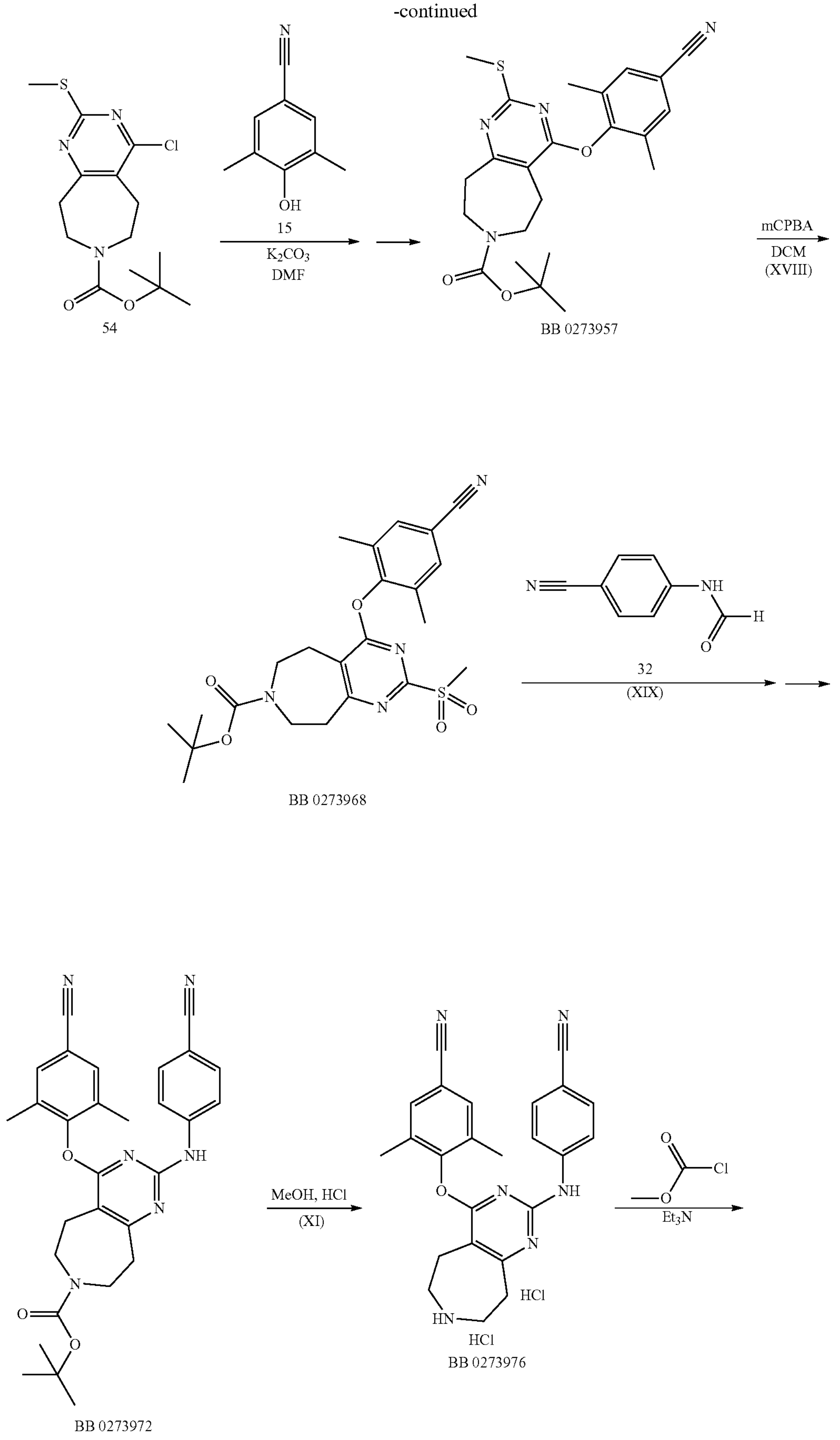

-continued
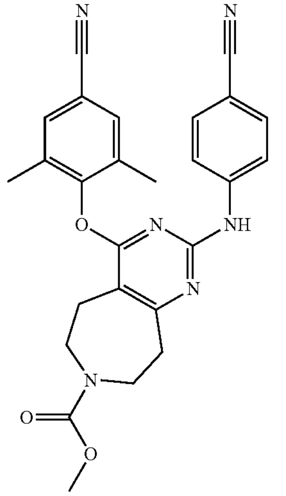
BB 0274134
BB 0274134
$^1$H NMR (400 MHz, DMSO-$d_6$, δ, ppm): 2.09 (s, 6H), 3.03 (broadened singlet, 4H), 3.64 (s, 7H), 7.41 (s, 4H), 7.77 (s, 2H), 10.06 (s, 1H).
Weight Yield—0.095 g (82%)
LCMS m/z (M+H): 469
Example 57
Synthesis of 4-((2-((4-cyanophenyl)amino)-7-(methylsulfonyl)-6,7,8,9-tetrahydro-5H-pyrimido[4,5-d]azepine-4-yl)oxy)-3,5-dimethylbenzonitrile
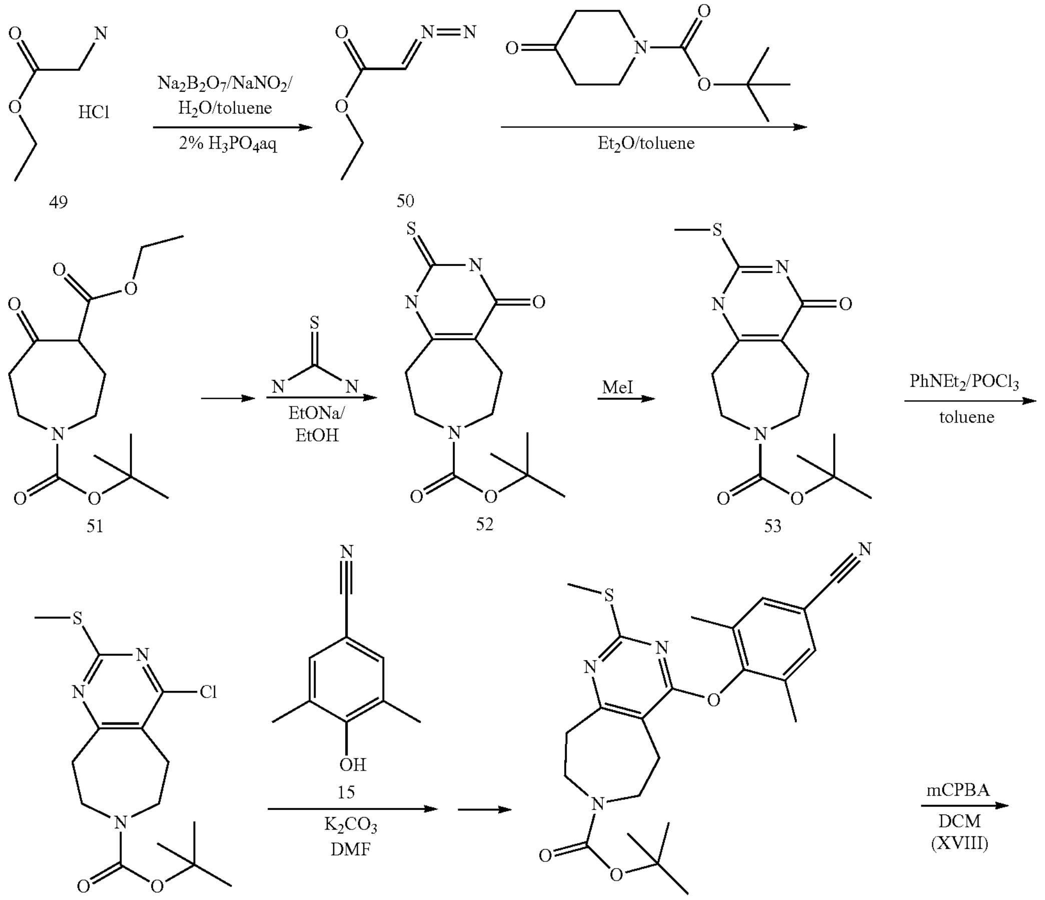
49 50 51 52 53 54 15 BB 0273957

-continued
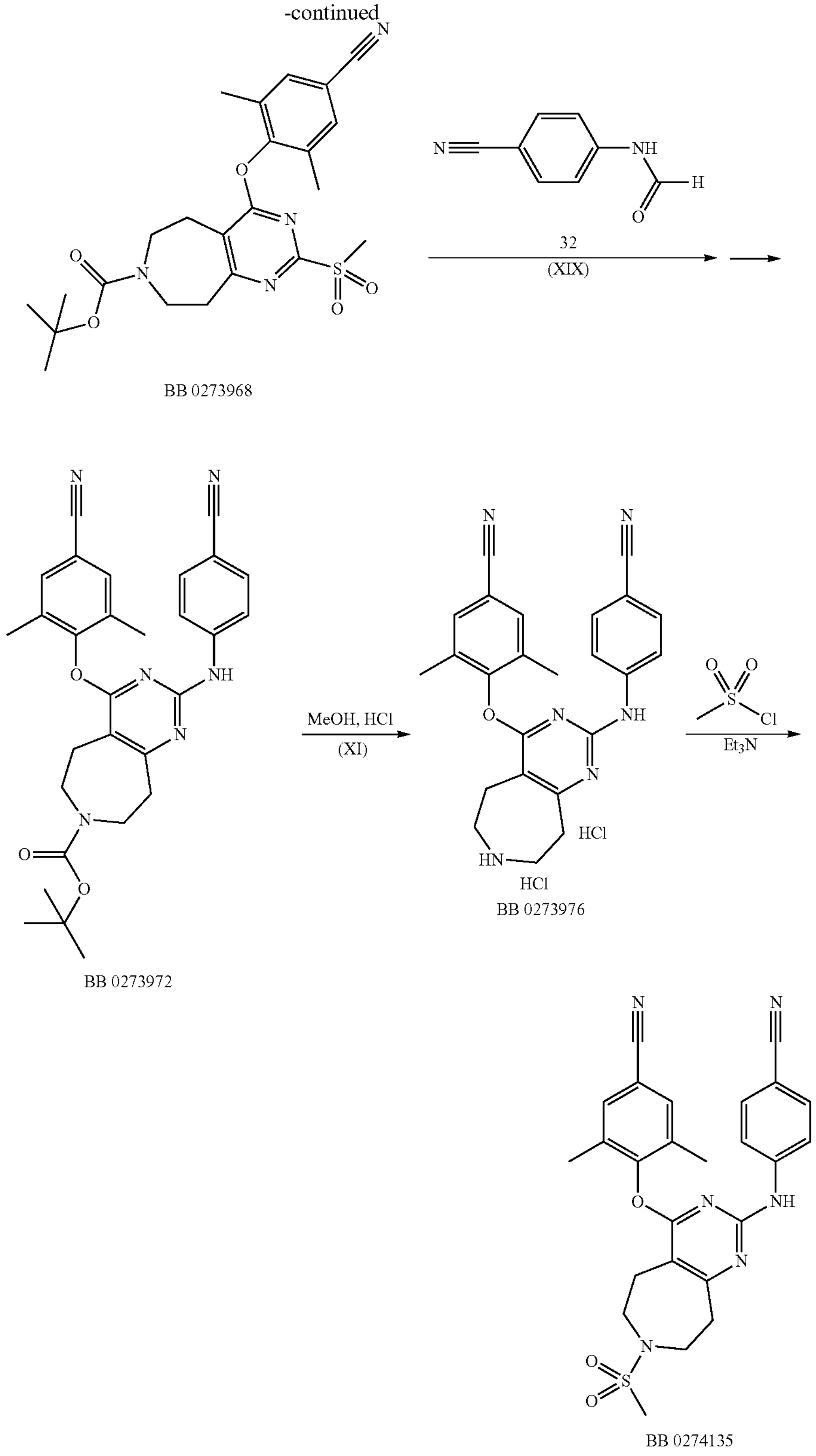
BB 0274135
$^1$H NMR (400 MHz, DMSO-$d_6$, δ, ppm): 2.10 (broadened singlet, 6H), 2.94 (s, 3H), 3.02-3.20 (m, 4H), 3.40-3.59 (m, 4H), 7.42 (s, 4H), 7.78 (s, 2H), 10.09 (s, 1H).
Weight Yield—0.08 g (75%)
LCMS m/z (M+H): 489

Example 58
Synthesis of 4-((2-((4-cyanophenyl)amino)-6-(pyridine-4-ylmethyl)-5,6,7,8-tetrahydropyrido[4,3-d] pyrimidine-4-yl)oxy)-3,5-dimethylbenzonitrile
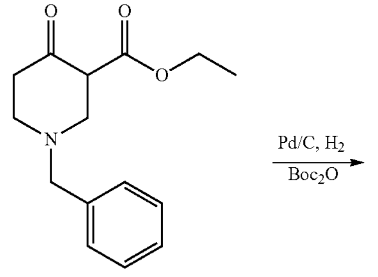
11
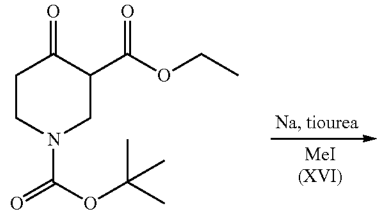
12
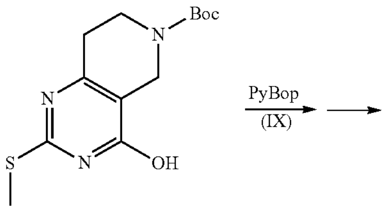
13
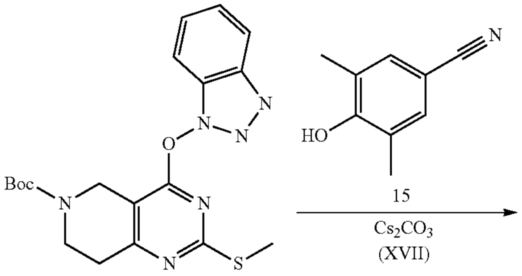
14
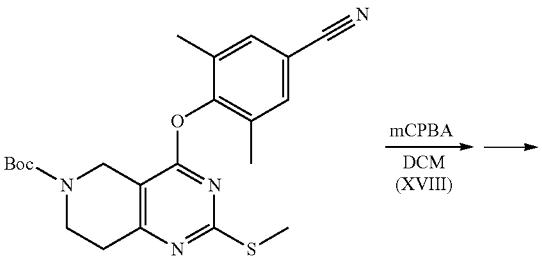
BB 0273947
-continued
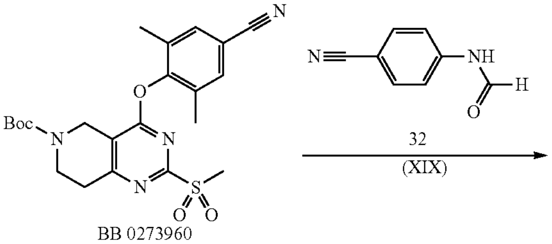
BB 0273960
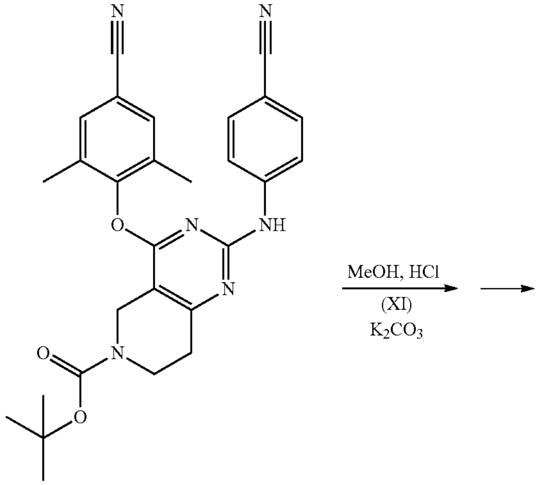
BB 0273961
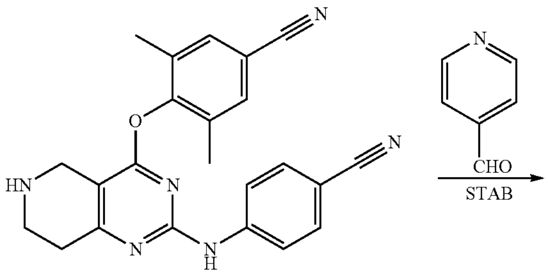
BB 0273963
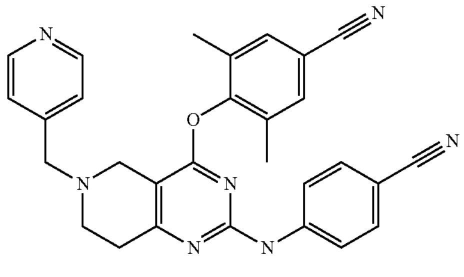
BB 0274137
BB 0274137
$^1$H NMR (400 MHz, $CDCl_3$, δ, ppm): 2.12 (s, 6H), 2.90 (dd, J=15.1 Hz, 4.8 Hz, 4H), 3.71 (s, 2H), 3.81 (s, 2H), 7.31-7.41 (m, 6H), 7.45 (s, 2H), 8.58-8.60 (m, 2H).
Weight Yield—0.026 g (38%)
LCMS m/z (M+H): 488

Example 59
Synthesis of 4-((2-((4-cyanophenyl)amino)-6-(pyridine-3-ylmethyl)-5,6,7,8-tetrahydropyrido[4,3-d]pyrimidine-4-yl)oxy)-3,5-dimethylbenzonitrile
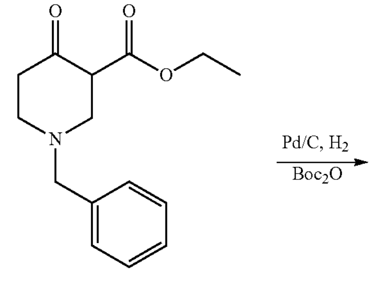
11
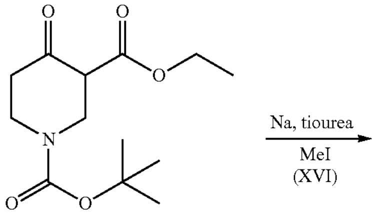
12
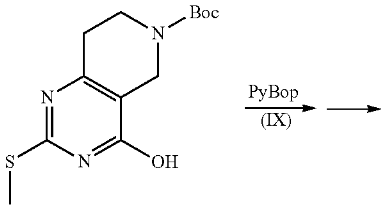
13
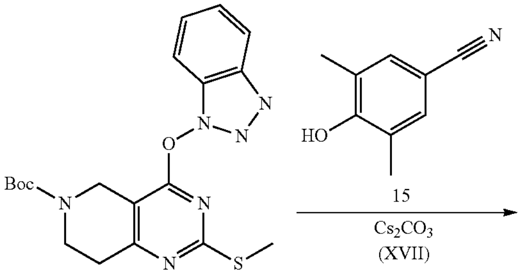
14
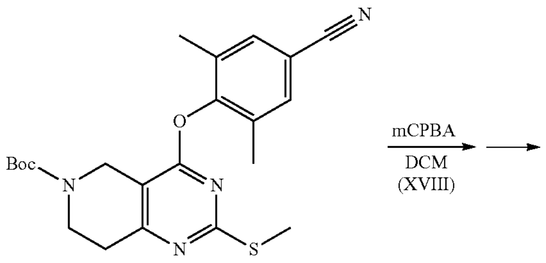
BB 0273947
-continued
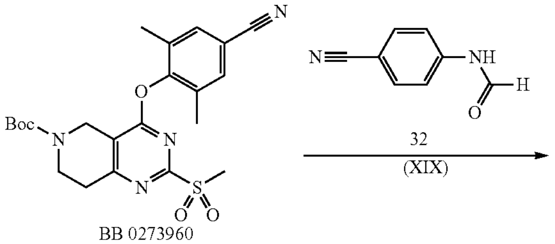
BB 0273960
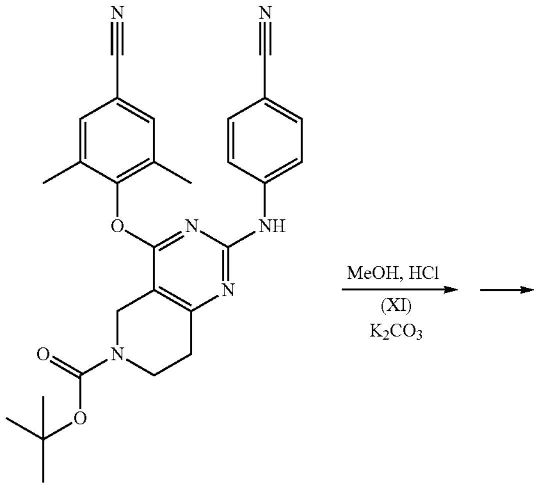
BB 0273961
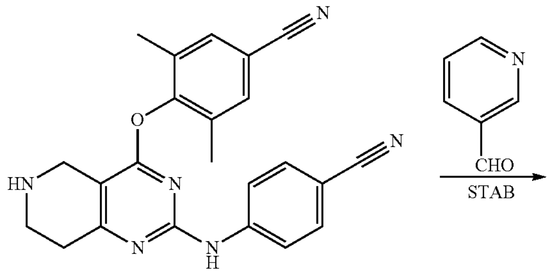
BB 0273963
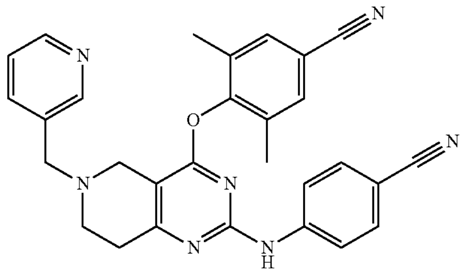
BB 0274138
BB 0274138
$^1$H NMR (400 MHz, $CDCl_3$, δ, ppm): 2.12 (s, 6H), 2.80-3.00 (m, 4H), 3.71 (s, 2H), 3.81 (s, 2H), 7.28-7.41 (m, 4H), 7.46 (s, 2H), 7.50 (dd, J=7.9 Hz, 4.8 Hz, 1H), 7.77 (d, J=7.8 Hz, 1H), 8.19 (dt, J=7.9 Hz, 1.9 Hz, 1H), 8.53-8.68 (m, 1H).
Weight Yield—0.030 g (40%)
LCMS m/z (M+H): 488

Example 60
Synthesis of 4-((2-((4-cyanophenyl)amino)-6-(2-hydroxybenzyl)-5,6,7,8-tetrahydropyrido[4,3-d]pyrimidine-4-yl)oxy)-3,5-dimethylbenzonitrile
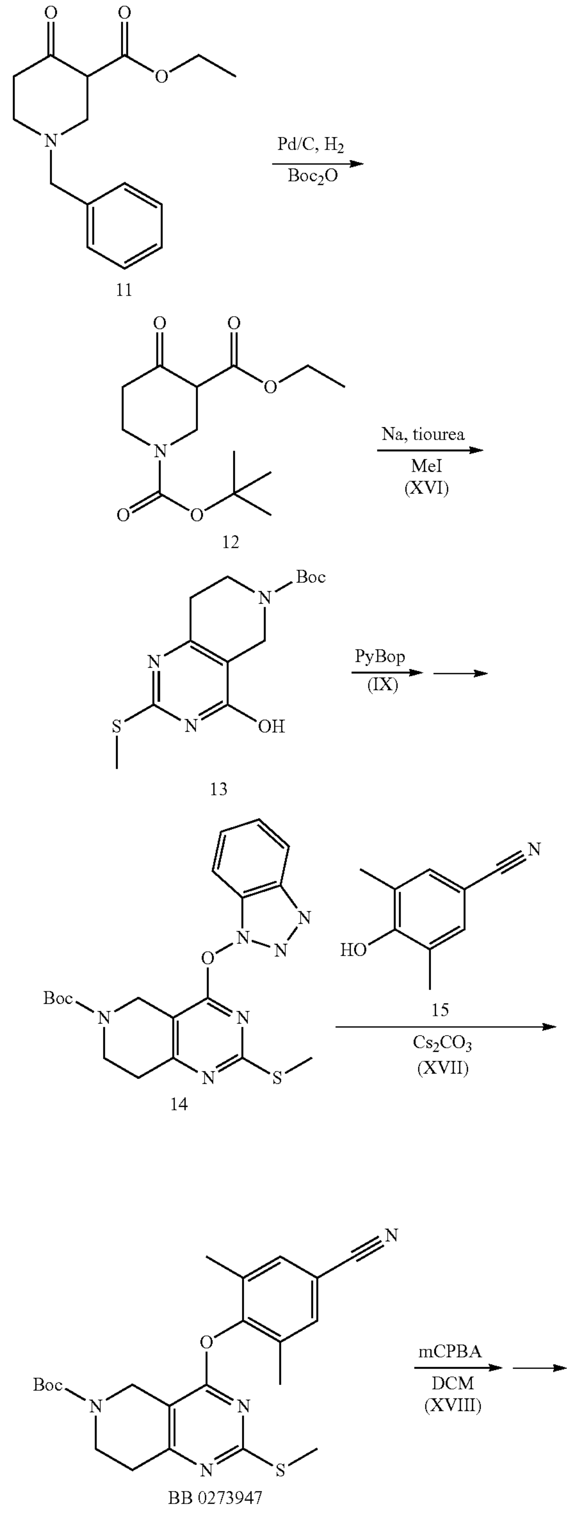
-continued
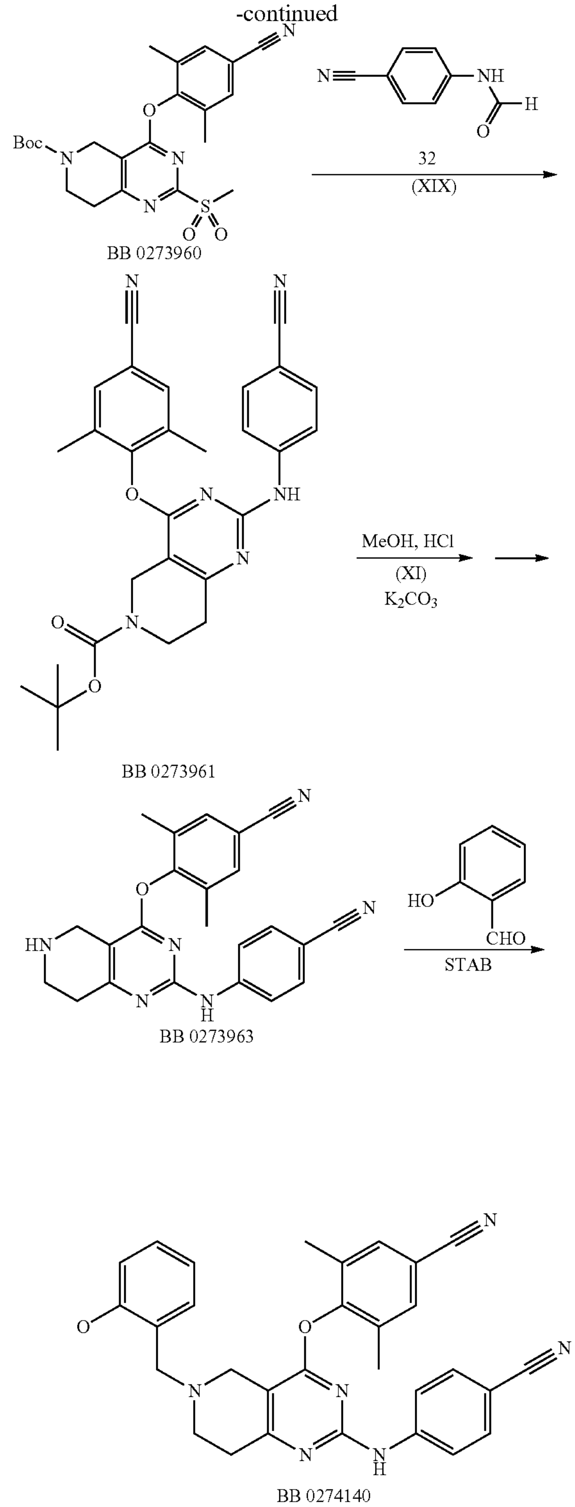
BB 0274140
$^1$H NMR (400 MHz, $CDCl_3$, δ, ppm): 2.14 (s, 6H), 3.00 (d, J=6.6 Hz, 4H), 3.83 (broadened singlet, 2H), 4.01 (s, 2H), 6.83-6.92 (m, 2H), 7.02-7.11 (m, 2H), 7.33-7.38 (m, 2H), 7.39-7.44 (m, 2H), 7.47 (s, 2H).
Weight Yield—0.033 g (41%)
LCMS m/z (M+H): 503

Example 61
Synthesis of 4-((2-((4-cyanophenyl)amino)-6-(2-(prop-2-in-1-yloxy)benzyl)-5,6,7,8-tetrahydropyrido[4,3-d]pyrimidine-4-yl)oxy)-3,5-dimethylbenzonitrile
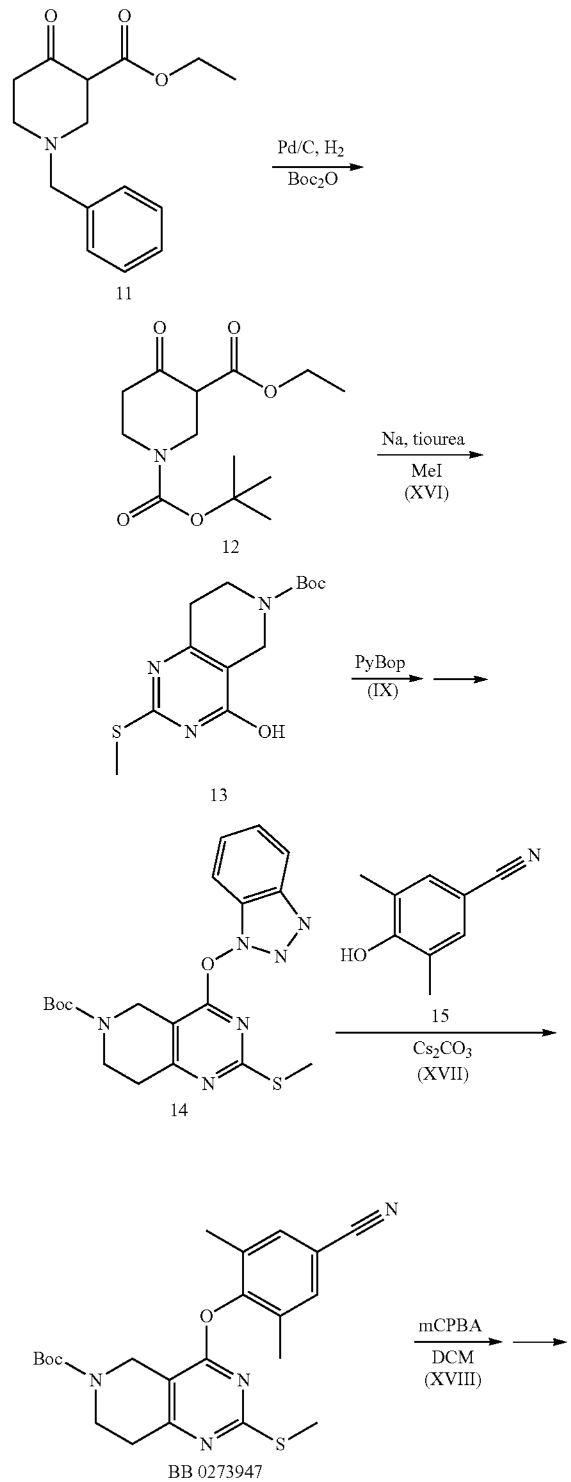
-continued
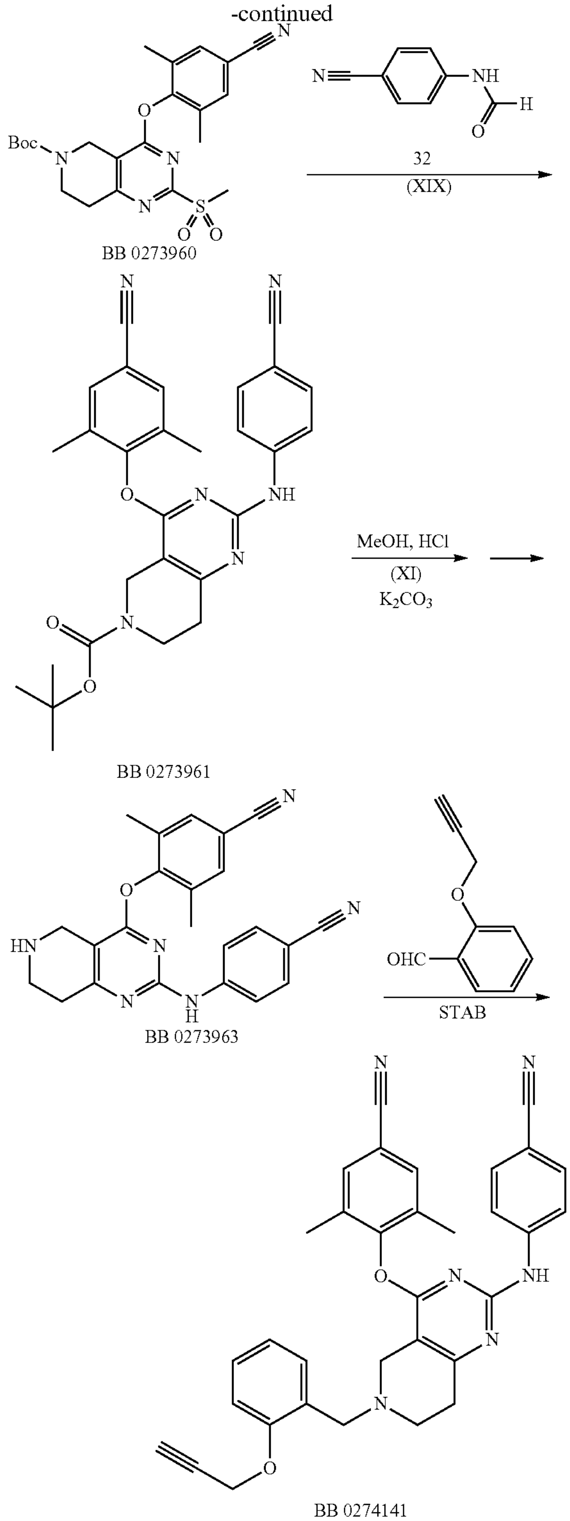
BB 0274141
$^1H$ NMR (400 MHz, $CDCl_3$, δ, ppm): 2.13 (s, 6H), 2.51 (dt, J=10.6 Hz, 2.4 Hz, 2H), 2.90 (s, 4H), 3.78 (s, 2H), 3.87 (s, 2H), 4.75 (dd, J=8.3 Hz, 2.4 Hz, 2H), 6.95-7.07 (m, 2H), 7.25-7.33 (m, 4H), 7.33-7.38 (m, 2H), 7.45 (s, 2H).
Weight Yield—0.062 g (70%)
LCMS m/z (M+H): 541

Example 62
Synthesis of 3-(4-(4-cyano-2,6-dimethylphenoxy)-2-((4-cyanophenyl)amino)-8,9-dihydro-5H-pyrimido[4,5-d]azepine-7(6H)-yl)propane acid
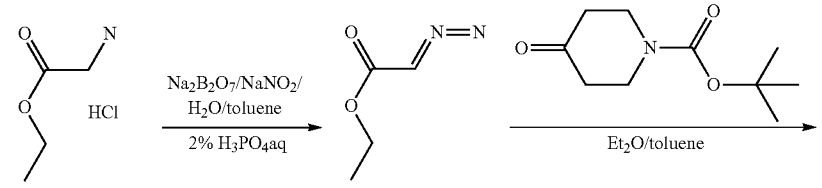
49 50
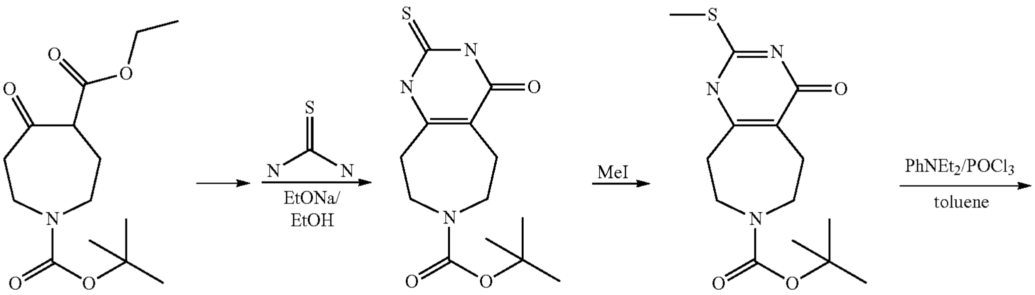
51 52 53
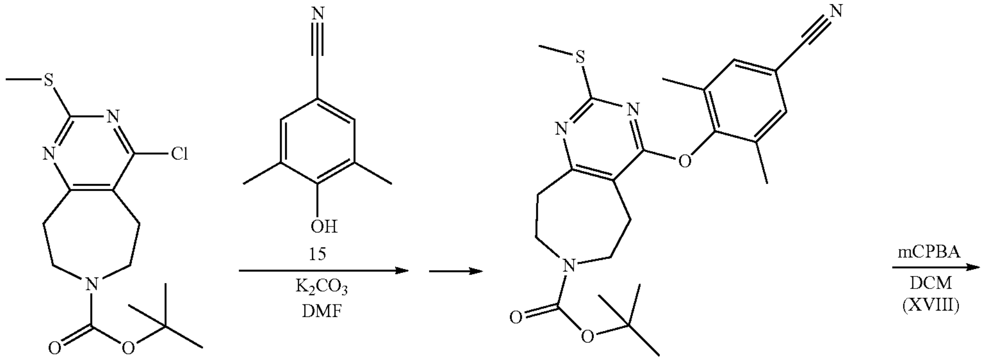
54 BB 0273957
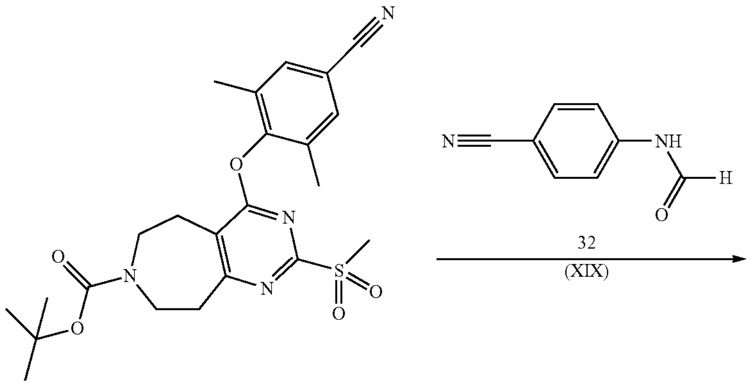
BB 0273968

-continued
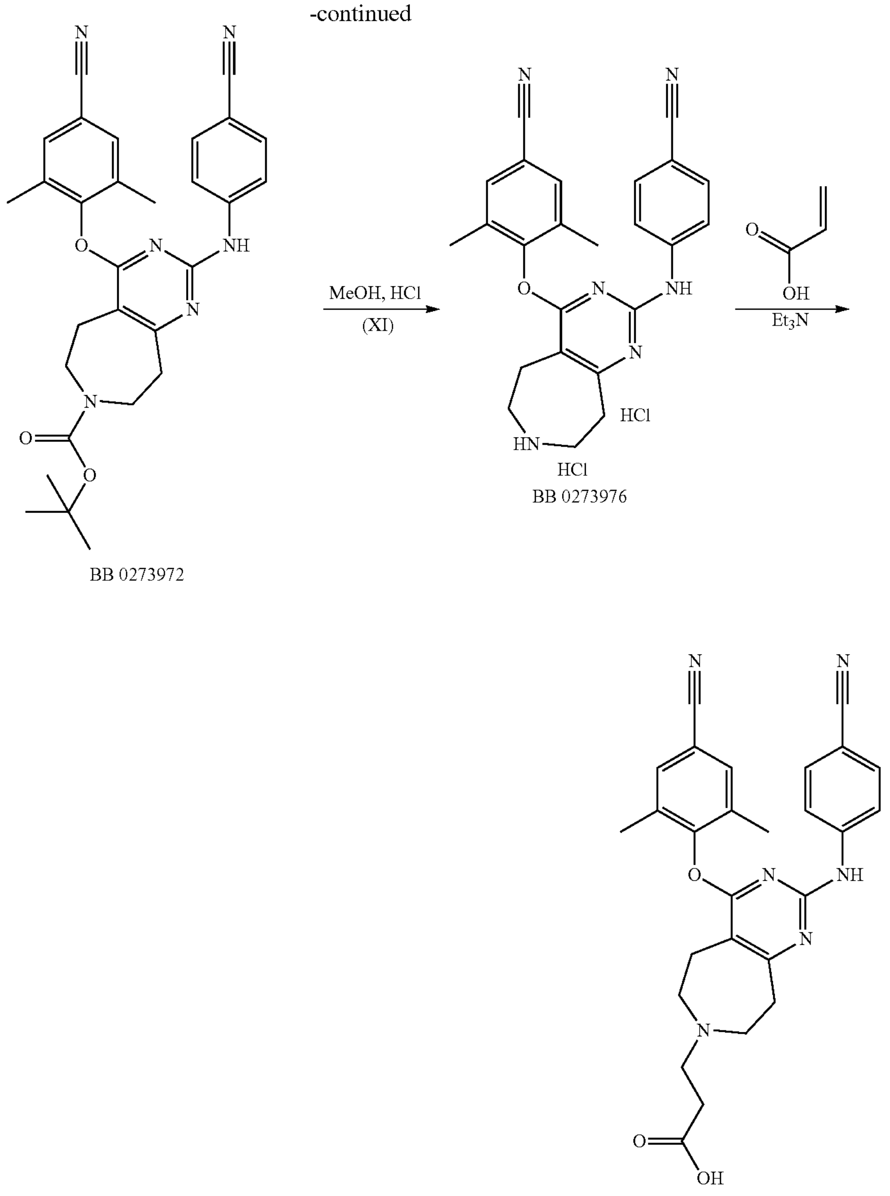
BB 0273972
BB 0273976
BB 0274143
BB 0274143
$^1$H NMR (400 MHz, DMSO-$d_6$, δ, ppm): 2.01-2.22 (m, 6H), 2.60-2.82 (m, 2H), 3.16 (broadened singlet, 10H), 7.43 (broadened singlet, 4H), 7.79 (s, 2H), 10.09 (broadened singlet, 1H).
Weight Yield—0.09 g (33%)
LCMS m/z (M+H): 483
Example 63
Synthesis of 4-((7-allyl-2-((4-cyanophenyl)amino)-6,7,8,9-tetrahydro-5H-pyrimido[4,5-d]azepine-4-yl)oxy)-3,5-dimethylbenzonitrile
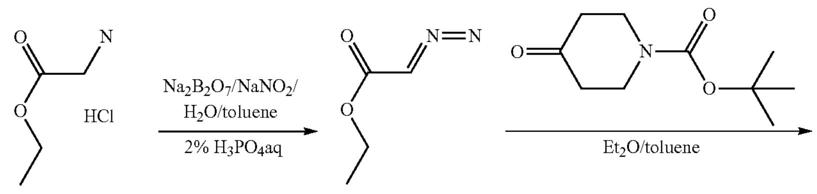
49
50

-continued
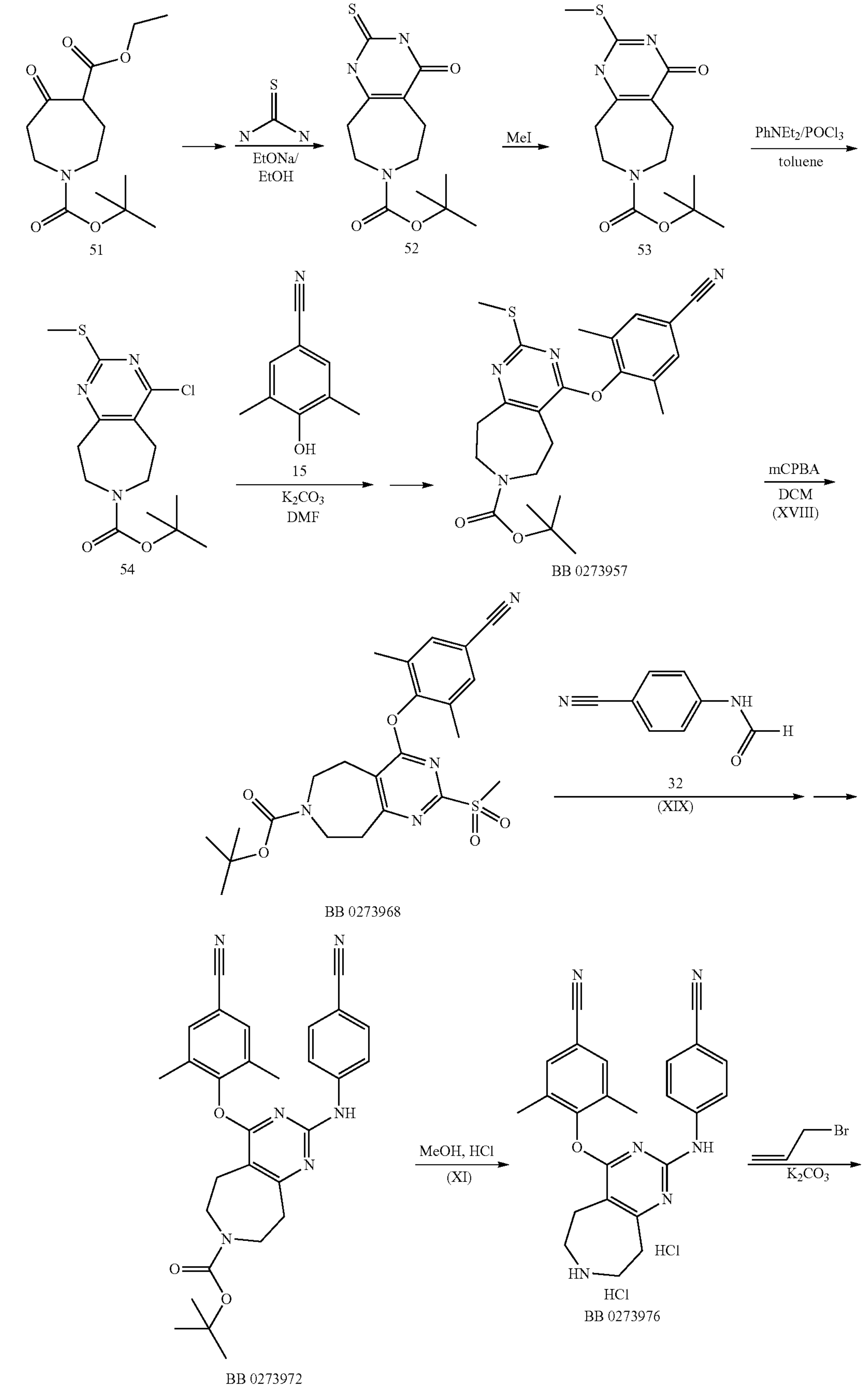
51 52 53
54 15 BB 0273957
32 BB 0273968
BB 0273972 BB 0273976

-continued
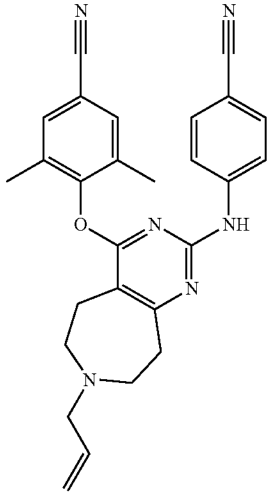
BB 0274144
BB 0274144
$^1H$ NMR (400 MHz, $CDCl_3$, δ, ppm): 2.15 (s, 6H), 2.61-2.81 (m, 4H), 3.07 (broadened singlet, 4H), 3.19 (d, J=6.2 Hz, 2H), 5.15-5.29 (m, 2H), 5.82-6.03 (m, 1H), 7.11 (s, 1H), 7.28-7.33 (m, 2H), 7.34-7.41 (m, 2H), 7.48 (s, 2H).
Weight Yield—0.011 g (17%)
LCMS m/z (M+H): 451
Example 64
Synthesis of 4-((7-acetyl-2-((4-cyanophenyl)amino)-6,7,8,9-tetrahydro-5H-pyrimido[4,5-d]azepine-4-yl)oxy)-3,5-dimethylbenzonitrile
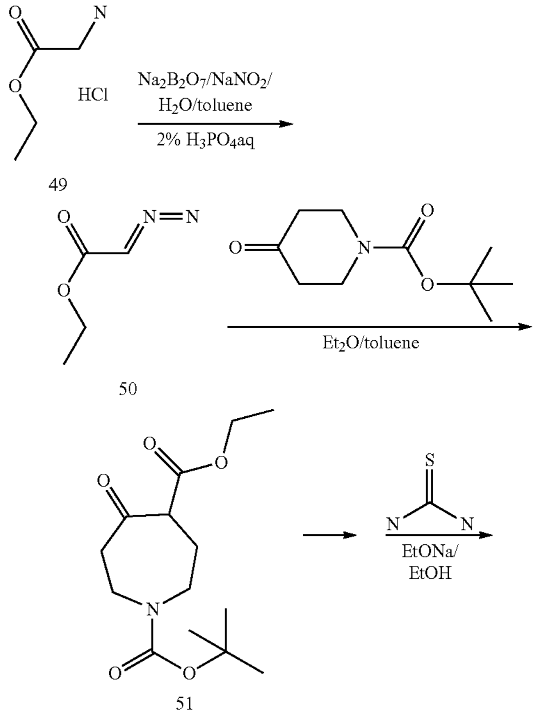
-continued
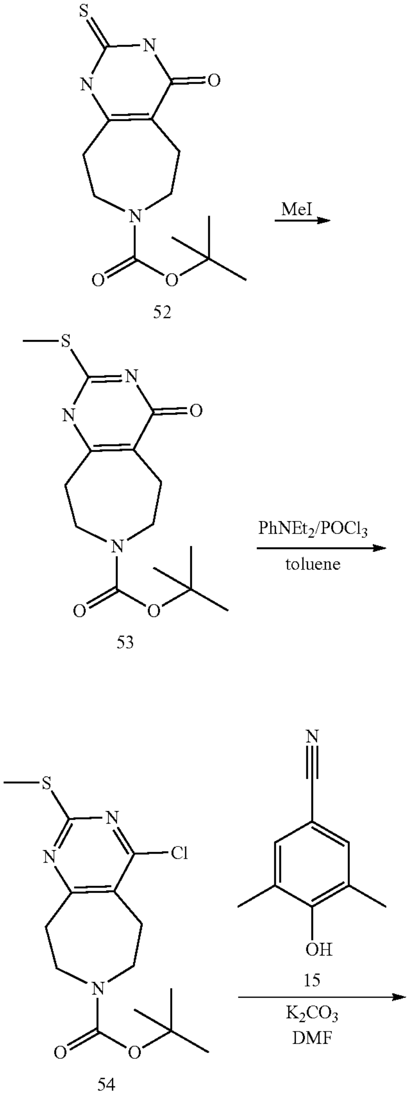

-continued
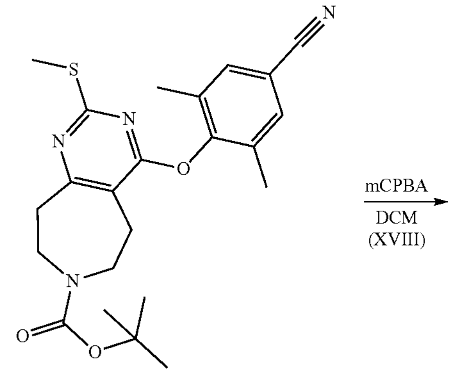
BB 0273957
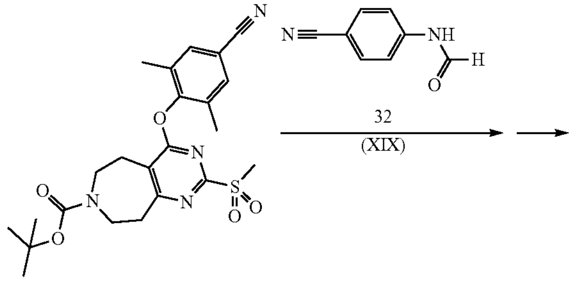
BB 0273698
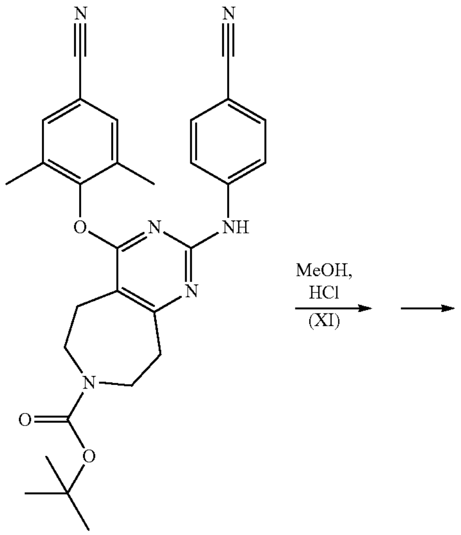
BB 0273972
-continued
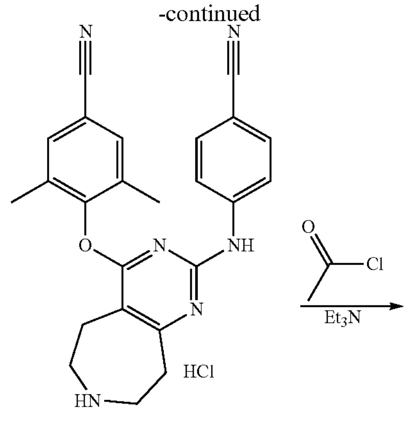
BB 0273976
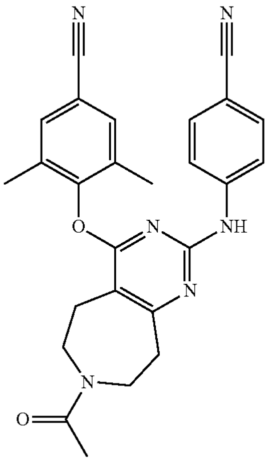
BB 0274145
BB 0274145
$^1$H NMR (400 MHz, DMSO-$d_6$, δ, ppm): 2.10 (broadened singlet, 9H), 2.98 (broadened singlet, 2H), 3.09 (broadened singlet, 2H), 3.70 (broadened singlet, 4H), 7.41 (broadened singlet, 4H), 7.78 (broadened singlet, 2H), 10.06 (broadened singlet, 1H).
Weight Yield—0.074 g (69%)
LCMS m/z (M+H): 453
Example 65
Synthesis of 4-((7-(2-(1H-imidazole-1-yl)acetyl)-2-((4-cyanophenyl)amino)-6,7,8,9-tetrahydro-5H-pyrimido[4,5-d]azepine-4-yl)oxy)-3,5-dimethylbenzonitrile
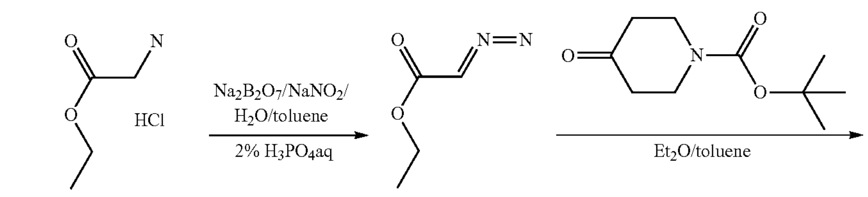
49
50

-continued
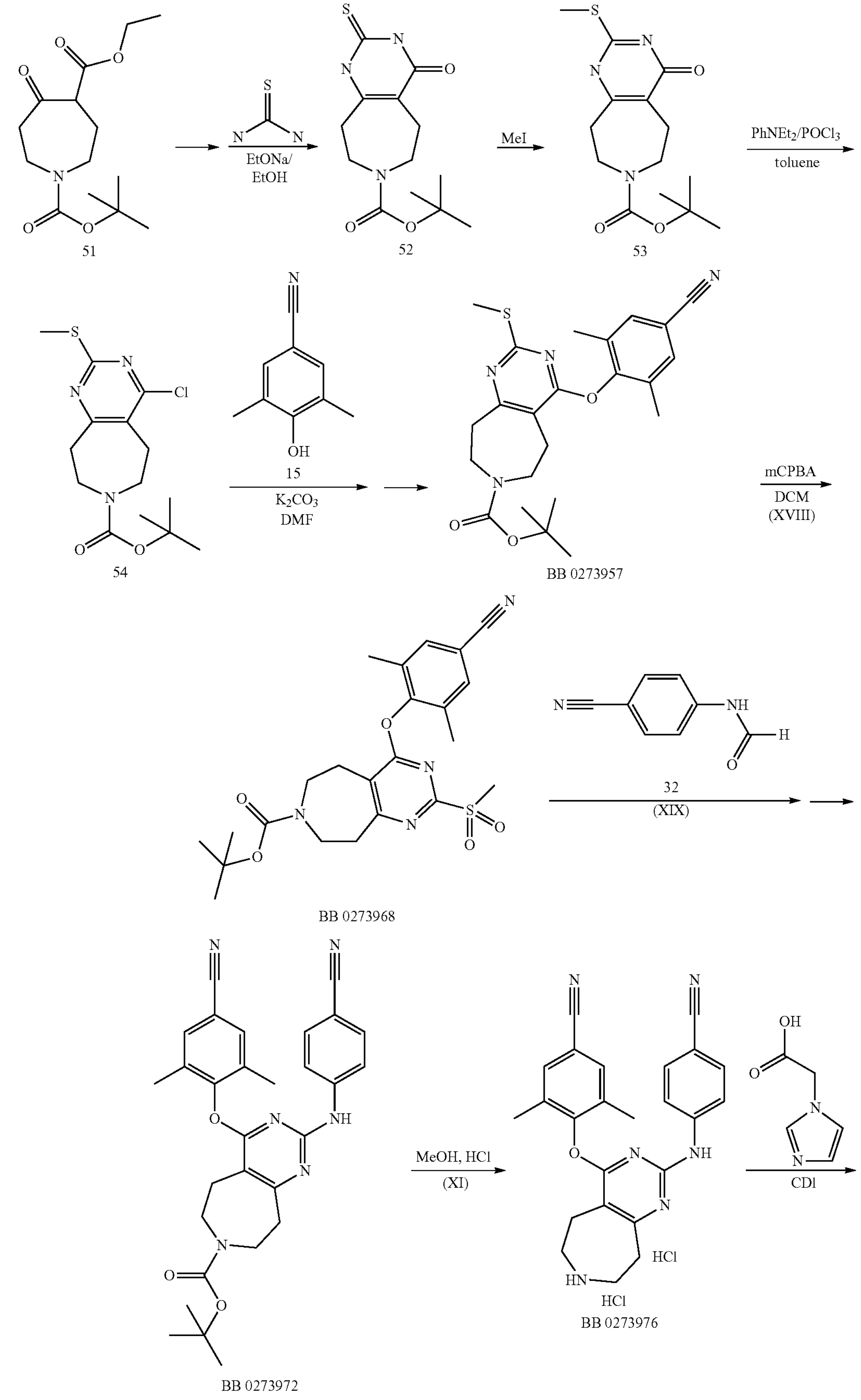
51
52
53
54
BB 0273957
BB 0273968
BB 0273972
BB 0273976

-continued
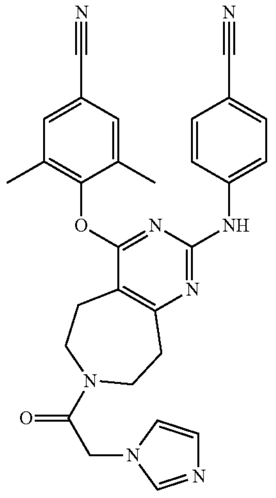
BB 0274227
BB 0274227
$^1H$ NMR (400 MHz, DMSO-$d_6$, δ, ppm): 2.11 (d, J=10.2 Hz, 6H), 3.03 (broadened singlet, 2H), 3.17 (broadened singlet, 2H), 3.76 (broadened singlet, 4H), 5.13 (d, J=6.1 Hz, 2H), 6.90 (broadened singlet, 1H), 7.10 (d, J=7.40 Hz, 1H), 7.43 (d, J=5.8 Hz, 4H), 7.61 (d, J=6.7 Hz, 1H), 7.79 (d, J=6.7 Hz, 2H), 10.08 (broadened singlet, 1H).
Weight Yield—0.011 g (21%)
LCMS m/z (M+H): 519
Example 66
Synthesis of 4-((2-((4-cyanophenyl)amino)-7-(2-(methyl-1H-imidazole-1-yl)acetyl)-6,7,8,9-tetra-hydro-5H-pyrimido[4,5-d]azepine-4-yl)oxy)-3,5-dimethylbenzonitrile
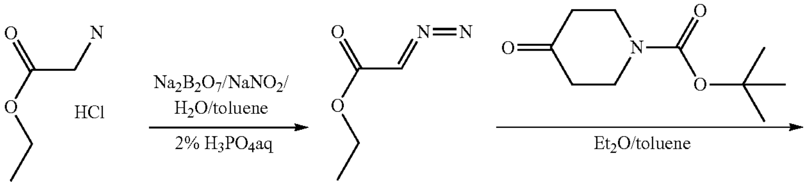
49 50
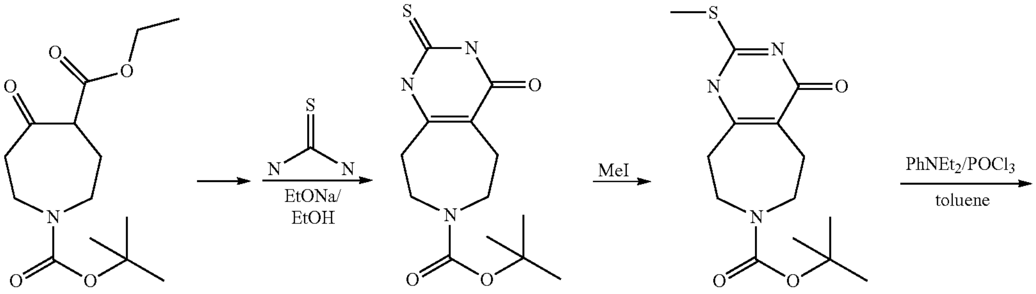
51 52 53

-continued
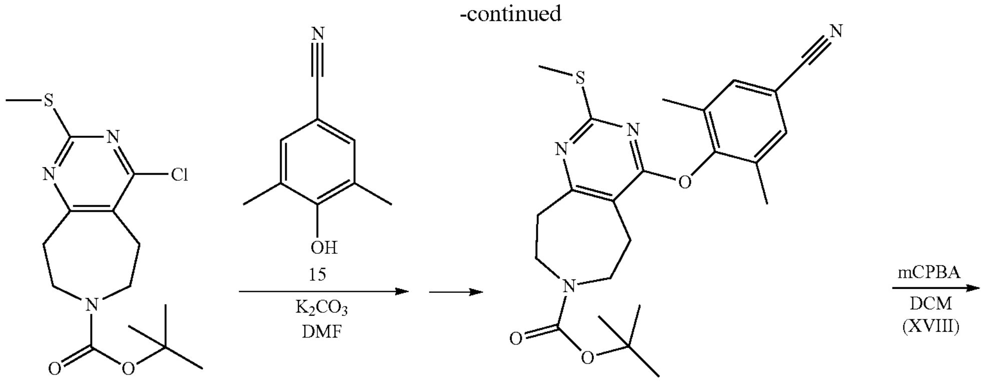
54 BB 0273957
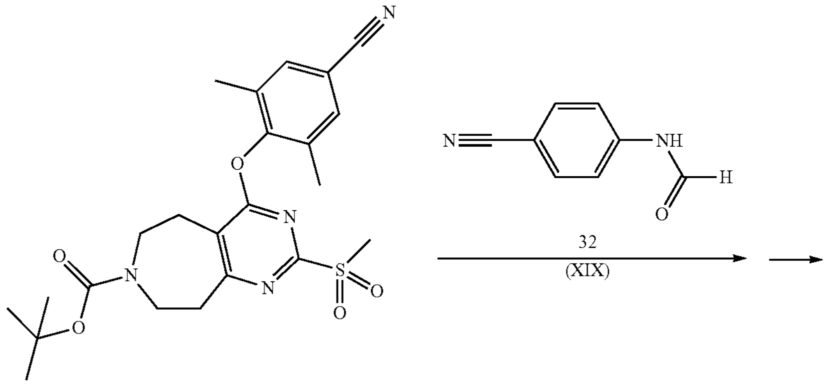
BB 0273968
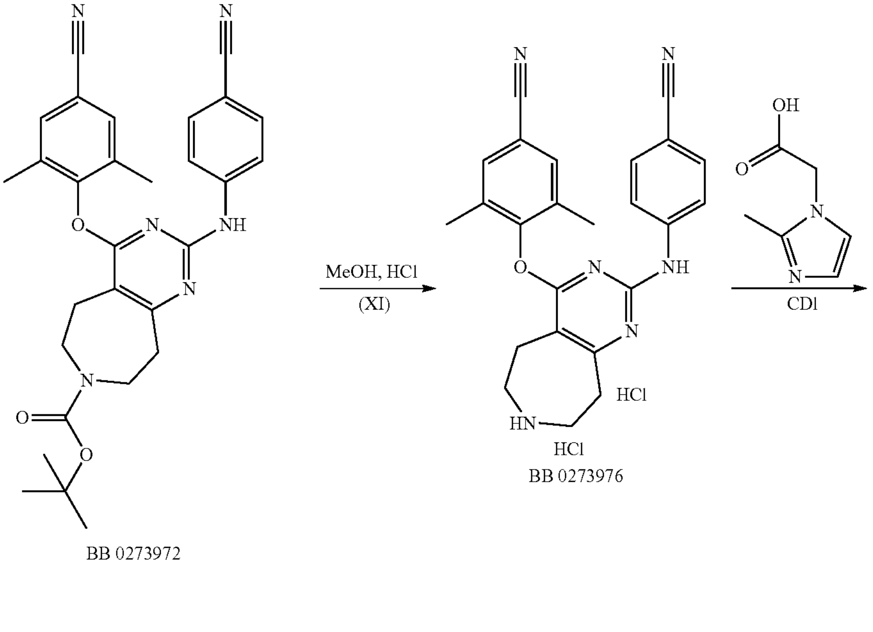
BB 0273972

-continued

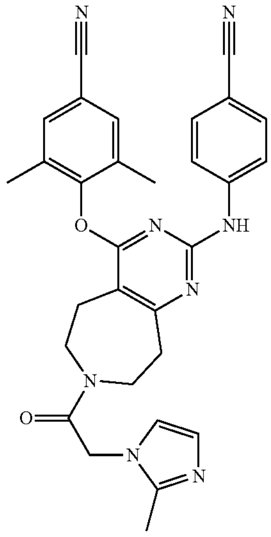

BB 0274236

BB 0274236

$^{1}H$ NMR (400 MHz, DMSO-$d_6$, δ, ppm): 2.00-2.23 (m, 9H), 2.92-3.25 (m, 4H), 3.77 (broadened singlet, 4H), 5.02 (d, J=13.0 Hz, 2H), 6.69 (d, J=5.2 Hz, 1H), 6.96 (d, J=11.4 Hz, 1H), 7.43 (d, J=6.8 Hz, 4H), 7.79 (d, J=7.5 Hz, 2H), 10.08 (broadened singlet, 1H).

M=0.038 g (41%)

LCMS m/z (M+H): 533

Example 67

Synthesis of 4-((6-(2-amino-3-(1H-imidazole-5-yl)propanoyl)-2-((4-cyanophenyl)amino)-5,6,7,8-tetrahydropyrido[4,3-d]pyrimidine-4-yl)oxy)-3,5-dimethylbenzonitrile

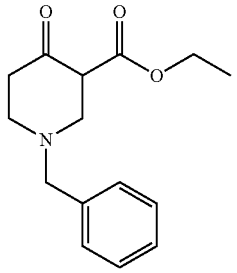

11

Pd/C, $H_2$
$Boc_2O$

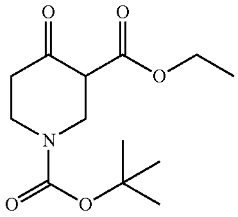

12

Na, tiourea
MeI
(XVI)

-continued

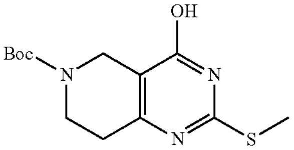

13

PyBop
(IX)

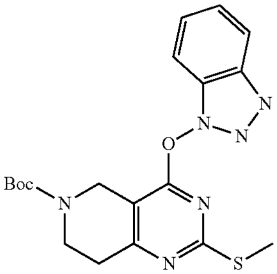

14

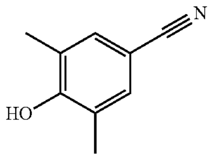

15

$Cs_2CO_3$
(XVII)

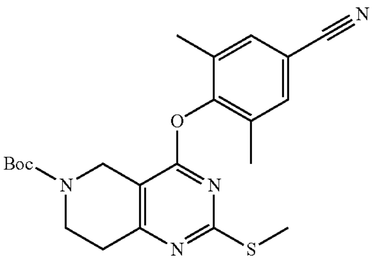

BB 0273947 mCPBA
DCM
(XVIII)

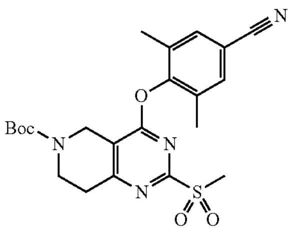

BB 0273960

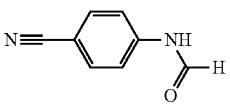

32

(XIX)

-continued

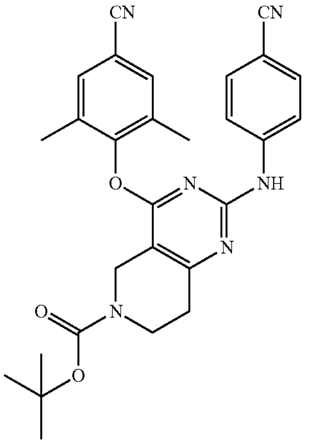

BB 0273961

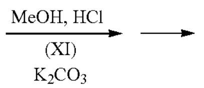

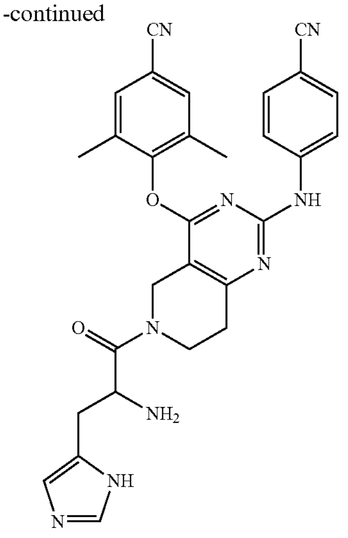

BB 0275622

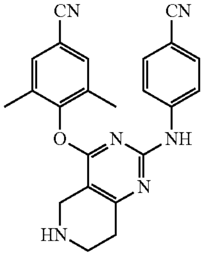

BB 0273963

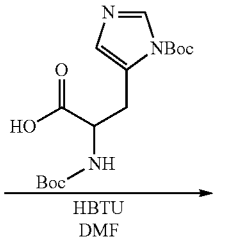

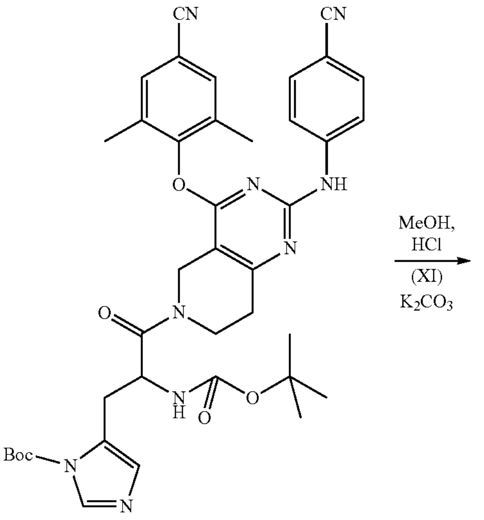

BB 0275622

$^1$H NMR (400 MHz, $CDCl_3$, δ, ppm): 2.42 (s, 5H), 2.51-2.68 (m, 1H), 2.73-2.92 (m, 1H), 3.01-3.30 (m, 2H), 3.74-3.96 (m, 2H), 4.05-4.33 (m, 1H), 4.61-4.77 (m, 1H), 4.82-4.97 (m, 1H), 6.94 (d, J=0.9 Hz, 1H), 7.37 (s, 2H), 7.47 (dd, J=4.9, 1.0 Hz, 1H), 7.63 (d, J=8.7 Hz, 2H), 7.83 (d, 2H) M=0.006 g (33%)

LCMS m/z (M+H): 535

Evaluation of HIV reproduction inhibition/protection of human cells by anti-HIV products of the present invention was conducted by measuring change in living cells concentration in experimental wells with MT-4 cells infected with HIV-1, as well as by the production of viral protein p24 with adding different concentrations of compounds according to the present invention.

Antiviral activity of products against HIV-1 subtype A strain 12RU 69831 was determined, when the cell culture was infected with a constant dose of virus, corresponding to 300 CCID50.

Results of IC50 determination of compounds according to the present invention are provided in table 1.

TABLE 1

| Activity of compounds according to the present invention against human immunodeficiency virus HIV-1 subtype A | |
|---|---|
| Compound | Activity against HIV-1 12RU 69831 strain (subtype A), µM |
| BB0273459 | 74.3452 |
| BB0274100 | 33.7972 |
| BB0274101 | 8.80281 |
| BB0274102 | 0.00341 |
| BB0274103 | 228.260 |
| BB0274111 | 533.088 |
| BB0274118 | 0.32442 |
| BB0274119 | 102.739 |
| BB0274120 | 108.280 |
| BB0274121 | 18.7265 |
| BB0274122 | 18.9274 |

TABLE 1-continued

Activity of compounds according to the present invention against human immunodeficiency virus HIV-1 subtype A

| Compound | Activity against HIV-1 12RU 69831 strain (subtype A), μM |
|---|---|
| BB0274123 | 2.06611 |
| BB0274124 | 342.424 |
| BB0274125 | 82.1428 |
| BB0274126 | 45.3020 |
| BB0274127 | 12.0967 |
| BB0274128 | 113.114 |
| BB0274129 | 1.03921 |
| BB0274130 | 240.000 |
| BB0274131 | 0.66666 |
| BB0274132 | 0.90909 |
| BB0274133 | 10.4722 |
| BB0274134 | 0.09594 |
| BB0274135 | 6.13496 |
| BB0274137 | 0.00799 |
| BB0274015 | 29.8805 |
| BB0274016 | 4880.48 |
| BB0274021 | 0.01022 |
| BB0274025 | 3215.43 |
| BB0274026 | 0.36398 |
| BB0274027 | 37.037 |
| BB0274028 | 16.194 |
| BB0274051 | 0.00552 |
| BB0274052 | 0.12745 |
| BB0274063 | 230.263 |
| BB0274064 | 493.421 |
| BB0274138 | 0.00676 |
| BB0274140 | 27.8330 |
| BB0274141 | 173.752 |
| BB0274143 | 0.71014 |
| BB0274144 | 1.62971 |
| BB0274145 | 1.68874 |
| BB0274227 | 0.01252 |
| BB0274236 | 0.04878 |
| BB0273774 | 223.844 |
| BB0273775 | 295.399 |
| BB0273892 | 1,223.77 |
| BB0273943 | 346.303 |
| BB0273961 | 42.2535 |
| BB0273963 | 7.55667 |
| BB0273964 | 0.14526 |
| BB0273965 | 1.73077 |
| BB0273969 | 10683.7 |
| BB0273972 | 117.416 |
| BB0273976 | 0.00583 |
| BB0274009 | 290.502 |
| BB0274010 | 0.06201 |
| BB0274011 | 27.1318 |
| BB0274012 | 5.81395 |
| BB0274014 | 5.97609 |
| BB0274065 | 41.118 |
| BB0274072 | 4.065 |
| BB0274073 | 57.425 |
| BB0274074 | 83.333 |
| BB0274075 | 5.802 |
| BB0274080 | 0.414 |
| BB0274095 | 11.333 |
| BB0274097 | 663.967 |
| BB0274098 | 0.046 |
| BB0274099 | 0.152 |
| BB0275622 | 0.032 |
| BB0274239 | 359.0485 |
| BB0274312 | 34.823 |
| BB0274337 | 204.938 |

Features mentioned in the specification or in the claims expressed in special forms and terms for the implementation of the claimed function or method or way of achievement of the claimed result may be used separately or in any combination of such features to implement the invention in its different forms.

The present invention is described with a reference to illustrations and examples with a purpose of clarification and understanding of the invention essence. It is obvious for the person skilled in the art that within the scope and claims of the invention, different changes and modifications are possible. Consequently, it is assumed that the specification just illustrates the invention and does not limit its scope. Scope of the invention is determined with a reference to the claims of the invention including the whole scope of equivalents covered by the claims.

All patents, patent applications and publications cited in the specification are included into the specification as a reference on a full scale in each case at the same extent, as if each patent, patent application and publication were cited separately.

It is also to be understood that the following claims are intended to cover all of the generic and specific features of the invention herein described, and all statements of the scope of the invention which, as a matter of language, might be said to fall there between. Now that the invention has been described.

The invention claimed is:

1. A compound of formula I:

(1)

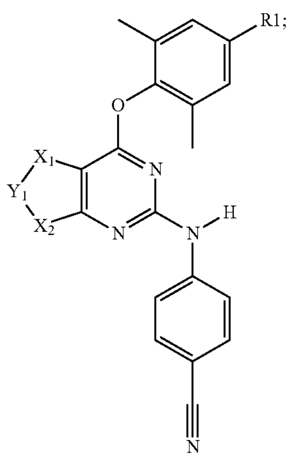

wherein $R^1$ is selected from the group consisting of H, CN, CN—CH═CH—, C═O, CH═CH—COOH, substituted or unsubstituted 4-6-membered heterocyclyl containing 1-2 O heteroatoms, aminocarbonyl, $NH_2$, substituted or unsubstituted $C_{1-6}$alkyl, halogen, substituted or unsubstituted $C_{1-6}$alkyloxy, $NHR^9$, $NR^9R^{10}$, —C(═O)—$NHR^9$, —C(═O)—$NR^9R^{10}$, —C(═O)—$R^9$, —CH═N—NH—C(═O)—$R^9$, substituted or unsubstituted $C_{1-6}$alkyloxy$C_{1-6}$alkyl, substituted or unsubstituted $C_{2-6}$alkenyl, substituted or unsubstituted $C_{2-6}$alkynyl, —C(═N—O—$R^8$)—$C_{1-4}$ alkyl, $R^7$, and —$R^b$—$R^7$;

wherein $X^1$ and $X^2$ are each a $(CH_2)_n$ substituent, wherein n is a number from 1 to 3 and is selected independently for $X_1$ and $X_2$;

wherein $Y^1$ is selected from the group consisting of —O—, —S—, —S(═O)—, —S(═O)$_2$—,

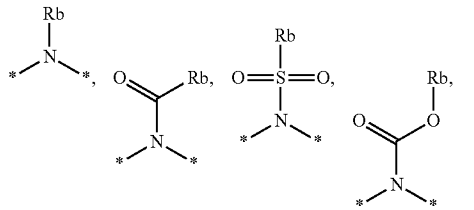

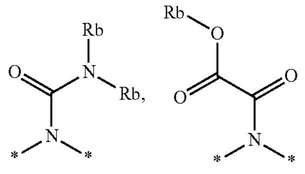

and

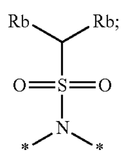

wherein $R^b$ is selected from the group consisting of —H, cyano, aminocarbonyl, substituted or unsubstituted —$C_1$-$C_6$-alkyl, substituted or unsubstituted —$C_2$-$C_6$-alkenyl, substituted or unsubstituted —$C_2$-$C_6$-alkynyl, substituted or unsubstituted —$C_3$-$C_6$-aryl, substituted or unsubstituted 4-6-membered-heteroaryl containing 1 to 4 heteroatoms wherein the heteroatoms are independently selected from N, S or O, substituted or unsubstituted —$C_3$-$C_9$-cycloalkyl, substituted or unsubstituted 4-9-membered heterocyclyl containing 1 to 4 heteroatoms wherein the heteroatoms are independently selected from N, S, or O, $R^7$, and $R^9$;

wherein $R^7$ is selected from the group consisting of monocyclic, bicyclic or tricyclic, saturated, partially saturated or aromatic carbocycle or monocyclic, bicyclic or tricyclic, saturated, partially saturated or aromatic 4-6 membered heterocycle, containing 1 to 4 heteroatoms, independently selected from a group S, N and O, wherein each of the mentioned above carbocyclic or heterocyclic fragments may be optionally substituted by one, two, three, four or five substituents, each of which is independently selected from halogen, hydroxy, mercapto, $C_{1-6}$alkyl, hydroxy$C_{1-6}$alkyl, amino$C_{1-6}$alkyl, mono- and di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, —C(═N—O—$R^8$), $R^{7a}$, —Rb—$R^{7a}$, and $R^{7a}$—$C_{1-4}$alkyl;

wherein $R^{7a}$ is selected from the group consisting of monocyclic, bicyclic or tricyclic, saturated, partially saturated or aromatic carbocycle or monocyclic, bicyclic or tricyclic, saturated, partially saturated or aromatic 4-6 membered heterocycle, containing 1 to 4 heteroatoms, independently selected from a group S, N and O, wherein each of the mentioned above carbocyclic or heterocyclic fragments may be optionally substituted by one, two, three, four or five substituents, each of which is independently selected from halogen, hydroxy, mercapto, $C_{1-6}$alkyl, hydroxy$C_{1-6}$alkyl, amino$C_{1-6}$alkyl, mono- or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, and —CH(═N—O—$R^8$);

wherein $R^8$ is hydrogen, $C_{1-4}$alkyl, aryl or aryl$C_{1-4}$alkyl;

wherein each of $R^9$ and $R^{10}$ independently are hydrogen; cyano, aminocarbonyl, hydroxy group; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; —CH(═$NR^{11}$) or $R^7$, wherein each of the $C_{1-6}$alkyl groups are independently substituted by one or two substituents, each of which is independently selected from hydroxy, $C_{1-6}$alkyloxy, hydroxy$C_{1-6}$alkyloxy, carboxyl, $C_{1-6}$alkyloxycarbonyl, cyano, amino, aminocarbonyl, imino, mono- and di($C_{1-4}$alkyl)amino, polyhalomethyl, polyhalomethyloxy; polyhalomethylthio, —S(═O)$_p$$R^8$, —NH—S(═O)$_p$ $R^8$, —C(═O)$R^8$, —NHC(═O)H, —C(═O)NHN$H_2$, NHC(═O)$R^8$, C(═NH)$R^8$, and $R^7$;

and pharmaceutically acceptable salts thereof.

2. The compound of claim 1, wherein $R^1$ is selected independently from H, —CN, —CH═CH—CN, —C═O, or —CH═CH—COOH.

3. The compound of claim 1, wherein $R^1$ is a 4-6-membered heterocyclyl containing 1-2 heteroatom O.

4. The compound of claim 1, wherein $R^1$ is oxetane, tetrahydrofuran or tetrahydropyran.

5. The compound of claim 1, wherein $Y^1$ is —O—, —S—, —S(═O)— or —S(═O)$_2$—.

6. The compound of claim 1, wherein $Y^1$ is

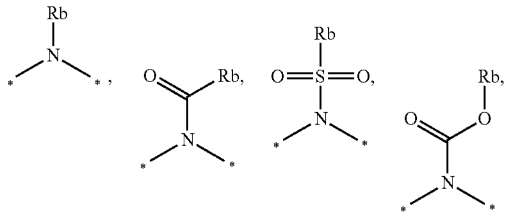

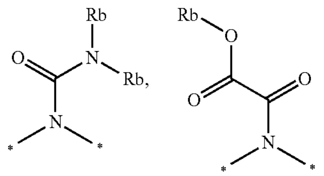

or

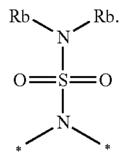

7. The compound of claim 1, wherein $Y^1$ is

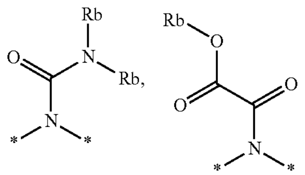

or

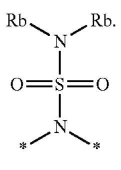

8. The compound of claim 1, wherein $R^b$ is substituted or unsubstituted methyl, ethyl, propyl, n-propyl, isopropyl, butyl, n-butyl, sec-butyl, tert-butyl, or pentyl.

9. The compound of claim 1, wherein $R^b$ is substituted or unsubstituted ethenyl, 1-propenyl, 2-propenyl, 1-butenyl, 2-butenyl, 3-butenyl, 2-methyl-1-propenyl, or 2-methyl-2-propenyl.

10. The compound of claim 1, wherein $R^b$ is substituted or unsubstituted phenyl.

11. The compound of claim 1, wherein $R^b$ is substituted or unsubstituted thienyl, pyrrolyl, imidazolyl, pyrazolyl, pyridyl, pyrimidinyl, pyridazinyl, triazinyl, tetrazolyl, benzo[b]thienyl, isobenzofuranyl, isoindolyl, or benzimidazolyl.

12. The compound of claim 1, wherein $R^b$ is substituted or unsubstituted cyclopropyl, cyclopentyl, cyclohexyl, bicyclo[2.2.2]octanyl, or spiro[5.5]undecanyl.

13. The compound of claim 1, wherein $R^b$ is substituted or unsubstituted pyrimidine, piperidine, azetidine, morpholine, piperazine, pyrrolidine, tetrahydropyran, furan, pyrrol, pyrazine, imidazole, or pyrazole.

14. The compound of claim 1, wherein $Y^1$ is

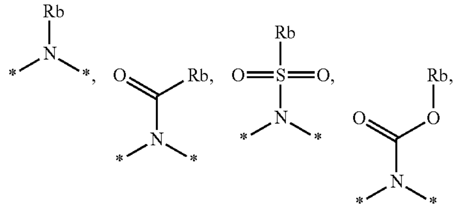

wherein $R^b$ is substituted or unsubstituted -5-6-membered-heteroaryl or heterocyclyl, containing 1 to 4 heteroatoms, independently selected from N, S and/or O.

15. The compound of claim 1, wherein $Y^1$ is

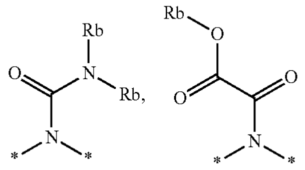

or

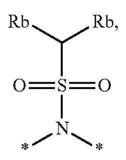

wherein $R^b$ is substituted or unsubstituted —$C_3$-$C_6$-aryl or substituted or unsubstituted —$C_3$-$C_9$-cycloalkyl.

16. The compound of claim 1, wherein a $(CH_2)_n$ type linker attaches $R^b$ of $Y^1$ to a moiety.

17. A compound selected from the group consisting of:

4-((4-(2,6-Dimethylphenoxy)-6,7-dihydro-5H-cyclopenta[d]pyrimidine-2-yl)amino)-benzonitrile;

4-(2,6-Dimethylphenoxy)-N-(piperidine-4-yl)-6,7-dihydro-5H-cyclopenta[d]pyrimidine-2-amine;

Ethylic ether 4-(((6-benzyl-4-(4-cyano-2,6-dimethylphenoxy)-5,6,7,8-tetrahydropyrido[4,3-d]pyrimidine-2-yl)amino)methyl)benzoic acid;

Ethylic ether 4-(((6-benzyl-4-(2,6-dimethylphenoxy)-5,6,7,8-tetrahydropyrido[4,3-d]pyrimidine-2-yl)amino)methyl)benzoic acid;

4-(((7-Benzyl-4-(2,6-dimethylphenoxy)-5,6,7,8-tetrahydropyrido[3,4-d]pyrimidine-2-yl)amino)methyl)benzonitrile;

N-(1-Benzylpiperidine-4-yl)-4-(2,6-dimethylphenoxy)-5,6,7,8-tetrahydroquinazoline-2-amine;

N-(1-Benzylpiperidine-4-yl)-4-(2,6-dimethylphenoxy)-6,7-dihydro-5H-cyclopenta[d]pyrimidine-2-amine;

4-((2-((4-Cyanophenyl)amino)-7-methyl-5,6,7,8-tetrahydropyrido[3,4-d]pyrimidine-4-yl)oxy)-3,5-dimethylbenzonitrile;

4-((4-(4-Formyl-2,6-dimethylphenoxy)-7-methyl-5,6,7,8-tetrahydro[3,4-d]pyrimidine-2-yl)amino)benzonitrile;

Tert-butyl 4-(4-(1,3-dioxolane-2-yl)-2,6-dimethylphenoxy)-2-((4-cyanophenyl)amino)-8,9-dihydro-5H-pyrimido[4,5-d]azepine-7(6H)-carboxylate;

Tert-butyl 2-((4-cyanophenyl)amino)-4-(4-formyl-2,6-dimethylphenyoxy)-8,9-dihydro-5H-pyrimido[4,5-d]azepine-7(6H)-carboxylate;

Tert-butyl 4-(4-cyano-2,6-dimethylphenoxy)-2-((4-cyanophenyl)amino)-7,8-dihydropyrido[4,3-d]pyrimidine-6(5H)-carboxylate;

4-((2-((4-Cyanophenyl)amino)-5,6,7,8-tetrahydropyrido[4,3-d]pyrimidine-4-yl)oxy)-3,5-dimethylbenzonitrile;

4-((2-((4-Cyanophenyl)amino)-6-(methylsulfonyl)-5,6,7,8-tetrahydropyrido[4,3-d]pyrimidine-4-yl)oxy)-3,5-dimethylbenzonitrile;

Ethyl 4-(4-cyano-2,6-dimethylphenoxy)-2-((4-cyanophenyl)amino)-7,8-dihydropyrido[4,3-d]pyrimidine-6(5H)-carboxylate;

(E)-3-(4-((7-(Tert-butoxycarbonyl)-2-((4-cyanophenyl)amino)-6,7,8,9-tetrahydro-5H-pyrimido[4,5-d]azepine-4-yl)oxy)-3,5-dimethylphenyl)acrylic acid;

Tert-butyl 4-(4-(4-cyano-2, 6-dimethylphenoxy)-2-((4-cyanophenyl) amino)-6,7,8,9-tetrahydro-5H-pyrimido[4,5-d]azepine-7-carbonyl)piperidine-1-carboxylate;

4-((2-((4-Cyanophenyl)amino)-6,7,8,9-tetrahydro-5H-pyrimido[4,5-d]azepine-4-yl)oxy)-3,5-dimethylbenzonitrile;

Tert-butyl 2-((4-cyanophenyl)amino)-4-(4-(2-cyanovinyl)-2,6-dimethylphenoxy)-8,9-dihydro-5H-pyrimido[4,5-d]azepine-7(6H)-carboxylate;

4-((2-((4-Cyanophenyl)amino)-7-picolynoyl-6,7,8,9-tetrahydro-5H-pyrimido[4,5-d]azepine-4-yl)oxy)-3,5-dimethylbenzonitrile;

4-((2-((4-Cyanophenyl)amino)-7-isonicotinoyl-6,7,8,9-tetrahydro-5H-pyrimido[4,5-d]azepine-4-yl)oxy)-3,5-dimethylbenzonitrile;

4-((2-((4-Cyanophenyl)amino)-7-nicotinoyl-6,7,8,9-tetrahydro-5H-pyrimido[4,5-d]azepine-4-yl)oxy)-3,5-dimethylbenzonitrile;

4-((2-((4-Cyanophenyl)amino)-7-(pyridine-2-ylmethyl)-6,7,8,9-tetrahydro-5H-pyrimido[4,5-d]azepine-4-yl)oxy)-3,5-dimethylbenzonitrile;

4-((2-((4-Cyanophenyl)amino)-7-(pyridine-3-ylmethyl)-6,7,8,9-tetrahydro-5H-pyrimido[4,5-d]azepine-4-yl)oxy)-3,5-dimethylbenzonitrile;

4-((2-((4-Cyanophenyl)amino)-7-(pyridine-4-ylmethyl)-6,7,8,9-tetrahydro-5H-pyrimido[4,5-d]azepine-4-yl)oxy)-3,5-dimethylbenzonitrile;

4-((2-((4-Cyanophenyl)amino)-6,7,8,9-tetrahydro-5H-pyrimido[4,5-d]azepine-4-yl)oxy)-3,5-dimethylbenzonitrile;

Tert-butyl 4-(4-(4-cyano-2,6-dimethylphenoxy)-2-((4-cyanophenyl)amino)-6,7,8,9-tetrahydro-5H-pyrimido[4,5-d]asein-7-carbonyl)piperidine-1-carboxylate;

4-((2-((4-Cyanophenyl)amino)-7-(piperidine-4-carbonyl)-6,7,8,9-tetrahydro-5H-pyrimido[4,5-d]azepine-4-yl)oxy)-3,5-dimethylbenzonitrile;

Tert-butyl 4-(4-(4-cyano-2,6-dimethylphenoxy)-2-((4-cyanophenyl)amino)-8,9-dihydro-5H-pyrimido[4,5-d]azepine-7(6H)-yl)piperidine-1-carboxylate;

4-((2-((4-Cyanophenyl)amino)-7-(piperidine-4-yl)-6,7,8,9-tetrahydro-5H-pyrimido[4,5-d]azepine-4-yl)oxy)-3,5-dimethylbenzonitrile;

4-((6-(2-Aminoacetyl)-2-((4-cyanophenyl)amino)-5,6,7,8-tetrahydropyrido[4,3-d]pyrimidine-4-yl)oxy)-3,5-dimethylbenzonitrile;

4-((2-((4-Cyanophenyl)amino)-6-(2-(3-hydroxyazetidine-1-yl)acetyl)-5,6,7,8-tetrahydropyrido[4,3-d]pyrimidine-4-yl)oxy)-3,5-dimethylbenzonitrile;

4-({2-[(4-Cyanophenyl)amino]-6-[2-(morpholine-4-yl)acetyl]-5H,6H,7H,8H-pyrido[4,3-d]pyrimidine-4-yl}oxy)-3,5-dimethylbenzonitrile;

4-({2-[(4-Cyanophenyl)amino]-6-[2-(4,4-difluoropiperidine-1-yl)acetyl]-5H,6H,7H,8H-pyrido[4,3-d]pyrimidine-4-yl}oxy)-3,5-dimethylbenzonitrile;

4-((2-((4-Cyanophenyl)amino)-7-(cyclopropanecarbonyl)-5,6,7,8-tetrahydro-[4,3-d]pyrimidine-4-yl)oxy)-3,5-dimethylbenzonitrile;

4-({2-[(4-Cyanophenyl)amino]-6-(morpholine-4-carbonyl)-5H,6H,7H,8H-pyrido[4,3-d]pyrimidine-4-yl}oxy)-3,5-dimethylbenzonitrile;

4-({2-[(4-Cyanophenyl)amino]-6-(4-methylpiperazine-1-carbonyl)-5H,6H,7H,8H-pyrido[4,3-d]pyrimidine-4-yl}oxy)-3,5-dimethylbenzonitrile;

Tert-butyl 2-(4-(4-cyano-2,6-dimethylphenoxy)-2-((cyanophenyl)amino)-6,7,8,9-tetrahydro-5H-pyrimido[4,5-d]azepine-7-carbonyl)pyrrolidine-1-carboxylate;

(R)-Tert-butyl 2-(4-(4-cyano-2,6-dimethylphenoxy)-2-((cyanophenyl)amino)-6,7,8,9-tetrahydro-5H-pyrimido[4,5-d]azepine-7-carbonyl)pyrrolidine-1-carboxylate;

(S)-Tert-butyl 2-(4-(4-cyano-2,6-dimethylphenoxy)-2-((cyanophenyl)amino)-6,7,8,9-tetrahydro-5H-pyrimido[4,5-d]azepine-7-carbonyl)pyrrolidine-1-carboxylate;

4-((2-((4-Cyanophenyl)amino)-7-(tetrahydro-2H-pyran-4-yl)-6,7,8,9-tetrahydro-5H-pyrimido[4,5-d]azepine-4-yl)oxy)-3,5-dimethylbenzonitrile;

4-((2-((4-Cyanophenyl)amino)-7-(5-methylfuran-2-yl)methyl)-6,7,8,9-tetrahydro-5H-pyrimido[4,5-d]azepine-4-yl)oxy)-3,5-dimethylbenzonitrile;

4-((2-((4-Cyanophenyl)amino)-7-(1-methyl-1H-pyrrol-2-yl)methyl)-6,7,8,9-tetrahydro-5H-pyrimido[4,5-d]azepine-4-yl)oxy)-3,5-dimethylbenzonitrile;

4-((2-((4-Cyanophenyl)amino)-7-(4-hydroxybenzyl)-6,7,8,9-tetrahydro-5H-pyrimido[4,5-d]azepine-4-yl)oxy)-3,5-dimethylbenzonitrile;

4-((2-((4-Cyanophenyl)amino)-7-(1-methoxypropane-2-yl)-6,7,8,9-tetrahydro-5H-pyrimido[4,5-d]azepine-4-yl)oxy)-3,5-dimethylbenzonitrile;

Tert-butyl 2-(4-(4-cyano-2,6-dimethylphenoxy)-2-((4-cyanophenyl)amino)-5,6,7,8-tetrahydropyrido[4,3-d]pyrimidine-6-carbonyl)pyrrolidine-1-carboxylate;

4-((2-((4-Cyanophenyl)amino)-6-(pyrrolidine-2-carbonyl)-5,6,7,8-tetrahydropyrido[4,3-d]pyrimidine-4-yl)oxy)-3,5-dimethylbenzonitrile;

4-((6-(Azetidine-3-carbonyl)-2-((4-cyanophenyl)amino)-5,6,7,8-tetrahydropyrido[4,3-d]pyrimidine-4-yl)oxy)-3,5-dimethylbenzonitrile;

4-((2-((4-Cyanophenyl)amino)-6-(pyrazine-2-carbonyl)-5,6,7,8-tetrahydropyrido[4,3-d]pyrimidine-4-yl)oxy)-3,5-dimethylbenzonitrile;

(S)-Tert-butyl (1-(4-(4-cyano-2,6-dimethylphenoxy)-2-((4-cyanophenyl)amino)-7,8-dihydropyrido[4,3-d]pyrimidine-6(5H)-yl)-1-oxopropane-2-yl)carbamate;

(S)-4-((6-(2-Aminopropanoyl)-2-((4-cyanophenyl)amino)-5,6,7,8-tetrahydropyrido[4,3-d]pyrimidine-4-yl)oxy)-3,5-dimethylbenzonitrile;

(S)-Tert-butyl (1-(4-(4-cyano-2,6-dimethylphenoxy)-2-((4-cyanophenyl)amino)-7,8-dihydropyrido[4,3-d]pyrimidine-6(5H)-yl)-1-oxo-3-phenylpropane-2-yl) carbamate;

(S)-4-((6-(2-Amino-3-phenylpropanoyl)-2-((4-cyanophenyl)amino)-5,6,7,8-tetrahydropyrido[4,3-d]pyrimidine-4-yl)oxy)-3,5-dimethylbenzonitrile;

4-((2-((4-Cyanophenyl)amino)-7-(2-morpholineoEthyl)-6,7,8,9-tetrahydro-5H-pyrimido[4,5-d]azepine-4-yl)oxy)-3,5-dimethylbenzonitrile;

(R)-Tert-butyl (1-(4-(4-cyano-2,6-dimethylphenoxy)-2-((4-cyanophenyl)amino)-7,8-dihydropyrido[4,3-d]pyrimidine-6(5H)-yl)-3-hydroxy-1-oxopropane-2-yl)carbamate;

Tert-butyl (1-(4-(4-cyano-2,6-dimethylphenoxy)-2-((4-cyanophenyl)amino)-7,8-dihydropyrido[4,3-d]pyrimidine-6(5H)-yl)-4-(methylthio)-1-oxobutane-2-yl)carbamate;

4-({6-[2-Amino-3-(1H-imidazole-5-yl)propanoyl]-2-[(4-cyanophenyl)amino]-5H,6H,7H,8H-pyrido[4,3-d]pyrimidine-4-yl}oxy)-3,5-dimethylbenzonitrile;

4-((6-(2-Amino-3-(1H-pyrazole-4-yl)propanoyl)-2-((4-cyanophenyl)amino)-5,6,7,8-tetrahydropyrido[4,3-d]pyrimidine-4-yl)oxy)-3,5-dimethylbenzonitrile;

Tert-butyl 4-(2-((tert-butoxycarbonyl)amino)-3-(4-(4-cyano-2,6-dimethylphenoxy)-2-((4-cyanophenyl)amino)-7,8-dihydropyrido[4,3-d]pyrimidine-6(5H)-yl)-3-oxopropyl)-1H-pyrazole-1-carboxylate;

(R)-4-((6-(2-Amino-3-hydroxypropanoyl)-2-((4-cyanophenyl)amino)-5,6,7,8-tetrahydropyrido[4,3-d]pyrimidine-4-yl)oxy)-3,5-dimethylbenzonitrile;

(S)-Tert-butyl (1-(4-(4-cyano-2,6-dimethylphenoxy)-2-((4-cyanophenyl)amino)-7,8-dihydropyrido[4,3-d]pyrimidine-6(5H)-yl)-3-(4-hydroxyphenyl)-1-oxopropane-2-yl)carbamate;

(S)-4-((6-(2-Amino-3-(4-hydroxyphenyl)propanoyl)-2-((4-cyanophenyl)amino)-5,6,7,8-tetrahydropyrido[4,3-d]pyrimidine-4-yl)oxy)-3,5-dimethylbenzonitrile;

(R)-Tert-butyl (1-(4-(4-cyano-2,6-dimethylphenoxy)-2-((4-cyanophenyl)amino)-7,8-dihydropyrido[4,3-d]pyrimidine-6(5H)-yl)-3-methyl-1-oxobutane-2-yl)carbamate;

(R)-4-((6-(2-Amino-3-methylbutanoyl)-2-((4-cyanophenyl)amino)-5,6,7,8-tetrahydropyrido[4,3-d]pyrimidine-4-yl)oxy)-3,5-dimethylbenzonitrile;

(S)-Tert-butyl (1-(4-(4-cyano-2,6-dimethylphenoxy)-2-((4-cyanophenyl)amino)-7,8-dihydropyrido[4,3-d]pyrimidine-6(5H)-yl)-4-methyl-1-oxopentane-2-yl)carbamate;

(S)-4-((6-(2-Amino-4-methylpentanoyl)-2-((4-cyanophenyl)amino)-5,6,7,8-tetrahydropyrido[4,3-d]pyrimidine-4-yl)oxy)-3,5-dimethylbenzonitrile;

(S)-di-Tert-butyl (6-(4-(4-cyano-2,6-dimethylphenoxy)-2-((4-cyanophenyl)amino)-7,8-dihydropyrido[4,3-d]pyrimidine-6(5H)-yl)-6-oxohexane-1,5-diyl)dicarbamate;

(S)-4-((2-((4-Cyanophenyl)amino)-6-(2,6-diaminohexanoyl)-5,6,7,8-tetrahydropyrido[4,3-d]pyrimidine-4-yl)oxy)-3,5-dimethylbenzonitrile;

4-((7-(2-Chloroacetyl)-2-((4-cyanophenyl)amino)-6,7,8,9-tetrahydro-5H-pyrimido[4,5-d]azepine-4-yl)oxy)-3,5-dimethylbenzonitrile;

Methyl 4-(4-cyano-2,6-dimethylphenoxy)-2-((4-4-cyanophenyl) amino)-8,9-dihydro-5H-pyrimido[4,5-d]azepine-7(6H)-carboxylate;

4-((2-((4-Cyanophenyl)amino)-7-(methylsulfonyl)-6,7,8,9-tetrahydro-5H-pyrimido[4,5-d]azepine-4-yl)oxy)-3,5-dimethylbenzonitrile;

4-((2-((4-Cyanophenyl)amino)-6-(pyridine-4-ylmethyl)-5,6,7,8-tetrahydropyrido[4,3-d]pyrimidine-4-yl)oxy)-3,5-dimethylbenzonitrile;

4-((2-((4-Cyanophenyl)amino)-6-(pyridine-3-ylmethyl)-5,6,7,8-tetrahydropyrido[4,3-d]pyrimidine-4-yl)oxy)-3,5-dimethylbenzonitrile;

4-((2-((4-Cyanophenyl)amino)-6-(2-hydroxybenzyl)-5,6,7,8-tetrahydropyrido[4,3-d]pyrimidine-4-yl)oxy)-3,5-dimethylbenzonitrile;

4-((2-((4-Cyanophenyl)amino)-6-(2-(prop-2-in-1-yloxy)benzyl)-5,6,7,8-tetrahydropyrido[4,3-d]pyrimidine-4-yl)oxy)-3,5-dimethylbenzonitrile;

3-(4-(4-Cyano-2,6-dimethylphenoxy)-2-((4-cyanophenyl)amino)-8,9-dihydro-5H-pyrimido[4,5-d]azepine-7(6H)-yl)propanoic acid;

4-((7-Allyl-2-((4-cyanophenyl)amino)-6,7,8,9-tetrahydro-5H-pyrimido[4,5-d]azepine-4-yl)oxy)-3,5-dimethylbenzonitrile;

4-((7-Acetyl-2-((4-cyanophenyl)amino)-6,7,8,9-tetrahydro-5H-pyrimido[4,5-d]azepine-4-yl)oxy)-3,5-dimethylbenzonitrile;

4-((7-(2-(1H-Imidazole-1-yl)acetyl)-2-((4-cyanophenyl)amino)-6,7,8,9-tetrahydro-5H-pyrimido[4,5-d]azepine-4-yl)oxy)-3,5-dimethylbenzonitrile;

4-((2-((4-Cyanophenyl)amino)-7-(2-(methyl-1H-imidazole-1-yl)acetyl)-6,7,8,9-tetrahydro-5H-pyrimido[4,5-d]azepine-4-yl)oxy)-3,5-dimethylbenzonitrile;

4-(4-Cyano-2,6-dimethylphenoxy)-2-[(4-cyanophenyl)amino]-5H,6H,7H,8H-pyrido[4,3-d]pyrimidine-6-sulfonamide;

Methyl 2-{2-[(4-cyanophenyl)amino]-4-(4-formyl-2,6-dimethylphenoxy)-5H,6H,7H,8H,9H-pyrimido [4,5-d]azepine-7-yl}-2-oxoacetate;

4-(4-Cyano-2,6-dimethylphenoxy)-2-[(4-cyanophenyl)amino]-N-(oxane-4-yl)-4aH,5H,6H,7H,8H,8aH-pyrido[4,3-d]pyrimidine-6-carboxamide;

and pharmaceutically acceptable salts thereof.

18. A pharmaceutical composition having activity against reverse transcriptase, the composition comprising:

a therapeutically effective amount of the compound of claim 1; and at least one carrier, excipient or diluent.

19. The pharmaceutical composition of claim 18, further comprising at least one compound selected from HIV protease inhibitors, nucleoside reverse transcriptase inhibitors, non-nucleoside reverse transcriptase inhibitors, CCR5 antagonists, or viral cell entry inhibitors.

20. The pharmaceutical composition of claim 18, wherein the HIV reverse transcriptase contains at least one mutation compared to Wild type HIV.

21. The pharmaceutical composition of claim 18, wherein the HIV reverse transcriptase has reduced sensitivity to Efavirenz, Nevirapine, Doravirine or Delavirdine.

22. A pharmaceutical composition having activity against reverse transcriptase, the composition comprising:

a therapeutically effective amount of the compound of claim 17; and at least one carrier, excipient or diluent.

23. The pharmaceutical composition of claim 22, further comprising at least one compound selected from HIV protease inhibitors, nucleoside reverse transcriptase inhibitors, non-nucleoside reverse transcriptase inhibitors, CCR5 antagonists, or viral cell entry inhibitors.

24. A pharmaceutical composition for the treatment or prevention of human immunodeficiency virus (HIV) comprising:

a therapeutically effective amount of the compound of claim 1; and at least one carrier, excipient or diluent.

25. The pharmaceutical composition of claim 24, further comprising at least one compound selected from the group consisting of HIV protease inhibitors, nucleoside reverse transcriptase inhibitors, non-nucleoside reverse transcriptase inhibitors, CCR5 antagonists, and viral cell entry inhibitors.

26. A pharmaceutical composition for the treatment or prevention of human immunodeficiency virus (HIV) comprising:

a therapeutically effective amount of the compound of claim 17; and at least one carrier, excipient or diluent.

27. The pharmaceutical composition of claim 26, further comprising at least one compound selected from the group consisting of HIV protease inhibitors, nucleoside reverse transcriptase inhibitors, non-nucleoside reverse transcriptase inhibitors, CCR5 antagonists, and viral cell entry inhibitors.

28. A method of treating or preventing HIV in a patient comprising administering a therapeutically effective amount of the compound of claim 1 to the patient in need thereof.

29. The method of claim 28, wherein the therapeutically effective amount of the compound is a daily dose of approximately 0.1 to approximately 500 mg/kg body weight in parenteral infusion.

30. The method of claim 28, wherein a daily dose is administered as a single dose or in 1-5 divided doses.

31. A method of treating or preventing HIV in a patient comprising administering a therapeutically effective amount of the compound of claim 19 to the patient in need thereof.

32. The method of claim 31, wherein the therapeutically effective amount of the compound is a daily dose of approximately 0.1 to approximately 500 mg/kg body weight in parenteral infusion.

33. The method of claim 31, wherein a daily dose is administered as a single dose or in 1-5 divided doses.

* * * * *